US011667903B2

(12) United States Patent
Yeo et al.

(10) Patent No.: US 11,667,903 B2
(45) Date of Patent: Jun. 6, 2023

(54) TRACKING AND MANIPULATING CELLULAR RNA VIA NUCLEAR DELIVERY OF CRISPR/CAS9

(71) Applicant: The Regents of the University of California, La Jolla, CA (US)

(72) Inventors: Eugene Yeo, La Jolla, CA (US); David A. Nelles, La Jolla, CA (US); Mark Fang, La Jolla, CA (US); Ranjan Batra, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 522 days.

(21) Appl. No.: 16/794,918

(22) Filed: Feb. 19, 2020

(65) Prior Publication Data

US 2020/0239863 A1 Jul. 30, 2020

Related U.S. Application Data

(60) Division of application No. 16/054,298, filed on Aug. 3, 2018, now abandoned, which is a continuation of application No. 15/359,567, filed on Nov. 22, 2016, now abandoned.

(60) Provisional application No. 62/259,014, filed on Nov. 23, 2015.

(51) Int. Cl.
| | |
|---|---|
| *C12N 15/113* | (2010.01) |
| *A61K 48/00* | (2006.01) |
| *C12N 9/22* | (2006.01) |
| *C12N 15/11* | (2006.01) |
| *A61K 38/46* | (2006.01) |

(52) U.S. Cl.
CPC ............. *C12N 9/22* (2013.01); *A61K 38/465* (2013.01); *A61K 48/0058* (2013.01); *C12N 15/111* (2013.01); *C12N 15/113* (2013.01); *C07K 2319/09* (2013.01); *C07K 2319/80* (2013.01); *C12N 2310/10* (2013.01); *C12N 2310/20* (2017.05); *Y02A 50/30* (2018.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 5,034,506 A | 7/1991 | Summerton et al. | |
| 5,166,315 A | 11/1992 | Summerton et al. | |
| 5,185,444 A | 2/1993 | Summerton et al. | |
| 5,214,134 A | 5/1993 | Weis et al. | |
| 5,216,141 A | 6/1993 | Benner | |
| 5,235,033 A | 8/1993 | Summerton et al. | |
| 5,264,562 A | 11/1993 | Matteucci | |
| 5,264,564 A | 11/1993 | Matteucci | |
| 5,405,938 A | 4/1995 | Summerton et al. | |
| 5,434,257 A | 7/1995 | Matteucci et al. | |
| 5,466,677 A | 11/1995 | Baxter et al. | |
| 5,470,967 A | 11/1995 | Huie et al. | |
| 5,489,677 A | 2/1996 | Sanghvi et al. | |
| 5,539,082 A | 7/1996 | Nielsen et al. | |
| 5,541,307 A | 7/1996 | Cook et al. | |
| 5,561,225 A | 10/1996 | Maddry et al. | |
| 5,596,086 A | 1/1997 | Matteucci et al. | |
| 5,602,240 A | 2/1997 | De Mesmaeker et al. | |
| 5,608,046 A | 3/1997 | Cook et al. | |
| 5,610,289 A | 3/1997 | Cook et al. | |
| 5,618,704 A | 4/1997 | Sanghvi et al. | |
| 5,623,070 A | 4/1997 | Cook et al. | |
| 5,633,360 A | 5/1997 | Bischofberger et al. | |
| 5,663,312 A | 9/1997 | Chaturvedula | |
| 5,677,437 A | 10/1997 | Teng et al. | |
| 5,677,439 A | 10/1997 | Weis et al. | |
| 5,714,331 A | 2/1998 | Buchardt et al. | |
| 5,719,262 A | 2/1998 | Buchardt et al. | |
| 6,013,639 A | 1/2000 | Peyman et al. | |
| 6,461,864 B1 | 10/2002 | Soriano et al. | |
| 6,471,996 B1 | 10/2002 | Sokoll et al. | |
| 6,472,375 B1 | 10/2002 | Hoon et al. | |
| 7,078,387 B1 | 7/2006 | Leiden et al. | |
| 8,697,359 B1 | 4/2014 | Zhang | |
| 9,074,199 B1 | 7/2015 | Chavez et al. | |
| 11,453,891 B2 | 9/2022 | Yeo et al. | |
| 2002/0068709 A1 | 6/2002 | Orum et al. | |
| 2015/0056702 A1 | 2/2015 | Conway | |
| 2015/0056705 A1 | 2/2015 | Conway et al. | |
| 2015/0071899 A1 | 3/2015 | Liu et al. | |
| 2015/0232844 A1 | 8/2015 | Ozsolak | |
| 2015/0353905 A1 | 12/2015 | Weiss | |
| 2016/0214276 A1 | 7/2016 | Liu | |
| 2016/0215276 A1 | 7/2016 | Liu et al. | |
| 2016/0238593 A1 | 8/2016 | Biyden et al. | |
| 2016/0289659 A1 | 10/2016 | Doudna et al. | |

(Continued)

FOREIGN PATENT DOCUMENTS

| | | |
|---|---|---|
| CN | WO 2001/75097 | 10/2011 |
| CN | 106103705 | 11/2016 |

(Continued)

OTHER PUBLICATIONS

Cong et al., Mol. Ther., May 2014, 22, Supplement 1, Abstract 551.*
Supplementary Partial European Search Report in European Appln. No. 19788702.9, dated Jun. 11, 2021, 12 pages.
Adamala et al., "Programmable RNA-binding protein composed of repeats of a single modular unit," Proceedings of the National Academy of Sciences, May 10, 2016, 113(19):E2579-E2588.
Bjerke et al., "Recent Advances in CRISPR Base Editing: From A to RNA," Biochemistry, Jan. 26, 2018, vol. 57, pp. 886887.
Cox et al., "RNA editing with CRISPR_Cas13," Science, 2017, 358(6366):1019-1027.
Durand et al., "The inside out of lentiviral vectors," Viruses, Feb. 2011, 3(2):132-159.
Extended European Search Report in EP Appln. No. 18799398, dated May 15, 2020, 11 pages.

(Continued)

*Primary Examiner* — Ileana Popa
(74) *Attorney, Agent, or Firm* — Fish & Richardson P.C.

(57) ABSTRACT

Cas9 polypeptides which target RNA and method of using them are provided.

20 Claims, 25 Drawing Sheets

Specification includes a Sequence Listing.

(56) References Cited

U.S. PATENT DOCUMENTS

| | | |
|---|---|---|
| 2016/0304846 A1 | 10/2016 | Liu et al. |
| 2016/0362667 A1 | 12/2016 | Donohue et al. |
| 2017/0073670 A1 | 3/2017 | Nishida et al. |
| 2018/0073012 A1 | 3/2018 | Liu et al. |
| 2018/0208924 A1 | 7/2018 | Fukuda et al. |
| 2018/0273576 A1 | 9/2018 | Hogrefe et al. |
| 2019/0062724 A1 | 2/2019 | Hsu et al. |
| 2021/0079366 A1 | 3/2021 | Zhang et al. |
| 2021/0332344 A1 | 10/2021 | Yeo et al. |
| 2021/0340197 A1 | 11/2021 | Yeo et al. |
| 2022/0127621 A1 | 4/2022 | Yeo et al. |
| 2022/0204978 A1 | 6/2022 | Yeo et al. |
| 2022/0220473 A1 | 7/2022 | Yeo et al. |

FOREIGN PATENT DOCUMENTS

| | | |
|---|---|---|
| CN | 108103090 | 6/2018 |
| CN | 110055284 | 7/2019 |
| JP | 2015-506669 | 3/2015 |
| WO | WO 1998/39352 | 9/1998 |
| WO | WO 1999/14226 | 3/1999 |
| WO | WO 2000/066604 | 11/2000 |
| WO | WO 2009/066758 | 5/2009 |
| WO | WO 2012/068627 | 5/2012 |
| WO | WO 2013/058404 | 4/2013 |
| WO | WO 2013/082548 | 6/2013 |
| WO | WO 2013/130684 | 9/2013 |
| WO | WO 2014/093622 | 6/2014 |
| WO | WO 2014/093635 | 6/2014 |
| WO | WO 2014/093661 | 6/2014 |
| WO | WO 2014/113493 | 7/2014 |
| WO | WO 2014/191518 | 12/2014 |
| WO | WO 2014/191521 | 12/2014 |
| WO | WO 2015/006294 | 1/2015 |
| WO | WO 2015/048690 | 4/2015 |
| WO | WO 2015/089277 | 6/2015 |
| WO | WO 2015/089351 | 6/2015 |
| WO | WO 2016/019655 | 2/2016 |
| WO | WO 2016/097212 | 6/2016 |
| WO | WO 2016/106236 | 6/2016 |
| WO | WO 2016/183402 | 11/2016 |
| WO | WO 2016/191684 | 12/2016 |
| WO | WO 2016/196655 | 12/2016 |
| WO | WO 2016/196805 | 12/2016 |
| WO | WO 2016/201138 | 12/2016 |
| WO | WO 2017/010556 | 1/2017 |
| WO | WO 2017/053312 | 3/2017 |
| WO | WO 2017/091630 | 6/2017 |
| WO | WO 2017/219027 | 12/2017 |
| WO | WO 2018/002697 | 1/2018 |
| WO | WO 2018/027078 | 2/2018 |
| WO | WO 2018/154387 | 8/2018 |
| WO | WO 2018/183703 | 10/2018 |
| WO | WO 2019/006471 | 1/2019 |
| WO | WO 2019/040664 | 2/2019 |
| WO | WO 2019/060746 | 3/2019 |
| WO | WO 2019/204828 | 10/2019 |

OTHER PUBLICATIONS

Fernanda et al., "Current strategies for site-directed RNA editing using ADARs," Methods, 2018, 156:16-24.

Fukuda et al., "Construction of a guide-RNA for site-directed RNA mutagenesis utilising intracellular A-to-I RNA editing," Sci Rep, 2017, 7:41478.

German-Retana et al., "Mutational analysis of plant cap-binding protein eIF4E reveals key amino acids involved in biochemical functions and potyvirus infection," Journal of virology, Aug. 1, 2008, 82(15):7601-7612.

Hanswillemenke et al., "Site-Directed RNA Editing in Vivo Can Be Triggered by the Light-Driven Assembly of an Artificial Riboprotein," J Am Chem Soc, 2015, 137(50):15875-81.

Hermonat & Muzyczka, "Use of adeno-associated virus as a mammalian DNA cloning vector: transduction of neomycin resistance into mammalian tissue culture cells," Proc. Natl. Acad. Sci. USA, 1984, 81:6466-6470.

Higuchi et al., "RNA editing of AMPA receptor subunit GluR-B: a base-paired intron-exon structure determines position and efficiency," Cell, 1993, 75(7):1361-70.

Hua et al. "Peripheral SMN restoration is essential for long-term rescue of a severe spinal muscular atrophy mouse model." Nature, 2011, 478(7367):123-6.

International Preliminary Report on Patentability in International Appln. No. PCT/US2018/031913, dated Nov. 12, 2019, 9 pages.

International Search Report and Written Opinion dated Aug. 2, 2018, from application No. PCT/US2018/031913.

Konermann et al., "Genome-scale transcriptional activation by an engineered CRISPR-Cas9 complex," Nature, 2015, 517(7356):583-588.

Konermann et al., "Transcriptome engineering with RNA-targeting type VI-D CRISPR effectors," Cell, Apr. 19, 2018, 173(3): 27 Pages.

Kotterman et al., "Viral Vectors for Gene Therapy: Translational and Clinical Outlook," Annual Review of Biomedical Engineering, 2015, 17:63-89.

Kuttan & Bass, "Mechanistic insights into editing-site specificity of ADARs," PNAS, 2012, 109(48):E3295-E3304.

Lebkowski et al., "Adeno-associated virus: a vector system for efficient introduction and integration of DNA into a variety of mammalian cell types," Mol. Cell. Biol., 1988, 8:3988-3996.

Matthews et al., "Structures of human ADAR2 bound to dsRNA reveal base-flipping mechanism and basis for site selectivity," Nature structural & molecular biology, May 2016, 23(5): 23 Pages.

McMahon et al., "TRIBE: Hijacking an RNA-Editing Enzyme to Identify Cell-Specific Targets of RNA-Binding Proteins," Cell, 2016, 165(3):742-53.

Montiel-Gonzalez et al "An efficient system for selectively altering genetic information within mRNAs." Nucleic Acids Res., 2016, 44:e157.

Montiel-Gonzalez et al., "Correction of mutations within the cystic fibrosis transmembrane conductance regulator by site-directed RNA editing," PNAS, 2013, 110(45):18285-90.

Nishikura, "A-to-I editing of coding and non-coding RNAs by ADARs," Nat Rev Mol Cell Biol, 2016, 17(2):83-96.

O'Keefe et al., "Scaleable manufacture of HIV-1 entry inhibitor griffithsin and validation of its safety and efficacy as a topical microbicide component," Proc. Nat. Acad. Sci. USA, 2009, 106(15):6099-6104.

PCT International Preliminary Report on Patentability in International Appln. No. PCT/US2019/028580, dated Oct. 29, 2020, 9 pages.

PCT International Search Report and Written Opinion in International Appln. No. PCT/US2019/028580, dated Aug. 27, 2019, 14 pages.

Phelps et al., "Recognition of duplex RNA by the deaminase domain of the RNA editing enzyme ADAR2," Nuc. Acid Res., 2015, 43(2):1123-1132.

Schellenberger et al., "A recombinant polypeptide extends the in vivo half-life of peptides and proteins in a tunable manner," Nat Biotechnol., 2009, 27(12):1186-1190.

Schlesinger & Dubensky, "Alphavirus vectors for gene expression and vaccines," Curr. Opin. Biotechnol., 1999, 10(5):434-439.

Schneider et al "Optimal guideRNAs for re-directing deaminase activity of hADAR1 and hADAR2 in trans." Nucleic Acids Res., 2014, 42:e87.

Wang et al., "Unbiased detection of off-target cleavage by CRISPR-Cas9 and TALENs using integrase-defective lentiviral vectors," Nature biotechnology, Feb. 2015, 33(2): 5 Pages.

Wold and Toth, "Adenovirus Vectors for Gene Therapy, Vaccination and Cancer Gene Therapy," Curr. Gene. Ther., 2013, 13(6):421-433.

Wright et al., "Biology and Applications of CRISPR Systems: Harnessing Nature's Toolbox for Genome Engineering," Cell, 2016, 164(1-2):29-44.

Yan et al., "Cas13d is a compact RNA-targeting type VI CRISPR effector positively modulated by a WYL-domain-containing accessory protein," Molecular cell, Apr. 19, 2018 70(2):327-339.

(56) References Cited

OTHER PUBLICATIONS

Ying et al., "Cancer therapy using a self-replicating RNA vaccine," Nat. Med., 1999, 5(7):823-827.
Zetsche et al., A split-Cas9 architecture for inducible genome editing and transcription modulation, Nature biotechnology, Feb. 2015, 33(2): 3 Pages.
Allocca et al., "Novel adeno-associated virus serotypes efficiently transduce murine photoreceptors," Journal of virology, Oct. 15, 2007, 81(20):11372-11380.
Asokan et al., "The AAV vector toolkit: poised at the clinical crossroads," Molecular Therapy, Apr. 1, 2012, 20(4):699-708.
Basolo et al., "RET protein expression has no prognostic impact on the long-term outcome of papillary thyroid carcinoma," European journal of endocrinology, Nov. 1, 2001, 145(5):599-604.
Borghardt et al., "Inhaled Therapy in Respiratory Disease: The Complex Interplay of Pulmonary Kinetic Processes," Canadian Respiratory Journal, 2018, 1-11.
Braasch et al., "Novel antisense and peptide nucleic acid strategies for controlling gene expression," Biochemistry, Apr. 9, 2002,41(14):4503-4510.
Brezgin et al., "Dead Cas systems: types, principles, and applications," International journal of molecular sciences, Jan. 2019, 20(23):6041, 26 pages.
Cai et al., "Quantitative assessment of mRNA cap analogues as inhibitors of in vitro translation," Biochemistry, Jun. 29, 1999, 38(26):8538-8547.
Chen et al., "Structure-guided design, synthesis, and evaluation of guanine-derived inhibitors of the eIF4E mRNA-cap interaction," Journal of medicinal chemistry, Apr. 26, 2012, 55(8):3837-3851.
Cokol et al., "Finding nuclear localization signals," EMBO reports, Nov. 1, 2000, 1(5):411-415.
De Mesmaeker et al., "Antisense oligonucleotides," Accounts of Chemical Research, Sep. 1, 1995, 28(9):366-374.
Deer et al., "High-level expression of proteins in mammalian cells using transcription regulatory sequences from the Chinese hamster EF-1α gene," Biotechnology progress, 2004, 20(3):880-889.
Deyle et al., "Adeno-associated vims vector integration," Current opinion in molecular therapeutics, Aug. 2009, 11(4):442-447.
Durocher et al., "High-level and high-throughput recombinant protein production by transient transfection of suspension-growing human 293-EBNA1 cells," Nucleic Acids Research, 2002, 30(2), 9 pages.
Esakova et al.,"Of proteins and RNA: the RNase P/MRP family," Rna, Sep. 1, 2010, 16(9):1725-1747.
Extended European Search Report in EP Appln. No. 19788702.9, dated Oct. 13, 2021, 11 pages.
Freitas et al., "Mechanisms and signals for the nuclear import of proteins," Current genomics, Dec. 2009, 10(8):550-557.
Gebeyehu et al., "Novel biotinylated nucleotide-analogs for labeling and colorimetric detection of DNA," Nucleic acids research, Jun. 11, 1987, 15(11):4513-4534.
GenBank Accession No. FJ209302, "*Homo sapiens* MALAT1-associated small cytoplasmic RNA, complete sequence," Dec. 2, 2008, 1 pages.
Hamajima et al., "Intranasal administration of HIV-DNA vaccine formulated with a polymer, carboxymethylcellulose, augments mucosal antibody production and cell-mediated immune response," Clinical immunology and immunopathology, Aug. 1, 1998, 88(2):205-210.
Heasman, "Morpholino oligos: making sense of antisense?" Developmental biology, Mar. 15, 2002, 243(2):209-214.
International Preliminary Report on Patentability in International Appln. PCT /US2020/028501, dated Oct. 28, 2021, 10 pages.
International Preliminary Report on Patentability in International Appln. PCT/US2020/028546, dated Oct. 28, 2021, 11 pages.
Kadokura et al., "Solid-phase synthesis of a 5'-terminal TMG-capped trinucleotide block of U1 snRNA," Tetrahedron Letters, Dec. 10, 2001, 42(50):8853-8856.

Khani et al., "AAV-mediated expression targeting of rod and cone photoreceptors with a human rhodopsin kinase promoter," Investigative ophthalmology & visual science, Sep. 1, 2007, 48(9):3954-3961.
Kirsebom, "RNase P RNA mediated cleavage: substrate recognition and catalysis," Biochimie, Oct. 1, 2007, 89(10):1183-1194.
Konermann et al., "Transcriptome engineering with RNA-targeting type VI-D CRISPR effectors," Cell, Apr. 19, 2018, 173(3):665-676.
Kormann et al., "Expression of therapeutic proteins after delivery of chemically modified mRNA in mice," Nature biotechnology, Feb. 2011, 29(2):154-157.
Koshkin et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron, Apr. 2, 1998, 54(14):3607-3630.
Lai et al., "Unexpected diversity of RNase P, an ancient tRNA processing enzyme: challenges and prospects," FEBS letters, Jan. 21, 2010, 584(2):287-296.
Martin, "Ein neuer Zugang zu 2'-O-Alkylribonucleosiden und Eigenschaften deren Oligonucleotide," Helvetica Chimica Acta, Mar. 22, 1995, 78(2):486-504.
Massie et al., "Inducible overexpression of a toxic protein by an adenovirus vector with a tetracycline-regulatable expression cassette," Journal of Virology, Mar. 1, 1998, 72(3):2289-2296.
Mingozzi et al., "Therapeutic in vivo gene transfer for genetic disease using AAV: progress and challenges," Nature reviews genetics, May 2011, 12(5):341-355.
Muzyczka, "Use of adeno-associated virus as a general transduction vector for mammalian cells," Viral expression vectors, 1992, 97-129.
Nasevicius et al., "Effective targeted gene 'knockdown' in zebrafish," Nature genetics, Oct. 2000, 26(2):216-220.
Nielsen "Sequence-selective recognition of DNA by strand displacement with a thymine-substituted polyamide," Science, Dec. 6, 1991, 254(5037):1497-1500.
Ohkubo et al.,"Efficient solid-phase synthesis of oligodeoxynucleotides having a 5'-terminal 2, 2, 7-trimethylguanosine pyrophosphate linkage," Bioorganic & medicinal chemistry, Jul. 1, 2009, 17(13):4819-4824.
Pang et al., "Comparative analysis of in vivo and in vitro AAV vector transduction in the neonatal mouse retina: effects of serotype and site of administration," Vision research, Feb. 1, 2008, 48(3):377-385.
Singh et al., "LNA (locked nucleic acids): synthesis and high-affinity nucleic acid recognition," Chemical communications, 1998, (4):455-456.
Soukarieh et al., "Design of nucleotide-mimetic and non-nucleotide inhibitors of the translation initiation factor eIF4E: Synthesis, structural and functional characterisation," European journal of medicinal chemistry, Nov. 29, 2016, 124:200-217.
Strenkowska et al., "Cap analogs modified with 1, 2-dithiodiphosphate moiety protect mRNA from decapping and enhance its translational potential. Nucleic acids research," Nov. 16, 2016, 44(20):9578-9590.
Wahlestedt et al., "Potent and nontoxic antisense oligonucleotides containing locked nucleic acids," Proceedings of the National Academy of Sciences, May 9, 2000, 97(10):5633-5638.
Walczak et al., "A novel route for preparing 5' cap mimics and capped RNAs: phosphate-modified cap analogues obtained via click chemistry," Chemical science, 2017, 8(1):260-267.
Wang et al., "Cyclohexene nucleic acids (CeNA): serum stable oligonucleotides that activate RNase H and increase duplex stability with complementary RNA," Journal of the American Chemical Society, Sep. 13, 2000, 122(36):8595-8602.
Warren et al., "Highly efficient reprogramming to pluripotency and directed differentiation of human cells with synthetic modified mRNA," Cell stem cell, Nov. 5, 2010, 7(5):618-630.
Xu et al., "A CRISPR-dCas toolbox for genetic engineering and synthetic biology," Journal of molecular biology, Jan. 4, 2019, 431(1):34-47.
Wang et al., "Probing RNA recognition by human ADAR2 using a high-throughput mutagenesis method," Nucleic acids research, Nov. 2016, 44(20):9872-9880.

(56) References Cited

OTHER PUBLICATIONS

Akerstrom et al., "A physicochemical study of protein G, a molecule with unique immunoglobulin G-binding properties," J. Biol. Chem., 1986, 261: 10,240-10,247.
Bashor C.J. et al., Using engineered scaffold interactions to reshape MAP kinase pathway signaling dynamics. Science, 2008, 319(5869):1539-1543.
Batra R. et al., Loss of MBNL Leads to Disruption of Developmentally Regulated Alternative Polyade in RNA-Mediated Disease; Mol. Cell. (Oct. 2014) 56(2):311-322.
Bennett C.F. et al., RNA targeting therapeutics: molecular mechanisms of antisense oligonucleotides as a therapeutic platform, Anmi Rev Pharmacol Toxlcol. (2010) 50: 259-293.
Bertrand E. et al., Localization of ASH1 mRNA particles in living yeast. Mol Cell (1998) 2(4):437-445.
Beuth B. et al., StructL1re of a Mycobacterivm tuberculosis NusA-RNA complex. EMBO J (2005) 24:3576-3587.
Bjorck et al., "Purification and some properties of *Streptococcal* protein G, a novel IgG-binding reagent," J. Immunol., 1984, 133:969-974.
Braddock Q.T. et al., StrL1cture and dynamics of KH domains from FBP bound to single-stranded DNA, Nature, 2002, 415:1051-1056.
Buchan J.R. et al., Eukaryotic stress granules: the ins and outs of translation. Mol Cell (2009) 36:932-941.
Buxbaum A.R. et al., Single beta-actin mRNA detection in neurons reveals a mechanism for regulating its translatability, Science, 2014, 343:(6169):419-422.
Cao et al., "A universal strategy for regulating mRNA translation in prokaryotic and eukaryotic cells" NARS, 2015, 43(8): 4353-4362.
Cencic R. et al., Protospacer adjacent motif (PAM)-distal sequences engage CRISPR Cas9 DNA target cleavage. PloS One (2014) 9(10): e109213 (13 pages).
Chen B. et al., Dynamic imaging of genomic loci in living human cells by an optimized CRISPR/Cas system, Cell, 2013, 155:1479-1491.
Cheong C.G. et al., Engineering RNA sequence specificity of Pumilio repeats. Proc Natl Acad Sci U, 2006, 103:13635-13639.
Cho S.W. et al., Targeted genome engineering in human cells with the Cas9 RNA-guided endonuclease. Nat Biotechnol. (2013) 31 (3): 230-232.
Chou H.H. et al., Picky: oligo microarray design for large genomes. Bioinformatics. (2004) 20(17):2893-28902.
Cong L. et al., Multiplex genome engineering using CRISPR/Cas systems. Science (2013) 339(6121):819-823.
Cooke et al., "Targeted translational regulation using the PUF protein family scaffold" PNAS, 2011, 108(38):15870-15875.
DeJesus-Hernandez M. et al., Expanded GGGGCC hexanucleotide repeat in noncoding region of C9ORF72 causes chromosome 9p-linked FTD and ALS. Neuron (2011) 72(2): 245-256.
Delebecque C.J. et al., Organization of intracellular reactions with rationally designed RNA assemblies. Science (2011) 333(6041): 470-474.
Doench et al., "Rational design of highly active sgRNAs for CRISPR-Cas9-mediated gene inactivation," Nature biotechnology, 2014, 32(12):1262-7.
Dong et al., Hum. Gene Ther., 1996, 7: 2101-2112; Abstract.
Donnelly C.J. et al., Limited availability of ZBP1 restricts axonal mRNA localization and nerve regeneration capacity. EMBO J (2011) 30(22): 4665-4677.
Dow L.E. et al., Inducible in vivo genome editing with CRISPR-Cas9. Nature Biotechnol. (Feb. 2015 epublished) 33(4):390-394 (14 pages).
Dueber J.E. et al., Synthetic protein scaffolds provide modL11ar control over metabolic flux. Nat. Biotechnol. (2009) 27(8): 753-759.
Eliasson et al., "Chimeric IgG-binding receptors engineered from *Staphylococcal* protein A and *Streptococcal* protein G," J. Biol. Chem., 1988, 263:4323-4327.
ENCODE Project ConsortiL.1m, The; An integrated encyclopedia of ONA elements in the human genome. Nature (2012) 489(7414): 57-74.

Esvelt K.M. et al., Orthogonal Cas9 proteins for RNA guided gene regulation and editing. Nat. Methods (2013) 10(11):1116-1121.
Filipovska A. et al., A universal code for RNA recognition by PUF proteins. Nat Chem Biol. (2011) 7:425-427.
Fouts D.E. et al., Functional recognition of fragmented operator sites by R17/MS2 coat protein, a translational repressor, Nucleic Acids Res., 1997, 25(22):4464-4473.
Fu et al., Improving CRISPR-Gas nuclease specificity using truncated guide RNAs. Nat Biotechnol., 2014, 32(3):279-284.
Fusco D. et al., Single mRNA molecules demonstrate probabilistic movement in living mammalian cells, Curr. Biol., 2003, 13(2):161-167.
Garcia J.F. et al., MS2 coat proteins bound to yeast mRNAs block 5' to 3' degradation and trap mRNA decay products: implications for the localization of mRNAs by MS2-MCP system. RNA (2015) 21(8):1393-1395.
Geisler S. et al., RNA in unexpected places: long non-coding RNA functions in diverse cellular contexts, Nat. Rev. Mol. Cell. Biol., 2013, 14(11):699-712.
Gentz et al., "Bioassay for trans-activation using purified human immunodeficiency virus tat-encoded protein: trans-activation requires mRNA synthesis," Proc. Natl. Acad. Sci., 1989, 86:821-824.
Gerstberger S. et al., Evolutionary conservation and expression of human RNA-binding proteins and their role in human genetic disease, Adv. Exp. Med. Biol., 2014 825:1-55.
Gilbert L.A. et al., CRISPR-mediated modular RNA guided regulation of transcription in eukaryotes, Cell, 2013, 154(2):442-451, (20 pages).
Graham et al., "Resources for the design of CRISPR gene editing experiments," Genome Biol. 2015; 16:260.
Graveley 8.R. et al., Arginine/serine-rich domains of SR proteins can function as activators of pre-mRNA splicing, Mol. Cell, 1998, 1:765-771.
Gritsenko et al., "Sequence features of viral and human Internal Ribosome Entry Sites predictive of their activity," PLoS Comput Biol, 2017, 13(9):e1005734.
Guss et al., "Structure of the IgG-binding regions of *Streptococcal* protein G," EMBO J., 1986, 5:1567-1575.
Hale et al., RNA-guided RNA cleavage by a CRISPR RNA-Cas protein complex. Cell (2009) 139(5):945-956.
Halo T. L. et al., NanoFlares for the detection, isolation, and culture of live tumor cells from human blood. PNAS (2014) 111 (48):17104-17109.
Hendel A. et al., Chemically modified guide RNAs enhance CRISPR-Cas genome editing in human primary cells. Nature Biotech. (2015) 33:985-989.
Hjelm et al., "Immunologically active and structurally similar fragments of protein A from *Staphylococcus aureus*," Eur. J. Biochem., 1975, 57:395-403.
Ho T.H. et al., Colocalization of muscleblind with RNA foci is separable from mis-regulation of alternative splicing in myotonic dystrophy; J Cell Sci. (2005) 118(13): 2923-2933.
Hsu et al., "Development and applications of CRISPR-Cas9 for genome engineering," Cell, 2014, 156(6):1262-1278.
Hua Y, et al., Antisense masking of an hnRNP A1/A2 intronic splicing silencer corrects SMN2 splicing in transgenic mice. Am J HL1m Genet. (2008) 82(4): 834-848.
Hua Y. et al., Antisense correction of SMN2 splicing in the CNS rescues necrosis in a type III SMA mouse model. Genes Oev. (2010) 24(15): 1634-1644.
Hua Y. et al., Peripheral SMN restoration is essential for long-term rescue of a severe spinal muscular atrophy mouse model. NatLJre. (2011) 478(7367):123-126.
Hwang W.Y. et al., Efficient In Vivo Genome Editing Using RNA•Guided Nucleases. Nat Biotechnol. (2013) 31(3): 227-229 (12 pages).
International Search Report and Written Opinion dated May 8, 2017 for corresponding Application PCT/US2016/063429, filed Nov. 22, 2016; 22 pages.
International Search Report and Written Opinion in Application No. PCT/US19/28580, dated Aug. 27, 2019, 14 pages.
Jiang F, "Structures of a CRISPR-Cas9 R-loop complex primed for DNA cleavage," Science, 2016, 351(6275):867-71.

(56) References Cited

OTHER PUBLICATIONS

Jinek M. et al., RNA-programmed genome editing in human cells. elife (2013) 2: e00471 (9 pages).

Kedersha N. et al., Mammalian stress granules and processing bodies. Methods Enzymol. (2007) Chapter 5; 431: 61-81.

Kelley et al., "Versatility of chemically synthesized guide RNAs for CRISPR-Cas9 genome editing," J. of Biotechnology, 2016, 233:74-83.

Kislauskis et al., "Sequences Responsible for Intracellular Localization of U.-Actin Messenger RNA also Affect Cell Phenotype," Journal of Cell Biology, 1994, 127(2):441-451.

Kodama et al., "An improved bimolecular fluorescence complementation assay with a high signal-to-noise ratio," Biotechniques, 2010, 49(5):793-805.

Kodama Y. et al., An improved bimolecular fluorescence complementation assay with a high signal signal to-noise ratio. Biotechniques. (Nov. 2010) 49(5): 793-805.

Kuscu C. et al., Genome-wide analysis reveals characteristics of off-target sites bound by the Cas9 endonuclease. Nat Biotechnol. (2014) 32(7): 677-683.

Laird-Offringa I.A. et al., Analysis of RNA-binding proteins by in vitro genetic selection: Identification of an amino acid residue important for locking U1A onto its RNA target. Proc Natl Acad Sci USA, 1995, 92:11859-11863.

Li D. et al., Heritable gene targeting in the mouse and rat using a CRISPR-Cas system. Nat Biotechnol. (2013) 31 (8): 681-683.

Li Y.R. et al., Stress granules as crucibles of ALS pathogenesis. J Cell Biol. (2013) 201(3): 361-372.

Lionnett. et al., A transgenic mouse for in vivo detection of endogenous labeled mRNA. Nat Methods (2011) 8(2): 165-170.

Lovci M.T. et al., Rbfox proteins regulate alternative mRNA splicing through evolutionarily conserved RNA bridges. Nat Struct Mol Biol., 2013, 20(12):1434-1442 (23 pages).

Lu J. et al., MicroRNA expression profiles classify human cancers. Nature (2005) 435(7043):834-838.

MacKenzie T.A. et al., Stromal Expression of miR-21 Identifies High-Risk Group in Triple-Negative Breast Cancer. Am J. Pathol. (Dec. 2014) 184(12):3217-3225.

Maddalo D. et al., In vivo engineering of oncogenic chromosomal rearrangements with the CRISPR/Cas9 system. Nature (Dec. 2014) 516(7531): 423-427.

Mali P. et al., CAS9 transcriptional activators for target specificity screening and paired nickases for cooperative genome engineering, Nat Biotech. (2013) 31 (9): 833-838; XP055299678.

Mali P. et al., RNA-Guided Human Genome Engineering via Cas9. Science (2013) 339(6121):823-826.

Manders E.M. et al., Dynamics of three-dimensional replication patterns during the S-phase, analyzed by double labelling of DNA and confocal microscopy. J Cell Sci. (1992) 103 (Pt 3): 857-862.

Meng L. et al., Towards a therapy for Angelman syndrome by targeting a long non-coding RNA. Nature (Feb. 2015) 518(7539): 409-412 (20 pages).

Mohr et al., "CRISPR guide RNA design for research applications," FEBS Journal, 2016, 283(17):3232-38.

Muddashetty R.S. et al., Reversible inhibition of PSD-95 mRNA translation by miR-125a, FMRP phosphorylation, and mGILJR signaling. Moi Ceil (2011) 42(5): 673-688.

Nakayama et al., Simple and efficient CRISPR/Cas9-mediated targeted mutagenesis in Xenopus tropicaiis. Genesis (2013) 51 (12): 835•843.

Nelles D. et al., Programmable RNA Tracking in Live Cells with CRISPR/Cas9. Cell (Mar. 2016) 165(2): 488-496; XP029496630.

Nelles et al., Applications of Cas9 as an RNA-programmed RNA-binding protein. Bioessays (Jul. 2015) 37(7): 732-739, e-publ. Apr. 16, 2015.

Nissim-Rafinia M. et al., Splicing regulation as a potential genetic modifier. Trends Genet. (2002), 18(3):123-127.

O'Connell M.R. et al., Programmable RNA recognition and cleavage by CRISPR/Cas9. Nature, (2014) 516: 263-266.

Ozawa T. et al., imaging dynamics of endogenous mitochondrial RNA in single living cells. Nat. Methods, 2007, 4(5):413-419.

Paige J.S. et al., RNA mimics of green fluorescent protein. Science (2011) 333: 642-646.

Park H.Y. et al., Visualization of dynamics of single endogenous mRNA labeled in live mouse, Science (Jan. 2014) 343:6196-422-424.

Partial International Search Report dated Feb. 28, 2017 for corresponding Application No. PCT/US2016/063429.

Pasca et al. "Using iPSC-derived neurons to uncover cellular phenotypes associated with Timothy syndrome," Nat Med, 2011, 17:1657-62.

Pasca S.P. et al., Using IPSC-derived neurons to uncover cellwiar phenotypes associated with Timothy Syndrome. Nat Med. (2011) 17(12):1657-1662.

Passini M.A. et al., Antisense oligonucleotides delivered to the mouse CNS ameliorate symptoms of severe spinal muscular atrophy. Science Transl Med. (2011) 3(72): 72ra18 (21 pages).

Price et al., Cas9-mediated targeting of viral RNA in eukaryotic cells. Proc Natl Acad Sci USA (May 2015) 112(19): 6164-6169.

Qi L.S. et al., Repurposing CRISPR as an RN.A-guided platform for sequence-specific control of gene expression, Cell, 2013, 152(5):1173-1183 (22 pages).

Rackham O. et al., Visualization of RNA protein interactions in living cells: FMRP and IMP1 interact on mRNAs. EMBO J., 2004, 23(16):3346-3355.

Rahdar M. et al., Synthetic CRISPR RNA-Cas9-guided genome editing in human cells. PNAS (Nov. 2015) pp. E711 0-E7117; XP055264777.

Rath A.K. et al., Genetically encoded tools for RNA imaging in living cells. Curr Opin Biotechnol., 2014, 31:42-49.

Renton A.E. et al., A hexanucleotide repeat expansion in C9ORF72 is the cause of chromosome 9p21-linked ALS-FTD. Neuron (2011) 72(2): 257-268.

Sachdeva G. et al., In vivo co-localization of enzymes on RNA scaffolds increases metabolic production in a geometrically dependent manner, Nucleic Acids Res., 2014, 42(14):9493-9503.

Sambrook & Russel, Molecular Cloning (3rd ed., CSHL Press, 2001).

Sampson T.R. et al., A CRISPR/Cas system mediates bacterial innate immune evasion and virulence, Nature, 2013, 497:254-257.

Sander et al., CRISPR-Cas systems for editing, regulating and targeting genomes. Nat Biotechnol. (2014) 32(4): 347-355.

Schindelin J. et al., Fiji: an open-source platform for biological-image analysis. Nat Methods (2012) 9(7):676-682.

Shestakova E.A. et al., The physiological significance of beta-actin mRNA localization in determining cell polarity and directional motility, Proc Natl Acad Sci USA, 2001, 98(13):7045-7050.

Shin I. et al., Live-cell imaging of Pol II promoter activity to monitor gene expression with RNA IMAGEtag reporters. Nucleic Acids Res (2014) 42(11): e90 (9 pages).

Sikkema, "An Fc-binding protein," Amer. Biotech. Lab., 1989, 7:42.

Sjoquist et al., "Protein A isolated from *Staphylococcus aureus* after digestion with lysostaphin," Eur. J. Biochem., 1972, 29:572-578.

Staals R.H. et al., RNA Targeting by the Type III-A CRISPR-Cas Csm Complex of Thermus thermophilus, Mol Cell, 2014, 56:518-530.

Stepto et al., "Modelling C9ORF72 hexanucleotide repeat expansion in amyotrophic lateral sclerosis and frontotemporal dementia," Acta Neuropathol., 2014, 127(3):377-89.

Sternberg S.H. et al., DNA interrogation by the CRISPR RNA-guided endonuclease Cas9. Nature, 2014, 507:(7490):62-67.

Strack R.L. et al., A superfolding Spinach2 reveals the dynamic nature of trinucleotide repeat-containing RNA, Nat Methods, 2013, 10(12):1219-1224.

Sunbul M. et al., Contact-mediated quenching for RNA imaging in bacteria with a fluorophore-binding aptamer, Angew Chem Int. Ed Engl, 2013, 52(50):13401-13404.

Swiech L. et al., In vivo interrogation of gene function in the mammalian brain using CRISPR-Cas9. Nature Biotechnol., (Jan. 2015) 33(1):102-106 (22 pages).

(56) References Cited

OTHER PUBLICATIONS

Tourriere H. et al., The RasGAP.associated endoribonuclease G3BP assembles stress granules. J Cell Biol., 2003, 160(6):823-831.
Tyagi S. et al., Molecular beacons: Probes that fluoresce upon hybridization. Nat Biotechnol. (1996) 14:303-308.
Unsworth H. et al., mRNA escape from stress granule sequestration is dictated by localization to the endoplasmic reticulum, FASEB J. (2010) 24(9): 3370-3380.
Urnov F.D. et al., Genome editing with engineered zinc finger nucleases, Nat Rev Genet. (2010) 11(9): 636-646.
Wang X. et al., Crystal structure of a Pumilio homology domain. Mol Cell (2001) 7: 855-865.
Wang X. et al., Modular recognition of RNA by a human pumilio-homology domain. Cell (2002) 110(4):501-512.
Wang Y. et al., Engineering splicing factors with designed specificities; Nat Methods. (2009) 6(11):825-830.
Wernersson R. et al., OligoWiz 2.0—Integrating sequence feature annotation into the design of microarray probes, Nucleic Acids Res., 2005, 33 (Web Server issue): W611-5.
Weyn-Van. Hentenryci< S.M. et al., HITS-CLIP and integrative modeling define the Rbfox splicing-regulatory network linked to brain development and autism. Cell Rep. (Mar. 2014) 6(6):1139-52 (26 pages).
Wiedenheft B., et al., RNA-guided genetic silencing systems in bacteria and archaea, Nature, 2012, 482(7385):331-338.
Wilson et al., "The structure of an antigenic determinant in a protein," Cell, 1984, 37:767-778.
Wright et al., "Rational design of a split-Cas9 enzyme complex," Proc Natl Acad Sci USA, 2015, 112(10):2984-9.
Wu et al., "Target specificity of the CRISPRCas9 system," Quant Biol. 2014, 2(2):59-70.
Yang et al., Effective gene targeting in rabbits using RNA-guided Cas9 nucleases. J Mol Cell Biol. (2014) 6(1):97-99.
Yeo G.W. et al., An RNA code for the FOX2 splicing regulator revealed by mapping RNA-protein interactions in stem cells. Nat Strict Mol Biol. (2009) 16(2): 130-137 (18 pages).
Zambrowicz et al., "Disruption of overlapping transcripts in the ROSA beta geo 26 gene trap strain leads to widespread expression of beta-galactosidase in mouse embryos and hematopoietic cells," Proc. Natl. Acad. Sci., 1997, 94:3789-3794.
Zetsche et al., "A split-Cas9 architecture for inducible genome editing and transcription modulation," Nat Biotechnol., 2015, 33(2):139-42.
Zhang et al., Treatment of type 1 myotonic dystrophy by engineering site-specific RNA endonucleases that target (CUG)(n), Mol. Ther., 2014, 22(2):312-320.
Zuris et al., Efficient Delivery of Genome-Editing Proteins in vitro and in vivo, Nature Biotechnol., 2015, 33(1):73-80.
PCT International Preliminary Report on Patentability in International Appln. No. PCT/US2019/049182, dated Mar. 11, 2021, 7 pages.
PCT International Preliminary Report on Patentability in International Appln. No. PCT/US2019/049197, dated Mar. 11, 2021, 9 pages.
Choudhury et al., "Engineering RNA endonucleases with customized sequence specificities," Nature communications, Oct. 23, 2012, 3(1):1-18.
Hwang et al., "Efficient genome editing in zebrafish using a CRISPR-Cas system," Nature biotechnology, Mar. 2013, 31(3):227-229.
Kanadia et al., "A muscleblind knockout model for myotonic dystrophy," Science, Dec. 12, 2003, 302(5652):1978-1980.
Koren et al., "Cell-penetrating peptides: breaking through to the other side," Trends in molecular medicine, Jul. 1, 2012, 18(7):385-393.
Long et al., "Postnatal genome editing partially restores dystrophin expression in a mouse model of muscular dystrophy," Science, Jan. 22, 2016, 351(6271):400-403.

Miyanohara et al., "Potent spinal parenchymal AAV9-mediated gene delivery by subpial injection in adult rats and pigs," Molecular Therapy—Methods & Clinical Development, Jan. 1, 2016, 3:16046, 10 pages.
Mouisel et al., "Outcome of acetylcholinesterase deficiency for neuromuscular functioning," Neuroscience research, Aug. 1, 2006, 55(4):389-396.
Nishimasu, et al. "Crystal structure of Cas9 in complex with guide RNA and target DNA," Cell, Feb. 27, 2014, 156(5):935-949.
Orengo et al., "Expanded CTG repeats within the DMPK 3' UTR causes severe skeletal muscle wasting in an inducible mouse model for myotonic dystrophy," Proceedings of the National Academy of Sciences, Feb. 19, 2008, 105(7):2646-2651.
Trans1T-LT1 Transfection Reagent Data Sheet, Mirus Bio, 2017, 6 pages.
Wheeler et al., "Correction of C1C-1 splicing eliminates chloride channelopathy and myotonia in mouse models of myotonic dystrophy," The Journal of clinical investigation, Dec. 3, 2007, 117(12):3952-3957.
Yang et al., "A dual AAV system enables the Cas9-mediated correction of a metabolic liver disease in newborn mice," Nature biotechnology, Mar. 2016, 34(3):334-338.
Zuris et al., "Cationic lipid-mediated delivery of proteins enables efficient protein-based genome editing in vitro and in vivo," Nature biotechnology, Jan. 2015, 33(1):73-80.
Hinnebusch, "Molecular Mechanism of Scanning and Start Codon Selection in Eukaryotes," Microbiology and Molecular Biology Reviews, Sep. 2011, 75(3):434-467.
International Preliminary Report on Patentability in International Appln. No. PCT/US2016/063429, dated May 29, 2018, 12 pages.
International Search Report and Written Opinion in International Appln. No. PCT/US2020/028501, dated Sep. 25, 2020, 12 pages.
International Search Report and Written Opinion in International Appln. No. PCT/US2020/028546, dated Jul. 14, 2020, 13 pages.
Anant et al., "Molecular mechanisms of apolipoprotein B mRNA editing," Current opinion in lipidology, Apr. 1, 2001, 12(2):159-165.
Blanc et al., "C-to-U RNA editing: mechanisms leading to genetic diversity," Journal of Biological Chemistry, Jan. 17, 2003, 278(3):1395-1398.
Cichowski et al., "NF1 tumor suppressor gene function: narrowing the Gap," Cell, Feb. 23, 2001, 104(4):593-604.
De Zoysa et al., "Posttranscriptional RNA pseudouridylation," The enzymes, Jan. 1, 2017, 41:151-167.
Du et al., "m 6 A RNA methylation controls neural development and is involved in human diseases," Molecular neurobiology, Mar. 2019, 56(3):1596-1606.
GenBank Accession No. NM_019852.4, "*Homo sapiens* methyltransferase like 3 (METTL3), mRNA," Oct. 21, 2018, 6 pages.
Guzzi et al., "Pseudouridylation of tRNA-derived fragments steers translational control in stem cells," Cell, May 17, 2018, 173(5): 40 pages.
Huang et al., "Inducing nonsense suppression by targeted pseudouridylation," nature protocols, Apr. 2012, 7(4):789-800.
Jia et al., "N 6-methyladenosine in nuclear RNA is a major substrate of the obesity-associated FTO," Nature chemical biology, Dec. 2011, 7(12):885-887.
Karijolich et al., "Converting nonsense codons into sense codons by targeted pseudouridylation," Nature, Jun. 2011, 474(7351):395-398.
Karijolich et al., "Transcriptome-wide dynamics of RNA pseudouridylation," Nature reviews Molecular cell biology, Oct. 2015, 16(10): 5 pages.
Li et al., "Targeted mRNA demethylation using an engineered dCas13b-ALKBH5 fusion protein," Nucleic acids research, Jun. 4, 2020, 48(10):5684-5694.
Maity et al., "N6-methyladenosine modification in mRNA: machinery, function and implications for health and diseases," The FEBS journal, May 2016, 283(9):1607-1630.
Mukhopadhyay et al., "C→ U editing of neurofibromatosis 1 mRNA occurs in tumors that express both the type II transcript and apobec-1, the catalytic subunit of the apolipoprotein B mRNA-editing enzyme," The American Journal of Human Genetics, Jan. 1, 2002, 70(1):38-50.

(56) References Cited

OTHER PUBLICATIONS

PCT International Search Report and Written Opinion in International Appln. No. PCT/US2019/049182, dated Dec. 6, 2019, 11 pages.
PCT International Search Report and Written Opinion in International Appln. No. PCT/US2019/049197, dated Dec. 12, 2019, 12 pages.
Shi et al., "YTHDF3 facilitates translation and decay of N 6-methyladenosine-modified RNA," Cell research, Mar. 2017, 27(3):315-328.
Skuse et al., "The neurofibromatosis type I messenger RNA undergoes base-modification RNA editing," Nucleic acids research, Feb. 1, 1996, 24(3):478-486.
Vu et al., "C-to-U editing and site-directed RNA editing for the correction of genetic mutations," Bioscience trends, Jun. 30, 2017, 11(3):243-253.
Warda et al., "Human METTL16 is a N6-methyladenosine (m6A) methyltransferase that targets pre-mRNAs and various non-coding RNAs," EMBO reports, Nov. 2017, 18(11):2004-2014.
Xiao et al., "Functionality and substrate specificity of human box H/ACA guide RNAs," Rna, Jan. 1, 2009, 15(1):176-186.
Xiao et al., "Nuclear m6A reader YTHDC1 regulates mRNA splicing," Molecular cell, Feb. 18, 2016, 61(4):507-519.
Yamanaka et al., "A novel translational repressor mRNA is edited extensively in livers containing tumors caused by the transgene expression of the apoB mRNA-editing enzyme," Genes & development, Feb. 1, 1997, 11(3):321-333.
Zaganelli et al., "The pseudouridine synthase RPUSD4 is an essential component of mitochondrial RNA granules," Journal of Biological Chemistry, Mar. 17, 2017, 292(11):4519-4532.
Batra et al., "Elimination of Toxic Microsatellite Repeat Expansion RNA by RNA-Targeting Cas9," Cell, 2017, 170(5):889-912.e10.
Jinek et al., "A programmable dual RNA-guided DNA endonuclease in adaptive bacterial immunity," Science, 2012, 337(6096):816-821.
Wojciechowska et al., "Cellular toxicity of expanded RNA repeats: focus on RNA foci," Human Molecular Genetics, 2011, 20:3811-3821.
GenBank Accession No. NP 001124150.1, "eukaryotic translation initiation factor 4E isoform 3 [*Homo sapiens*]," Sep. 3, 2019, 3 pages.

\* cited by examiner

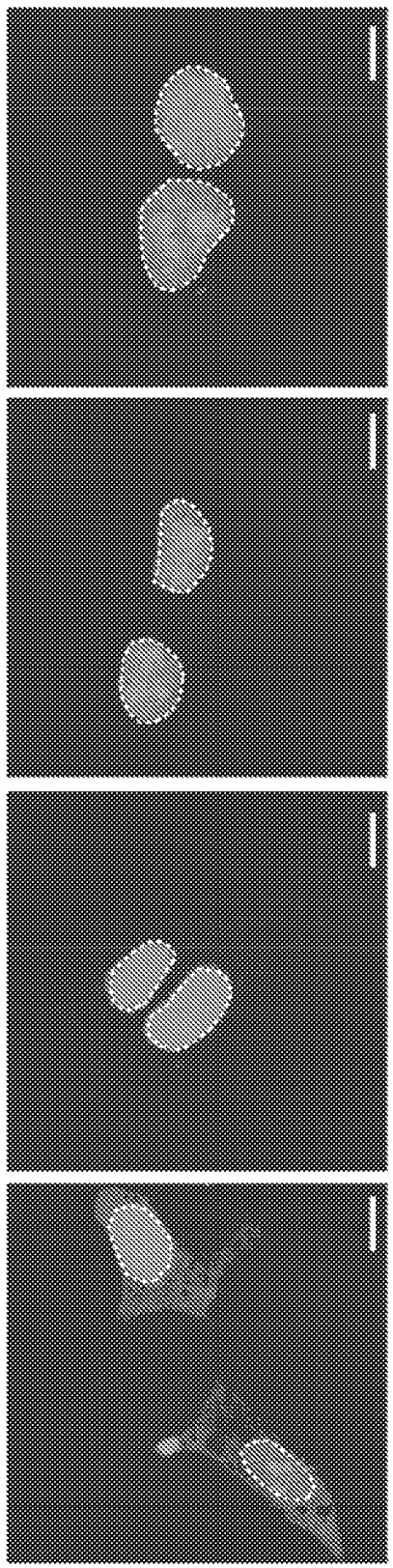
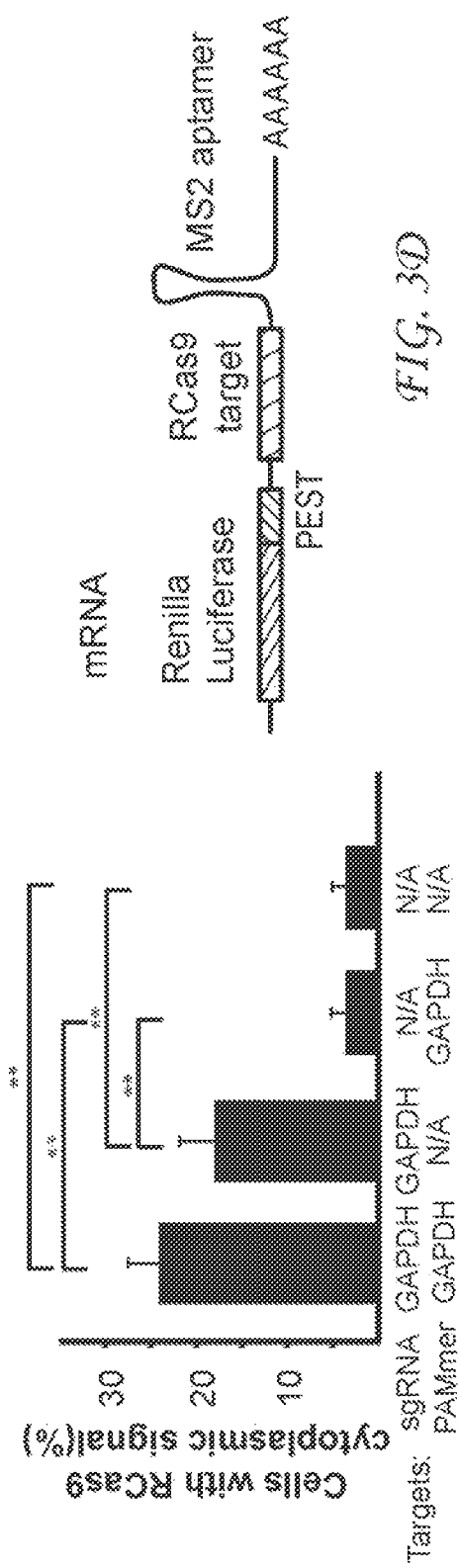
FIG. 3B
FIG. 3C
FIG. 3D

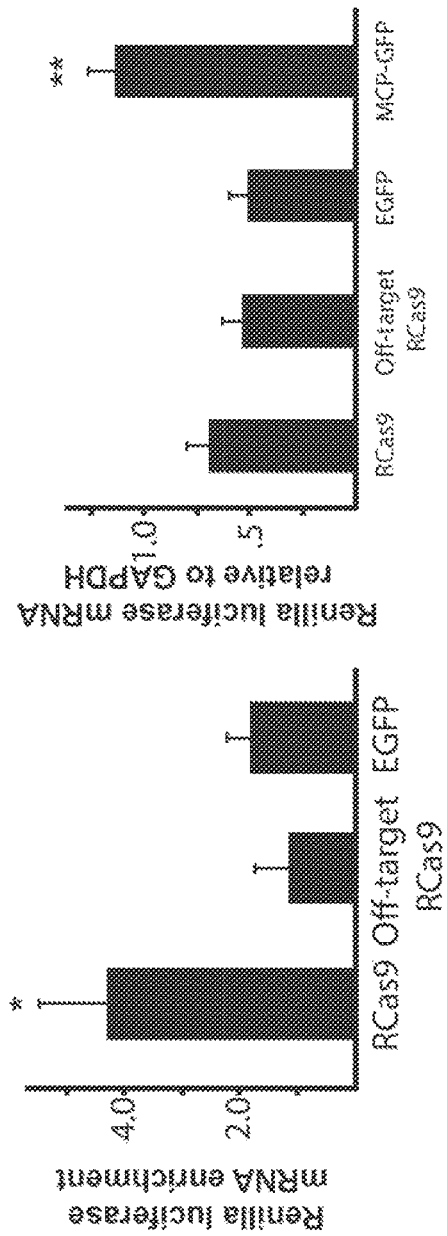
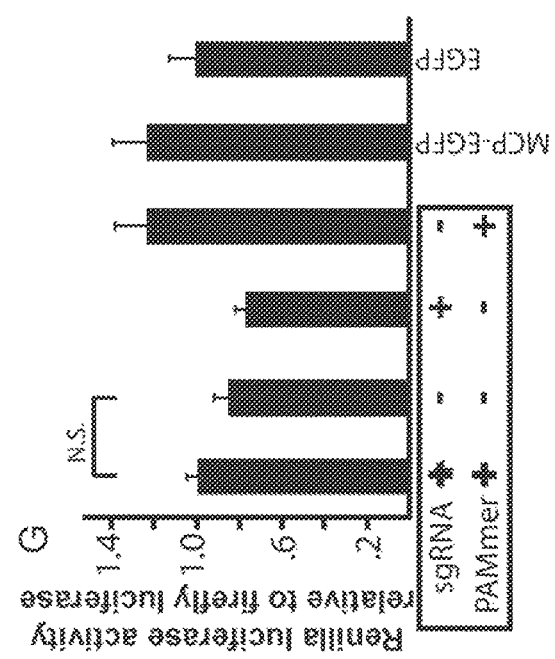
FIG. 3E  FIG. 3F  FIG. 3G

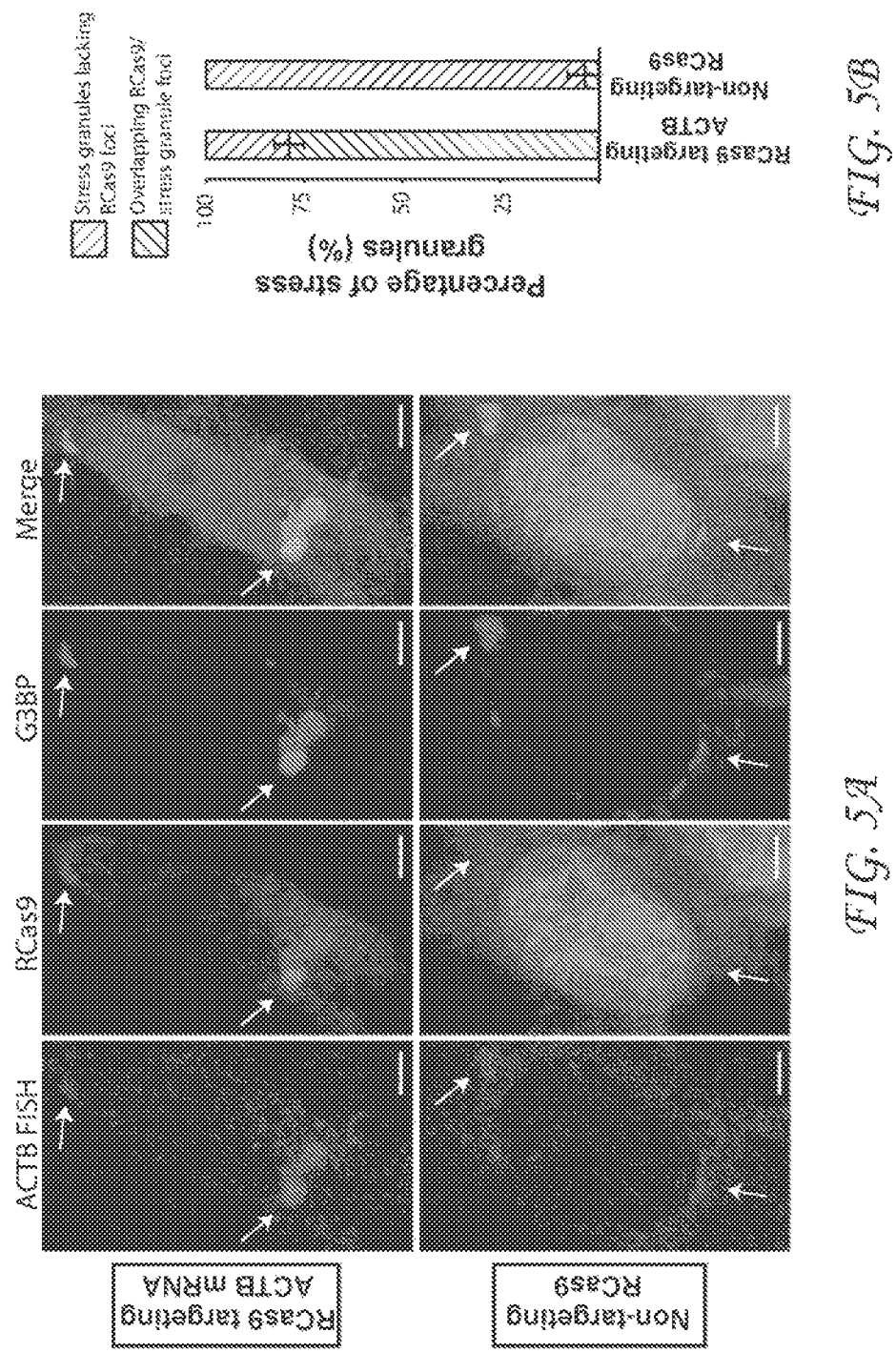

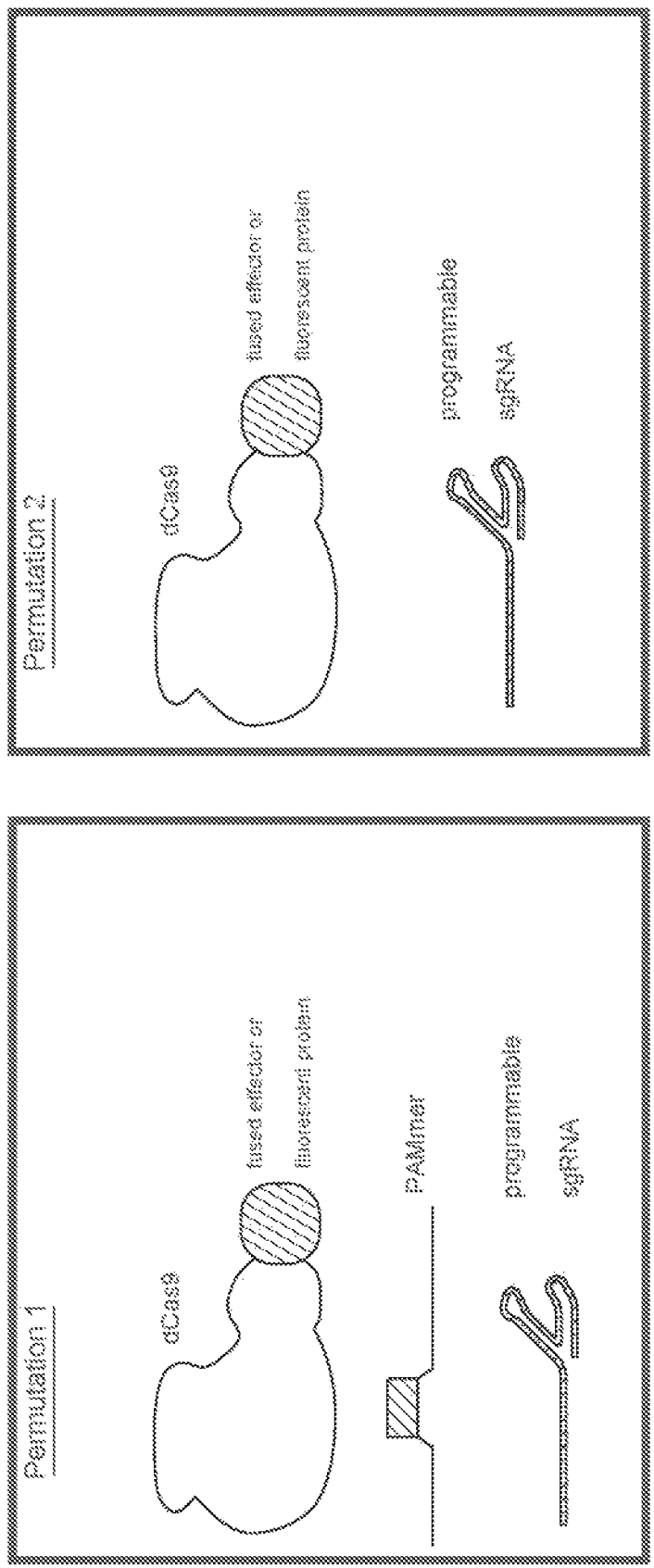
FIG. 7A1

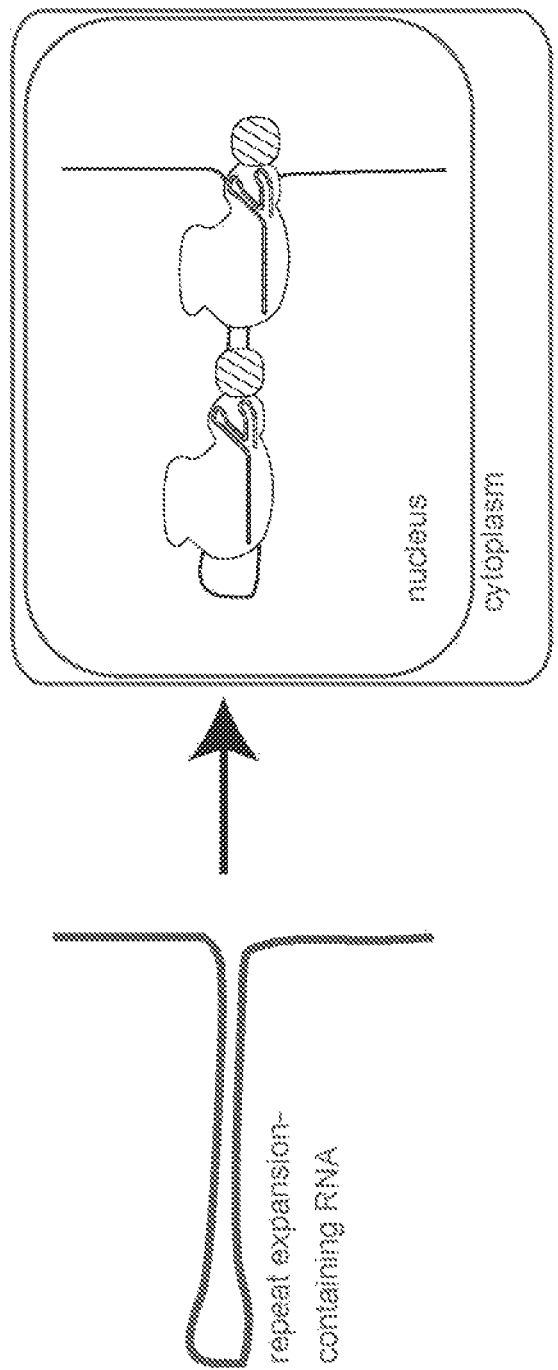
FIG. 7A2

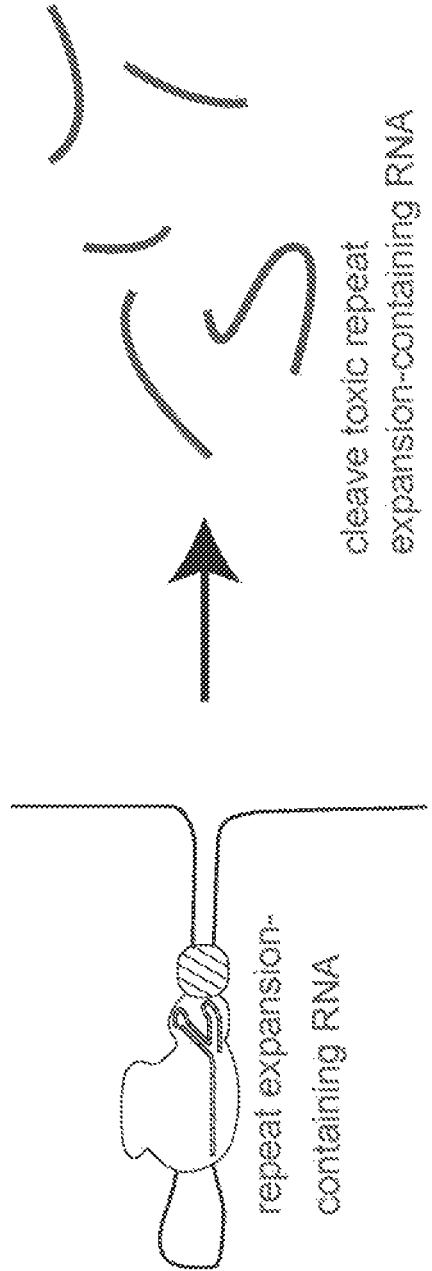
FIG. 7A3

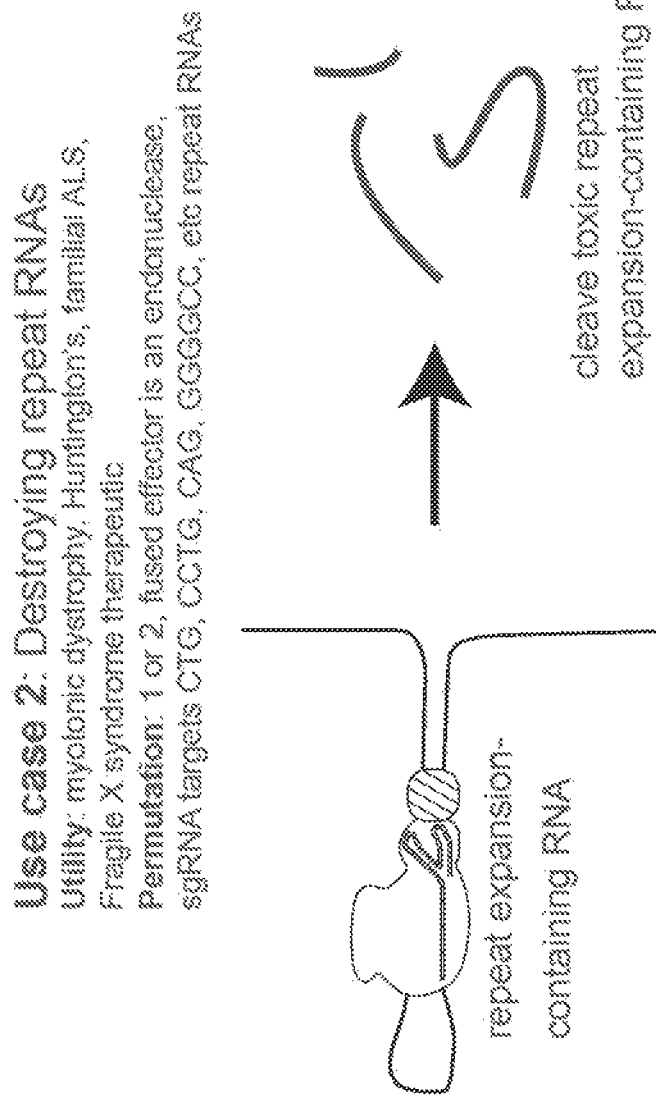
FIG. 7D1

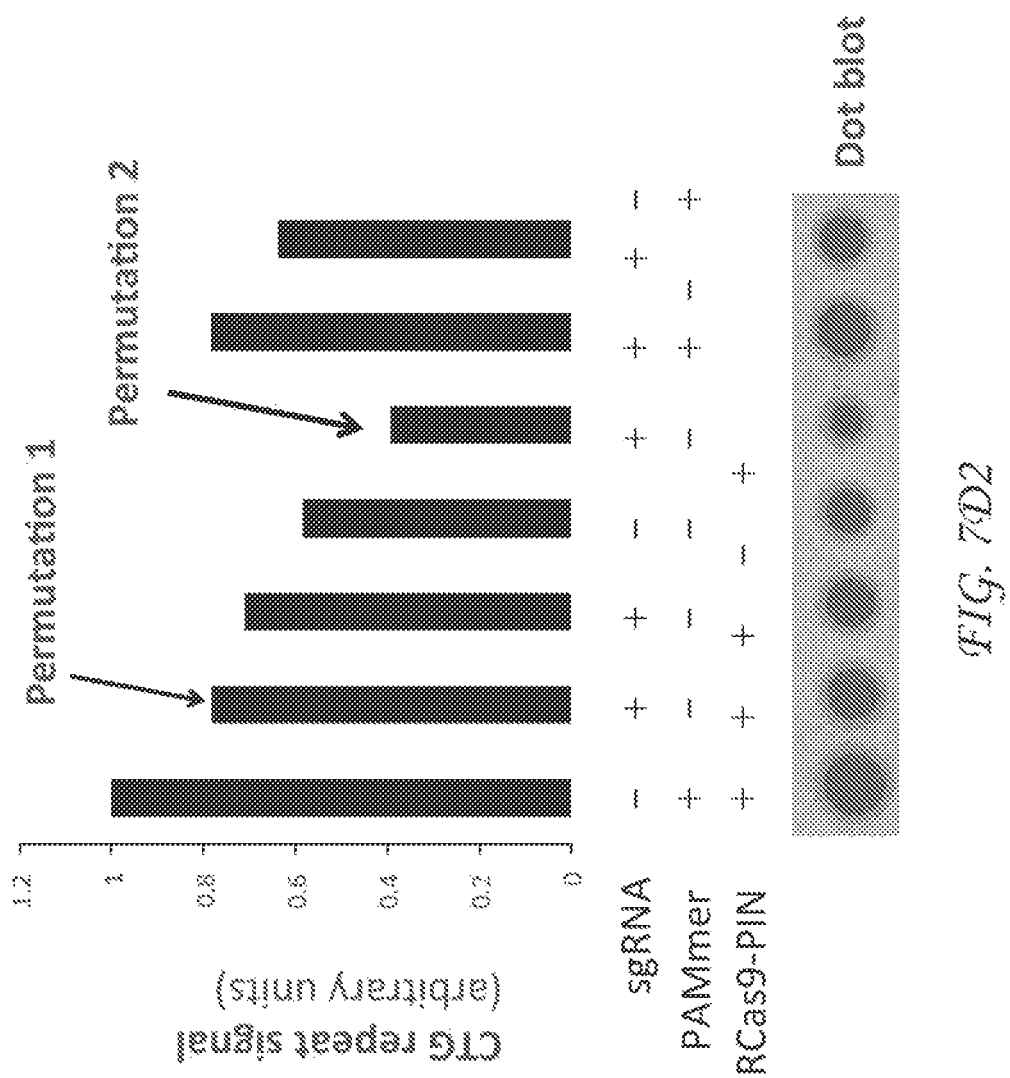
FIG. 7D2

US 11,667,903 B2

TRACKING AND MANIPULATING CELLULAR RNA VIA NUCLEAR DELIVERY OF CRISPR/CAS9

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. In particular, this application claims the benefit of priority to U.S. Provisional Application Ser. No. 62/259,014, entitled "TRACKING AND MANIPULATING CELLULAR RNA VIA NUCLEAR DELIVERY OF CRISPR/CAS9," filed Nov. 23, 2015, the disclosures of which are hereby incorporated by reference herein in their entireties.

STATEMENT REGARDING FEDERALLY SPONSORED R&D

This invention was made with government support under NIH Grant/Contract Numbers HG004659 and NS075449 awarded by the National Institutes of Health of the United States of America. The government has certain rights in the invention.

REFERENCE TO SEQUENCE LISTING, TABLE, OR COMPUTER PROGRAM LISTING

The present application is being filed along with a Sequence Listing in electronic format. The Sequence Listing is provided as a file entitled UCSD097-001A_SEQLIST.TXT, created Nov. 22, 2016, which is 105 Kb in size. The information in the electronic format of the Sequence Listing is incorporated herein by reference in its entirety.

BACKGROUND OF THE INVENTION

Field of the Invention

The present application relates to genetic engineering, and in alternative embodiments, provides Cas9 polypeptides which have been engineered to bind to RNA.

Description of the Related Art

Current methods for tracking RNA, determining the amount of RNA, or modifying the amount or structure of RNA suffer from various drawbacks. Improved methods and compositions for implementing them are provided herein.

SUMMARY OF THE INVENTION

Some embodiments are described in the following numbered paragraphs:
1. An engineered nucleoprotein complex comprising:
(a) a Cas9 polypeptide, and
(b) a recombinant or synthetics single guide RNA (sgRNA) which is engineered or designed to comprise:
 (1) on its 5' end, all RNA sequence that recognizes by hybridization (that hybridizes to or binds to) a target RNA and
 (2) on its 3' end: (i) an RNA sequence capable of binding to or associating with the Cas9 polypeptide (a Cas9 polypeptide-binding "scaffold sequence"), or (ii) a linker that binds or covalently or non-covalently links the 5' RNA-hybridizing or binding end of the sgRNA with the Cas9 polypeptide,
wherein optionally the nucleoprotein complex does not comprise a PAMmer oligonucleotide,
and optionally the Cas9 polypeptide:
 (1) is a, or is derived from a bacterial or archaeal Cas9 polypeptide,
 (2) lacks a domain, or a portion of a domain, of a corresponding wild type (WT) Cas9 polypeptide, wherein optionally the domain is an HNH and/or RuvC nuclease domain of Cas9, comprises a ββα-metal fold comprising or including a Cas9 polypeptide active site, or combinations thereof;
 (3) lacks DNase, or DNA cleaving, capability or activity, nickase activity, or combinations thereof, wherein optionally the DNase, or DNA cleaving capability or activity is removed by modification (mutation) or removal of all or part of: an HNH and/or RuvC nuclease domain of Cas9, a Cas9 polypeptide DNase active site or a ββα-metal fold that comprising a Cas9 polypeptide active site, or combinations thereof,
 (4) lacks all or part of: an HNH and/or RuvC nuclease domain of Cas9, a Cas9 polypeptide DNase active site, a ββα-metal fold that comprising a Cas9 polypeptide active site, or combinations thereof, thereby optionally reducing the size of the polypeptide, optionally facilitating packaging of a Cas9-coding nucleotide in a viral or other delivery vector, or
 (5) is a variant of a WT Cas9 polypeptide, and has one or more amino acid mutations that result in reduced DNase or nuclease activity relative to a corresponding WT Cas9 polypeptide.
or optionally the archaeal or bacterial Cas9 polypeptide is, comprises or is derived from: a *Haloferax mediteranii*, a *Mycobacterium tuberculosis*, a *Francisella tularensis* subsp. *novicida*, a *Pasteurella multocida*, a *Neisseria meningitidis*, a *Campylobacter jejune*, a *Streptococcus thermophilus* LMD-9 CRISPR 3, a *Campylobacter lari* CF89-12, a *Mycoplasma gallisepticum* str. F, a *Nitratifractor salsuginis* str DSM 16511, a *Parvibaculum lavamentivorans*, a *Roseburia intestinalis*, a *Neisseria cinerea*, a *Gluconacetobacter diazotrophicus*, an *Azospirillum* B510, a *Sphaerochaeta globus* str. Buddy, a *Flavobacterium columnare*, a *Fluviicola taffensis*, a *Bacteroides coprophilus*, a *Mycoplasma* mobile, a *Lactobacillus farciminis*, a *Streptococcus pasteurianus*, a *Lactobacillus johnsonii*, a *Staphylococcus pseudintermedius*, a *Filifactor alocis*, a *Treponema denticola*, a *Legionella pneumophila* str. Paris, a *Sutterella wadsworthensis*, a *Corynebacter diphtheriac*, or a *Streptococcus aureus*; a *Francisella novicida* (optionally a *Francisella novicida* Cpf1) or a *Natronobacterium gregoryi* Argonaute modified or repurposed to target RNA, wherein optionally the sgRNA 3' end or "scaffold sequence" comprises all or part of, or is derived from, the wild type (WT) cognate guide nucleic acid of each of these respective bacteria or archaeal organisms.

2. The engineered nucleoprotein complex of Claim 1, wherein the 5' RNA-hybridizing or binding end of the sgRNA is between about 15 to 25, or 20, 21, 22 nucleotides in length, and the RNA sequence capable of binding to or associating with the Cas9 polypeptide is between about 85 and 100, or 90, 91, 92, 93, 94 or 95 nucleotides in length, and optionally the Cas9 polypeptide is adapted to be associated with, fused with, or that binds to or is covalently or non-covalently linked to, an effector polypeptide, a targeting agent, an enzyme, and/or a detectable moiety, wherein optionally the effector polypeptide comprises an RNA modifying polypeptide, wherein optionally the Cas9 polypeptide is a recombinant or synthetic polypeptide, wherein optionally the target RNA is (or the RNA sequence that recognizes by hybridization, or hybridizes to or binds to, the target RNA, is antisense to:) a messenger RNA (mRNA), ribosomal RNA (rRNA), signal recognition particle RNA (SRP RNA), transfer RNA (tRNA), small nuclear RNA (snRNA), small nucleolar RNA (snoRNA), antisense RNA (aRNA), long noncoding RNA (lncRNA), microRNA (miRNA), piwi-interacting RNA (piRNA), small interfering RNA (siRNA), short hairpin RNA (shRNA), retrotransposon RNA, viral genome RNA, or viral noncoding RNA.

3. The engineered nucleoprotein complex of any one of Claims 1 or 2, wherein said Cas9 polypeptide is noncovalently associated with said effector polypeptide, targeting agent, detectable moiety, or RNA modifying polypeptide.

4. The engineered nucleoprotein complex of any one of Claims 1 or 2, wherein said Cas9 polypeptide is fused to or covalently linked to said effector polypeptide, targeting agent, detectable moiety, and optionally the effector polypeptide is or comprises an RNA modifying polypeptide, and optionally the targeting agent is or comprises: a cytoplasmic polyadenylation element binding protein (CPEB), a zinc finger binding protein (ZBP), TIA-1 (a 3'UTR mRNA binding protein), a PSF (a protein component of spliceosomes) or a DNA-binding domain (DBD) of PSF, fragile X mental retardation protein (FMRP), IGF-II mRNA-binding protein (IMP)-1 (IMP1), IMP2, IMP3, a cytoskeleton binding protein, a transmembrane protein, or an engineered protein comprising a combination of domains of these aforementioned proteins to generate a combinatorial trafficking phenomena.

and optionally the enzyme is involved in the modification of synthesis of a compound, optionally wherein the compound is a polypeptide or a nucleic acid, and optionally the association of the Cas9 polypeptide on a target RNA creates a local accumulation of intermediate products in a biosynthetic pathway to amplify the production of a medically- or technologically-useful compound compared to free-floating biosynthetic enzymes.

5. The engineered nucleoprotein complex of any one of Claims 1-4, wherein said RNA modifying polypeptide comprises a splicing factor or an RNA splicing domain, optionally a RBFOX2 domain-containing protein, a protein known to influence RNA splicing, or an RNA cleaving domain (endonuclease), optionally as a PIN domain-containing protein.

6. The engineered nucleoprotein complex of any one of Claims 1-5, wherein said Cas9 polypeptide is covalently bound to the single guide RNA (sgRNA) by the linker.

7. The engineered nucleoprotein complex of any one of Claims 1-6, wherein said single guide RNA (sgRNA) carries extensions of, or comprises, secondary RNA structures in the 3' end scaffold sequence.

8. The engineered nucleoprotein complex of any one of Claims 1-7, wherein said single guide RNA (sgRNA) comprises one or more point mutations that improve expression levels of the single guide RNAs via removal of partial or full transcription termination sequences or sequences that destabilize sgRNAs after transcription via action of trans-acting nucleases by at least about 5%, 10%, 15% or more.

9. The engineered nucleoprotein complex of any one of Claims 1-8, wherein said single guide RNA (sgRNA) comprises an alteration or an additional nucleotide or chemical moiety at the 5' end which stabilizes said single guide RNA against degradation.

10. The engineered nucleoprotein complex of Claim 9, wherein said additional nucleotide or chemical moiety at the 5' end of said single guide RNA (sgRNA) is selected from the group consisting of 2'O-methyl, phosphorothioates, and thiophosphonoacetate linkages and bases, and optionally the alteration or additional chemical moiety for chemical stabilization comprises a 2'-F, locked nucleic acid (LNA), a 2'-O-methoyethyl, or a unlocked nucleic acid (UNA).

11. The engineered nucleoprotein complex of an one of Claims 1-10, wherein said single guide RNA comprises one or more methylphosphonate, thiophosponoaceteate, or phosphorothioate linkages, optionally that reduce RNA nuclease activity on the sgRNA by at least about 5%, 10%, 15% or more.

12. The engineered nucleoprotein complex of any one of Claims 1-11, wherein said single guide RNA (sgRNA) comprises an alteration or an additional nucleotide or chemical moiety at the 5' end which improves RNA targeting by at least about 5%, 10%, 15% or more.

13. The engineered nucleoprotein complex of any one of Claims 1-12, wherein said single guide RNA comprises 2'-fluorine, 2'O-methyl, and/or 2'-methoxyethyl base modifications in the spacer or scaffold region of the sgRNA to improve target recognition or reduce nuclease activity on the single guide RNA by at least about 5%, 10%, 15% or more.

14. The engineered nucleoprotein complex of any one of Claims 1-13, wherein said single guide RNA comprises sufficient sequence antisense to the target RNA to allow it to hybridize under physiological conditions to at least about 5%, 10%, 15%, or between about 5% and 20%, or more of the target RNA.

15. The engineered nucleoprotein complex of any one of Claims 1-14, wherein said single guide RNA comprises a sequence that is antisense to or complementary to at least a portion of the target RNA, wherein said portion is optionally at least about 5%, 10%, 15% or more of the target RNA, or between about 5% and 20%, or more of the target RNA.

16. The engineered nucleoprotein complex of any one of Claims 1-15, further comprising a CRISPR-targeting RNA (crRNA) and a trans-activating cRNA (tracrRNA), wherein said Cas9 polypeptide is complexed with or linked to, or covalently or non-covalently associated with, the CRISPR-targeting RNA (crRNA) in combination with the trans-activating cRNA (tracrRNA).

17. The engineered nucleoprotein complex of any one of Claims 1-16, wherein said RNA modifying polypeptide is further complexed with, or is linked to covalently or non-covalently, an antisense oligonucleotide.

18. The engineered nucleoprotein complex of Claim 17, wherein said antisense oligonucleotide comprises at least one modified nucleotide.

19. The engineered nucleoprotein complex of Claim 18, wherein said at least one modified nucleotide is selected from the group consisting of 2'OMe RNA and 2'OMe DNA nucleotides.

20. The engineered nucleoprotein complex of any one of Claims 1-19, wherein said nucleoprotein complex further comprises a PAMmer oligonucleotide, and optionally the PAMmer also carries a 5' overhang which is required to maintain target specificity conferred by the sgRNA.

21. The engineered nucleoprotein complex of Claim 20, wherein said PAMmer oligonucleotide comprises one or more modified bases or linkages.

22. The engineered nucleoprotein complex of Claim 21, wherein said one or more modified bases or linkages are selected from the group consisting of locked nucleic acids and nuclease stabilized linkages.

23. The engineered nucleoprotein complex of any one of Claims 1-22, wherein said engineered nucleoprotein complex is adapted to be delivered to the nucleus of a cell.

24. The engineered nucleoprotein complex of Claim 23, wherein said engineered nucleoprotein complex is adapted to be co-exported with a target RNA out of said nucleus.

25. The engineered nucleoprotein complex of any one of Claim 23 or 24, wherein said Cas9 polypeptide comprises, or further comprises, optionally is fused or linked to a nuclear localization signal, one or more linker peptides, XTEN peptides, or optionally, an SV40 nuclear localization signal.

26. The engineered nucleoprotein complex of any one of Claims 1-25, wherein said Cas9 polypeptide is nuclease null.

27. The engineered nucleoprotein complex of any one of Claims 1-26, wherein said target RNA comprises a repeat sequence, and the 5' end RNA sequence that recognizes by hybridization (that hybridizes to or binds to) the target RNA comprises a sequence capable of hybridizing to, or is complementary to, the repeat sequence.

28. The engineered nucleoprotein complex of Claim 27, wherein said repeat sequence is selected from the group consisting of CTG, CCTG, CAG, GGGGCC, and any combination thereof.

29. The engineered nucleoprotein complex of Claim 27 or 28, wherein said target RNA is associated with a disease or condition or infection, and optionally the disease or condition is caused by or is associated with a RNA microsatellite repeat expansion.

30. The engineered nucleoprotein complex of Claim 29, wherein said disease, condition, or infection is selected from the group consisting of myotonic dystrophy, Huntington's disease, familial ALS, cancer, spinal muscular atrophy, spinocerebellar ataxia, Fragile X-associated tremor/ataxia syndrome, Spinal-bulbar muscular dystrophy, Oculapharyngeal muscular dystrophy, Fragile X syndrome, a viral or bacterial infection, wherein optionally the viral infection is a Herpesviridae or herpes simplex virus, a human immunodeficiency virus, Epstein Barr virus, hepatitis virus, Hepatitis A, Hepatitis B, Hepatitis C, Hepatitis D, Hepatitis E, Zika virus, enteroviruses, Human Papillomavirus (HPV), influenza virus, Marburg virus, Ebola virus, Mumps virus, cytomegalovirus, rotavirus, Rubella virus, Varicella zoster virus, severe acute respiratory syndrome (SARS) coronavirus, a Paramyxoviridae or measles virus, West Nile virus, Yellow fever virus, or Dengue fever virus infection.

31. The engineered nucleoprotein complex of any of claims 1 to 30, wherein said Cas9 polypeptide is associated with an effector polypeptide, wherein the polypeptide is a toxic protein.

32. The engineered nucleoprotein complex of any of claims 1 to 31, wherein said Cas9 polypeptide is fused to, bound to, or associated with an effector polypeptide, a targeting agent, an enzyme or a detectable agent or moiety, wherein optionally the Cas9 polypeptide is a recombinant or synthetic polypeptide.

33. The engineered nucleoprotein complex of Claim 32, wherein said detectable agent or moiety comprises a detectable polypeptide or composition which has been fused or linked to said Cas9 polypeptide.

34. The engineered nucleoprotein complex of Claim 33, wherein said detectable polypeptide comprises a polypeptide which is inactivated when said detectable polypeptide is in the nucleus of a cell.

35. The engineered nucleoprotein complex of Claim 34, wherein said detectable polypeptide is not detectable when said detectable polypeptide is in the nucleus of a cell but is detectable when said detectable polypeptide is not in the nucleus of the cell.

36. The engineered nucleoprotein complex of Claim 35, wherein said detectable polypeptide is detectable when it is not in the nucleus of the cell via an association with another agent which is detectable.

37. The engineered nucleoprotein complex of any one of Claims 32-36, wherein said detectable polypeptide is a fluorescent, split fluorescent, or luminescent polypeptide, or said delectable agent or moiety comprises a fluorescent, split fluorescent, or luminescent agent.

38. The engineered nucleoprotein complex of Claim 37 wherein said fluorescent polypeptide comprises or is a green fluorescent protein (GFP) or an enhanced GFP.

39. The engineered nucleoprotein complex of any one of Claims 1-38, wherein said single guide RNA (sgRNA) comprises one or more point mutations that improves expression levels of the single guide RNAs by at least 5%, 10%, 15% or more via removal of partial or full transcription termination sequences or sequences that destabilize single guide RNAs after transcription via action of trans-acting nucleases.

40. The engineered nucleoprotein complex of any one of Claims 1-39, wherein said Cas9 polypeptide is complexed with a CRISPR-targeting RNA (crRNA) in combination with a trans-activating cRNA (tracrRNA).

41. The engineered nucleoprotein complex of any one of Claims 1-40, wherein said Cas9 polypeptide is further complexed with an antisense oligonucleotide, wherein the antisense oligonucleotide comprises a PAMmer oligonucleotide which is complementary to a sequence in the target RNA.

42. The engineered nucleoprotein complex of Claim 41, wherein sad PAMmer oligonucleotide comprises at least one modified nucleotide.

43. The engineered nucleoprotein complex of Claim 20, wherein said at least one modified nucleotide is selected from the group consisting of 2'OMe RNA and 2'OMe DNA nucleotides.

44. The engineered nucleoprotein complex of any one of Claims 1-43, wherein said Cas9 polypeptide is adapted to be delivered to the nucleus of a cell.

45. The engineered nucleoprotein complex of Claim 44, wherein said Cas9 polypeptide is adapted to be co-exported with a target RNA out of said nucleus.

46. A vector comprising a nucleic acid, or nucleic acids, optionally vector or vectors, encoding the engineered nucleoprotein complex of any one of Claims 1-45, wherein optionally the vector is, comprises or is derived from an adenovirus, an adeno-associated virus (AAV), a retrovirus, a herpes simplex virus, a human immunodeficiency virus (HIV), or a synthetic vector.

47. A cell comprising, or having contained therein:
(a) the engineered nucleoprotein complex of any of claims 1-45; or
(b) a nucleic acid, or nucleic acids, optionally vector or vectors, encoding the engineered nucleoprotein complex of any one of Claims 1-45,
wherein optionally the cell is a mammalian cell or a human cell.

48. A chimeric nucleic acid encoding the engineered nucleoprotein complex of any one of Claims 1-45, wherein optionally the nucleic acid is a recombinant or synthetic nucleic acid, wherein optionally the nucleic acid is operably linked to a constitutive or an inducible promoter.

49. The nucleic acid of Claim 48, wherein the expression of one or more of the Cas9 polypeptide, the sgRNA, the PAMmer oligonucleotide, the effector polypeptide, the detectable moiety, or combinations thereof, is controlled by a regulatable or constitutive promoter.

50. A vector comprising the nucleic acid of any of Claims 48 or 49, wherein optionally the vector is, comprises or is derived from an adenovirus, an adeno-associated virus (AAV), a retrovirus, a herpes simplex virus, a human immunodeficiency virus (HIV), or a synthetic vector.

51. A cell or tissue comprising: the engineered nucleoprotein complex of any on of Claims 1-45; the nucleic acid of Claims 48 or 49; or the vector of Claim 50.

52. A method of treating, preventing, ameliorating or reducing the symptoms of a disease or condition, or infection, in a mammalian or a human subject comprising administering to said mammalian or human subject:
(a) the engineered nucleoprotein complex of any of claims 1-45, wherein said Cas9 polypeptide is adapted to be associated with, or that binds to or is covalently or non-covalently linked to, an effector polypeptide wherein optionally the effector polypeptide comprises an RNA modifying polypeptide; or
(b) a nucleic acid, or nucleic acids, optionally vector or vectors, encoding the engineered nucleoprotein complex of any one of Claims 1-45, wherein said Cas9 polypeptide is adapted to be associated with, or that binds to or is covalently or non-covalently linked to, an effector polypeptide wherein optionally the effector polypeptide comprises an RNA modifying polypeptide, and wherein the nucleic acid is, or nucleic acids are, expressed intracellularly and express the engineered nucleoprotein complex, (c) pharmaceutical composition comprising
  (i) the engineered nucleoprotein complex of any of claims 1-45, wherein said Cas9 polypeptide is adapted to be associated with, or that binds to or is covalently or non-covalently linked to, an effector polypeptide wherein optionally the effector polypeptide comprises an RNA modifying polypeptide; or
  (ii) a nucleic acid, or nucleic acids, optionally vector or vectors, encoding the engineered nucleoprotein complex of any one of Claims 1-45, wherein said Cas9 polypeptide is adapted to be associated with, or that binds to or is covalently or non-covalently linked to, an effector polypeptide wherein optionally the effector polypeptide comprises an RNA modifying polypeptide,
and optionally an excipient,
and optionally the pharmaceutical compound is formulated for enteral or parenteral delivery, or for intravenous (IV) delivery; or
(d) a cell or tissue of claim 51;
thereby modifying an RNA in a cell and treating, preventing, or ameliorating or reducing the symptoms of the disease or condition, or infection,
wherein optionally the engineered nucleoprotein complex or the nucleic acid or vector encoding the Cas9 polypeptide is carried or contained in a nanoparticle, a particle, a micelle or a liposome or lipoplex, a polymersome, a polyplex or a dendrimer, which optionally can further comprise or express a cell penetrating moiety or peptide.

53. The method of Claim 52, wherein the nucleic acid or nucleic acids encoding one or all of the components of the engineered nucleoprotein complex is/are carried by or is/are contained in a single vector, or each component (the Cas9 polypeptide, the sgRNA, the effector polypeptide, or a combination of components, is carried by or is contained in a separate vector,
and optionally the vector or vectors are adenovirus vectors, or one or more adeno-associated virus (AAV) vectors, a retrovirus, a herpes simplex virus, a human immunodeficiency (HIV), or a synthetic vector.

54. The method of Claim 52 or 53, wherein the expression of one or more of the Cas9 polypeptide, the sgRNA, the PAMmer oligonucleotide, the effector polypeptide, or combinations thereof is controlled by a regulatable or constitutive promoter.

55. The method of any of Claims 52-54, wherein the nucleic acid encoding the single guide RNA (sgRNA) is carried by or is contained in the same vector as the nucleic acid encoding the Cas9 polypeptide, optionally adenovirus or AAV vectors, a retrovirus, a herpes simplex virus, a human immunodeficiency virus (HIV), or a synthetic vector.

56. The method of any of Claims 52-55, wherein the nucleic acid encoding the sgRNA and the nucleic acid encoding the Cas9 polypeptide are carried by or is contained in different vectors, optionally adenovirus or AAV vectors, a retrovirus, herpes simplex virus, a human immunodeficiency virus (HIV), or a synthetic vector.

57. The method of any of Claims 52-56 wherein the nucleic acid encoding the effector polypeptide, optionally a RNA modifying polypeptide, is carried by same or is carried by or is contained in a separate vector, optionally an AAV vector, a retrovirus, a herpes simplex virus, a human immunodeficiency virus (HIV), or a synthetic vector.

58. The method of any one of Claims 52-57, wherein the disease or condition is caused by a repeat sequence selected from the group consisting of CTG, CCTG, CAG, GGGGCC, and any combination thereof.

59. The method of Claim 52-58, wherein said disease, condition, or infection is caused by or is associated with a RNA microsatellite repeat expansion, or is selected from the group consisting of myotonic dystrophy, Huntington's disease, familial ALS, cancer, spinal muscular atrophy, spinocerebellar ataxia, Fragile X-associated tremor/ataxia syndrome, Spinal-bulbar muscular dystrophy, Oculopharyngeal muscular dystrophy, Fragile X syndrome, a viral or bacterial infection, wherein optionally the viral infection is a Herpesviridae or herpes simplex virus, a human immunodeficiency virus, Epstein Barr virus, hepatitis virus, Hepatitis A, Hepatitis B, Hepatitis C, Hepatitis E, Zika virus, enteroviruses, Human Papillomavirus (HPV), influenza virus, Marburg virus, Ebola virus, Mumps virus, cytomegalovirus, rotavirus, Rubella, virus, Varicella zoster virus, severe acute respiratory syndrome (SARS) coronavirus, a Paramyxoviridae or measles virus, West Nile virus, Yellow fever virus, or Dengue fever virus infection.

60. The method of any one of Claims 52-59, wherein the administration route is selected from the group consisting of oral, pulmonary, intraperitoneal (ip), intravenous (iv), intramuscular (im), subcutaneous (sc), transdermal, buccal, nasal, sublingual, ocular, rectal and vaginal.

61. A method of expressing the engineered nucleoprotein complex of any of claims 1-45, comprising introducing a vector of Claims 46 or 50 or a nucleic acid of claims 48 or 49 into a cell under conditions in which said cell expresses said nucleoprotein complex.

62. A method of tracking a target RNA or measuring the amount of a target RNA in a cell comprising administering to the cell engineered nucleoprotein complex of any of claims 1-45, wherein said Cas9 polypeptide is adapted to be associated with, or that binds to or is covalently or non-covalently linked to, a detectable moiety, and allowing the engineered nucleoprotein complex to bind to said target RNA in said cell and determining the location of said target RNA in said cell or determining the amount of said target RNA in said cell.

63. The method of Claim 61, wherein said engineered nucleoprotein complex binds to said target RNA in a nucleus of said cell and is subsequently co-exported from said nucleus with said target RNA.

64. The method of any one of Claims 63 or 64, wherein the location of said target RNA in said cell or the amount of said target RNA in said cell is determined using a fluorescence microscopy or equivalent thereof.

65. A method of modifying the amount or structure of a target RNA in a cell in vitro or in vivo comprising allowing an engineered nucleoprotein complex of any one of Claims 1-45, wherein said Cas9 polypeptide is adapted to be associated with, or that binds to or is covalently or non-covalently linked to, an effector polypeptide wherein optionally the effector polypeptide comprises an RNA modifying polypeptide, to bind to said target RNA in said cell under conditions in which the amount or structure of said target RNA in said cell is modified.

66. A method of modifying the amount or structure of a target RNA in a cell in vitro or in vivo comprising expressing one or more components of the engineered nucleoprotein complex of any one of Claims 1-45, wherein said Cas9 polypeptide is adapted to be associated with, or that binds to or is covalently or non-covalently linked to, an effector polypeptide wherein optionally the effector polypeptide comprises an RNA modifying polypeptide, in a cell under conditions in which the amount or structure of said target RNA in said cell is modified, wherein the one or more components of the engineered nucleoprotein complex comprises a Cas9 polypeptide, a sgRNA, a PAMmer oligonucleotide, an effector protein, a detectable moiety, or combinations thereof.

67. A method of measuring RNA content or dynamics in a sample, comprising: introducing the engineered nucleoprotein complex of any one of Claims 1-45, wherein said Cas9 polypeptide is adapted to be associated with, or that binds to or is covalently or non-covalently linked to, a detectable moiety, into said sample; and
observing, detecting or measuring the amount of the detectable agent in said sample.

68. The method of Claim 67, comprising introducing a nucleic acid of Claims 48 or 49 or a vector of Claims 46 or 50 into said sample under conditions in which said Cas9 polypeptide is expressed.

69. The method of Claims 67 or 68, further comprising introducing a single guide RNA.

70. The method of any one of Claims 67-69, further comprising introducing a PAMmer oligonucleotide.

71. The method of any one of Claims 67-70, wherein said sample comprises or is derived from a tissue, a biopsy, a serum or blood sample, or a sputum sample.

72. The method of any one of Claims 67-71, wherein said sample comprises a plurality of cells.

73. The method of any one of Claims 67-72, comprising measuring the expression level or abundance of a target RNA in said sample.

74. The method of any one of Claims 67-73, comprising diagnosing a disease, condition, or infection of said sample, or in an individual from which said sample was derived, of said sample based on the expression level or abundance of said target RNA in said sample, 75. and optionally the target RNA is derived from a viral or bacterial infection, wherein optionally the viral infection is a Herpesviridae or herpes simplex virus, a human immunodeficiency virus, Epstein Barr virus, hepatitis virus, Hepatitis A, Hepatitis B, Hepatitis C, Hepatitis D, Hepatitis E, Zika virus, enteroviruses, Human Papillomavirus (HPV), influenza virus, Marburg virus, Ebola virus, Mumps virus, cytomegalovirus, rotavirus, Rubella virus, Varicella zoster virus, severe acute respiratory syndrome (SARS) coronavirus, a Paramyxoviridae or measles virus, West Nile virus, Yellow fever virus, or Dengue fever virus infection.

76. The method of any one of Claims 67-74, wherein said target RNA comprises a repeat sequence.

77. The method of Claim 75, wherein said repeat sequence is selected from the group consisting of CTG, CCTG, CAG, GGGGCC, and any combination thereof.

78. The method of Claim 75 or 76, wherein said repeat sequence is associated with a disease, condition, or infection.

79. The method of Claim 77, Wherein said disease or condition is caused by or is associated with a RNA microsatellite repeat expansion, or is selected from the group consisting of myotonic dystrophy, Huntington's disease, familial ALS, cancer, spinal muscular atrophy, spinocerebellar ataxia, Fragile X-associated tremor/ataxia syndrome, Spinal-bulbar muscular dystrophy, Oculopharyngeal muscular dystrophy, and Fragile X syndrome.

80. A method of modifying a target RNA in a sample, comprising:
introducing the engineered nucleoprotein complex of any one of Claims 1-44, wherein said Cas9 polypeptide is adapted to be associated with, or that binds to or is covalently or non-covalently linked to, an effector polypeptide wherein optionally the effector polypeptide comprises an RNA modifying polypeptide, into said sample; and
modifying said target RNA in said sample using the RNA modifying polypeptide.

81. The method of Claim 79, comprising introducing a nucleic acid of Claim 45 or 49 or a vector of claim 50 into said sample under conditions in which said Cas9 polypeptide is expressed.

82. The method of Claim 79 or 80, further comprising introducing a single guide RNA.

83. The method of any one of Paragraphs 79-81, further comprising introducing a PAMmer oligonucleotide.

84. The method of any one of Claims 79-82, wherein said sample comprises a tissue.

85. The method of any one of Claims 79-83, wherein said sample comprises a plurality of cells.

86. The method of any one of Claims 79-84, comprising modifying the amount of target RNA in said sample.

87. The method of Claim 85, wherein said target RNA comprises a repeat sequence.

88. The method of Claim 86, wherein said repeat sequence is selected from the group consisting of CTG, CCTG, CAG, GGGGCC, and any combination thereof.

89. The method of Claim 86 or 87, wherein said repeat sequence is associated with a disease.

90. The method of Claim 88, wherein said disease is caused by or is associated with a RNA microsatellite repeat expansion, or is selected from the group consisting of myotonic dystrophy, Huntington's disease, familial ALS, cancer, spinal muscular atrophy, spinocerebellar ataxia, Fragile X-associated tremor/ataxia syndrome, Spinal-bulbar muscular dystrophy, Oculopharyngeal muscular dystrophy, and Fragile X syndrome.

91. A pharmaceutical composition comprising
   (a) the engineered nucleoprotein complex of any of claims 1-45, wherein said Cas9 polypeptide is adapted to be associated with, or that binds to or is covalently or non-covalently linked to, an effector polypeptide wherein optionally the effector polypeptide comprises an RNA modifying polypeptide; or
   (b) a middle acid, or nucleic acids, optionally vector or vectors, encoding the engineered nucleoprotein complex of any one of Claims 1-45, wherein said Cas9 polypeptide is adapted to be associated with, or that binds to or is covalently or non-covalently linked to, an effector polypeptide wherein optionally the effector polypeptide comprises an RNA modifying polypeptide,
   and optionally an excipient,
   and optionally the pharmaceutical compound is formulated for enteral or parenteral delivery, or for intravenous (IV) delivery.

92. The pharmaceutical composition of Claim 90, wherein the engineered nucleoprotein complex or the nucleic acid or vector encoding the nucleoprotein complex is carried in a nanoparticle, a particle, a micelle or a liposome or lipoplex, a polymersome, a polyplex or a dendrimer, which optionally can further comprise or express a cell penetrating moiety or peptide.

93. The pharmaceutical composition of Claim 91, wherein the nanoparticle or particle comprises lipids, polymers, hydrogel, or a combination thereof.

94. The pharmaceutical composition of any one of Claims 90-93, wherein the sgRNA is contained in the same vector as the Cas9 polypeptide, or is contained in a different vector as the Cas9 polypeptide.

95. The pharmaceutical composition of any one of Claims 90-94, wherein the nucleic acid encoding the Cas9 polypeptide and the nucleic acid encoding the sgRNA is carried in one or more vectors, optionally adenovirus vectors or adeno-associated virus (AAV) vectors, a retrovirus, a herpes simplex virus, a human immunodeficiency virus (HIV), or a synthetic vector.

96. A recombinant or synthetic Cas9 polypeptide.
   wherein the Cas9 polypeptide:
   (a) is a, or is derived from a, bacterial or archaeal Cas9 polypeptide; and
   (b)
   (i) lacks a domain, or a portion of a domain, of a corresponding wild type (WT) Cas9 polypeptide, wherein optionally the domain is an HNH and/or RuvC nuclease domain of Cas9, comprises a ββα-metal fold comprising or including a Cas9 polypeptide active site, or combinations thereof;
   (ii) lacks DNase, or DNA cleaving, capability or activity, or nickase activity, wherein optionally the DNase, or DNA cleaving capability or activity is removed by modification (mutation) or removal of all or part of: an HNH and/or RuvC nuclease domain of Cas9, a Cas9 polypeptide DNase active site or a ββα-metal fold that comprising a Cas9 polypeptide active site, or combinations thereof,
   (iii) lacks all or part of: an HNH and/or RuvC nuclease domain of Cas9, a Cas9 polypeptide DNase active site or a ββα-metal fold that comprising a Cas9 polypeptide active site, or combinations thereof, thereby optionally reducing the size of the polypeptide, optionally facilitating packaging of a Cas9-coding nucleotide in a viral or other delivery vector, or
   (iv) is a variant of a WT Cas9 polypeptide, and has one or more amino acid mutations that result in reduced DNase or nuclease activity relative to a corresponding WT Cas9 polypeptide,
   and optionally the archaeal or bacterial Cas9 polypeptide is, comprises or is derived from: a *Haloferax mediteranii*, a *Mycobacterium tuberculosis*, a *Francisella tularensis* subsp. *novicida*, a *Pasteurella multocida*, a *Neisseria meningitidis*, a *Campylobacter jejune*, a *Streptococcus thermophilus* LMD-9 CRISPR 3, a *Campylobacter lari* CF89-12, a *Mycoplasma gallisepticum* str. F, a *Nitratifractor salsuginis* str DSM 16511, a *Parvibaculum lavamentivorans*, a *Roseburia intestinalis*, a *Neisseria cinerea*, a *Gluconacetobacter diazotrophicus*, an *Azospirillum* B510, a *Sphaerochaeta globus* str. Buddy, a *Flavobacterium columnare*, a *Fluviicola taffensis*, a *Bacteroides coprophilus*, a *Mycoplasma mobile*, a *Lactobacillus farciminis*, a *Streptococcus pasteurianus*, a *Lactobacillus johnsonii*, a *Staphylococcus pseudintermedius*, a *Filifactor alocis*, a *Treponema denticola*, a *Legionella pneumophila* str. Paris, a *Sutterella wadsworthensis*, a *Corynebacter diphtheriae*, or a *Streptococcus aureus*; a *Francisella novicida* (optionally a *Francisella novicida* Cpf1) or a *Natronobacterium gregoryi* Argonaute modified or repurposed to target RNA.

wherein optionally the Cas9 polypeptide further comprises an sgRNA, wherein optionally the sgRNA comprises a "scaffold sequence" capable of binding to or associating with the Cas9 polypeptide comprising all or part of, or is derived from, the wild type (WT) cognate guide nucleic acid of the wild type (WT) bacteria or archaeal organism from which the Cas9 polypeptide was derived,
   and optionally the sgRNA further comprises on its 5" end, an RNA sequence that recognizes by hybridization (that hybridizes to or binds to) a target RNA,
   and optionally the Cas9 polypeptide is adapted to be associated with, fused to, or that binds to or is covalently or non-covalently linked to, an effector polypeptide, a targeting agent, an enzyme, and/or a detectable moiety, wherein optionally the effector polypeptide comprises an RNA modifying polypeptide.

97. A recombinant or synthetic nucleic acid encoding the Cas9 polypeptide of claim 95, wherein optionally the nucleic acid is a chimeric nucleic acids encoding the Cas9 polypeptide of claim 95 and an sgRNA.

97. A vector comprising or having contained therein the nucleic acid claim 98, wherein optionally the vector is, comprises or is derived from an adenovirus, an adeno-associated virus (AAV), a retrovirus, a herpes simplex virus, a human immunodeficiency virus (HIV), or a synthetic vector 98. A cell or tissue comprising or having contained therein the Cas9 polypeptide of claim 95, or the nucleic acid of claim 96.

99. A Cas9 polypeptide which has been engineered to recognize a target RNA and which is adapted to be associated with an RNA modifying polypeptide.

100. The Cas9 polypeptide of Claim 99, wherein said Cas9 polypeptide is adapted to noncovalently associate with said RNA modifying polypeptide.

101. The Cas9 polypeptide of Claim 100, wherein said Cas9 polypeptide is fused to said RNA modifying polypeptide.

102. The Cas9 polypeptide of any one of Claims 99-101, wherein said RNA modifying polypeptide is a splicing factor.

103. The Cas9 polypeptide of any one of Claims 99-102, wherein said Cas9 polypeptide is complexed with a single guide RNA.

104. The Cas9 polypeptide of Claim 103, wherein said single guide RNA carries extensions of secondary structures in the single guide RNA scaffold sequence.

105. The Cas9 polypeptide of any one of Claims 103 or 104, wherein said single guide RNA comprises one or more point mutations that improve expression levels of the single guide RNAs via removal of partial or full transcription termination sequences or sequences that destabilize single guide RNAs after transcription via action of trans-acting nucleases.

106. The Cas9 polypeptide of any one of Claims 103-105, wherein said single guide RNA comprises an alteration at the 5' end which stabilizes said single guide RNA against degradation.

107. The Cas9 polypeptide of any one of Claims 103-106, wherein said single guide RNA comprises an alteration at the 5' end which improves RNA targeting.

108. The Cas9 polypeptide of any one of Claims 107, wherein said alteration at the 5' end of said single guide RNA is selected from the group consisting of 2'O-methyl, phosphorothioates, and thiophosphonoacetate linkages and bases.

109. The Cas9 polypeptide of any one of Claims 103-108, wherein said single guide RNA comprises 2'-fluorine, 2'-O-methyl, and/or 2'-methoxyethyl base modifications in the spacer or scaffold region of the sgRNA to improve target recognition or reduce nuclease activity on the single guide RNA.

110. The Cas9 polypeptide of any one of Claims 103-109, wherein said single guide RNA comprises one or more methylphosphonate, thiophosponoaceteate, or phosphorothioate linkages that reduce nuclease activity on the target RNA.

111. The Cas9 polypeptide of any one of Claims 103-110, wherein said single guide RNA hybridizes to at least a portion of the target RNA.

112. The Cas9 polypeptide of any one of Claims 103-111, wherein said single guide RNA comprises a sequence that is complementary to at least a portion of the target RNA.

113. The Cas9 polypeptide of any one of Claims 103-112, wherein said Cas9 polypeptide is complexed with a clustered regularly interspaced short palindromic repeats (CRISPR)-targeting RNA (crRNA) in combination with a trans-activating cRNA (tracrRNA).

114. The Cas9 polypeptide of any one of Claims 103-113, wherein said RNA modifying polypeptide is further complexed with an antisense oligonucleotide.

115. The Cas9 polypeptide of Claim 114, wherein said antisense oligonucleotide comprises at least one modified nucleotide.

116. The Cas9 polypeptide of Claim 115, wherein said at least one modified nucleotide is selected from the group consisting of 2'OMe RNA and 2'OMe DNA nucleotides.

117. The Cas9 polypeptide of any one of Claims 114-116, wherein said antisense oligonucleotide comprises a PAMmer oligonucleotide.

118. The Cas9 polypeptide of Claim 117, wherein said PAMmer oligonucleotide comprises one or more modified bases or linkages.

119. The Cas9 polypeptide of Claim 118, wherein said one or more modified bases or linkages are selected from the group consisting of locked nucleic acids and nuclease stabilized linkages.

120. The Cas9 polypeptide of any one of Claims 119, wherein said Cas9 polypeptide is adapted to be delivered to the nucleus of a cell.

121. The Cas9 polypeptide of Claim 120, wherein said Cas9 polypeptide is adapted to be co-exported with a target RNA out of said nucleus.

122. The Cas9 polypeptide of any one of Claim 120 or 121, wherein said Cas9 polypeptide comprises a nuclear localization signal.

123. The Cas9 polypeptide of any one of Claims 99-122, wherein said Cas9 polypeptide is nuclease null.

124. The Cas9 polypeptide of any one of Claims 103-123, wherein said target RNA comprises a repeat sequence.

125. The Cas9 polypeptide of Claim 124, wherein said repeat sequence is selected from the group consisting of CTG, CCTG, CAG, GGGGCC, and any combination thereof.

126. The Cas9 polypeptide of Claim 124 or 125, wherein said target RNA is associated with a disease.

127. The Cas9 polypeptide of Claim 126, wherein said disease is selected from the group consisting of myotonic dystrophy, Huntington's disease, familial ALS, cancer, spinal muscular atrophy and Fragile X syndrome.

128. A method of treating or ameliorating a disease in a human subject comprising administering a nucleic acid encoding the Cas9 polypeptide of any one of Claims 99-127 to said human subject.

129. The method of Claim 128, wherein the nucleic acid encoding the Cas9 polypeptide is carried by an adeno-associated virus (AAV) vector.

130. The method of Claim 128 or 129, further comprising administering a nucleic acid encoding the sgRNA.

131. The method of Claim 130, wherein the nucleic acid encoding the sgRNA is carried by the AAV vector.

132. The method of Claim 131, wherein the nucleic acid encoding the sgRNA is carried by a second AAV vector.

133. The method of any one of Claims 128-132, wherein the disease is caused by a repeat sequence selected from the group consisting of CTG, CCTG, CAG, GGGGCC, and any combination thereof.

134. The method of any one of Claims 128-133, said disease is selected from the group consisting of myotonic dystrophy, Huntington's disease, familial ALS, cancer, spinal muscular atrophy and Fragile X syndrome.

135. The method of any one of Claims 128-134, wherein the administration route is selected from the group consisting of oral, pulmonary, intraperitoneal (ip), intravenous (iv), intramuscular (im), subcutaneous (sc), transdermal, buccal, nasal, sublingual, ocular, rectal and vaginal.

136. A pharmaceutical composition comprising a nucleic acid encoding the Cas9 polypeptide of any one of Claims 99-127 and an excipient.

137. The pharmaceutical composition of Claim 136, wherein the nucleic acid encoding the Cas9 polypeptide is carried in a nanoparticle.

138. The pharmaceutical composition of Claim 137, wherein the nanoparticle comprises lipids, polymers, hydrogel, or a combination thereof.

139. The pharmaceutical composition of any one of Claims 136-138, further comprising a nucleic acid encoding the sgRNA.

140. The pharmaceutical composition of any one of Claims 136-139, wherein the nucleic acid encoding the Cas9 polypeptide or the nucleic acid encoding the snRNA is carried in one or more adeno-associated virus (AAV) vectors.

141. A Cas9 polypeptide which has been engineered to recognize a target RNA, wherein said Cas9 polypeptide is associated with a detectable agent.

142. The Cas9 polypeptide of Claim 141, wherein said detectable agent comprises a detectable polypeptide which has been fused to said Cas9 polypeptide.

143. The Cas9 polypeptide of Claim 142, wherein said detectable polypeptide comprises a polypeptide which is inactivated when said detectable polypeptide is in the nucleus of a cell.

144. The Cas9 polypeptide of Claim 143, wherein said detectable polypeptide is not detectable when said detectable polypeptide is in the nucleus of a cell but is detectable when said detectable polypeptide is not in the nucleus of the cell.

145. The Cas9 polypeptide of Claim 144, wherein said detectable polypeptide is detectable when it is not in the nucleus of the cell via an association with another agent which is detectable.

146. The Cas9 polypeptide of any one of Claims 141-145 wherein said detectable polypeptide is a fluorescent polypeptide.

147. The Cas9 polypeptide of Claim 146 wherein said fluorescent polypeptide comprises enhanced GFP.

148. The Cas9 polypeptide of any one of Claims 141-147, wherein said Cas9 polypeptide is complexed with a single guide RNA.

149. The Cas9 polypeptide of Claim 148, wherein said single guide RNA carries extensions of secondary structures in the single guide RNA scaffold sequence.

150. The Cas9 polypeptide of any one of Claim 148 or 149, wherein said single guide RNA comprises one or more point mutations that improves expression levels of the single guide RNAs via removal of partial or full transcription termination sequences or sequences that destabilize single guide RNAs after transcription via action of trans-acting nucleases.

151. The Cas9 polypeptide of any one of Claims 148-150, wherein said single guide RNA comprises an alteration at the 5' end which stabilizes said single guide RNA against degradation.

152. The Cas9 polypeptide of any one of Claims 148-151, wherein said single guide RNA comprises an alteration at the 5' end which improves RNA targeting.

153. The Cas9 polypeptide of any one of Claims 148-152, wherein said alteration at the 5' end of said single guide RNA is selected from the group consisting of 2'O-methyl, phosphorothioates, and thiophosphonoacetate linkages and bases.

154. The Cas9 polypeptide of any one of Claims 148-153, wherein said single guide RNA comprises 2'-fluorine, 2'O-methyl, and/or 2'-methoxyethyl base modifications in the spacer or scaffold region of the sgRNA to improve target recognition or reduce nuclease activity on the single guide RNA.

155. The Cas9 polypeptide of any one of Claims 148-154, wherein said single guide RNA comprises one or more methylphosphonate, thiophosponoaceteate, or phosphorothioate linkages that reduce nuclease activity on the target RNA.

156. The Cas9 polypeptide of any one of Claims 148-155, wherein said single guide RNA hybridizes to at least a portion of the target RNA.

157. The Cas9 polypeptide of any one of Claims 148-156, wherein said single guide RNA comprises a sequence that is complementary to at least a portion of the target RNA.

158. The Cas9 polypeptide of any one of Claims 148-157, wherein said Cas9 polypeptide is complexed with a CRISPR-targeting RNA (crRNA) in combination with a trans-activating cRNA (tracrRNA).

159. The Cas9 polypeptide of any one of Claims 148-158, wherein said Cas9 polypeptide is further complexed with an antisense oligonucleotide which is complementary to a sequence in the target RNA.

160. The Cas9 polypeptide of Claim 159, wherein said antisense oligonucleotide comprises at least one modified nucleotide.

161. The Cas9 polypeptide of Claim 160, wherein said at least one modified nucleotide is selected from the group consisting of 2'OMe RNA and 2'OMe DNA nucleotides.

162. The Cas9 polypeptide of any one of Claims 159-161, wherein said antisense oligonucleotide comprises a PAMmer oligonucleotide.

163. The Cas9 polypeptide of Claim 162, wherein said PAMmer oligonucleotide comprises one or more modified bases or linkages.

164. The Cas9 polypeptide of Claim 163, wherein said one or more modified bases or linkages are selected from the group consisting of locked nucleic acids and nuclease stabilized linkages.

165. The Cas9 polypeptide of any one of Claims 141-164, wherein said Cas9 polypeptide is adapted to be delivered to the nucleus of a cell.

166. The Cas9 polypeptide of Claim 165, wherein said Cas9 polypeptide is adapted to be co-exported with a target RNA out of said nucleus.

167. The Cas9 polypeptide of any one of Claims 165 or 166, wherein said Cas9 polypeptide comprises a nuclear localization signal.

168. The Cas9 polypeptide of any one of Claims 141-167, wherein said Cas9 polypeptide is nuclease null.

169. The Cas9 polypeptide of any one of Claims 141-168, wherein said target RNA comprises a repeat sequence.

170. The Cas9 polypeptide of Claim 169, wherein said repeat sequence is selected from the group consisting of CTG, CCTG, CAG, GGGGCC, and any combination thereof.

171. The Cas9 polypeptide of Claim 169 or 170, wherein said target RNA is associated with a disease.

172. The Cas9 polypeptide of Claim 171, wherein said disease is selected from the group consisting of myotonic dystrophy, Huntington's disease, familial ALS, cancer, spinal muscular atrophy and Fragile X syndrome.

173. A nucleic acid encoding the Cas9 polypeptide of any one of Claims 141-172.

174. A vector comprising the nucleic acid of Claim 173.

175. A cell comprising the nucleic acid of Claim 173, or the sector of Claim 174.

176. A method of expressing the Cas9 polypeptide of any one of Claims 141-172 comprising introducing a nucleic acid of Claim 172 or a vector of Claim 174 into a cell under conditions in which said cell expresses said Cas9 polypeptide.

177. A method of tracking a target RNA or measuring the amount of a target RNA in a cell comprising allowing a Cas9 polypeptide of any one of Claims 141-172 to bind to said target RNA in said cell and determining the location of said target RNA in said cell or determining the amount of said target RNA in said cell.

178. The method of Claim 177, wherein said Cas9 polypeptide binds to said target RNA in a nucleus of said cell and is subsequently co-exported from said nucleus with said target RNA.

179. The method of any one of Claims 177 or 178, wherein the location of said target RNA in said cell or the amount of said target RNA in said cell is determined using fluorescence microscopy.

180. A nucleic acid encoding the Cas9 polypeptide of any one of Claims 99-127.

181. A vector comprising the nucleic acid of Claim 180.

182. A cell comprising the nucleic acid of Claim 180 or the vector of Claim 181.

183. A method of expressing the Cas9 polypeptide of any one of Claims 99-127 comprising introducing a nucleic acid of Claim 180 or a vector of Claim 181 into a cell under conditions in which said cell expresses said Cas9 polypeptide.

184. A method of modifying the amount or structure of a target RNA in a cell comprising allowing a Cas9 polypeptide of any one of Claims 99-127 to bind to said target RNA in said cell under conditions in which the amount or structure of said target RNA in said cell is modified.

185. A method of measuring RNA content or dynamics in a sample, comprising:
introducing the Cas9 polypeptide of any one of Claims 141-172 into said sample; and
observing the detectable agent in said sample.

186. The method of Claim 185, comprising introducing a nucleic acid of Claim 131 or a vector of Claim 132 into said sample under conditions in which said Cas9 polypeptide is expressed.

187. The method of Claim 87 or 88, further comprising introducing a single guide RNA.

188. The method of any one of Claims 87-89, further comprising introducing an antisense oligonucleotide.

189. The method of any one of Claims 87-90, wherein said sample comprises a tissue.

190. The method of any one of Claims 87-91, wherein said sample comprises a plurality of cells.

191. The method of any one of Claims 87-92, comprising measuring the content of a target RNA in said sample.

192. The method of Claim 93, comprising diagnosing a disease condition of said sample based on the content of said target RNA in said sample.

193. The method of Claim 94, wherein said disease is selected from the group consisting of myotonic dystrophy, Huntington's disease, familial ALS, cancer, spinal muscular atrophy and Fragile X syndrome.

194. A method of modifying a target RNA in a sample, comprising:
introducing the Cas9 polypeptide of any one of Claims 141-172 into said sample; and
modifying said target RNA in said sample using the RNA modifying polypeptide.

195. The method of Claim 96, comprising introducing a nucleic acid of Claim 180 or a vector of Claim 181 into said sample under conditions in which said Cas9 polypeptide is expressed.

196. The method of Claim 194 or 195, further comprising introducing a single guide RNA.

197. The method of any one of Claims 194-196, further comprising introducing an antisense oligonucleotide.

198. The method of any one of Claims 194-197, wherein said sample comprises a tissue.

199. The method of any one of Claims 194-198, wherein said sample comprises a plurality of cells.

200. The method of any one of Claims 194-199, comprising modifying a target RNA in said sample.

201. The method of Claim 200, wherein said target RNA comprises a repeat sequence.

202. The method of Claim 201, wherein said repeat sequence is selected from the group consisting of CTG, CCTG, CAG, GGGGCC, and any combination thereof.

203. The method of Claim 201 or 202, wherein said repeat sequence is associated with a disease.

204. The method of Claim 203, wherein said disease is selected from the group consisting of myotonic dystrophy, Huntington's disease, familial ALS, cancer, spinal muscular atrophy and Fragile X syndrome.

BRIEF DESCRIPTION OF THE DRAWINGS

FIG. 1A. *S. pyogenes* Cas9 and single guide RNA (sgRNA) complexes bound to DNA or RNA. The Cas9:sgRNA complex may require a DNA NGG motif referred to as the protospacer adjacent motif (PAM). In the case of DNA binding, the PAM is supplied by the DNA target itself. The mechanism of DNA targeting by Cas9 is described extensively (Sander J D, Joung J K. CRISPR-Cas systems for editing, regulating and targeting genomes. *Nat Biotechnol.* 2014;32(4):347-55; Sternberg S H, Redding S, Jinek M, Greene E C, Doudna J A. DNA interrogation by the CRISPR RNA-guided endonuclease Cas9. *Nature.* 2014;507(7490):62-7; Wu X, Kriz A J, Sharp P A. Target specificity of the CRISPR-Cas9 system. *Quant Biol.* 2014;2(2):59-70; Jiang F, Taylor D W, Chen J S, Kornfeld J E, Zhou K, Thompson A J, Nogales E, Doudna J A. Structures of a CRISPR-Cas9 R-loop complex primed for DNA cleavage. *Science,* 2016; 351(6275):867-71).

FIG. 1B: In alternative embodiments, RNA-targeted Cas9 (RCas9) relies upon a short oligonucleotide called the PAMmer to supply the PAM motif. By utilizing a mismatched PAMmer, specificity of RCas9 for RNA while avoiding the encoding DNA is achieved. The PAMmer also carries a 5' overhang which is required to maintain target specificity conferred by the sgRNA. As a result, it is hypothesized that the 5' end of the PAMmer is at least partially dehybridized from the target RNA as Cas9-mediated unwinding of the PAMmer:target RNA duplex may confer an energetic cost that is recovered when the sgRNA hybridizes the target RNA.

FIG. 3B. An RCas9 system was delivered to HEK293T cells with an sgRNA and PAMmer targeting the 3'UTR of GAPDH or sgRNA and PAMmer targeting a sequence from λ bacteriophage which should not be present in human cells targeting sequence "N/A"). Cellular nuclei are outlined with a dashed white line.

FIG. 3C. A chart demonstrating the fraction of cells with a cytoplasmic RCas9 signal.

FIG. 3D. A schematic of a Renilla luciferase mRNA construct carrying a target site for RCas9 adjacent to an MS2 aptamer. The construct contains a PEST protein degradation signal to reveal any translational effects of RCas9 binding to the mRNA.

FIG. 3E. A chart demonstrating RNA immunoprecipitation of EGFP after transient transfection of the RCas9 system targeting the luciferase mRNA compared to non-targeting sgRNA and PAMmer or EGFP alone. Scale bars represent 10 microns.

FIG. 3F. A chart comparing the amounts of Renilla luciferase mRNA after transient transfection of the RCas9 system targeting the luciferase mRNA compared to non-targeting sgRNA and PAMmer or EGFP alone. No significant change in RNA abundance was revealed which contrasts with the increase in mRNA amount in the presence of MCP-EGFP. Scale bars represent 10 microns.

FIG. 3G. A chart comparing the amounts of Renilla luciferase protein after transient transfection of the RCas9 system targeting the luciferase mRNA compared to non-targeting sgRNA and PAMmer or EGFP alone. No significant change in the amount of Renilla luciferase protein was revealed. Scale bars represent 10 microns.

FIG. 5A. Tracking of mRNA trafficking to stress granules. An exemplary RCas9 system targeting β-actin mRNA was delivered to HEK293T cells expressing G3BP1, a protein known to be efficiently trafficked to stress granules, fused to mCherry. We oxidatively stressed the cells with sodium arsenite and measured localization of RCas9 and G3BP1.

FIG. 5B. RCas9 and G3BP1 signal distribution was measured in stressed cells (200 μM sodium arsenite) with the fraction of G3BP1+ stress granules with RCas9 foci reported. Error bars are standard deviation calculated from 30-40 cells from each of three biological replicates (90-120 cells total) and RCas9 overlapping foci were defined as accumulations of RCas9 signal >50% brighter than surrounding cytoplasmic signal with overlapping G3BP1 foci.

FIG. 7A2. Use Case 1 describes tracking the presence, localization, and movement of a target RNA, such as repeat-containing RNAs, with applications in diagnostics and research (data supporting this use case is described in FIGS. 7B and 7C). Repeat-containing RNAs cause a host of disease including, myotonic dystrophy, familial ALS, Huntington's disease, and many other conditions.

FIG. 7A3. Use case 2 describes an exemplary therapeutic application of RCas9 in living cells that utilizes a fused endonuclease (effector) protein to Cas9 that destroys targeted RNAs. This general principle can be used to cleave a variety of disease causing RNAs that cause various conditions ranging from neurodegeneration to cancer. Data supporting this application in the context of targeting the repeat-containing RNA that causes myotonic dystrophy is described in FIG. 7D2.

FIG. 7A4. RNA splicing use case 3 describes alteration of RNA splicing with RCas9. Dysfunctional RNA splicing is linked to many diseases including cancer and spinal muscular atrophy (SMA). This use case involves an effector comprising a splicing factor or other protein that alters RNA splicing that is targeted to pre-mRNAs to alter splicing. Data supporting this use case is described in FIG. 7E.

FIG. 7D1. Data demonstrating cleavage of RNA using an exemplary RCas9 system (use case 2). Here, the RNA that causes myotonic dystrophy (composed of repeating CUG RNA bases) was targeted in living human cells using both permutation 1 and 2 of the RCas9 system.

FIG. 7D2. Application of the permutation 2 of the RNA-cleaving RCas9 system (use case 2) resulted in a large reduction of the amount of CUG repeat-containing RNA (~35% RNA levels compared to no RCas9 system present, bar on far left). The bar graph represents a quantification of the Northern dot blot (below).

FIGS. 7B-D demonstrate that RCas9 is capable of cleaving CTG repeat RNA. This data demonstrates that an associated molecular phenotype (MBNL1 distribution) is reversed to at healthy pattern upon RCas9-mediated cleavage of the RNA.

DETAILED DESCRIPTION OF THE PREFERRED EMBODIMENT

Figure 1:
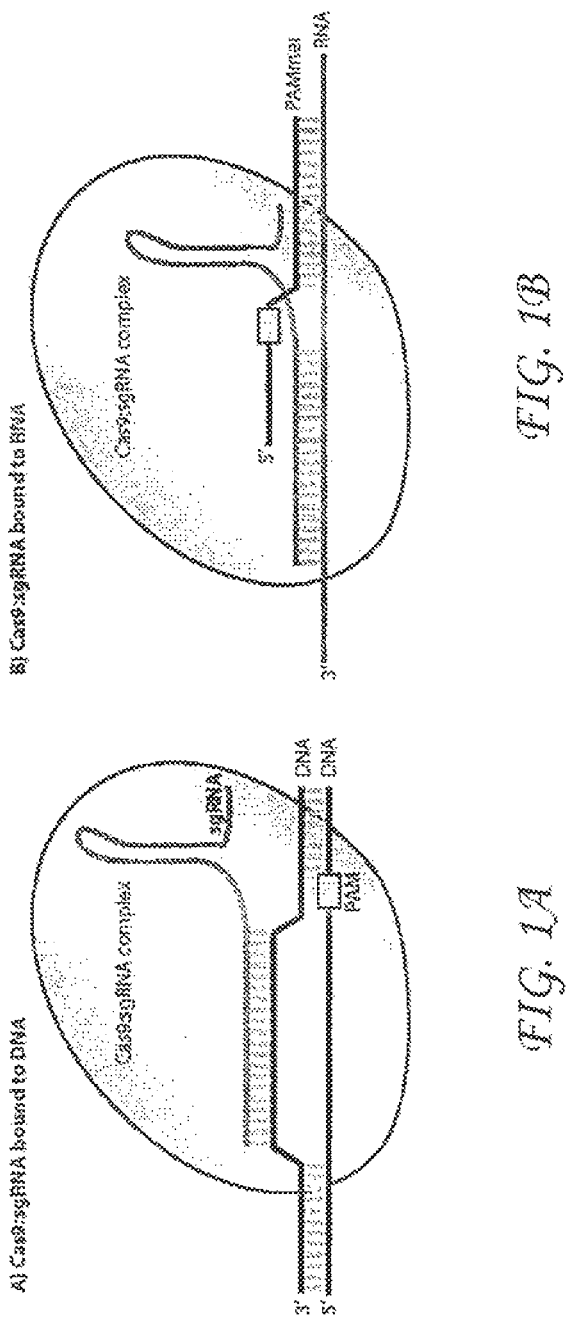
FIG. 7A1. Alternative embodiments ("Permutation 1, Permutation 2") and uses for exemplary RNA-targeting Cas9 (RCas9). Permutations 1 and 2 describe which in some embodiments may be the minimal components for measuring and manipulating RNA with an exemplary RNA-targeting Cas9. The RCas9 system is composed of the *Streptococcus pyogenes* Cas9 protein, a single guide RNA, and a short oligonucleotide known as the PAMmer (permutation 1) OR *Streptococcus pyogenes* Cas9 protein and a single guide RNA only. Each use case (1-3) describes a distinct technological or biomedical exemplary application of the RCas9 system in the context of living cells.

All publications, patents, and patent applications mentioned in this specification are herein incorporated by reference in their entireties for all purposes to the same extent as if each individual publication, patent, or patent application was specifically and individually indicated to be incorporated by reference. For example, PCT/US14/53301 is herein incorporated by reference in its entirety for all purposes.

Definitions

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "associated" or "associated with" can mean that two or more moieties, such as chemical groups, nucleotides, oligonucleotides, proteins or peptides are linked to each other, either covalently or non-covalently. For example, a protein may be associated with a nucleotide, a fluorescent agent, or another protein. An association can mean that two or more proteins or peptides form a fusion protein. An association can be a physical association. In some instances two or more proteins or peptides are "tethered", "attached", or "linked" to one another. An association may be a covalent bond between two proteins or peptides.

As used herein, a "polypeptide" includes proteins, fragments of proteins, and peptides, whether isolated from natural sources, produced by recombinant techniques, or chemically synthesized. A polypeptide may have one or more modifications, such as a post-translational modification (such as glycosylation, etc.) or any other modification (such as pegylation, etc.). The polypeptide may contain one or more non-naturally-occurring amino acids (such as an amino acid with a side chain modification). Polypeptides described herein typically comprise at least about 10 amino acids.

As used herein, the term "sample" can refer to a composition comprising targets. Suitable samples for analysis by the disclosed methods, devices, and systems include cells, tissues, organs, or organisms or compositions obtained from cells, tissues or organisms.

As used herein, the term "specifically binds" refers to the binding specificity of a specific binding pair. Hybridization by a target-specific nucleic acid sequence of a particular target polynucleotide sequence in the presence of other potential targets is one characteristic of such binding. Specific binding involves two different nucleic acid molecules wherein one of the nucleic acid molecules specifically hybridizes with the second nucleic acid molecule through chemical or physical means. The two nucleic acid molecules are related in the sense that their binding with each other is such that they are capable of distinguishing their binding partner from other assay constituents having similar characteristics. The members of the binding component pair are referred to as ligand and receptor (anti-ligand), specific binding pair (SBP) member and SBP partner, and the like.

"Polynucleotide," or "nucleotide," as used interchangeably herein, refer to polymers of nucleotides of any length, and include DNA and RNA. A polynucleotide or nucleotide sequence could be either double-stranded or single-stranded. When a polynucleotide or nucleotide sequence is single stranded, it could refer to either of the two complementary strands. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (such as methyl phosphonates, phosphotriesters, phosphoamidates, cabamates, etc.) and with charged linkages (such as phosphorothioates, phosphorodithioates, etc.), those containing pendant moieties, such as, for example, proteins (such as nucleases, toxins, antibodies, signal peptides, ply-L-lysine, etc.), those with intercalators (such as acridine, psoralen, etc.), those containing chelators (such as metals, radioactive metals, boron, oxidative metals, etc.), those containing alkylators, those with modified linkages (such as alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping groups moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by $P(O)S$ ("thioate"), $P(S)S$ ("dithioate"), "$(O)NR_2$" ("amidate"), $P(O)R$, $P(O)OR'$, $CO$ or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

As used herein, "improve" means a change of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100%, 125%, 150%, 175%, 200%, 225%, 250%, 275%, 300%, 350%, 400%, 450%, 500%, 600%, 700%, 800%, 900%, 1000% or more or any value between any of the listed values. Alternatively, "improve" could mean a change of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, "complexed" means non-covalently linked to or associated with.

As used herein, "nuclease null" may refer to a polypeptide with reduced nuclease activity, reduced endo- or exo- DNAse activity RNAse activity, reduced nickase activity, or reduced ability to cleave DNA and/or RNA.

As used herein, "reduced nuclease activity" means decline in nuclease, nickase, DNAse, or RNAse activity of at least about 1%, 2%, 5%, 10%, 15%, 20%, 25%, 30%, 35%, 40%, 35%, 50%, 55%, 60%, 65%, 70%, 75%, 80%, 85%, 90%, 95%, 100% or more or any value between any of the listed values. Alternatively, "reduced nuclease activity" may refer to a decline of at least about 1-fold, 1.5-fold, 2-fold, 3-fold, 4-fold, 5-fold, 6-fold, 7-fold, 8-fold, 9-fold, 10-fold, 15-fold, 20-fold, 30-fold, 40-fold, 50-fold, 60-fold, 70-fold, 80-fold, 90-fold, 100-fold, 500-fold, 1000-fold, 2000-fold or more or any value between any of the listed values.

As used herein, a "trafficking agent or agents" may refer to any polypeptide that directs the nucleoprotein complex to a desired location in a cell, such as a cytoplasmic polyadenylation element binding protein (CPEB), a zinc finger binding protein (ZBP), TIA-1 (a 3'UTR mRNA binding protein), a PSF (a protein component of spliceosomes) or a DNA-binding domain (DBD) of PSF, fragile X mental retardation protein (FMRP), IGF-II mRNA-binding protein (IMP)-1 (IMP1), IMP2, IMP3, a cytoskeleton binding protein, a transmembrane protein, or an engineered protein comprising a combination of domains of these aforementioned proteins to generate a combinatorial trafficking phenomena.

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5× Denhardt's solution, 5× SSPE, 0.2% SDS at 42° C., followed by washing in 0.2× SSPE, 0.2% SDS, at 42° C. High stringency conditions can be provided, for example, by hybridization in 50% formamide, 5× Denhardt's solution, 5× SSPE, 0.2% SDS at 42° C., followed by washing in 0.1× SSPE, and 0.1% SDS at 65° C.

Low stringency hybridization refers to conditions equivalent to hybridization in 10% formamide, 5× Denhardt's solution, 6× SSPE, 0.2% SDS at 22° C. followed by washing in 1× SSPE, 0.2% SDS, at 37° C. Denhardt's solution contains 1% Ficoll, 1% polyvinylpyrolidone, and 1% bovine serum albumin (BSA), 20× SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art.

RNA-Targeting Cas9 Polypeptides (RCas9)

Some embodiments disclosed herein provide Cas9 polypeptide which has been engineered to recognize a target RNA, wherein the Cas9 polypeptide is associated with an effector. In some embodiments, the Cas9 polypeptide is a *Streptococcus pyogenes* Cas9 polypeptide. In some embodiments, the Cas9 polypeptide comprises a mutation, such as D10A, H840A, or both (SEQ ID NO: 31), in the *Streptococcus pyogenes* Cas9 polypeptide.

Some embodiments relate to a version of the Cas9 polypeptide-comprising nucleoprotein complex as provided herein is involved in the clustered regularly interspaced short palindromic repeats (CRISPR)/Cas9, or CRISP/Cas9, system that has been repurposed or engineered to target RNA instead of DNA in living cells. This repurposed or engineered Cas9 polypeptide-comprising nucleoprotein complex binds to RNA is referred to herein as RCas9. CRISPR has revolutionized genome engineering by allowing simply-programmed recognition of DNA in human cells and supported related technologies in imaging and gene expression modulation. We have developed an analogous means to target RNA using an RCas9, or with CRISPR/Cas9. In some embodiment, nucleoprotein complexes as provided herein comprise a Cas9 protein, a single guide RNA (sgRNA), and optionally an (chemically-modified or synthetic) antisense PAMmer oligonucleotide. The PAMmer is an antisense oligonucleotide that serves to simulate a DNA substrate for recognition by Cas9 via hybridization to the target RNA. Together, the Cas9 protein and sgRNA components allow recognition of hypothetically any RNA sequence Thus, in alternative embodiments, compositions and methods provided herein provide solutions to persistent problems in many fields of basic biology and therapy. As a tool for basic biology and drug development, this technology has already supported nondestructive measurement of RNA localization and gene expression in living cell (see discussion below). From a therapeutic perspective, compositions and methods provided herein allow targeted alteration of RNA compositions via alteration of RNA splicing or RNA editing to reverse RNA features that are implicated in diseases such as cancer and neurodegeneration. The nucleoprotein complexes as provided herein stand apart from the state of the art as the first simply reprogrammable, nucleic acid-guided RNA binding protein.

In some embodiments, exemplary nucleoprotein complexes as provided herein are associated with, or comprise, a detectable agent, such as a fluorescent agent, a fluorescent protein, an enzyme, or the like. In some embodiments, the fluorescent protein is a green fluorescent protein (GFP), an enhanced GFP (EGFP (SEQ ID NO: 30)), a blue fluorescent protein or its derivatives (EBFP, EBFP2, Azurite, mKalama1), a cyan fluorescent protein or its derivatives (ECFP, Cerulean, CyPet, mTurquoise2), a yellow fluorescent protein and its derivatives (YFP, Citrine, Venus, YPet), UnaG, dsRed, eqFP611, Dronpa, TagRFPs, KFP, EosFP, Dendra, IrisFP, etc., or fragments thereof. In some embodiments, a fluorescent protein may be split into two halves, each fused with a Cas9 polypeptide, so that when the two Cas9 polypeptides bind to adjacent RNA targets, the two halves of the fluorescent protein come into close proximity of each other and generate a fluorescent signal. For example, the fluorescent protein Venus can be split into two halves: an N-terminal portion and a C-terminal portion. In some embodiments, the N-terminal portion comprises residues 1-155 or 1-173 (SEQ ID NO: 25). In some embodiments, the N-terminal portion comprises an I152L mutation (SEQ ID NO: 24; I152L reduced background complementation mutant, from Kodama et al Biotechniques, 2010 November, 49(5): 793-805). In some embodiments, the C-terminal portion comprises residues 155-238 (SEQ ID NO: 26). In some embodiments, the enzyme is luciferase (Gaussia, Renilla, Firefly variants), tobacco etch virus. (TEV) protease, ubiquitin, horse radish peroxidase, or a toxin such as diphtheria toxin, etc. In some embodiments, the enzyme may be split into two halves, each fused with a Cas9 polypeptide, so that when the two Cas9 polypeptides bind to adjacent RNA targets, the two halves of the enzyme come into close proximity of each other and create the enzymatic activity. In some embodiments, the enzyme is involved in the modification of synthesis of a compound. In some embodiments, the compound is a polypeptide or a nucleic acid. In some embodiments, the association of the Cas9 polypeptide on a target RNA creates a local accumulation of intermediate products in a biosynthetic pathway to amplify the production of a medically- or technologically-useful compound compared to free-floating biosynthetic enzymes.

In some embodiments, the nucleoprotein complexes as provided herein are associated with an effector polypeptide such as a nuclease that cleaves RNA, such as, a PIN domain protein, such as human SMG6 (SEQ ID NO: 27), or fragments thereof. In some embodiments, nucleoprotein complexes as provided herein are associated with an RNA binding protein, such as, human RBFOX1 (SEQ ID NO: 28), Human RBFOX2 (SEQ ID NO: 29), or the like, or fragments thereof. In some embodiments, the Cas9 polypeptide is associated with a splicing factor, or fragments thereof. In some embodiments, the nuclease, RNA binding protein, or splicing factor may be split into two halves, each fused with a Cas9 polypeptide, so that when the two Cas9 polypeptides bind to adjacent RNA targets, the two halves of the nuclease, RNA binding protein, or splicing factor come into close proximity of each other and create the enzymatic activity.

In some embodiments, nucleoprotein complexes as provided herein are further associated with or comprise one or more nuclear localization signals, one or more stable, inert linker peptides such as XTEN peptides, or combinations thereof. XTEN peptides have been used to extend the serum half-life of translationally fused biologic drugs by increasing their hydrodynamic radius, acting as a protein-based functional analog to chemical PEGylation. As XTEN peptides are chemically stable, non-cationic, non-hydrophobic, and predicted to adopt an extended, unstructured conformation. XTEN-based linker peptides can function as stable, inert linker sequences to join Cas9 polypeptides to an effector polypeptide, such as an RNA modifying polypeptide, or to a detectable moiety.

Truncated Cas9 Polypeptides

Truncated versions of *Streptococcus pyogenes* Cas9 that are capable of binding RNA are advantageous in terms of their ability to specifically alter target RNA but not DNA sequences while reducing the size of Cas9 protein to fit in adeno-associated viral vectors (AAV). In some embodiments, the nucleoprotein complexes comprise truncated versions of Cas9 that lack part or all of the DNA-cleaving HNH, RuvC domains, or combinations thereof, which facilitate both of these important features by eliminating the DNA-cleaving ability of Cas9 (producing a nuclease-null Cas9) and reducing its size. In some embodiments, AAV vectors capable of delivering ~4.5 kb are used for packaging of transgenes. In some embodiments, AAVs capable of packaging large transgenes such as about 4.6 kb, 4.7 kb, 4.8 kb, 4.9 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.5 kb, 8.0 kb, 9.0 kb, 10.0 kb, 11.0 kb, 12.0 kb, 13.0 kb, 14.0 kb, 15.0 kb, or larger are used.

In other embodiments, the nucleoprotein complexes comprise truncations lacking all or portions of other domains that contact specific DNA residues (such as the PAMmer-interaction-domain, or PAM-ID domain), all or portions of the Rec domain, or combinations thereof, providing further reductions in size that maintain the ability of Cas9 to bind RNA. By fusing nuclease-null Cas9 to effectors such as the PIN domain or other effectors that act on RNA but not DNA, these embodiments provide means to alter RNA while not targeting the encoding DNA.

In some embodiments, the Cas9 active sites (10 and 840) are mutated to Alanine (D10A and H840A) to eliminate the cleavage activity of *Streptococcus pyogenes* Cas9, producing nuclease-deficient or dCas9. The RuvC domain is distributed among 3 non-contiguous portions of the dCas9 primary structure (residues 1-60, 719-775, and 910-1099). The Rec lobe is composed of residues 61-718. The HNH domain is composed of residues 776-909. The PAM-ID domain is composed of residues 1100-1368.

The REC lobe be considered the structural scaffold for recognition of the sgRNA and target DNA/RNA. The NUC lobe contains the two nuclease domains (HNH and RuvC), plus the PAM-interaction domain (PAM-ID), which recognizes the PAM sequence. In some embodiments, the 98-nucleotide sgRNA can similarly be broken into two major structural components: the first contains the target-specific guide or "spacer" segment (nucleotides 1-20) plus the repeat-tetraloop-anti-repeat and stem-loop 1 (SL1) regions; the second contains stem-loops 2 and 3 (SL2, SL3). In some embodiments, the guide-through-SL1 RNA segment is bound mainly by the Cas9 REC lobe. In some embodiments, the SL2-SL3 segment is bound mainly by the NUC lobe.

A recent study demonstrated that 1368-amino acid *Streptococcus pyogenes* Cas9 can be split into two polypeptides comprising the REC lobe (amino acids 56-714) and the NUC lobe (amino acids 1-57 fused to 729-1368), which can be combined in trans to form a functional nuclease (Wright A V, Sternberg S H, Taylor D W, Staahl B T, Bardales J A, Kornfeld J E, Doudna J A. Rational design of a split-Cas9 enzyme complex. *Proc Natl Acad Sci USA*. 2015;112(10): 2984-9). The study results demonstrate that Cas9 construct missing the entire NUC lobe can assemble with sgRNA with high affinity: albeit significantly lower affinity than full-length Cas9. Currently, it is unknown how affinity changes in this range affect either DNA-editing efficiency of CRISPR/Cas9 or its ability to target RNA in cells.

In some embodiments, a minimal construct of SpCas9 is engineered that will recognize a target RNA sequence with high affinity and guide its fused PIN RNA endonuclease domain to a model RNA for destruction. In some embodiments, the smallest construct will be a REC-only construct. In some embodiments, the constructs will comprise less minimized constructs lacking the HNH, PAM-ID, parts of each domain, lacking both of each domains, or combinations thereof. In some embodiments, the HNH domain will be excised by inserting a five-residue flexible linker between residues 77 and 909 (ΔHNH). In some embodiments, all or part of the PAM-ID are removed. In some embodiments, truncating Cas9 at residue 1098 (ΔPAM-ID #1), fusing residues 1138 and 1345 with an 8-residue linker (ΔPAM-ID #2), or fusing residues 1138 with 1200 and 1218 with 1339 (with 5-residue and 2-residue linkers, respectively: ΔPAM-ID #3) are used to remove all or part of the PAM-ID. The ΔPAM-ID #2 and 3 constructs will retain elements of the PAM-ID that contribute to binding of the sgRNA repeat-anti-repeat (residues 1099-1138) and SL2-SL3 (residues 1200-1218 and 1339-1368) segments. In some embodiments, the HNH deletion will be combined with the three PAM-ID deletions.

In some embodiments, the nucleoprotein complex may comprise a Cas9 polypeptide that lacks all or part of (1) an HNH domain, (2) at least one RuvC nuclease domain, (3) a Cas9 polypeptide DNase active site, (4) a ββα-metal fold comprising a Cas9 polypeptide active site, or (5) a Cas9 polypeptide that lacks all or part of one or more of the HNH domain, at least one RuvC nuclease domain, a Cas9 polypeptide DNase active site, and/or a ββα-metal fold comprising a Cas9 polypeptide active site as compared to a corresponding wild type (WT) Cas9 polypeptide and wherein, the complex may or may not comprise a PAMmer oligonucleotide.

Single Guide RNA (sgRNA)

In some embodiments, nucleoprotein complexes as provided herein are complexed with a single guide RNA (sgRNA). In some embodiments, the single guide RNA carries extensions of secondary structures in the single guide RNA scaffold sequence. In some embodiments, the single guide RNA comprises one or more point mutations that improve expression levels of the single guide RNAs via removal of partial or full transcription termination sequences or sequences that destabilize single guide RNAs after transcription via action of trans-acting nucleases. In some embodiments, the single guide RNA comprises an alteration at the 5' end which stabilizes said single guide RNA against degradation. In some embodiments, the single guide RNA comprises an alteration at the 5' end which improves RNA targeting. In some embodiments, the alteration at the 5' end of said single guide RNA is selected from the group consisting of 2'O-methyl, phosphorothioates, and thiophosphonoacetate linkages and bases. In some embodiments, the single guide RNA comprises 2'-fluorine, 2'O-methyl, and/or 2'-methoxyethyl base modifications in the spacer or scaffold region of the sgRNA to improve target recognition or reduce nuclease activity on the single guide RNA. In some embodiments, the single guide RNA comprises one or more methylphosphonate, thiophosponoaceteate, or phosphorothioate linkages that reduce nuclease activity on the target RNA.

In some embodiments, the single guide RNA can recognize the target RNA, for example, by hybridizing to the target RNA. In some embodiments, the single guide RNA comprises a sequence that is complementary to the target RNA. In some embodiments, the single guide RNA has a length that is, is about, is less than, or is more than, 10 nt, 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 300 nt, 400 nt, 500 nt, 1,000 nt, 2,000 nt, or a range between any two of the above values. In some embodiments, the single guide RNA can comprise one or more modified nucleotides.

In alternative embodiments, a variety of RNA targets can be recognized by the single guide RNA. For example, a target RNA can be messenger RNA (mRNA), ribosomal RNA (rRNA), signal recognition particle RNA (SRP RNA), transfer RNA (tRNA), small nuclear RNA (snRNA), small nucleolar RNA (snoRNA), antisense RNA (aRNA), long noncoding RNA (lncRNA), microRNA (miRNA), piwi-interacting RNA (piRNA), small interfering RNA (siRNA), short hairpin RNA (shRNA), retrotransposon RNA, viral genome RNA, viral noncoding RNA, or the like. In some embodiments, a target RNA can be an RNA involved in pathogenesis or a therapeutic target for conditions such as cancers, neurodegeneration, cutaneous conditions, endocrine conditions, intestinal diseases, infectious conditions, neurological disorders, liver diseases, heart disorders, autoimmune diseases, or the like.

In some embodiments, a target RNA can comprise a repeat sequence. For example, the repeat sequence can be CTG, CCTG, CAG, GGGGCC, or any combination thereof. In some embodiments, the repeat sequence is associated with a disease, for example, myotonic dystrophy, Huntington's disease, familial ALS, cancer, spinal muscular atrophy, Fragile X syndrome, etc.

PAMmer Oligonucleotide

In some embodiments, nucleoprotein complexes as provided herein are further complexed with an antisense oligonucleotide which is complementary to a sequence in the target RNA. In some embodiments, the antisense oligonucleotide comprises a PAMmer oligonucleotide. In some embodiments, the antisense oligonucleotide comprises at least one modified nucleotide. In some embodiments, the at least one modified nucleotide is selected from the group consisting of 2'OMe RNA and 2'OMe DNA nucleotides. In some embodiments, the PAMmer oligonucleotide comprises one or more modified bases or linkages. In some embodiments, the one or more modified bases or linkages are selected from the group consisting of locked nucleic acids and nuclease stabilized linkages. In some embodiments, the antisense oligonucleotide is complementary to a sequence that is in close proximity to the target RNA. For example, the antisense oligonucleotide can be complementary to a sequence that is about 10 nt, 20 nt, 30 nt, 40 nt, 50 nt, 60 nt, 70 nt, 80 nt, 90 nt, 100 nt, from the target RNA. In some embodiments, the antisense oligonucleotide has a length that is, is about, is less than, or is more than, 10 nt, 20 nt, 30 nt, 40 nt, 50 nt, 60 nt, 70 nt, 80 nt, 90 nt, 100 nt, 110 nt, 120 nt, 130 nt, 140 nt, 150 nt, 160 nt, 170 nt, 180 nt, 190 nt, 200 nt, 300 nt, 400 nt, 500 nt, 1,000 nt, 2,000 nt, or a range between any two of the above values. In some embodiments, the antisense oligonucleotide comprises RNA, DNA, or both.

Nucleic Acids Encoding Cas9 Polypeptides

Some embodiments disclosed herein provide nucleic acids that encode the Cas9 polypeptides, sgRNAs, or fusion proteins of the nucleoprotein complexes as provided herein, optionally associated with an effector or detectable moiety, such as a detectable reagent or an RNA modifying polypeptide, e.g., an RNA endonuclease.

The nucleic acids may be naturally occurring nucleic acids DNA, RNA, or nucleic acids including peptide nucleic acid (PNA), Morpholino and locked nucleic acid (LNA), as well as glycol nucleic acid (GNA) and threose nucleic acid (TNA). Both single-stranded and double-stranded nucleic acids may be used for the present disclosure. In some embodiments, the nucleic acid is a recombinant DNA molecule.

In some embodiments, the Cas9 polypeptides as encoded herein comprise archaeal or bacterial Cas9 polypeptides. In some embodiments the Cas9 polypeptide is, comprises or is derived from: *Haloferax mediteranii, Mycobacterium tuberculosis, Francisella tidarensis* subsp. *novicida, Pasteurella multocida, Neisseria meningitidis, Campylobacter jejune, Streptococcus thermophilius* LMD-9 CRISPR 3, *Campylobacter lari* CF89-12, *Mycoplasma gallisepticum* str. F, *Nitratifractor salsuginis* str. DSM 16511, *Parvibaculum lavamentivorans, Roseburia intestinalis, Neisseria cinerea, Gluconacetobacter diazotrophicus, Azospirillum* B510, *Sphaerochaeta globus* str. Buddy, *Flavobacterium columnare, Fluviicola taffensis, Bacteroides coprophilus, Mycoplasma mobile, Lactobacillus farciminis, Streptococcus pasteurianus, Laciobacillus johnsonii, Staphylococcus pseudintermedius, Filifactor alocis, Treponema denticola, Legionella pneumophila* str. Paris, *Sutterella wadsworthensis, Corynebacter diphtheriae,* or *Streptococcus aureus*; a *Francisella novicida* (optionally a *Francisella novicida* Cpf1) or a *Natronobacterium gregoryi* Argonaute modified or repurposed to target RNA, wherein optionally the sgRNA 3' end or "scaffold sequence" comprises all or part of, or is derived from, the wild type (WT) cognate guide nucleic acid of each of these respective bacteria or archaeal organisms.

As used herein, "operatively linked" or "linked operatively" refer to the situation in which part of a linear DNA sequence can influence the other parts of the same DNA molecule. For example, when a promoter controls the transcription of the coding sequence, it is operatively linked to the coding sequence.

Some embodiments disclosed herein provide genetically engineered recombinant vectors comprising nucleic acid molecules encoding exemplary Cas9 polypeptides, sgRNAs, or fusion proteins of an exemplary Cas9 polypeptide optionally associated with an effector or detectable moiety, such as a detectable reagent or an RNA modifying polypeptide, e.g., an RNA endonuclease. Vectors used can include those that are suitable for expression in a selected host, whether prokaryotic or eukaryotic, for example, phage, plasmid, and viral vectors. Viral vectors may be either replication competent or replication defective retroviral vectors. Viral propagation generally will occur only in complementing host cells comprising replication defective vectors, for example, when using replication defective retroviral vectors in methods provided herein viral replication will not occur. Vectors may comprise Kozak sequences (Lodish et al., Molecular Cell Biology, 4th ed., 1999) and may also contain the ATG start codon. Promoters that function in a eukaryotic host include SV40, LTR, CMV, EF-1α, white cloud mountain minnow β-actin promoter, etc.

Copy number and positional effects are considered in designing transiently and stably expressed vectors. Copy number can be increased by, for example, dihydrofolate reductase amplification. Positional effects can be optimized by, for example, Chinese hamster elongation factor-1 vector pDEF38 (CHEF1), ubiquitous chromatin opening elements (UCOE), scaffold/matrix-attached region of human (S/MAR), and artificial chromosome expression (ACE) vectors, as well as by using site-specific integration methods known in the art. The expression constructs containing the vector and gene of interest will further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

Considering the above-mentioned factors, exemplary vectors suitable for expressing exemplary Cas9 polypeptides, sgRNAs, and/or fusion proteins of a Cas9 polypeptide, optionally associated with an effector or detectable moiety, such as a detectable reagent or an RNA modifying polypeptide in bacteria include pTT vectors, are available e.g., from Biotechnology Research Institute (Montreal, Canada), pQE70, pQE60, and pQE-9, available from Qiagen (Mississauga, Ontario, Canada); vectors derived from pcDNA3, available from Invitrogen (Carlsbad, Calif.); pBS vectors, Phagescript vectors. Bluescript vectors, pNH8A, pNH6a, pNH18A, pNH46A, available from Stratagene (La Jolla, Calif.); and ptrc99a, pKK223-3, pKK233-3, pDR540, pRIT5 available from Pharmacia (Peapack, N.J.). Among suitable eukaryotic vectors are pWLNEO, pSV2CAT, pOG44, pXT1, and pSG available from Stratagene (La Jolla, Calif.); and pSVK3, pBPV, pMSG and pSVL, available from Pharmacia (Peapack, N.J.).

Vectors for expressing exemplary Cas9 polypeptides, sgRNAs, or fusion proteins of a Cas9 polypeptide, optionally associated with an effector or detectable moiety, such as a detectable reagent or an RNA modifying polypeptide include those comprising a pTT vector backbone (Durocher et al., Nucl. Acids Res. 30:E9 (2002)). Briefly, the backbone of a pTT vector may be prepared by obtaining pIRESpuro/EGFP (pEGFP) and pSEAP basic vector(s), for example from Clontech (Palo Alto, Calif.), and pcDNA3.1, pCDNA3.1/Myc-(His)6 and pCEP4 vectors can be obtained from, for example, Invitrogen (Carlsbad, Calif.). As used herein, the pTT5 backbone vector can generate a pTT5-Gateway vector and be used to transiently express proteins in mammalian cells. The pTT5 vector can be derivatized to pTT5-A, pTT5-B, pTT5-D, pTT5-E, pTT5-H, and pTT5-I, for example. As used herein, the pTT2 vector can generate constructs for stable expression in mammalian cell lines.

A pTT vector can be prepared by deleting the hygromycin (BsmI and SalI excision followed by fill-in and ligation) and EBNA1 (ClaI and NsiI excision followed by fill-in and ligation) expression cassettes. The ColEI origin (FspI-SalI fragment, including the 3' end of the β-lactamase open reading frame (ORF) can be replaced with a FspI-SalI fragment from pcDNA3.1 containing the pMBI origin (and the same 3' end of β-lactamase ORF). A Myc-(His)6 C-terminal fusion tag can be added to SEAP (HindIII-HpaI fragment from pSEAP-basic) following in-frame ligation in pcDNA3.1/Myc-His digested with HindIII and EcoRV. Plasmids can subsequently be amplified in *E. coli* (DH5α) grown in LB medium and purified using MAXI prep columns (Qiagen, Mississauga, Ontario, Canada). To quantify, plasmids can be subsequently diluted in, for example, 50 mM Tris-HCl pH 7.4 and absorbencies can be measured at 260 nm and 280 nm. Plasmid preparations with A260/A280 ratios between about 1.75 and about 2.00 are suitable for producing the Fc-fusion constructs.

The expression vector pTT5 allows for extrachromosomal replication of the cDNA driven by a cytomegalovirus (CMV) promoter. The plasmid vector pCDNA-pDEST40 is a Gateway-adapted vector which can utilize a CMV promoter for high-level expression. SuperGlo GFP variant (sgGFP) can be obtained from Q-Biogene (Carlsbad, Calif.). Preparing as pCEP5 vector can be accomplished by removing the CMV promoter and polyadenylation signal of pCEP4 by sequential digestion and self-ligation using SalI and XbaI enzymes resulting in plasmid pCEP4Δ. A GblII fragment from pAdCMV5 (Massie et al., J. Virol. 72:2289-2296 (1998)), encoding the CMV5-poly(A) expression cassette ligated in BglII-linearized pCEP4Δ, resulting in the pCEP5 vector.

Vectors for expressing exemplary Cas9 polypeptides, sgRNAs or fusion proteins of a Cas9 polypeptide, optionally associated with an effector or detectable moiety, such as a detectable reagent or an RNA modifying polypeptide can include those comprising vectors optimized for use in CHO-S or CHO-S-derived cells, such as pDEF38 (CHEF1) and similar vectors (Running Deer et al., Biotechnol, Prog. 20:880-889 (2004)). The CHEF vectors contain DNA elements that lead to high and sustained expression in CHO cells and derivatives thereof. They may include, but are not limited to, elements that prevent the transcriptional silencing of transgenes.

Vectors may include a selectable marker for propagation in a host. In alternative embodiments, a selectable marker is used that allows the selection of transformed cells based on their ability to thrive in the presence or absence of a chemical or other agent that inhibits an essential cell function. The selectable markers confer a phenotype on a cell expressing the marker, so that the cell can be identified under appropriate conditions. Suitable markers, therefore, include genes coding for proteins which confer drug resistance or sensitivity thereto, impart color to, or change the antigenic characteristics of those cells transfected with a molecule encoding the selectable marker, when the cells are grown in an appropriate selective medium.

Suitable selectable markers include dihydrofolate reductase or G418 for neomycin resistance in eukaryotic cell culture; and tetracycline, kanamycin, or ampicillin resistance genes for culturing in E. coli and other bacteria. Suitable selectable markers also include cytotoxic markers and drug resistance markers, whereby cells are selected by their ability to grow on media containing one or more of the cytotoxins or drugs; auxotrophic markers, by which cells are selected for their ability to grow on defined media with or without particular nutrients or supplements, such as thymidine and hypoxanthine; metabolic markers for which cells are selected, for example, for ability to grow on defined media containing a defined substance, for example, an appropriate sugar as the sole carbon source; and markers which confer the ability of cells to form colored colonies on chromogenic substrates or cause cells to fluoresce.

As mentioned above, vectors for the expression of exemplary Cas9 polypeptides, sgRNA, or fusion proteins of an exemplary Cas9 polypeptide optionally associated with an effector or detectable moiety, such as a detectable reagent or an RNA modifying polypeptide can also be constructed in retroviral vectors. One such vector, the ROSA geo retroviral vector, which maps to mouse chromosome six, was constructed with the reporter gene in reverse orientation with respect to retroviral transcription, downstream of a splice acceptor sequence (U.S. Pat. No. 6,461,864; Zambrowiez et al., Proc. Natl. Acad. Sci. 94:3789-3794 (1997)). Infecting embryonic stem (ES) ceps with ROSA geo retroviral vector resulted in the ROSA geo26 (ROSA26) mouse strain by random retroviral gene trapping in the ES cells.

A DNA insert comprising nucleic acids (optionally contained in a vector or vectors) encoding exemplary Cas9 polypeptides, sgRNAs, or fusion proteins of a Cas9 polypeptide, optionally associated with an effector or detectable moiety, such as a detectable reagent or an RNA modifying polypeptide can be operatively linked to an appropriate promoter, such as the phage lambda PL promoter; the E. coli lac. trp. phoA, and tac promoters; the SV40 early and late promoters; and promoters of retroviral LTRs. Suitable vectors and promoters also include the pCMV vector with an enhancer, pcDNA3.1; the pCMV vector with an enhancer and an intron, pCIneo; the pCMV vector with an enhancer, an intron, and a tripartate leader, pTT2, and CHEF1. Other suitable vectors and promoters will be known to the skilled artisan. The promoter sequences include at least the minimum number of bases or elements necessary to initiate transcription of a gene of interest at levels detectable above background. Within the promoter sequence may be a transcription initiation site, as well as protein binding domains (consensus sequences) responsible for the binding of RNA polymerase. In alternative embodiments, eukaryotic promoters will often, but not always, contain "TATA" boxes and "CAT" boxes.

Some embodiments disclosed herein provide vectors for the in vivo expression of exemplary Cas9 polypeptides, sgRNAs, or fusion proteins of an exemplary Cas9 polypeptide, optionally associated with an effector or detectable moiety, such as a detectable reagent or an RNA modifying polypeptide in animals, including humans, under the control of a promoter that functions in a tissue-specific manner. For example, promoters that drive the expression of the Cas9 polypeptides sgRNAs, or fusion proteins of a Cas9 polypeptide associated, optionally associated with an effector or detectable moiety, such as a detectable reagent or an RNA modifying polypeptide may be liver-specific, as described in PCT/US06/00668.

A region of additional amino acids, particularly charged amino acids, may be added to the N-terminus of the polypeptide to improve stability and persistence in the host cell purification throughout and subsequent handling and storage. Also, amino acid moieties may be added to the polypeptide to facilitate purification. Such amino acids may or may not be removed prior to the final preparation of the polypeptide. The Cas9 polypeptides or fusion proteins of a Cas9 polypeptide, optionally associated with an effector or detectable moiety, such as a detectable reagent or an RNA modifying polypeptide can be fused to marker sequences, such as a peptide, that facilitates purification of the fused polypeptide. The marker amino acid sequence may be is hexa-histidine peptide such as the tag provided in a pQE vector (Qiagen, Mississauga, Ontario, Canada), among others, many of which are commercially available. As described in Gentz et al., Proc. Natl. Acad. Sci. 86:821-824 (1989), for instance, hexa-histidine provides for convenient purification of the fusion protein. Another peptide tag useful for purification, the hemagglutinin HA tag, corresponds to an epitope derived from the influenza hemagglutinin protein (Wilson et al., Cell 37:767-778 (1984)). Any of the above markers can be engineered using the polynucleotides or the polypeptides as provided herein.

The expression constructs can further contain sites for transcription initiation, termination, and, in the transcribed region, a ribosome binding site for translation. The coding portion of the transcripts expressed by the constructs can include a translation initiating codon at the beginning and a termination codon (UAA, UGA, or UAG) appropriately positioned at the end of the polypeptide to be translated.

Cells Expressing Cas9 Polypeptides

Some embodiments disclosed herein provide a cell line comprising the nucleic acid or nucleic acids (e.g., vector or vectors) that encode exemplary Cas9 polypeptides, sgRNAs, or fusion proteins of an exemplary Cas9 polypeptide associated with an effector or detectable moiety, such as a detectable reagent or an RNA modifying polypeptide. In some embodiments, the cell line transfected may be a prokaryotic cell line, a eukaryotic cell line, a yeast cell line, an insect cell line, an animal cell line, a mammalian cell line, a human cell line, etc. The proteins expressed in mammalian cells have been glycosylated properly. The mammalian cells can produce the Cas9 polypeptides, sgRNAs, or fusion proteins of a Cas9 polypeptide, optionally associated with an effector or detectable moiety, such as a detectable reagent or an RNA modifying polypeptide in this disclosure. Examples of useful mammalian host cell lines are HEK293, CHO, sp2/0, NSO, COS, BHK, PerC6. Many other cells can also be used as the expression and production host, and hence, are encompassed by this disclosure.

For recombinant production of the fusion proteins, molecular cloning method is used based on the molecular cloning protocols, for example those described in, Sambrook & Russel, Molecular Cloning (3rd ed., CSHL Press, 2001). The DNA sequences coding the fusion protein can be acquired by ordinary techniques, e.g. by whole gene synthesizing or spliced DNA fragments. Many vectors can be used. The vector components generally include, but are not limited to, one or more of the following: a signal sequence for the secretion of expressed proteins, one or more marker genes including the selection marker gene for the stable cell line screening in eukaryote cells, an origin of replication, an enhancer element, a promoter, and a transcription termination sequence, and poly A, etc.

Transfection of animal cells typically involves opening transient pores or "holes" in the cell membrane, to allow the uptake of material. Genetic material (such as supercoiled plasmid DNA or siRNA constructs), or even proteins such as antibodies, may be transfected. There are various methods of introducing foreign DNA into a eukaryotic cell. Transfection can be carried out using calcium phosphate, by electroporation, or by mixing a cationic lipid with the material to produce liposomes, which fuse with the cell membrane and deposit their cargo inside. Many materials have been used as carriers for transfection, which can be divided into three kinds: (cationic) polymers, liposomes and nanoparticles.

Exemplary Cas9 polypeptides or fusion proteins of an exemplary Cas9 polypeptide associated with an effector or detectable moiety, such as a detectable reagent or an RNA modifying polypeptide may be recovered from the cells by precipitation, ultracentrifugation, or chromatographic methods, including ion exchange chromatography, size exclusion chromatography, affinity chromatography, immunoaffinity chromatography, HPLC, etc. RP-HPLC may be used to further purify the recovered fusion protein. When the Cas9 polypeptides or fusion proteins of a Cas9 polypeptide associated with an effector or detectable moiety, such as a detectable reagent or an RNA modifying polypeptide are secreted, commercially available ultrafiltration membranes from Millipore, Amicon, Pellicon, etc. may be used to concentrate the supernatant.

In some embodiments, protein A affinity chromatography may be used to recover the Cas9 polypeptides or fusion proteins of a Cas9 polypeptide associated with an effector or detectable moiety, such as a detectable reagent or an RNA modifying polypeptide. Protein A is a cell wall component produced by several strains of Staphylococcus aureus and can be made in a recombinant fashion. It consists of a single polypeptide chain weighing approximately 42,000 daltons and contains little or no carbohydrate. Protein A binds specifically to the Fc region of most immunoglobulin molecules, including IgG (Sjoquist et al., Eur. J. Biochem. 29:572-578 (1972); Hjelm et al., Eur. J. Biochem. 57:395-403 (1975)).

Protein G affinity chromatography may also be used to purify the Cas9 polypeptides or fusion proteins of a Cas9 polypeptide associated with an effector or detectable moiety, such as a detectable reagent or an RNA modifying polypeptide. Protein G is a bacterial cell wall protein produced by group G streptococci and can also be made in a recombinant fashion. Like Protein A, Protein G binds to most mammalian immunoglobulins, primarily through their Fc regions (Bjorck et al., J. Immunol. 133:969-974 (1984); Guss et al., EMBO J. 5:1567-1575 (1986); Åkerström et al., J. Biol. Chem. 261;10,240-10,247 (1986)). Affinity chromatography using Cas9 binding molecules may further be used to purify Cas9 polypeptides of the disclosure. For example, Protein A/G is a genetically engineered protein that combines the IgG binding profiles of both Protein A and Protein G. Protein A/G is a gene fusion product, which can be secreted from, inter alia, nonpathogenic Bacillus. Protein A/G typically weighs approximately 50,000 daltons and was designed to contain four Fc binding domains from Proteins A and two from Protein G (Sikkema, Amer. Biotech. Lab. 7:42 (1989); Eliasson et al., J. Biol. Chem. 263:4323-4327 (1988)).

Methods of Tracking or Measuring the Amount of Target RNA

Some embodiments disclosed herein provide compositions for and methods of tracking a target RNA or measuring the amount of a target RNA in a sample, such as a cell, comprising allowing an exemplary Cas9 polypeptide disclosed herein to bind to said target RNA in said cell and determining the location of said target RNA in said cell or determining the amount of said target RNA in said cell. In some embodiments, the Cas9 polypeptide associated with a detectable agent as disclosed herein is introduced to the sample. In some embodiments, a single guide RNA that recognizes the target RNA, and/or an antisense oligonucleotide, such as a PAMmer oligonucleotide, is further introduced to the sample.

In some embodiments, exemplary Cas9 polypeptides bind to said target RNA in a nucleus of said cell and is subsequently co-exported from said nucleus with said target RNA. In some embodiments, the location of said target RNA in said cell or the amount of said target RNA in said cell is determined using fluorescence microscopy.

In some embodiments, the methods provided herein comprise measuring the content of a target RNA in said sample. In some embodiments, the methods comprise diagnosing a disease condition of said sample based on the content of said target RNA in said sample. In some embodiments, the disease is selected from the group consisting of myotonic dystrophy, Huntington's disease, familial ALS, cancer, spinal muscular atrophy and Fragile X syndrome, etc.

Methods of Modifying a Target RNA

Some embodiments disclosed herein provide methods of modifying a target in a sample comprising introducing exemplary Cas9 polypeptides disclosed herein into the sample and modifying said target RNA in said sample using an RNA modifying polypeptide, which in alternative embodiments can be linked or fused to an exemplary Cas9 polypeptide. In some embodiments, the exemplary Cas9 polypeptide associated with an RNA modifying polypeptide as disclosed herein is introduced to the sample. In some embodiments, a single guide RNA (sgRNA) that recognizes the target RNA, and/or an antisense oligonucleotide, such as a PAMmer oligonucleotide, is further introduced to the sample, and in some embodiments the sgRNA is associated with, or is co-expressed with, the Cas9 polypeptide.

In some embodiments, the RNA modifying polypeptide can fragment the target RNA. In some embodiments, the RNA modifying polypeptide can change the splicing of the target RNA.

In some embodiments, the methods comprise treating a disease condition of said sample by modifying said target RNA in said sample. In some embodiments, the disease is selected from the group consisting of myotonic dystrophy, Huntington's disease, familial ALS, cancer, spinal muscular atrophy and Fragile X syndrome, etc.

Current methods to target RNA in living cells rely on nucleic acid basepairing with antisense oligonucleotides (ASOs) or engineered RNA binding proteins. ASOs can unambiguously recognize target RNA, but are limited in their function to destruction of the target RNA or as a means to block association of other nucleic acids or protein to the RNA. Engineered RNA binding proteins are difficult and expensive to design, must be completely redesigned for every RNA target, target structured RNAs poorly, and their affinities for RNA can vary unpredictably. In contrast to ASOs, engineered RNA binding proteins can carry a variety of protein factors to alter the target RNA for therapy for RNA tracking. Certain Cas9 polypeptides and methods of using them are discussed in PCT/US2014/069730, entitled Methods and Compositions for Modifying a Single-Stranded Target Nucleic Acid, filed Dec. 11, 2014 and published as WO2015/089277, the disclosure of which is incorporated herein by reference in its entirety.

In alternative embodiments, exemplary RCas9 polypeptides and RCas9 complexes as provided herein combines the strengths of both of these approaches by allowing simply-programmed and strong RNA binding based on nucleic acid basepairing while carrying any protein factor to achieve the effect of choice on the target RNA. In alternative embodiments, exemplary RCas9 polypeptides and RCas9 complexes as provided herein also incorporate CRISPR-related technologies that include modified single guide RNAs that can recruit trans-acting protein factors, photo- and drug-activatable Cas proteins, and optogenetics-compatible Cas proteins.

There currently exist no widely-used methods of RNA localization tracking that are compatible with living cells. FISH protocols require destruction of the cells/tissues of interest, but there is great interest in non-destructive RNA tracking in living cells. In alternative embodiments, exemplary RNA-targeted Cas9 polypeptides and RCas9 complexes as provided herein can fill this important gap.

With respect to altering RNA splicing modulation, PUF protein splicing factors or 2'-O-methyl and 2'-O-2-methoxyethyl RNA oligonucleotides have drawbacks (Wang Y, Cheong C G, Hall T M, Wang Z, 2009. Engineering splicing factors with designed specificities. *Nat Methods* 6: 825-830). As mentioned above, there are no widely-used factors for splicing modulation due to the weaknesses of PUF proteins and oligonucleotides. In alternative embodiments, the need for improved splicing modulation for basic research and therapies can be addressed using exemplary RCas9 technology described herein.

Some embodiments described herein relate to the design and application of RCas9 for RNA tracking in living cells. In some embodiments, RCas9 comprises a mutant form of Cas9 protein fused to a fluorescent protein, a single guide RNA with expression in mammalian cells driven by a U6 polymerase III promoter, and an antisense oligonucleotide composed of 2'OMe RNA and DNA bases. These components may be delivered to the cellular nucleus with transfection reagents and bind mRNA forming the RCas9 complex. The RCas9 complex is subsequently exported from the nucleus while bound to the target RNA, allowing tracking of the target mRNA localization via fluorescence microscopy. Other embodiments allow measurement of RNA abundance in the cell, or fusion of Cas9 to splicing factors or other RNA-modifying enzymes to alter RNA features for therapy or research. In some embodiments, RCas9 is delivered to the cellular nucleus and subsequently co-exported with a targeted mRNA to be localized, detected or measured.

RCas9 RNA tracking has been compared herein to established methods of RNA tracking. Established methods such as fluorescence in situ hybridization require killing of the cells-of-interest, while RCas9 provided high quality RNA tracking measurements in living cells. Further, RCas9 supported tracking of RNAs as the translocated in the cytoplasm of living cells. We also demonstrate co-export of RCas9 from cellular nuclei in response to mRNA detection. By attaching a split or inactivated protein to RCas9 and localizing the other half or activating peptide to the cellular cytoplasm, we have successfully reconstituted split protein activity in response to RNA abundance.

In some embodiments, RCas9 provided herein is used for tracking RNA in living cells. Current methods of RNA tracking require killing cells of interest. Many diseases feature altered RNA localization patterns and drug development will require methods to track endogenous RNAs in diseased cells and in response to drug treatment.

In some embodiments, RCas9 provided herein is used for nondestructive isolation of cells based on gene expression. The RCas9 system can be used to create fluorescence readout of RNA abundance in living cells. This could allow isolation of circulating cancer cells in patient blood or from patient biopsies. These rare cells could be isolated based on their gene expression using RCas9 and be expanded and studied, allowing cancer detection long before development of tumors sufficiently large to identify with MRI or PET imaging.

In some embodiments, RCas9 provided herein is used for altering RNA composition in living cells. The ability for force binding of Cas9 fused to RNA-modifying enzymes will provide a fundamental tool to the rapidly growing field of RNA metabolism and processing. The Human Genome Project has shifted its focus to studying the importance of RNA and there is a profound lack of engineering tools for studying and utilizing the consequences of RNA processing.

The *Streptococcus pyogenes* CRISPR-Cas system has gained widespread application as a genome editing and gene regulation tool as simultaneous cellular delivery of the Cas9 protein and guide RNAs enables recognition of specific DNA sequences. As provided herein, the discovery and engineering of a Cas9 that can bind and cleave RNA in an RNA-programmable manner demonstrates the utility of exemplary systems and method as provided herein as a universal nucleic acid-recognition technology. In alternative embodiments, exemplary RNA-targeted Cas9 (RCas9) as provided herein allows identification and manipulation of RNA substrates in live cells, empowering the study of cellular gene expression, and could ultimately spawn patient- and disease-specific diagnostic and therapeutic tools. Here we describe the development of RCas9 and compare it to previous methods for RNA targeting, including engineered RNA binding proteins and other types of CRISPR-Cas systems. Provided are exemplary alternative uses ranging from live imaging of transcriptional dynamics to patient-specific therapies and applications in synthetic biology.

Introduction

The human genome project was completed more than a decade ago and sets the foundation for understanding the genetic basis of cell behavior in health and disease. Since then, efforts have shifted towards understanding the importance of functional genetic elements and how they affect gene expression (The ENCODE Project Consortium, 2012. An integrated encyclopedia of DNA elements in the human genome, *Nature* 489: 57-74). Since all cells of an individual contain largely the same DNA, the functional distinctions between cell types (a cardiomyocyte and a neuron, for instance) are closely linked to the portions of the genome that are transcriptionally active. As a result, measurement of transcribed RNA within individual cells reveals cellular identity and distinguishes healthy and disease states. For example, expression levels of a focused panel of RNA transcripts identified disease-associated aberrations in neuronal development in models of autism spectrum disorder (Pasca S P, Portmann T, Voineagu I, Yazawa M, et al. 2011. Using iPSC-derived neurons to uncover cellular phenotypes associated with Timothy syndrome, *Nat Med* 17; 1657-62). As another example, the expression of certain small non-coding RNAs known as microRNAs (miRs) is increasingly recognized as a characteristic signature of oncogenic transformation. Tumor microRNA signatures can serve as biomarkers informing the type of malignancy and associated clinical outcomes (Lu J, Getz G, Miska E A, Alvarez-Saavedra E. et al. 2005. MicroRNA expression profiles classify human cancers, *Nature* 435: 834-8; MacKenzie T A, Schwartz G N, Calderone H M, Graveel C R, et al. 2014. Stromal Expression of miR-21 Identifies High-Risk Group in Triple-Negative Breast Cancer, *Am J Pathol* 184: 3217-25). These studies and others make clear that tracking informative RNAs in vivo will be key to disease modeling, diagnostics and potentially therapeutics.

Due to the obvious impact of expressing specific RNAs on cell state and behavior, unraveling the mechanisms that affect the processing of these RNA has become very important. Following transcription, protein-encoding RNAs undergo a series of maturation steps that include alternative splicing, nuclear export and subcellular targeting, turnover and spatiotemporally restricted translation. These steps are mediated by RNA binding proteins (RBPs) and dysfunction of these factors and their RNA targets causes disease in humans (Gerstberger S, Hafner M, Ascano M, Tuschl T. 2014. Evolutionary conservation and expression of human RNA-binding proteins and their role in human genetic disease, *Adv Exp Med Biol* 825: 1-55). Altered subcellular distribution of RBPs caused by gain-of-function expanded RNA elements is also becoming a common theme in human disease. For example, expansion of an intronic hexanucleotide repeat within the C9ORF72 gene was recently recognized at the most frequently mutated genetic locus among two common neurodegenerative disorders, frontotemporal lobar degeneration and amyotrophic lateral sclerosis (DeJesus-Hernandez M, Mackenzie I R, Boeve B F, Boxer A L, et. al. 2011. Expanded GGGGCC hexanucleotide repeat in noncoding region of C9ORF72 causes chromosome 9p-linked FTD and ALS, *Neuron* 72: 245-56; Renton A E, Majounie E, Waite A, Simon-Sanchez J, et al. 2011. A hexanucleotide repeat expansion in C9ORF72 is the cause of chromosome 9p21-linked ALS-FTD, *Neuron* 72: 257-68). In vivo approaches to targeting the processing of endogenous RNA would open up basic biological understanding of development and disease as well as new avenues for therapies.

A recent publication has raised awareness of the potential of RNA-guided RNA recognition (O'Connell M R, Oakes B L, Sternberg S H, East-Seletsky A, et al. 2014. Programmable RNA recognition and cleavage by CRISPR/Cas9, *Nature* 516: 263-6). Here, we focus on the potential of repurposing and engineering Cas9, the effector nuclease of the *Streptcococcus pyogenes* CRISPR-Cas system that has been used to recognize DNA in mammalian cells, as an RNA-programmed RNA recognition technology.

Current RNA Recognition Modalities and Their Limitations

The development of designer RNA recognition factors will support a variety of advances in biology and medicine. Aside from targeted modulation of RNA processing and abundance, a designer RBP could generate completely novel activities in response to RNA recognition, such as generating a signal for noninvasive detection of cell state, promoting association of signaling proteins and their substrates only in particular cell types, or even ablating cells that display particular expression profiles. This broad potential has motivated the development of designer RNA recognition factors to varying degrees of success.

An ideal RNA recognition system would be capable of strong and specific binding to endogenous RNAs and display sufficient modularity for simple and predictable targeting. Inroads towards programmable RNA recognition have emerged based upon engineered natural nucleic acid binding proteins that are powerful for some applications but suffer from limited programmability, recognize too short a recognition sequence to be specific, and/or require large libraries of protein repeat sequences to target all possible RNA sequences. In contrast to direct recognition of nucleic acids by proteins, CRISPR-Cas (clustered regularly-interspaced short palindromic repeats) systems form bacterial adaptive immune systems and recognize invading nucleic acids with RNA-guided proteins.

An obvious strategy is the alteration or concatenation of natural RNA-binding protein domains. The identification of canonical RNA recognition protein domains such as KH and RRM led to attempts at identifying and modulating their natural RNA targets (Beuth B, Pennell S, Arnvig K B, Martin S R, et al. 2005. Structure of a Mycobacterium tuberculosis NusA-RNA complex, *EMBO J* 24: 3576-87; Braddock D T, Louis J M, Baber J L, Levens D, et al. 2002. Structure and dynamics of KH domains from FBP bound to single-stranded DNA, *Nature* 415: 1051-6; Laird-Offringa I A, Belasco J G. 1995. Analysis of RNA-binding proteins by in vitro genetic selection: identification of an amino acid residue important for locking U1A onto its RNA target, *Proc Natl Acad Sci USA* 92: 11859-63). These domains bind RNA in groups of 4-5 contiguous nucleotides. As a result, libraries of more than 1000 protein domains are required to recognize all 5-base RNA sequences. In contrast, PUF proteins contain repeat domains that recognize a single RNA nucleotide each so only four repeats are in principle required to recognize all possible RNA sequences. The crystal structures of natural PUF proteins were first described in 2001 (Wang X, Zamore P D, Hall T M. 2001. Crystal structure of a Pumilio homology domain, *Mol Cell* 7: 855-65) and revealed recognition of specific RNA bases that is largely determined by the amino acid side chains rather than the backbone. Since their initial discovery, the RNA specificity of PUF proteins has been decoded (Filipovska A, Razif M F, Nygard K K, Rackham O. 2011. A universal code for RNA recognition by PUF proteins. *Nat Chem Biol* 7: 425-7) and PUFs have been designed against a variety of RNA targets (Wang Y, Cheong C G, Hall T M, Wang Z. 2009. Engineering splicing factors with designed specificities. *Nat Methods* 6: 825-30). Furthermore, PUFs have been successfully fused to nucleolytic domains to target and destroy disease-associated RNA (Zhang W, Wang Y, Dong S, Choudhury R, et al. 2014. Treatment of type I myotonic dystrophy by engineering site-specific RNA endonucleases that target (CUG)(n) repeats. *Molecular therapy: J Am Soc Gene Ther* 22: 312-20). However, PUF proteins can only recognize 8 contiguous bases and local secondary structures can have a strong influence on RNA affinity, thus limiting their utility (Zhang W, Wang Y, Dong S, Choudhury R, et al. 2014. Treatment of type 1 myotonic dystrophy by engineering site-specific RNA endonucleases that target (CUG)(n) repeats. *Molecular therapy: J Am Soc Gene Ther* 22: 312-20).

Cas9 for RNA-Guided Nucleic Acid Recognition

While PUF, KH, and RRM proteins rely upon protein-RNA interactions to recognize RNA, nucleic acid base-pairing represents a simpler means of RNA recognition. The CRISPR-Cas bacterial immune system utilizes RNA-mediated base-pairing to recognize DNA, and has been successfully repurposed to target DNA in mammalian cells (Mali P, Yang L H, Esvelt K M, Aach J, et al. 2013. RNA-Guided Hutnan Genome Engineering via Cas9. *Science* 339: 823-6; Cho S W, Kim S, Kim J M, Kim J S. 2013. Targeted genome engineering in human cells with the Cas9 RNA-guided endonuclease. *Nat Biotechnol* 31: 230-2; Hwang W Y, Fu Y F, Reyon D, Maeder M L. et al. 2013. Efficient genome editing in zebrafish using a CRISPR-Cas system. *Nat Bio-*

*technol* 31: 227-9; Jinek M, East A, Cheng A, Lin S. et al. 2013. RNA-programmed genome editing in human cells. *eLife* 2: e00471). In bacteria and archaea, CRISPR-Cas forms the functional core of adaptive immune systems that are typically composed of a nuclease associated with a pair of RNAs called the trans-activating CRISPR RNA (tracrRNA) and CRIPSR RNA (crRNA). The tracrRNA and crRNA guide the CRISPR nuclease to invading plasmid or bacteriophage DNA by base-pairing for cleavage by the nuclease (FIG. 1A). Recently, a Type II CRISPR-Cas system from *S. pyogenes* was repurposed to target mammalian DNA by creation of an artificial combination of the tracrRNA and crRNA called the single guide RNA (sgRNA) (Mali P, Yang L H, Esvelt K M, Aach J, et al. 2013. RNA-Guided Hunan Genome Engineering via Cas9. *Science* 339: 823-6; Cong L, Ran F A, Cox D, Lin S, et al. 2013. Multiplex genome engineering using CRISPR/Cas systems. *Science* 339: 819-23). By allowing facile DNA targeting via the sgRNA sequence, RNA-programmed Cas9 is rapidly proving to be a popular means of genome editing and transcription modulation. The recent application of Cas9 to RNA targeting may support a similar shift in programmable RNA recognition based on RNA programming over engineered binding proteins.

RNA-targeted Cas9 (RCas9) is the subject of recent work from the Doudna lab that demonstrates strong and specific binding and subsequent cleavage of ssRNA by Cas9 in vitro. In FIGS. 1A and 1B, we compare this new approach to RNA recognition by Cas9 to DNA recognition. DNA targeting by Cas9 requires two features: an NGG sequence referred to as the protospacer adjacent motif (PAM) and a sgRNA carrying an antisense sequence adjacent to the PAM (FIG. 1A). These two features are also required for RNA targeting by Cas9, although the PAM motif is provided by a hybridized antisense oligonucleotide the PAMmer), which sits adjacent to the sgRNA antisense sequence after hybridization to the target RNA (FIG. 1B).

O'Connell and Oakes et al. also demonstrated that a 5' extension of the PAMmer beyond the PAM motif is required to generate specific RNA recognition programmed by the sgRNA. Shorter PAMmers lacking this extension promote Cas9:sgRNA binding that is independent of sgRNA sequence, but the sequence specificity of sgRNA-programmed RNA recognition is reconstituted by an extension of the PAMmer. This effect may be due to the energetic cost of Cas9-mediated unwinding of the PAMmer-RNA target duplex which is recovered only when the sgRNA hybridizes its target. Since the sgRNA is encodable and small (~100 bases), there is potential to generate large libraries of sgRNAs to target particular gene networks or screen the transcriptome. In contrast, the size of engineered RNA recognition proteins does not easily support large-scale screens. Although the cost associated with producing and distributing large libraries of modified oligonucleotide PAMmers will be an obstacle to work at this scale, future developments may allow the use of minimally modified oligonucleotides and leverage low-cost, high-throughput oligonucleotide synthesis technologies.

The aforementioned study was conducted exclusively in vitro and the strength and specificity of RNA-targeting Cas9 (RCas9) inside living cells or organisms is not yet known. Analogous to recent measurement of CRISPR-Cas off-target activities on genomic DNA (Cencic R, Miura H, Malina A, Robert F, et al. 2014. Protospacer adjacent motif (PAM)-distal sequences engage CRISPR Cas9 DNA target cleavage. *PLoS One* 9: e109213; Kuscu C, Arslan S, Singh R, Thorpe J, et al. 2014. Genome-wide analysis reveals characteristics of off-target sites bound by the Cas9 endonuclease. *Nat Biotechnol* 32: 677-83), extensive validation of the RCas9 binding specificity will be required in order to evaluate its potential as an intracellular, RNA-programmable RNA-binding protein. Along with its well-known ability to target DNA, the comprehensive ability of the *S. pyogenes* CRISPR-Cas system to target nucleic acids is now being established. The Information Box highlights major challenges that must be overcome for RCas9 to be applicable in vivo.

Information Box: In Vivo Applications of RCas9

An evaluation of the potential of RCas9 for RNA targeting in living organisms naturally begins by examining reported in vivo applications of Cas9 for genome editing. Delivery of Cas9 and the cognate sgRNA have been achieved by various means, including the use of viruses that encode Cas9 and the sgRNA (Swiech L, Heidenreich M, Banerjee A, Habib N, et al. 2015. In vivo interrogation of gene function in the mammalian brain using CRISPR-Cas9. *Nature Biotechnol* 33: 102-6; Maddalo D, Manchado E, Concepcion C P, Bonetti C, et al. 2014. In vivo engineering of oncogenic chromosomal rearrangements with the CRISPR/Cas9 system. *Nature* 516: 423-7), transgenic animals that allow drug-inducible expression of Cas9 (Dow L E, Fisher J, O'Rourke K P, Muley A. et al. 2015. Inducible in vivo genome editing with CRISPR-Cas9. *Nature Biotechnol* doi: 10.1038/nbt.3155), and delivery of Cas9 protein and sgRNA via anionic fusion proteins and cationic lipids (Zuris J A, Thompson D B, Shu Y, Guilinger J P, et al. 2015. Cationic lipid-mediated delivery of proteins enables efficient protein-based genome editing in vitro and in vivo. *Nature Biotechnol* 33: 73-80). Modulation of RNA splicing by RCas9 via targeting of a splicing factor fused to Cas9 to a pre-mRNA of interest, for instance, could be conducted in the central nervous system with an appropriately serotyped adenovirus. Splicing modulation in other tissues could be achieved with drug-inducible and tissue-specific expression of Cas9 and its sgRNA. But in all cases, an efficient means to deliver the RCas9 PAMmer to the appropriate tissues must be identified. By limiting the expression or delivery of either Cas9 or the sgRNA to the tissue of interest and conducting systemic administration of the PAMmer, it may be possible to achieve tissue-specific RCas9 activity. Highly stable modified oligonucleotides such as 2'-O-(2-methoxyethyl)-RNA have supported effective delivery and targeting of antisense RNAs in vivo (Meng L, Ward A J, Chun S, Bennett C F, et al. 2015. Towards a therapy for Angelman syndrome by targeting a long non-coding RNA. *Nature* 518: 409-12; Hua Y, Sahashi K, Hung G, Rigo F, et al. 2010. Antisense correction of SMN2 splicing in the CNS rescues necrosis in a type III SMA mouse model. *Genes Dev* 24: 1634-44; Passini M A, Bu J, Richards A M, Kinnecom C, et al. 2011. Antisense oligonucleotides delivered to the mouse CNS ameliorate symptoms of severe spinal muscular atrophy. *Science Transl Med* 3: 72ra18) and may prove useful in the RCas9 system as well. Thus, while these and similar approaches have been used to deliver one or two components of the RCas9 system in vivo, it remains to be seen which combination allows effective reconstitution of all three components. Further modifications in the PAMmer will be required to prevent destruction of the target RNA due to recognition by RNAse H, the cellular enzyme that degrades RNA in RNA-DNA hybrids. Careful adjustment of the PAMmer length and modifications will be important to maintain targeting specificity while avoiding recruitment of the RNAi machinery. Although RCas9 does not appear to cleave DNA in vitro, it remains to be seen if inadvertent DNA targeting may occur in vivo. Ultimately, the success of RCas9 in vivo will ultimately rely on its specificity and whether RCas9 destabilizes the target RNA or interferes with its translation.

Modulating Post-Transcriptional Gene Expression

Figure 2:
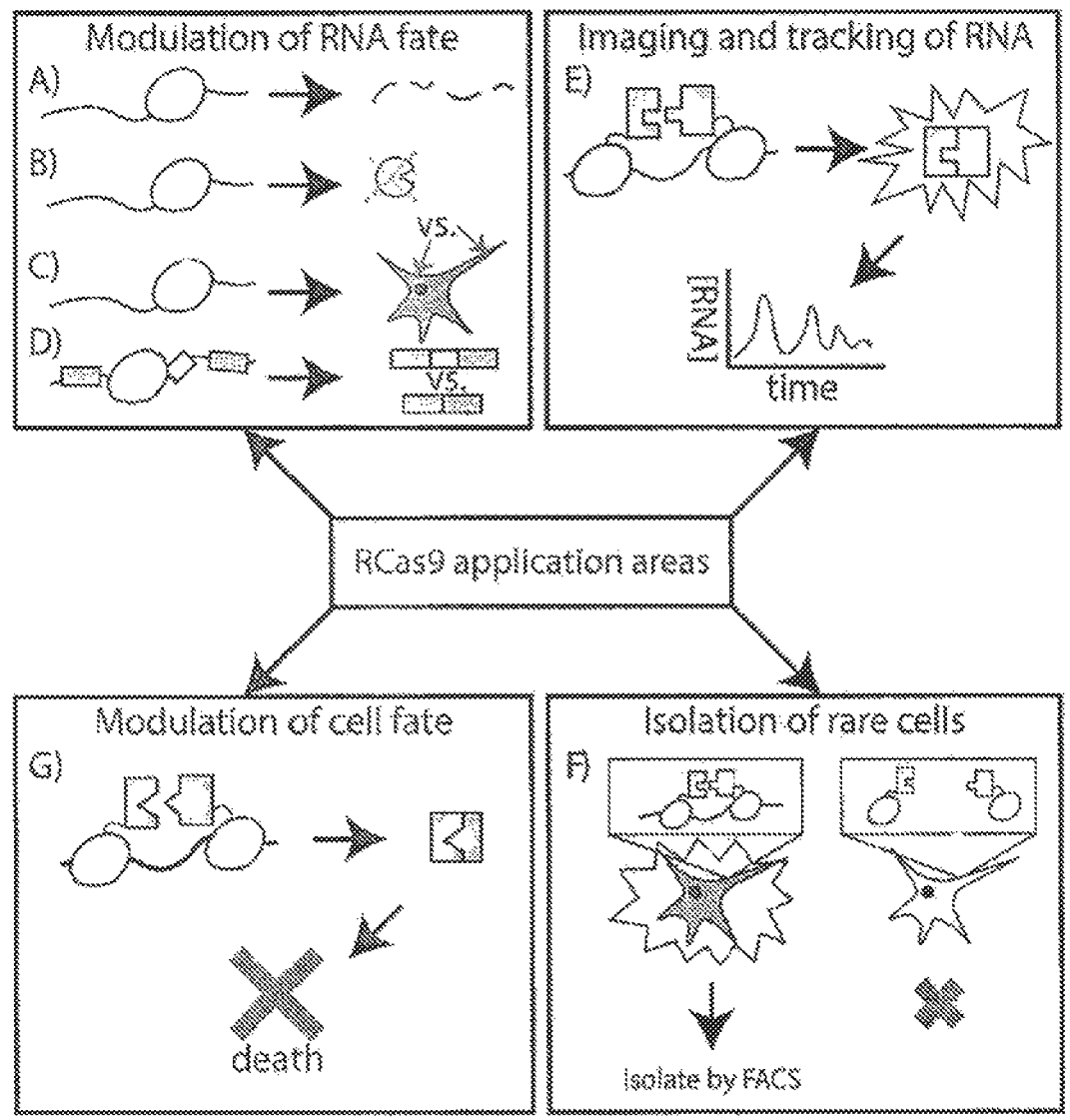
FIG. 2. Summary of exemplary RCas9 application areas. A-D describe means by which RNA fate can be manipulated by an exemplary RCas9 system as provided herein. A: With a nuclease-active version of Cas9, siRNA-intractable RNA targets could be cleaved. B: Conversely, gene expression could be amplified by tethering factors that prevent degradation of target RNAs. C: In alternative embodiments, by fusing Cas9 to a trafficking agent, RNAs could be forced, or are directed, to different sites of action in the cell for local translation or other activities, e.g., RNA nuclease activity. D: In alternative embodiments, the processing of pre-mRNAs is modulated by fusing Cas9 with a splicing factor to force differential exon choice. E: In alternative embodiments, along with altering RNA fate, RCas9 is used to track RNA abundance in time with split luminescent or fluorescent proteins whose complementation is guided by binding of adjacent Cas9 proteins on RNA. F: In alternative embodiments, split fluorescent proteins are used to reveal rare cells by their RNA content for isolation by FACS and subsequent study. G: In alternative embodiments, split toxic proteins or proteins that transform prodrugs to their active form are complemented in an RNA-dependent manner via fusion to Cas9.

Exemplary RCas9 polypeptides as provided herein utilize the inherent endonucleolytic activity of Cas9 to attenuate gene expression via cleavage of particular transcripts (FIG. 2A). While RNA interference (RNAi) supports effective RNA recognition and cleavage, RCas9-based gene knockdown can be useful in compartments or organelles where the RNAi machinery is not present or active. In alternative embodiments, the high affinity of RCas9 for RNA and dual recognition by both the sgRNA and PAMmer allows more specific RNA depletion than siRNAs or antisense oligonucleotides. Table 1 compares this and other applications of exemplary RCas9 to current methods and Table 2 compares RCas9 for RNA knockdown to RNAi in greater detail.

TABLE 1

Summary of exemplary RCas9 applications

| Application | State of the art | Limitations | RCas9-based approach | Main area of innovation |
|---|---|---|---|---|
| Targeted RNA knockdown (FIG. 2A) | siRNA, antisense oligonucleotides. | Efficiency limited by access to RNA silencing machinery and dependence on RNA structure. | Natural nucleolytic activity of Cas9. | Strong binding of Cas9 to target RNA may allow better knockdown efficiency; may allow knockdown in compartments lacking RNAi machinery. |
| RNA stabilization (FIG. 2B) | Coding region of GOI placed within stabilizing UTR contexts; | Requires targeted genetic manipulation or exogenous expression of GOI. | dCas9 fused to RNA stabilizing factor. | Potential first means to stabilize any unlabeled RNA. |
| RNA localization alteration (FIG. 2C) | Cis-acting sequence tags incorporated into transcript; these recruit tagged exogenous or endogenous localization factors. | Requires targeted genetic manipulation or exogenous expression of GOI. | dCas9 fused to RNA trafficking protein. | The high affinity of RCas9 for RNA could enable control of endogenous RNA localization. |
| RNA splicing alteration (FIG. 2D) | PUF proteins fused to splicing factors or splicing factor access blocked with antisense oligonucleotides. | PDFs limited to 8 base recognition sequences, oligonucleotides limited to splicing factor loss-of-function. | dCas9 fused to splicing factor targeted adjacent to or inside exons. | Potentially more specific alteration of splicing allowing either gain- or loss-of-function. |
| Imaging of RNA localization (FIG. 2E) | MS2 or Spinach labeling of RNA in conjunction with MS2-GFP protein or Spinach fluorophore. | Requires modification of target RNA. | dCas9 fused to fluorescent protein or split fluorescent protein. | May be effective means of revealing localization of any unlabeled RNA. |
| Time-resolved RNA measurements (FIG. 2E) | Incorporation of fluorescent or luminescent reporter at genomic locus near GOI. | Requires genetic modification. | dCas9 fused to split fluorescent or luminescent protein. | May be first means for time-resolved gene expression measurement without genetic modification. |
| Isolation of rare cells based on gene expression (FIG. 2F) | Identification of surface markers and antibodies for FACS. | Requires known surface marker for cell type of interest. | dCas9 fused to split fluorescent protein. | There are currently no high-sensitivity means to measure RNA content in live cells. |
| Death induction based in response to gene expression (FIG. 2G) | Incorporation of toxic protein at genomic locus near GOI. | Requires genetic modification, limited therapeutic potential. | dCas9 fused to split toxic protein. | Potentially first means to programmably target RNA profiles for death induction. |
| Substrate shuttling | Fusion of enzymes or incorporation of protein/protein interaction partners to create enzyme concatemers. | Results in constitutive substrate shuttling. | dCas9 fused to members of synthetic pathway targeting adjacent sites on an RNA. | First means to control substrate shuttling based upon RNA abundance. |

TABLE 2

Comparison of RNAi and exemplary RCas9 for gene knockdown

|  | RNA | RCas9 |
|---|---|---|
| Specificity | Specificity determined by at most ~21RNA nucleotides | Target recognized by both 20 nucleotids within the sgRNA and the 20+ nucleotide PAMmer. |

TABLE 2-continued

Comparison of RNAi and exemplary RCas9 for gene knockdown

| | RNA | RCas9 |
|---|---|---|
| Components | Engages endogenous RNA-induced silencing complex (RISC); requires delivery of siRNA only. | Requires delivery of Cas9 protein, sgRNA, and PAMmer oligonucleotide. |
| Localization | RISC mainly cytoplasmic; targeting nuclear RNAs difficult. | RCas9 potentially active in both nucleus and cytoplasm. |
| Influence of RNA structure | Efficiency dependent on RNA accessibility and structure. | Cas9's helicase activity may allow recognition of structured RNA sequences. |

Effective ways to enhance rather than decrease gene expression have been elusive. In alternative embodiments, by fusing Cas9 to a factor that stabilizes mature messenger RNAs, compositions and methods provided herein enhance protein production from particular transcripts (FIG. 2B). In alternative embodiments, another permutation of the CRISPR-Cas system CRISPR interference (CRISPRi) relies upon transcription modulators fused to a nuclease-null Cas9 (dCas9) that can enhance or repress gene expression by binding to particular genomic loci (Gilbert L A, Larson M H, Morsut L, Liu Z, et al. 2013. CRISPR-mediated modular RNA-guided regulation of transcription in eukaryotes. *Cell* 154: 442-51; Qi L S, Larson M H, Gilbert L A, Doudna J A, et al. 2013. Repurposing CRISPR as an RNA-guided platform for sequence-specific control of gene expression. *Cell* 152: 1173-83). While capable of strongly influencing gene expression, this approach does not allow isolation of the effects of RNA and protein gene products. By fusing Cas9 to translation enhancing factors, RCas9 may allow enhancement of protein expression of specific genes without altering RNA abundance in order to measure the specific importance of the protein gene product.

Another means by which cells control gene product activity is through the localization of RNA. In neurons, cell somata can be separated from synapses by centimeters or more, which presents a challenge to accumulating synaptic proteins at sufficient concentrations. After export from the nucleus, mRNAs involved in synaptic structure and activity such as postsynaptic density protein 95 (PSD-95) (Muddashetty R S, Nalavadi V C, Gross C, Yao X, et al. 2011. Reversible inhibition of PSD-95 mRNA translation by miR-125a, FMRP phosphorylation, and mGluR signaling. *Mol Cell* 42: 673-88) are transported through dendrites where they are translated near their site of action (FIG. 2C). By fusing Cas9 to a transport factor, the RCas9 system could be used to force transport to a chosen region of the cell such as pre- or postsynaptic terminals. In the case of regeneration of neuronal processes after injury, there is some evidence that localization of RNAs that encode cytoskeletal components are critical to regrowth of axons (Shestakova E A, Singer R H, Condeelis J. 2001. The physiological significance of beta-actin mRNA localization in determining cell polarity and directional motility. *Proc Natl Acad Sci USA* 98: 7045-50; Donnelly C J, Willis D E, Xu M, Tep C, et al. 2011. Limited availability of ZBP1 restricts axonal mRNA localization and nerve regeneration capacity. *EMBO J* 30: 4665-77). The ability to manipulate RNA localization in this context could be an important part of a regenerative therapy.

In alternative embodiments, exemplary RCas9 is used to alter the composition of RNAs. Pre-mRNA splicing is a vital step in mRNA biogenesis and tethering of splicing factors to the pre-mRNA has been shown to alter the inclusion or exclusion of sequences (Graveley B R, Maniatis T. 1998. Arginine/serine-rich domains of SR proteins can function as activators of pre-mRNA splicing. *Mol Cell* 1: 765-71). For instance, the splicing factor RBFOX2 has been shown to influence inclusion of exons depending on whether it binds up or downstream of alternative exons (Lovei M T, Ghanem D, Marr H, Arnold J, et al. 2013. Rbfox proteins regulate alternative mRNA splicing through evolutionarily conserved RNA bridges. *Nat Struct Mol Biol* 20: 1434-42; Weyn-Varthentenryck S M, Mele A, Yan Q, Sun S, et al. 2014. HITS-CLIP and integrative modeling define the Rbfox splicing-regulatory network linked to brain development and autism. *Cell Rep* 6: 1139-52; Yeo G W, Coufal N G, Liang T Y, Peng G E, et al. 2009. An RNA code for the FOX2 splicing regulator revealed by mapping RNA-protein interactions in stem cells. *Nat Struct Mol Biol* 16; 130-7). In alternative embodiments, by carefully choosing splicing factors and fusing them to exemplary Cas9, it may be possible to create designer splicing factors whose influence on splice site choice can be determined by RCas9 sequence binding. For instance, spinal muscular atrophy is caused by deletion of the gene SMN1 resulting in neuron death, but there is evidence that forced alteration of SMN2 splicing in SMN1-deficient cells can produce a SMN2 isoform that reconstitutes the activity of SMN1 (Hua Y, Vickers T A, Okunola H L, Bennett C F, et al. 2008. Antisense masking of an hnRNP A1/A2 intronic splicing silencer corrects SMN2 splicing in transgenic mice. *Am J Hum Genet* 82: 834-48). In alternative embodiments, this type of targeted splicing alteration is used in compositions and methods as provided herein to reverse a variety of diseases caused by aberrant splicing (Nissim-Rafinia M, Kerem B. 2002. Splicing regulation as a potential genetic modifier. *Trends Genet* 18: 123-7).

These are just a few examples of exemplary RCas9's as provided herein to modulate cellular RNA composition and cell behavior. In alternative embodiments, as universal nucleic acid-recognitions proteins, Cas proteins as provided herein allow targeting of particular RNAs genomic loci. For instance, long non-coding RNAs (lncRNAs) can recognize particular genomic loci and guide associated chromatin-modifying factors to dramatic effect on genome organization (Geisler S, Coller J. 2013. RNA in unexpected places: long non-coding RNA functions in diverse cellular contexts. *Nat Rev Mol Cell Biol* 14: 699-712). In alternative embodiments, exemplary RCas9 is fused to another Cas protein that utilizes an orthogonal sgRNA could be used to alter genome organization in a similar manner. By bringing targeted RNA in close proximity to a genomic locus of choice, this DNA- and RNA-binding Cas fusion can support studies of the function of lncRNAs in any genomic context. In alternative embodiments, the use of multiple Cas proteins with orthogonal sgRNAs also allows simultaneous and distinct alteration of multiple RNAs for instance by utilizing both nuclease-null and active Cas proteins. In alternative embodiments, However, it is currently unclear whether other Cas proteins are capable of RNA recognition, so it remains to be seen if RCas9 can target multiple RNAs simultaneously (Esvelt K M, Mali P, Braff J L, Moosburner M, et al. 2013. Orthogonal Cas9 proteins for RNA-guided gene regulation and editing. *Nat Methods* 10: 1116-21).

Imaging Applications

Several RNA recognition tools developed recently have enabled imaging of specific RNA species in live cells but suffer from several shortcomings (see (Rath A K, Rentmeister A. 2014. Genetically encoded tools for RNA imaging in living cells. *Curr Opin Biotechnol* 31C; 42-9) for an excellent review). In a manner analogous to visualizing proteins through fusion with fluorescent proteins, a set of RNA-based systems that rely on sequence tags incorporated in the RNA of interest can allow RNA visualization. These tags are specifically recognized by a protein moiety that binds strongly and specifically to the RNA tag. One popular approach utilizes bacteriophage MS2 coat protein (MCP) fused to a fluorescent protein (Bertrand E, Chartrand P, Schaefer M, Shenoy S M, et al. 1998. Localization of ASH1 mRNA particles in living yeast. *Mol Cell* 2: 437-45) recognizing a short RNA structural motif (a so-called 'hairpin'). The low signal-to-noise ratio due to background fluorescence from unbound probe can be improved by incorporating long arrays of tandemly repeated recognition elements, an approach that has allowed effective imaging of highly abundant RNAs in live cells (Park H Y, Lim H, Yoon Y J, Follenzi A, et al. 2014. Visualization of dynamics of single endogenous mRNA labeled in live mouse. *Science* 343: 422-4), but there is concern that such large tags can significantly perturb typical RNA behavior. An alternative approach is the incorporation of artificial RNA sequence tags that are bound by an exogenous small molecule fluorophore (Paige J S, Wu K Y, Jaffrey S R. 2011. RNA mimics of green fluorescent protein. *Science* 333: 642-6; Strack R L, Disney M D, Jaffrey S R. 2013. A superfolding Spinach2 reveals the dynamic nature of trinucleotide repeat-containing RNA. *Nat Methods* 10: 1219-24). By immobilizing the fluorophore in this aptamer tag, fluorescence signal can be generated by increasing quantum yield, separating a fluorophore-quencher pair, or by FRET (Paige J S, Wu K Y, Jaffrey S R. 2011. RNA mimics of green fluorescent protein. *Science* 333: 642-6; Shrack R L, Disney M D, Jaffrey S R. 2013. A superfolding Spinach2 reveals the dynamic nature of trinucleotide repeat-containing RNA. *Nat Methods* 10: 1219-24; Sunbul M, Jaschke A. 2013. Contact-mediated quenching for RNA imaging in bacteria with a fluorophore-binding aptamer. Angew Chem Int Ed Engl 52: 13401-4; Shin I, Ray J, Gupta V, Ilgu M, et al. 2014. Live-cell imaging of Pol II promoter activity to monitor gene expression with RNA IMAGEtag reporters. *Nucleic Acids Res* 42; e90). A third approach to suppress background fluorescence is the expression of two polypeptides that reconstitute a functional fluorescent protein when recruited to an RNA target by taking advantage of natural or artificial RNA binding domains (Rackham O, Brown C M. 2004. Visualization of RNA-protein interactions in living cells: FMRP and IMP1 interact on mRNAs. *EMBO J* 23: 3346-55). While all three methods have been tremendously useful and are widely used to study dynamics of RNA transport and localization, they require a tagged version of the RNA of interest either through genetic modification of the endogenous locus or by forced expression of an exogenous tagged version of the RNA. To illustrate, cells derived from a knock-in mouse harboring 24 MS2 hairpins in the 3'-untranslated region (UTR) of the beta-actin gene allowed the real time visualization of transcription from the modified allele, including the observation of transcriptional bursting upon serum stimulation (Lionnet T, Czaplinski K, Darzacq X, Shav-Tal Y, et al. 2011. A transgenic mouse for in vivo detection of endogenous labeled mRNA. *Nature Methods* 8: 165-70). However, the MCP-GFP fusion proteins need to be delivered to cells exogenously and this system is limited to only highly expressed RNAs. Furthermore, incomplete occupation of the MS2 hairpins reduces local signal and generates significant background noise due to unbound probe (Fusco D, Accornero N, Lavoie B, Shenoy S M, et al. 2003. Single mRNA molecules demonstrate probabilistic movement in living mammalian cells. *Curr Biol:* 13: 161-7). Another technology, molecular beacons, allows imaging of unmodified transcripts but suffer from high noise and cumbersome delivery (Tyagi S, Kramer F R. 1996. Molecular beacons: Probes that fluoresce upon hybridization. *Nat Biotechnol* 14: 303-8). RCas9 may circumvent these issues by allowing direct recognition of untagged RNAs with high specificity and low noise.

Exemplary alternative RCas9 applications as provided herein allow visualization of the abundance and/or localization of one or more endogenous RNAs simultaneously. By fusing an exemplary nuclease-null Cas9 to a fluorescent protein, it could be possible to visualize the localization of particular RNAs or RNA splice variants. In alternative embodiments, a pair of exemplary Cas9 proteins is fused to halves of split fluorescent protein such as Venus (Ozawa T, Natori Y, Sato M, Umezawa Y. 2007. Imaging dynamics of endogenous mitochondrial RNA in single living cells. *Nat Methods* 4: 413-9) and targeted to adjacent sites on an RNA (FIG. 2E). This will allow visualization of RNA localization with lower background than an intact fluorescent protein or measurement of the RNA content of individual cells. In alternative embodiments, this split protein approach is used to target adjacent exons in a differentially spliced transcript, allowing identification and isolation of individual cells that express particular RNA splice isoforms. In alternative embodiments, the identification of exemplary Cas proteins with orthogonal sgRNAs could allow targeting of multiple transcripts for localization or abundance measurements simultaneously, allowing multiplexed, live-cell measurement of RNA dynamics of individual cells.

In alternative embodiments, provided are applications of compositions and methods for endogenous RNA localization and abundance measurements in live cells. For example, characterization of somatic stem cells remains difficult because few surface markers exist for cell sorting-based identification and purification of these rare cells. Gene expression profiling remains the most effective way to identify rare cell types and in alternative embodiments, exemplary RCas9 as provided herein enables this type of nondestructive measurement so that rare cells can be preserved, expanded, and studied in isolation.

In alternative embodiments, provided are compositors and methods for RNA localization, which is important in cellular response to injury, stress, and some behaviors that promote cell polarity such as extension of neuronal processes. Stress granules are a type of RNA and protein cluster that sequester mRNA and protein and typically form in response to oxidative stress, heat, viral infection, or hypoxia (Kedersha N, Anderson P. 2007. Mammalian stress granules and processing bodies. *Methods Enzymol* 431: 61-81). Aberrant formation of RNA granules is implicated in many diseases, but the RNA components of these structures are only beginning to be described. In alternative embodiments, compositions and methods provided herein can image endogenous RNA trafficking to stress granules and support investigation of stress granule roles in health and disease. In order to understand the importance of RNA granules in disease, exemplary RCas9 can be used for time-resolved measurements of granule formation in response to stress, disease, or in drug screens where RNA localization may play a role in disease progression or regeneration of damaged tissues.

Synthetic Biology Applications

Provided herein are methods and compositions having industrial, clinical, and other technological utility. Like all engineering-oriented disciplines, provided herein are modularized, flexible platforms that can be tuned for diverse applications. The highly modular and programmable nature of exemplary RCas9 systems as provided herein can be used as a platform technology in synthetic biology. For example, in alternative embodiments, split enzymes are fused to Cas9 proteins whose activity is reconstituted upon binding to a target RNA such as complementation of split death-inducing proteins after detection of a cancer-linked RNA (FIG. 2G). In alternative embodiments, pathways involving successive protein/protein interactions are re-engineered by using RNA to scaffold interactions among exemplary Cas9 fusion proteins as provided herein. In alternative embodiments, scaffold proteins as provided herein can bind kinases and their substrates to strongly influence the output of a signaling pathway, and exemplary RCas9 polypeptides are used in the scaffolding of protein/protein interactions to control signaling in a gene expression-dependent manner. Another group used tethering of enzymes involved in the production of the drug precursor mevalonate, thereby increasing production of this small molecule (Dueber J E, Wu G C, Malmirchegini G R, Moon T S, et al. 2009. Synthetic protein scaffolds provide modular control over metabolic flux. *Nat Biotechnol* 27: 753-9). In principle, strong co-binding of exemplary Cas9 fusion proteins on a target RNA provides a new level of control over successive protein interactions or shuttling of metabolites.

Conclusions, General Concerns and Alternative Approaches

Progress in RNA targeting methods from their beginnings, when RBP domains were adapted to serve as sequence specificity determinants, to RCas9, with its target recognition by simple nucleic acid hybridization, is poised to closely parallel the development of DNA targeting technology. Here, zinc finger and TAL effector nucleases have recently given way to DNA recognition by the Cas9-bound sgRNA. While for DNA targeting applications, Cas9 and its sgRNA are sufficiently stable and nontoxic in mammalian cells, it remains to be seen whether all three components of the RCas9 system (Cas9, sgRNA, and PAMmer) can be delivered efficiently and, if so, successfully cooperate to bind target RNA. Alternative approaches to RNA-programmed RNA recognition are on the horizon. Type III-B CRISPR-Cas systems are known to target and cleave RNA as part of their normal activities in bacterial immunity. The effector complexes of these CRISPR systems from *Thermus thermophilus* (Staals R H, Zhu Y, Taylor D W, Kornfeld J E, et al. 2014. RNA Targeting by the Type III-A CRISPR-Cas Csm Complex of *Thermus thermophilus*. *Mol Cell* 56: 518-30) and *Pyrococcus furiosus* (Yeo G W, Coufal N G, Liang T Y, Peng G E, et al. 2009. An RNA code for the FOX2 splicing regulator revealed by mapping RNA-protein interactions in stem cells. *Nat Struct Mol Biol* 16: 130-7) have been characterized in detail and their nucleolytic activities reconstituted in vitro. While the natural ability of these complexes to recognize RNA is appealing, each complex is composed of 1-4 copies of six different proteins, which could pose challenges for its reconstitution in vivo. Cas9 from *Francisella novicida* targets a particular endogenous RNA in this organism in a RNA-guided manner, although the flexibility of this system to target chosen RNAs remains unclear (Sampson T R, Saroj S D, Llewellyn A C, Tzeng Y L, et al. 2013. A CRISPR/Cas system mediates bacterial innate immune evasion and virulence. *Nature* 497: 254-7).

In alternative embodiments, exemplary RCas9 polypeptides recognize untagged, endogenous RNA via simple base-pairing, and this represents a major advance in RNA targeting and is particularly critical in diagnostic or therapeutic applications. In alternative embodiments, exemplary RCas9 polypeptides and systems as provided herein are delivered efficiently to cells, cooperate to recognize RNA, with minimal unwanted destabilization or alteration of target RNA while also avoiding targeting of genomic DNA and off-target transcripts, and thereby provide new applications of RCas9 in basic and applied biology and in medicine.

Data provided herein demonstrates that exemplary RCas9 polypeptides and systems as provided herein are effective for nucleic acid-programmed recognition and tracking of untagged mRNA localization in living cells by CRISPR/Cas9.

Summary

In alternative embodiments, provided herein are RCas9 polypeptides and systems for RNA-programmed genome editing using CRISPR/Cas9 from *Streptococcus pyogenes* has enabled rapid and accessible alteration of genomic loci in a variety of organisms. In alternative embodiments, provided herein are flexible means to target RNA to allow alteration and imaging of endogenous RNA transcripts analogous to CRISPR/Cas-based genomic tools, but most RNA tracking methods rely on incorporation of exogenous tags. Here we demonstrate that exemplary nuclease-inactive *S. pyogenes* CRISPR/Cas9 can bind RNA in a nucleic acid-programmed manner and allow endogenous RNA tracking in living cells. We show that nuclear-localized RNA-targeting Cas9 (RCas9) is exported to the cytoplasm only in the presence of sgRNAs targeting mRNAs with distributions that correlate well with fluorescence in situ hybridization imaging. We also demonstrate time-resolved measurements of β-actin mRNA trafficking to stress granules. Our results establish the exemplary RCas9 as provided herein can be used to bind and track RNA in living cells in a programmable manner without the requirement of genetically encoded tags.

Introduction

Clustered Regularly-Interspaced Palindromic Repeats (CRISPRs) form the basis of adaptive immune systems in bacteria and archaea by encoding CRISPR RNAs that guide CRISPR-associated (Cas) nucleases to invading genetic material (Wiedenheft B., Sternberg, S. H., and Doudna, J. A. (2012). RNA-guided genetic silencing systems in bacteria and archaea. Nature 482, 331-338). Cas9 from the type II CRISPR system of *S. pyogenes* has been repurposed for genome engineering in eukaryotic organisms (Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPR-Cas system. Nat Biotechnol 31, 227-229; Li, D., Qiu, Z., Shao, Y., Chen, Y., Guan, Y., Liu, M., Li, Y., Gao, N., Wang, L., Lu, X., et al. (2013a). Heritable gene targeting in the mouse and rat using a CRISPR-Cas system. Nat Biotechnol 31, 681-683; Nakayama, T., Fish, M. B., Fisher, M., Oomen-Hajagos, J., Thomsen, G. H., and Grainger, R. M. (2013). Simple and efficient CRISPR/Cas9-mediated targeted mutagenesis in *Xenopus tropicalis*. Genesis 51, 835-843; Sander, J. D., and Joung, J. K. (2014). CRISPR-Cas systems for editing, regulating and targeting genomes. Nat Biotechnol. 32, 347-355; Yang, D., Xu, J., Zhu, T., Fan, J., Lai, L., Zhang, J., and Chen, Y. E. (2014). Effective gene targeting in rabbits using RNA-guided Cas9 nucleases. J Mol Cell Biol 6, 97-99) and is rapidly proving to be an efficient means of DNA targeting for other applications such as gene expression modulation (Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell. 152, 1173-1183) and imaging (Chen, B., Gilbert, L. A., Cimini, B. A., Schnitzbauer, J., Zhang, W., Li, G. W., Park, J., Blackburn, E. H., Weissman, J. S., Qi, L. S., et al. (2013). Dynamic imaging of genomic loci in living human cells by an optimized CRISPR/Cas system. Cell 155, 1479-1491). Cas9 and its associated single guide RNA (sgRNA) require two critical features to target DNA: a short DNA sequence of the form 5'-NGG-3' (where 'N'=any nucleotide) known as the protospacer adjacent motif (PAM) and an adjacent sequence on the opposite DNA strand that is antisense to the sgRNA. By supporting DNA recognition with specificity determined entirely by a short spacer sequence within the sgRNA, CRISPR/Cas9 provides uniquely flexible and accessible manipulation of the genome. Manipulating cellular RNA content, in contrast, remains problematic. While there exist robust means of attenuating gene expression via RNA interference and antisense oligonucleotides, other critical aspects of post-transcriptional gene expression regulation such as alternative splicing, subcellular trafficking, and spatiotemporally-restricted translation are largely intractable.

Analogous to the assembly of zinc finger nucleases (Urnov, F. D., Rebar, E. J., Holmes, M. C., Zhang, H. S., and Gregory, P. D. (2010). Genome editing with engineered zinc finger nucleases. Nat Rev Genet 11, 636-646) and transcription activator-like effector nucleases (TALEN) to recognize specific DNA sequences, efforts to recognize specific RNA sequences have focused on engineering RNA binding domains. For instance, the Pumilio and FBF homology (PUF) proteins carry well-defined modules capable of recognizing a single base each. However each module must be redesigned and validated for each RNA target and at most can only recognize 8 contiguous bases, which limits their utility for recognizing RNA substrates uniquely in the transcriptome. An alternative approach to recruiting proteins to specific RNA substrates is to introduce RNA aptamers into target RNAs, enabling specific and strong association of cognate aptamer binding proteins such as the MS2 coat protein (Fouts, D. E., True, H. L., and Celander, D. W. (1997). Functional recognition of fragmented operator sites by R17/MS2 coat protein, a translational repressor. Nucleic Acids Res 25, 4464-4473). This approach has enabled tracking RNA localization in living cells over time with high sensitivity (Buxbaum, A. R., Wu, B., and Singer, R. H. (2014). Single beta-actin mRNA detection in neurons reveals a mechanism for regulating its translatability. Science 343, 419-422) but relies upon laborious genetic manipulation of the target RNA in cells and is not suitable for recognition of arbitrary RNA sequences. Analogous to CRISPR/Cas9-based recognition of DNA, programmable RNA recognition based on nucleic acid specificity alone without the need for genetic manipulation or libraries of RNA binding proteins would greatly expand researchers' ability to modify the mammalian transcriptome and enable transcriptome engineering.

Although the CRISPR/Cas9 system has evolved to recognize double-stranded DNA, recent in vitro work has demonstrated that programmable targeting of RNAs with Cas9 is possible by providing the PAM as part of an exogenously added oligonucleotide (PAMmer) that hybridizes to the target RNA (O'Connell, M. R., Oakes, B. L., Sternberg, S. H., East-Seletsky, A., Kaplan, M., and Doudna, J. A. (2014). Programmable RNA recognition and cleavage by CRISPR/Cas9. Nature 516, 263-266). By taking advantage of the Cas9 target search mechanism that relies on PAM sequences (Sternberg, S. H., Redding, S., Jinek, M., Greene, E. C., and Doudna, J. A. (2014). DNA interrogation by the CRISPR RNA-guided endonuclease Cas9, Nature 507, 62-67), a mismatched PAM sequence in the PAMmer/RNA hybrid allows exclusive targeting of RNA and not the encoding DNA. The high affinity and specificity of RNA recognition by Cas9 in cell-free extracts and the success of genome targeting with Cas9 indicate the potential of CRISPR/Cas9 to support programmable RNA targeting in living cells.

To assess the potential of CRISPR/Cas9 to act as a programmable RNA binding protein in living cells, we measured the degree of nuclear expert of a nuclear localization signal-tagged nuclease-deficient Cas9-GFP fusion. We demonstrate that the sgRNA alone is sufficient to promote nuclear export of the Cas9 fusion without influencing the abundance of the targeted mRNA or abundance of protein encoded by the targeted mRNA. In order to evaluate whether RNA-targeted Cas9 (RCas9) signal patterns correspond with an established untagged RNA labeling method, we compared distributions of RCas9 and fluorescence in situ hybridization (FISH) targeting β-actin mRNA. We observed high correlation among FISH and RCas9 colocalization that was dependent on the presence of a PAMmer, indicating the importance of the PAM for efficient RNA targeting. In contrast to established untagged RNA localization measurements such as FISH, RCas9 supports temporally-resolved measurements of RNA localization. We demonstrate this capability by tracking β-actin localization to oxidative stress-induced RNA/protein accumulations called stress granules. This work establishes the ability of RCas9 to bind RNA in living cells and sets the foundation for manipulation of the transcriptome in addition to the genome by CRISPR/Cas9.

EXAMPLES

Figure 3A:
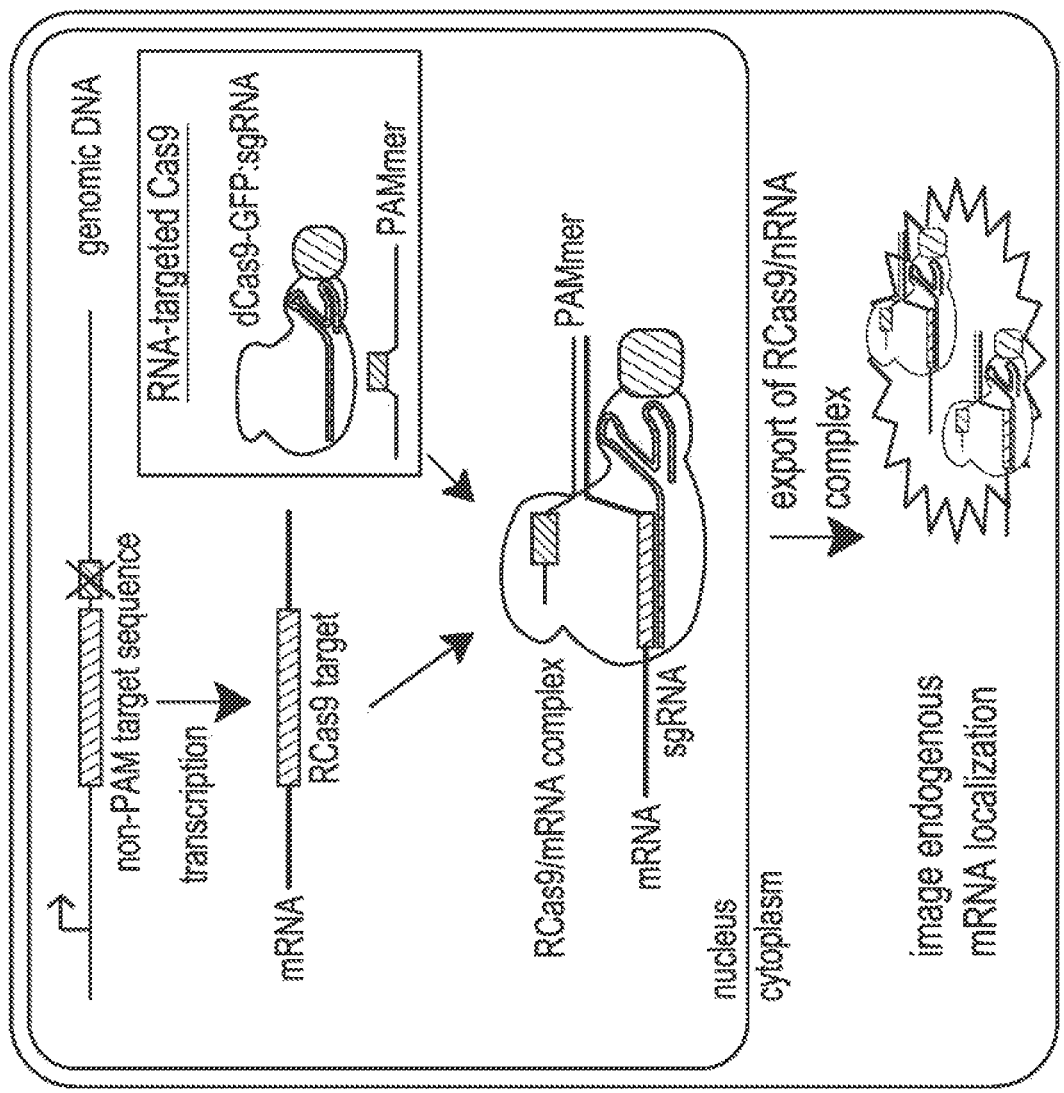
FIG. 3A. Targeting mRNA with RNA-targeted Cas9. In alternative embodiments, RNA-targeting of mRNA in human cells requires delivery of three components to the nucleus: an SV40 nuclear localization signal-tagged nuclease-inactive Cas9 and EGFP or mCherry fused to the C-terminus (dCas9-EGFP), an sgRNA with expression driven by the U6 polymerase III promoter, and a PAMmer composed of DNA and 2'-O-methyl RNA bases with a phosphodiester backbone. The sgRNA and PAMmer are antisense to adjacent regions of the target mRNA whose encoding DNA does not carry a PAM sequence. After formation of the RCas9/mRNA complex in the nucleus, the complex is exported to the cytoplasm.
Figure 6:
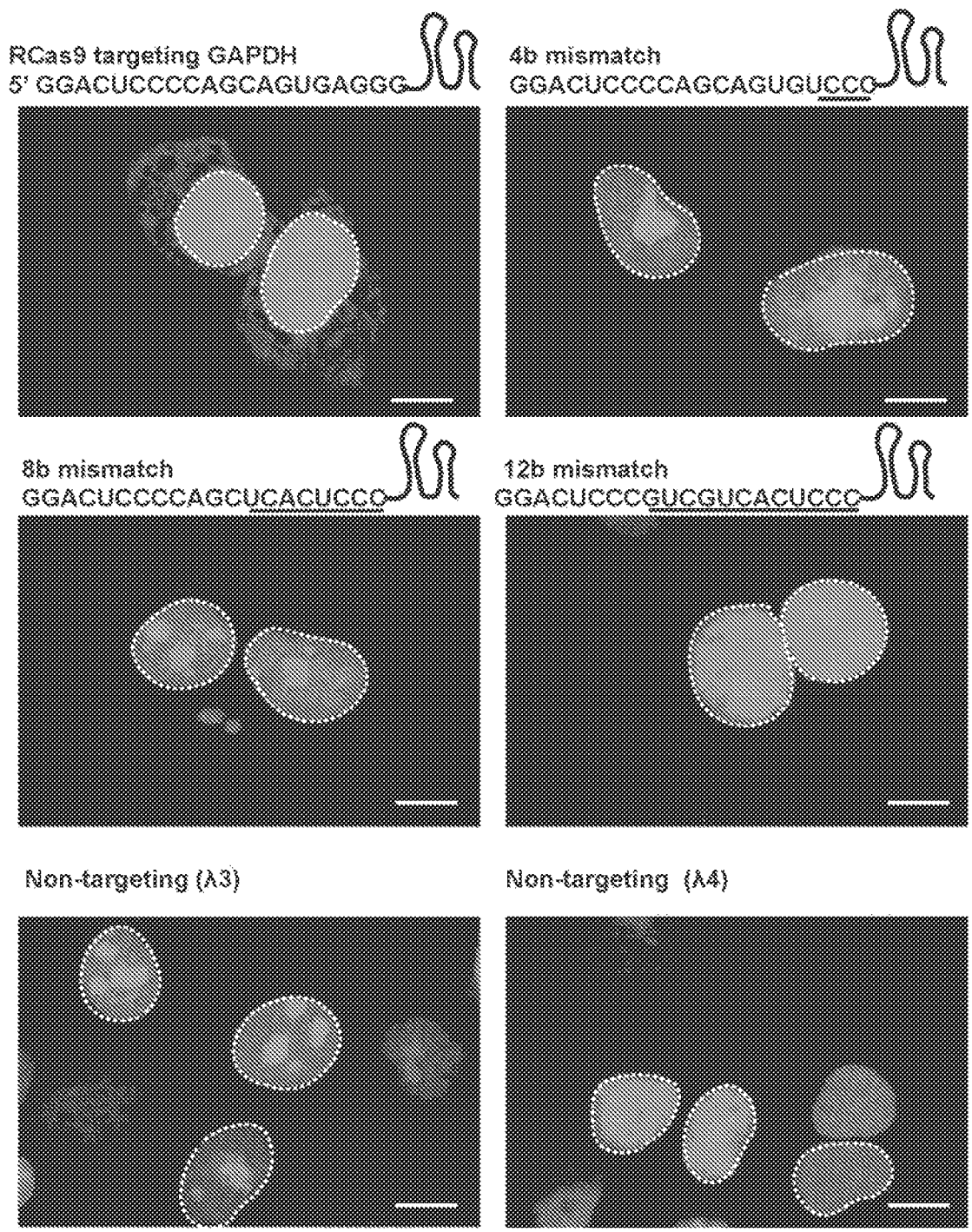
FIG. 6. Degree of nuclear export of dCas9-GFP in the presence of mismatches in the sgRNA seed sequence targeting GAPDH. 0, 4, 8, or 12-base mismatches in the seed sequence of an sgRNA targeting the 3'UTR of GAPDH were introduced and transfected with the RCas9 system. Degree of cytoplasmic signal was evaluated with confocal microscopy. An 8-base mismatch was sufficient to eliminate cytoplasmic signal. Further non-targeting controls were indistinguishable from a completely mismatched seed sequence (12-base mismatch). Cellular nuclei are outlined with a dashed white line. Scale bars represent 10 microns.

Example 1: RNA-Targeted Cas9 Export from Nucleus in Presence of sgRNA Targeting GAPDH mRNA As an initial assessment of the ability of RCas9 to recognize specific mRNA substrates in human cells, we tested if enhanced GFP (EGFP)-tagged Cas9 containing a nuclear localization signal can be co-exported from the nucleus with an mRNA in the presence of a cognate sgRNA and PAMmer designed to recognize that mRNA (FIG. 3A). Nuclease-null Cas9 (dCas9) was sandwiched between a SV40 nuclear localization signal sequence at the N-terminus and two at the C-terminus and was fused with the coding sequence for EGFP and cloned into a mammalian expression vector (NLS-dCas9-2xNLS-EGFP, abbreviated as dCas9-GFP). In a separate expression vector, a modified sgRNA scaffold with an extended stem-loop structure that improves association with Cas9 and mutations that eliminate a partial transcription termination sequence (Chen, B., Gilbert, L. A., Cimini, B. A., Schnitzbauer, J., Zhang, W., Li, G. W., Park, J., Blackburn, E. H., Weissman, J. S., Qi, L. S., et al. (2013). Dynamic imaging of genomic loci in living human cells by an optimized CRISPR/Cas system. Cell 155, 1479-1491) was driven by the U6 snRNA polymerase III promoter. The PAMmer was synthesized as a mixed DNA and 2'-O-methyl (2'OMe) RNA oligonucleotide using standard phosphoramidite chemistry and purified using HPLC (see Tables 3-4 for target, sgRNA and PAMmer sequences). As a proof-of-concept, we designed an sgRNA-PAMmer pair to target the 3' untranslated region (3'UTR) of GAPDH mRNA (FIG. 3B). As a negative control, we designed an sgRNA-PAMmer pair targeting the λ bacteriophage that is absent in human cells ("N/A" sgRNA and PAMmer). We observed that transiently transfected dCas9-GFP co-transfected with the negative control sgRNA and PAMmer is almost exclusively nuclear, with 3% of cells containing GFP signal in the cytoplasm (FIGS. 3B and 3C). When the negative control PAMmer is replaced with the GAPDH-targeting PAMmer, the results are identical. However, upon co-transfection of GAPDH-targeting sgRNA plasmid, we demonstrated that 24% and 17% of cells have GFP signal in the cytoplasm with and without a GAPDH-targeting PAMmer, respectively (FIGS. 3B and 3C). In both cases, the sgRNA targeting GAPDH result in a significant increase in the fraction of cells with cytoplasmic GFP signal compared to a non-targeting sgRNA. We also observed a loss of nuclear export with as few as 4 bases mismatched in the sgRNA seed sequence (See FIG. 6). Overall, these results are consistent with previous in vitro RNA pull-down experiments that demonstrate RNA binding by Cas9:sgRNA that is independent of but strengthened by the PAMmer (O'Connell et al., 2014). Thus, we demonstrate that RCas9 can be relocalized into the cytoplasm by programming the sgRNA-PAMmer to recognize a specific abundant mRNA in live cells.

TABLE 3

RNA target sequences

| Target | PAMmer target underlined, sgRNA target bold |
|---|---|
| GAPDH mRNA 3'UTR | CACAAGAGGAAGAGAGAGACCCTCACTGCTGGGG AGTCC (SEQ ID NO: 5) |
| β-actin mRNA 3'UTR | GAAGGTGACAGCAGTCGGTTGGAGCGAGCATCCC CCAAA (SEQ ID NO: 6) |
| λ2 bacteriophage | GCTCAATTTTGACAGCGGTCATGGCATTCCACTT ATCAC (SEQ ID NO: 7) |

TABLE 4

PAMmer (PAM in bold) and sgRNA (spacer in bold) sequences

| | |
|---|---|
| PAMmer, β-actin 3'UTR | mUCmGCmUCmCAmUGGmGAmCTmGCmUGmUCmACmCTmUC (SEQ ID NO: 8) |
| sgRNA, β-actin 3'UTR | GTTTGGGGGATGCTCGCTCCAGTTTAAGAGCTATGCTGGAAACAGCATA GCAAGTTTAAATAAGGCTAGTCCGTTATCAACTTGAAAAAGTGGCACCG AGTCGGTGCTTTTTTT (SEQ ID NO: 9) |
| PAMmer, GAPDH 3'UTR | mAGmUGmAGmGGmCGGmCTmCTmCTmUCmCTmCTmUGmUG (SEQ ID NO: 10) |
| sgRNA, GAPDH 3'UTR | GGACTCCCCAGCAGTGAGGGGTTTAAGAGCTATGCTGGAAACAGCATAG CAAGTTTAAATAAGGCTAGTCCGTTATCAACTTGAAAAAGTGGCACCGA GTCGGTGCTTTTTTT (SEQ ID NO: 11) |
| PAMmer, λ2 bacteriophage | mATmGCmCAmUGmUGGmGCmUGmUCmAAmAAmUTmGAmGc (SEQ ID NO: 12) |
| sgRNA, λ2 bacteriophage | GTGATAAGTGGAATGCCATGGTTTAAGAGCTATGCTGGAAACAGCATAG CAAGTTTAAATAAGGCTAGTCCGTTATCAACTTGAAAAAGTGGCACCGA GTCGGTGCTTTTTTT (SEQ ID NO: 13) |

Example 2: Recognition of an mRNA with RNA-Targeted Cas9 does not Alter RNA Translation or Stability To further characterize the interaction between RCas9 and a target mRNA, we directed RCas9 to the 3' untranslated region (UTR) of Renilla luciferase carrying a commonly-used RNA tag for RNA tracking from the MS2 bacteriophage (Fouts, D. E., True, H. L., and Celander, D. W. (1997). Functional recognition of fragmented operator sites by R17/MS2 coat protein, a translational repressor, Nucleic Acids Res 25, 4464-4473) and a sequence targeted by a previously validated sgRNA:PAMmer pair (O'Connell, M. R., Oakes, B. L., Sternberg, S. H., East-Seletsky, A., Kaplan, M., and Doudna, J. A. (2014). Programmable RNA recognition and cleavage by CRISPR/Cas9. Nature 516, 263-266) (FIG. 3D). RNA immunoprecipitation with an antibody recognizing EGFP revealed a four-fold greater association of luciferase mRNA to dCas9-EGFP in the presence of a cognate sgRNA and PAMmer, compared to non-targeting sgRNA or scrambled PAMmer or to EGFP protein alone (FIG. 3E). We next measured the effect of RCas9 targeting on luciferase mRNA abundance by quantitative RT-PCR. We observed no significant difference in the abundance of MS2-tagged luciferase mRNA in the presence of the targeting or non-targeting RCas9 system or EGFP alone. In contrast, co-expression of EGFP fused to the MS2 coat protein (MCP) recognizing the MS2 aptamer had a significant stabilizing effect which could be due to inhibition of RNA degradation by the MS2 system (Garcia, J. F., and Parker, R. (2015). MS2 coat proteins bound to yeast mRNAs block 5' to 3' degradation and trap mRNA decay products: implications for the localization of mRNAs by MS2-MCP system. RNA 21, 1393-1395) (FIG. 3F). We also considered potential effects of RCas9 targeting on translation (FIG. 3G) and observed that presence of the targeting sgRNA and PAMmer caused no significant changes in protein levels compared to non-targeting RCas9. Our results demonstrate that RCas9 recognition of RNA with an sgRNA and PAMmer avoids perturbation of RNA and protein levels associated with targeting via MCP-tagged GFP.

Figure 4A:
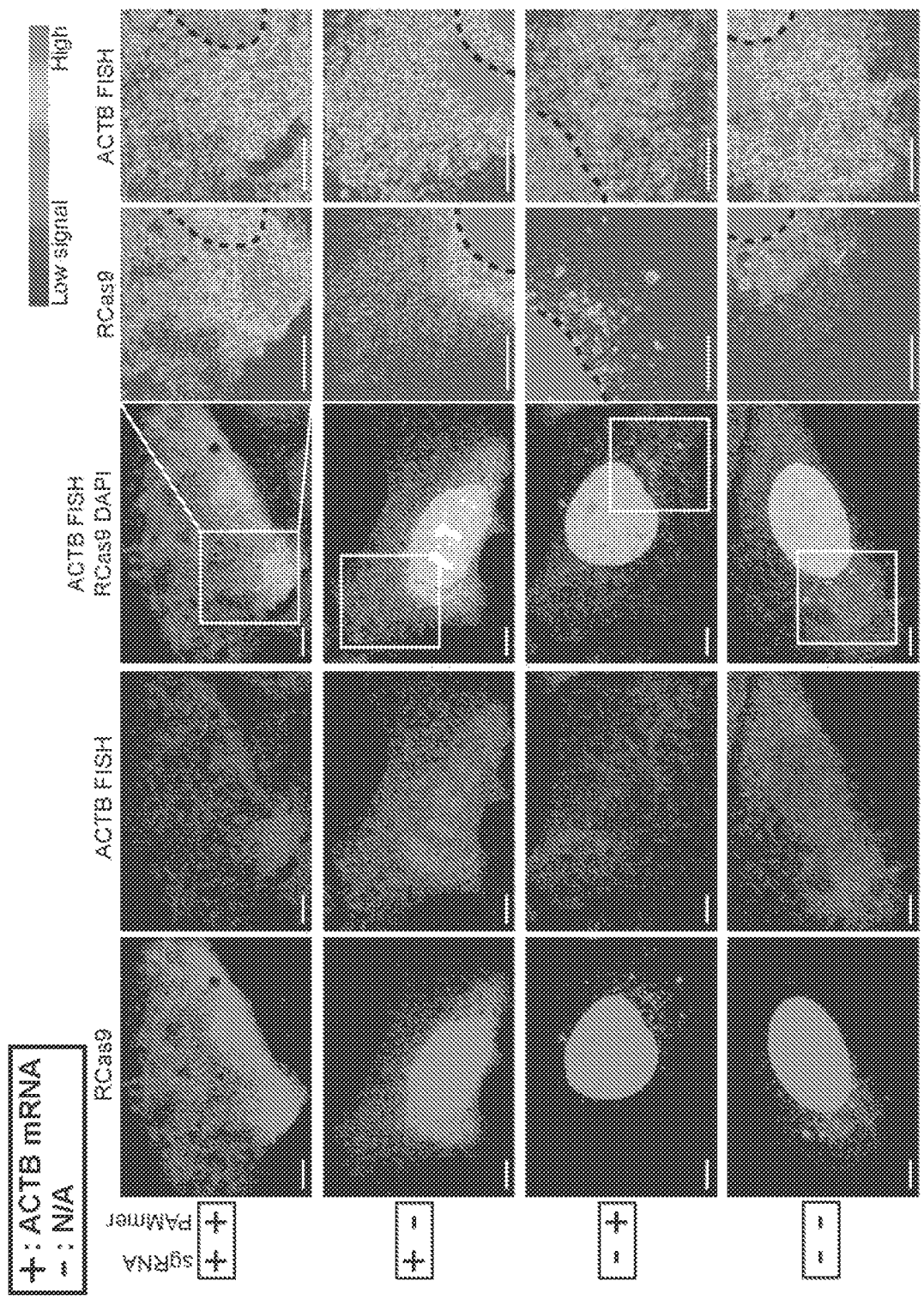
FIG. 4A. Tracking β-actin mRNA localization with RCas9. An exemplary RCas9 system was delivered to U2OS cells and the cells were subjected to FISH for β-actin mRNA. RCas9 with sgRNA and PAMmer targeting β-actin mRNA was compared to non-targeting sgRNA and PAMmer antisense to a sequence from λ bacteriophage ("-" sgRNA and "-" PAMmer). False color images on the right feature dotted lines that delineate the nucleus.
Figure 4B:
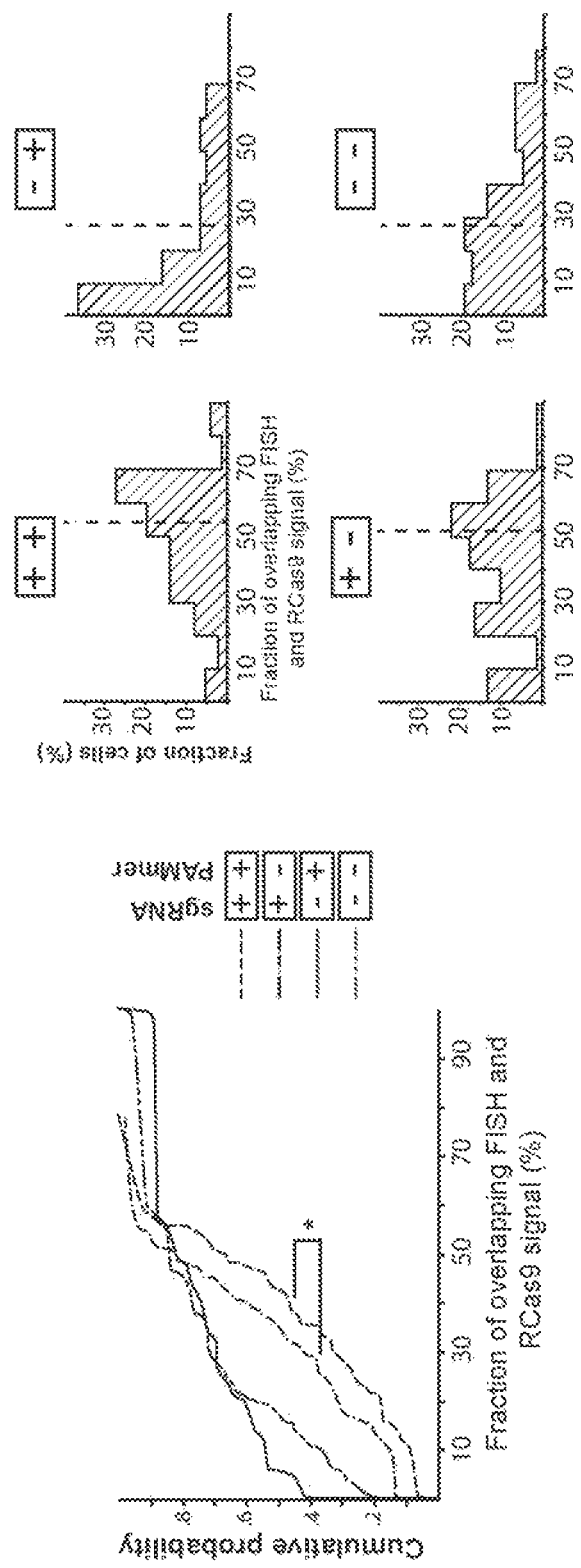
FIG. 4B. Pixel-by-pixel analysis of RCas9 and FISH colocalization in the form of the Mander's overlap coefficient is summarized using a cumulative distribution of the percent of cytoplasmic area with overlapping signal in 60-80 cells in each condition. Frequency histograms shown to the right demonstrate degree of overlap for each individual condition. The presence of the PAMmer produces a significantly greater colocalization among RCas9 and FISH in the presence of the sgRNA targeting β-actin mRNA (p=0.035, two-tailed Mann-Whitney Test). Scale bars represent 20 microns.

Example 3: RNA-Targeted Cas9 Signal Distributions Correlate with an Established Untagged RNA Localization Determination Method To assess whether RCas9 signal distributions correlate with an orthogonal method to measure RNA localization, we targeted the 3'UTR of β-actin ("+" sgRNA and "+" PAMmer) and compared dCas9-2xNLS-mCherry signal to RNA fluorescence in situ hybridization (FISH) for β-actin mRNA (FIG. 4A) and non-targeting sgRNA and PAMmer ("−" sgRNA" and "−" PAMmer with sequences corresponding to λ bacteriophage). By comparing the Mander's overlap coefficients that describe pixel-by-pixel overlap among FISH And RCas9 (Manders, E. M., Stap, J., Brakenhoff, G. J., van Driel, R., and Aten, J. A. (1992). Dynamics of three-dimensional replication patterns during the S-phase, analysed by double labelling of DNA and confocal microscopy. J Cell Sci 103 (Pt 3), 857-862) (FIG. 4B), we determined that the sgRNA primarily accounts for co-localization among FISH and RCas9 with maximal overlap in the presence of both sgRNA and PAMmer targeting β-actin mRNA. A non-targeting PAMmer results in a significantly less overlap (FIG. 4B) (p=0.035, Mann-Whitney Test) and produces a diffuse pattern of RCas9 signal in the cytoplasm that contrasts with the highly localized pattern revealed by FISH (FIG. 4A). This result is consistent with weaker binding of RCas9 with a non-targeting PAMmer observed in cell-free systems (O'Connell, M. R., Oakes, B. L., Sternberg, S. H., East-Seletsky, A., Kaplan, M., and Doudna, J. A. (2014). Programmable RNA recognition and cleavage by CRISPR/Cas9, Nature 516, 263-266). A non-targeting sgRNA results in largely nuclear retention of RCas9 signal with low correlation between cytoplasmic RCas9 signal and FISH (FIG. 4A-B). We conclude that maximal overlap between FISH and RCas9 signal distributions requires the presence of both cognate sgRNA and PAMmer.

Example. 4: Tracking RNA Trafficking to Stress Granules Over Time

Figure 5C:
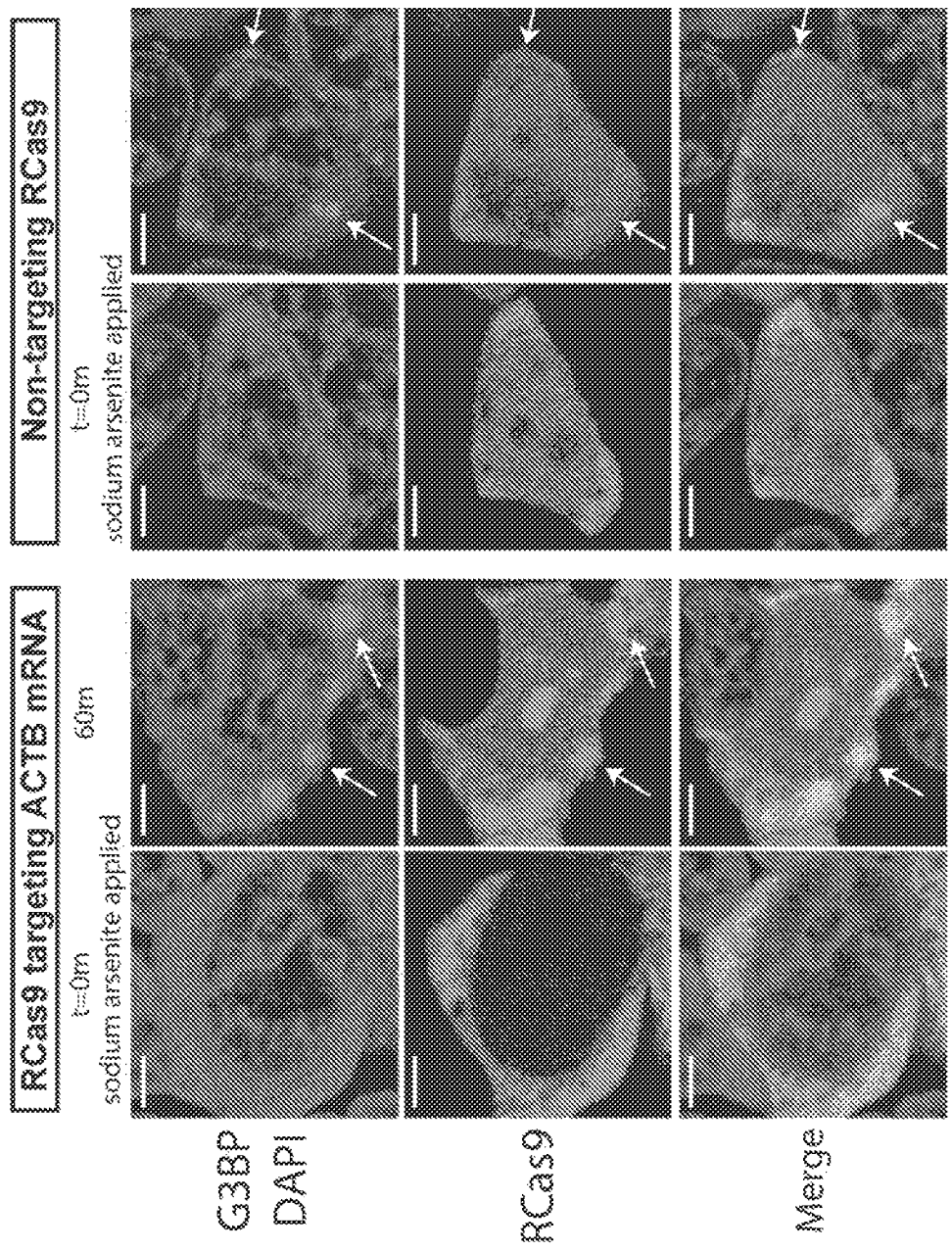
FIG. 5C. RNA trafficking to stress granules was imaged in real time using cells harboring RCas9 targeting β-actin mRNA. At time zero, cells were imaged and sodium arsenite applied. 60 minutes later, cells were imaged again and a comparison of RCas9 and G3BP1-positive stress granules revealed close correlation of foci only in the presence of sgRNA and PAMmer targeting β-actin mRNA.
Figure 5D:
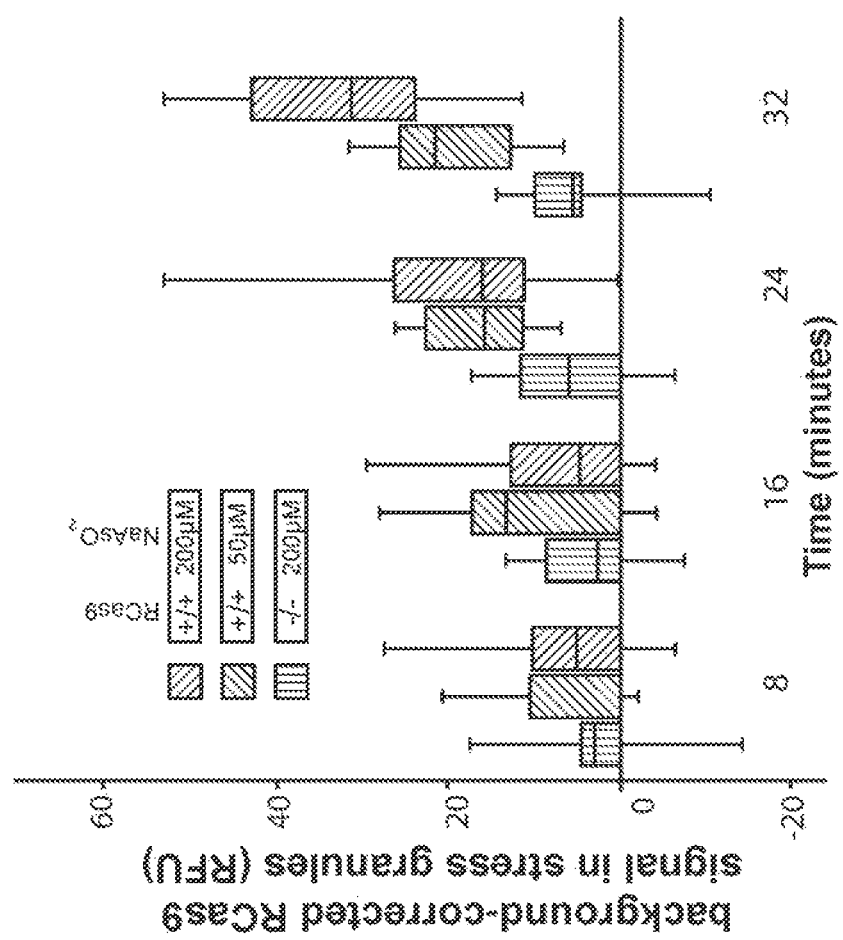
FIG. 5D. In a similar experiment, RCas9 targeting β-actin mRNA signal accumulation in stress granules was tracked over time. 8-11 stress granules were tracked in each condition with time points every 8 minutes for 32 minutes where narrow lines represent individual granules and the thick lines represent mean signal for each condition (see Methods for detailed procedure). Error bars represent standard error and scale bars represent 5 microns.

In addition to promoting local translation, trafficking of mRNA can also influence temporal programming of protein production (Buchan, J. R., and Parker, R. (2009). Eukaryotic stress granules: the ins and outs of translation. Mol Cell 36, 932-941). We therefore determined whether RCas9 supports tracking of mRNA to protein-RNA aggregates known as stress granules. Stress granules are translationally-silent protein and RNA accumulations that can form aberrantly and may influence disease progression in the nervous system (Li, Y. R., King, O. D., Shorter, J., and Gitler, A. D. (2013b). Stress granules as crucibles of ALS pathogenesis. J Cell Biol 201, 361-372) but there are limited means that can track the movement of endogenous RNA to these structures in live cells (Bertrand, E., Chartrand, P., Schaefer, M., Shenoy, S. M., Singer, R. H., and Long, R. M. (1998). Localization of ASH1 mRNA particles in living yeast. Mol Cell 2, 437-445). As β-actin mRNA is known to localize to stress granules (Unsworth, H., Raguz, S., Edwards, H. J., Higgins, C. F., and Yague, E. (2010). mRNA escape from stress granule sequestration is dictated by localization to the endoplasmic reticulum. FASEB J 24, 3370-3380) during oxidative stress, we simultaneously tracked β-actin mRNA using RCas9 and mCherry-fused to the Ras GTPase-activating protein-binding protein 1 (G3BP1) protein, a well-described marker for stress granules (Tourriere, H., Chebli, K., Zekri, L., Courselaud, B., Blanchard, J. M., Bertrand, E., and Tazi, J. (2003). The RasGAP-associated endoribonuclease G3BP assembles stress granules. J Cell Biol 160, 823-831). After application of sodium arsenite to induce cellular stress, wee observed accumulation of RCas9 signal to G3BP1-positive foci only in the presence of the RCas9 system targeting β-actin mRNA and not in the presence of non-targeting sgRNA and PAMmer (FIG. 5A). We quantified the degree of overlap among RCas9- and G3BP1-foci and determined that the majority of stress granules feature overlapping RCas9-foci (FIG. 5B). Next we tracked RCas9 signal in stressed cells over time in living cells (FIG. 5C). We observed accumulation of RCas9 signal in G3BP1-positive foci in a manner dependent on the presence of sgRNA and PAMmer targeting β-actin mRNA (FIG. 5C). We also observed that the rate and degree of RCas9 signal accumulation in stress granules is dependent on dosage of the stressor sodium arsenite (FIG. 5D). These results indicate the potential of RCas9 as a means to generate time-resolved, quantitative RNA localization measurements.

Discussion

This work demonstrates, to our knowledge, the first proof-of-principle that RCas9 can be utilized in living cells to bind target RNAs such as mRNAs with specificity determined entirely by simply-programmed sgRNA and PAMmers. In alternative embodiments, provided are RCas9 polypeptides and systems (complexes) that support the recognition of RNA sequences that are long enough for unique discrimination in the transcriptome which contrasts with engineered RNA-binding proteins such as PUF proteins (Cheong, C. G., and Hall, T. M. (2006). Engineering RNA sequence specificity of Pumilio repeats. Proc Natl Acad Sci USA 103, 13635-13639; Wang, X., McLachlan, J., Zamore, P. D., and Hall, T. M. (2002). Modular recognition of RNA by a human pumilio-homology domain. Cell 110, 501-512) that suffer from short RNA recognition sequences and require protein design, assembly and validation for each RNA target. Other CRISPR/Cas systems have demonstrated RNA binding in bacteria (Hale, C. R., Zhao, P., Olson, S., Duff, M. O., Graveley, B. R., Wells, L., Terns, R. M., and Terns, M. P. (2009). RNA-guided RNA cleavage by a CRISPR RNA-Cas protein complex. Cell 139, 945-956; Sampson, T. R., Saroj, S. D., Llewellyn, A. C., Tzeng, Y. L., and Weiss, D. S. (2013). A CRISPR/Cas system mediates bacterial innate immune evasion and virulence. Nature 497, 254-257) or eukaryotes (Price, A. A., Sampson, T. R., Rainer, H. K., Grakoui, A., and Weiss, D. S. (2015). Cas9-mediated targeting of viral RNA in eukaryotic cells. Proc Natl Acad Sci USA 112, 6164-6169), although these systems cannot discriminate RNA from DNA targets, feature RNA targeting rules that remain unclear, or rely on large protein complexes that may be difficult to reconstitute in mammalian cells. Further work varying the sgRNA spacer length (Fu, Y., Sander, J. D., Reyon, D., Caseio, V. M., and Joung, J. K. (2014). Improving CRISPR-Cas nuclease specificity using truncated guide RNAs. Nat Biotechnol 32, 279-284) and PAMmer length and chemical modifications will be required to determine the optimal RCas9 parameters.

In some embodiments, the nucleoprotein complexes provided herein does not include a PAMmer oligonucleotide. The RCas9 system described in "Methods and compositions for modifying a single stranded target nucleic acid" (WO 2015089277 A1) as utilize a PAMmer oligonucleotide. Using a unique nucleoprotein complex comprising an RCas9 polypeptide and a single guide RNA, but not to including a PAMmer oligonucleotide, to target RNA, we have demonstrated that this system recognizes and alters target RNA in the absence of a PAMmer. Despite the absence of a PAMmer, our results for this system indicate (1) a highly efficient alteration of targeted RNAs, and (2) RNA recognition in living eukaryotic cells. The fully encodable nature of this 2-component system enables the deployment of our system in a therapeutic context using viral vectors, nanoparticles, or other excipients that support delivery of DNA. Because PAMmer cannot be encoded in DNA due to chemical modifications that are required to stabilize and protect it from cellular enzymatic activities, earlier systems requiring a PAMmer were not fully encodable.

Alternative applications of exemplary RCas9 as provided herein measure or alter RNA splicing via targeting of split fluorescent proteins or splicing factors adjacent to alternatively spliced exons. In alternative embodiments, the nucleic acid-programmable nature of exemplary RCas9 as provided herein allows for multiplexed targeting (Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823) of RNA and the use of Cas9 proteins that bind orthogonal sgRNAs (Esvolt, K. M., Mali, P., Braff, J. L., Moosburner, M., Yaung, S. J., and Church, G. M. (2013). Orthogonal Cas9 proteins for RNA-guided gene regulation and editing. Nat Methods 10, 1116-1121), which can support distinct activities on multiple target RNAs simultaneously. In alternative embodiments, RNA targeting afforded by exemplary RCas9 as provided herein supports the development of sensors that recognize specific healthy or disease-related gene expression patterns and reprogram cell behavior via alteration of gene expression or concatenation of enzymes on a target RNA (Delebecque, C. J., Lindner, A. B., Silver, P. A., and Aldaye, F. A. (2011). Organization of intracellular reactions with rationally designed RNA assemblies. Science 333, 470-474; Sachdeva, G., Garg, A., Godding, D., Way, J. C., and Silver, P. A. (2014). In vivo co-localization of enzymes on RNA scaffolds increases metabolic production in a geometrically dependent manner. Nucleic Acids Res 42, 9493-9503). Efforts towards In alternative embodiments, Cas9 is delivered in vivo are underway (Dow, L. E., Fisher, J., O'Rourke, K. P., Muley, A., Kastenhuber, E. R., Livshits, G., Tschaharganch, D F., Socci, N. D., and Lowe, S. W. (2015). Inducible in vivo genome editing with CRISPR-Cas9, Nat Biotechnol 33, 390-394; Swiech, L., Heidenreich, M., Banerjee, A., Habib, N., Li, Y., Trombetta, J., Sur, M., and Zhang, F. (2015). In alternative embodiments, exemplary RCas9 as provided herein can be used for in vivo interrogation of gene function in the mammalian brain using CRISPR-Cas9. Nat Biotechnol 33, 102-106; Zuris, J. A., Thompson, D. B., Shu, Y., Guilinger, J. P., Bessen, J. L., Hu, J. H., Maeder, M. L., Joung, J. K., Chen, Z. Y., and Liu, D. R. (2015). In alternative embodiments, provided are cationic lipid-mediated delivery of exemplary RCas9 as provided herein to enable efficient protein-based genome editing in vitro and in vivo. Nat Biotechnol 33, 73-80), and these efforts combined with existing oligonucleotide chemistries (Bennett, C. F., and Swayze, E. E. (2010). RNA targeting therapeutics: molecular mechanisms of antisense oligonucleotides as a therapeutic platform. Annu Rev Pharmacol Toxicol 50, 259-293) could support in vivo delivery of the RCas9 systems as provided herein for targeted modulation of many features of RNA processing in living organisms.

Experimental Procedures

Plasmid Construction, PAMmer Synthesis, and Target Site Choice

The dCas9-2xNLS sequence was amplified from pHR-SFFV-dCas9-BFP-KRAB (a gift from Stanley Qi & Jonathan Weissman, Addgene plasmid #46911), tagged with a SV40 nuclear localization signal (NLS) on the N-terminus, and fused to EGFP or mCherry in pcDNA 3.1 (Invitrogen, Carlsbad Calif.) using Gibson assembly. A version lacking NLS on the N-terminus was also constructed. To construct the sgRNA scaffold construct, the human U6 polymerase III promoter with the modified sgRNA scaffold (Chen et al., 2013) was purchased as a gBlock from IDT with a BbsI restriction site at the 5' end of the sgRNA scaffold (see sequence in FIG. 6) and cloned into the multiple cloning site of pBlueScript II SK (+) (Agilent, Santa Clara, Calif.) using Gibson assembly. Phosphorylated oligonucleotides encoding the sgRNA sequences were ligated into BbsI-digested sgRNA scaffold construct to produce sgRNAs targeting the 3'UTR of GAPDH, β-actin, and renilla luciferase mRNAs (see FIG. 6). The luciferase-PEST construct for pull-down and abundance experiments was modified from plasmid xyz (gift from Jens Lykke-Anderson, UCSD). pCMV-Renilla luciferase is a version of the same construct lacking MS2 and RCas9 target sites.

RCas9 target sites were chosen with a combination of the IDT antisense oligonucleotide design tool and the microarray probe design tools Picky (Chou et al., 2004) and OligoWiz (Wernersson and Nielsen, 2005). We designed PAMmers against high-confidence sites with 8 bases on the 5' end beyond the PAM sequence. PAMmers were composed of mixed 2'OMe RNA and DNA bases and purified by HPLC (Integrated DNA Technologies, Coralville Iowa).

Cell Lines

U2OS and HEK293T cells were grown in Dulbecco's modified eagle medium (DMEM) supplemented with 10% fetal bovine serum, glutamax, and non-essential amino acids (Invitrogen). Cells were passaged every 3-4 days with TrypLE EXPRESS (Invitrogen) using standard methods and maintained in a humidified incubator at 37° C. with 5% $CO_2$.

GAPDH and β-Actin mRNA Targeting with RCas9

U2OS cells cultured as described above were passaged at ~80% confluency. Glass-bottom 96-well plates or chamber slides were coated with 20 µg/mL fibronectin in PBS for 2 h at 37° C., then the fibronectin solution was aspirated and 20,000 cells were plated in each well. 16 hours later, cells were transfected with the sgRNA and dCas9-2xNLS-EGFP plasmids using Lipofectamine 3000 (Invitrogen) according to the manufacturer's instructions. pCMV-Renilla luciferase was co-transfected in these experiments so that total transfected protein load was the same among various dosages of sgRNA and dCas9. The weight ratio of sgRNA and dCas9-EGFP (carrying a N-terminal NLS) plasmids ranged from 5:1 to 2.5:1, respectively, where the amount of dCas9-EGFP was fixed at 10% of total transfected material. Immediately after plasmid transfection, PAMmers were transfected using Lipofectamine RNAiMax (Invitrogen) according to manufacturer's instructions. 24 hours after transfection, cells were washed with PBS and fixed with 3.7% paraformaldehyde in PBS, permeabilized with 70% ethanol at 4° C. for one hour, and mounted using Prolong Gold Antifade mounting medium with DAPI (Invitrogen). Confocal microscopy was conducted using an Olympus FV1000 confocal microscope.

Nuclear export of RCas9 in the presence of sgRNA and PAMmer targeting the 3'UTR of GAPDH was analyzed by measuring the average signal in the nuclei and cytoplasm of individual cells. Cells with average cytoplasmic signal greater than 10% of the average nuclear signal were considered to have a cytoplasmic signal.

RNA Immunoprecipitation

HEK293T cells cultured as described above were passaged at 80% confluency and 600,000 cells were seeded in each well of 6-well tissue culture plates coated with poly-L-lysine. 16 hours later, cells were co-transfected with the RCas9 system as described above (dCas9-GFP with 2× internal NLS tags), or plasmids encoding MS2-EGFP or EGFP along with a plasmid encoding the model Renilla luciferase mRNA driven by a CMV promoter. 30 hours later, the growth media was aspirated and the cells were washed with PBS. 1% paraformaldehyde in PBS was applied to the cells, incubated for 10 minutes at room temperature, then the solution was aspirated and the cells washed twice with cold PBS. Next, the cells were scraped from the wells in cold PBS and the cell suspension was centrifuged as 800×g for 4 minutes to pellet the cells. The cells were washed once more, then resuspended in RIPA buffer with protease inhibitor (Roche) and sonicated for 5 minutes in a BIORUPTOR™ sonicator (50% duty cycle, 1 minute period). Insoluble material was pelleted after a high-speed centrifugation and the supernatant was applied to protein G DYNABEADS™ (Invitrogen) coated with mouse anti-GFP antibody (Roche). After overnight incubation at 4° C., the bead supernatant was retained and beads washed 3 times with RIPA buffer containing 0.02% Tween-20 and once with DNase buffer (350 mM Tris-HCl, pH 6.5; 50 mM MgCl$_2$; 5 mM DTT). The beads were resuspended in DNase buffer and TURBO™ DNase (Invitrogen) was added to 0.08 units/μL. The beads were incubated at 37° C. for 30 minutes, then proteinase K (NEB) was added to 0.1 U/μL and incubated with shaking at 37° C. for 30 minutes. Next, urea was added to 2.5 M and the beads were incubated with shaking at 37° C. for 30 minutes. The bead supernatant was collected and subjected to a two sequential phenol:chloroform:isoamyl alcohol (25: 24:1) extractions followed by three chloroform extractions. The RNA was precipitated and reverse transcribed using SuperScript III™ (Invitrogen) using random hexamer primers, and relative abundance of Renilla luciferase RNA on the beads was compared to the supernatant using qPCR (see Table 5 for primer sequences).

TABLE 5 qPCR primer sequences

| | |
|---|---|
| GAPDH forward primer | AAGGTGAAGGTCGGAGTCAAC (SEQ ID NO: 14) |

TABLE 5-continued qPCR primer sequences

| | |
|---|---|
| GAPDH reverse primer | GGGGTCATTGATGGCAACAATA (SEQ ID NO: 15) |
| Renilla luciferase forward primer | GTAACGCTGCCTCCAGCTAC (SEQ ID NO: 16) |
| Renilla luciferase reverse primer | GTGGCCCACAAAGATGATTT (SEQ ID NO: 17) |

Measurements of Influence of RCas9 on RNA Stability and Translation

HEK293T cells were cultured as described above, passaged and plated in 96- or 12-well tissue culture plates, and were co-transfected 24 h later with the RCas9 system (dCas9-GFP with 2× internal NLS tags) and the Renilla luciferase construct carrying MS2 and RCas9 binding sites in the 3'UTR. In the protein abundance measurements, a small amount of CMV-driven firefly luciferase vector (5% of total transfected plasmid) was co-transfected as a transfection control. For RNA stability measurements, RNA was isolated 24 h after transfection, DNase treated, reverse transcribed with Superscript III (Invitrogen) using dT(20) primers according the manufacturer's instructions. The amount of Renilla luciferase cDNA relative to GAPDH was then measured using qPCR. For the translation studies, Renilla and firefly luciferase protein were measured with the Dual Luciferase Kit (Promega) according to the manufacturer's instructions.

Fluorescence In Situ Hybridization for β-Actin mRNA

Stellaris FISH Probes recognizing human β-actin mRNA and labeled with Quasar 670™ (VSMF-2003-5. Biosearch Technologies, Inc., Petaluma, Calif.) were hybridized to cells 24 hours after transfection with the RCas9 system targeting β-actin mRNA. Hybridization was conducted according to the manufacturer's instructions. Confocal microscopy was conducted using an Olympus FV1000™ confocal microscope.

Overlap Analysis for Fluorescence In Situ Hybridization and RCas9

Colocalization analysis among FISH and RCas9 (dCas9-GFP with 2× internal NLS tags) targeting β-actin mRNA was conducted using the Coloc 2 plugin from the image analysis software FIJI™ (Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat Methods 9, 676-682). The cytoplasm of individual cells with similar dCas9-EGFP transfection levels was selected and the Coloc 2 analysis was conducted using default parameters. The Mander's overlap coefficient describing degree of overlap of the FISH signal with RCas9 for more than 60 cells in each condition was compiled and p-values were calculated with the two-tailed Mann-Whitney U test.

Tracking β-Actin mRNA Trafficking to Stress Granules

A HEK293T cell line was genetically modified with a fusion of mCherry to the C-terminus of Ras GTPase-activating protein-binding protein 1 (G3BP1) using CRISPR/Cas9. Briefly, a donor plasmid was constructed consisting of the mCherry ORF, a puromycin selection cassette, and flanking 1.5 kb homology arms directed at the G3BP1 locus. An sgRNA sequence targeting the C-terminus of G3BP1 was cloned into pSpCas9(BB)-2A-GFP (pX458) (gift from Feng Zhang, Addgene plasmid #48138) and co-transfected with the donor plasmid using Fugene HD (Roche) following the manufacturer's instructions. 48 hours after transfection, cells were selected with 1 µg/mL puromycin in growth medium for 14 days and mCherry-positive clones were selected and screened by PCR.

A clone with at least one modified allele was plated on glass chamber slides coated with fibronectin and transfected with the RCas9 system targeting the 3'UTR of β-actin mRNA as described above. 24 hours after transfection, cells were imaged with a Zeiss LSM 810™ confocal microscope with a stage incubator and sodium arsenite was applied to cells at concentrations ranging from 50 to 200 µM. Cells were maintained at 37° C. in a humidified atmosphere and 5% $CO_2$ and imaged at regular intervals.

Analysis of β-Actin mRNA Trafficking to Stress Granules

The average signal intensity in the RCas9 channel in areas with overlapping G3BP1-mCherry foci was recorded for each time point. Average signal intensity in the RCas9 channel surrounding G3BP1-mCherry foci was recorded as background and subtracted from the previous value to produce the background-adjusted RCas9 signal in stress granules.

Example 5: Tracking and Manipulating RNA Repeats Using RCas9 Plasmid Construction, PAMmer Synthesis, and Transfections The dCas9-2xNLS sequence was amplified from pHR-SFFV-dCas9-BFP-KRAB (a gift from Stanley Qi & Jonathan Weissman. Addgene plasmid #46911), tagged with two SV40 nuclear localization signals (NLS) on the C-terminus, and fused to EGFP or mCherry pCDNA 3.1 (Invitrogen, Carlsbad Calif.) using Gibson assembly. To construct the sgRNA scaffold construct, the human U6 polymerase III promoter with the modified sgRNA scaffold (Chen et al., 2013) was purchased as a gBlock from IDT with two BbsI restriction sites at the 5' end of the sgRNA scaffold (see table 1) and cloned into the multiple cloning site of pBlueScript II SK (+)™ (Agilent, Santa Clara, Calif.) using Gibson assembly. Phosphorylated oligonucleotides encoding the sgRNA sequences (with overhangs 5'CACC on the RNA antisense strand and 5'AAAC on the sense strand) were ligated into BbsI-digested sgRNA scaffold construct to produce sgRNAs targeting specific transcripts (see table 1). The SMA minigene construct was a gift from the Adrian Krainer lab. DM1 related 120 CTG repeats were present downstream of the CMV promoter in pCDNA 3.1 plasmid backbone for expression in mammalian cell lines. pCDNA3.1 PIN-XTEN-dCas9-2XNLS was constructed via amplification of the PIN domain from human cDNA from the SMG6 gene. The XTEN linker is a flexible linker used to isolate adjacent proteins domains. pCDNA 3.1 FOX2-dCas9-2xNLS was constructed via amplification of FOX2 from the Open Biosystem Human ORFeome™ and assembled with dCas9-2XNLS using Gibson assembly.

Figure 7A:
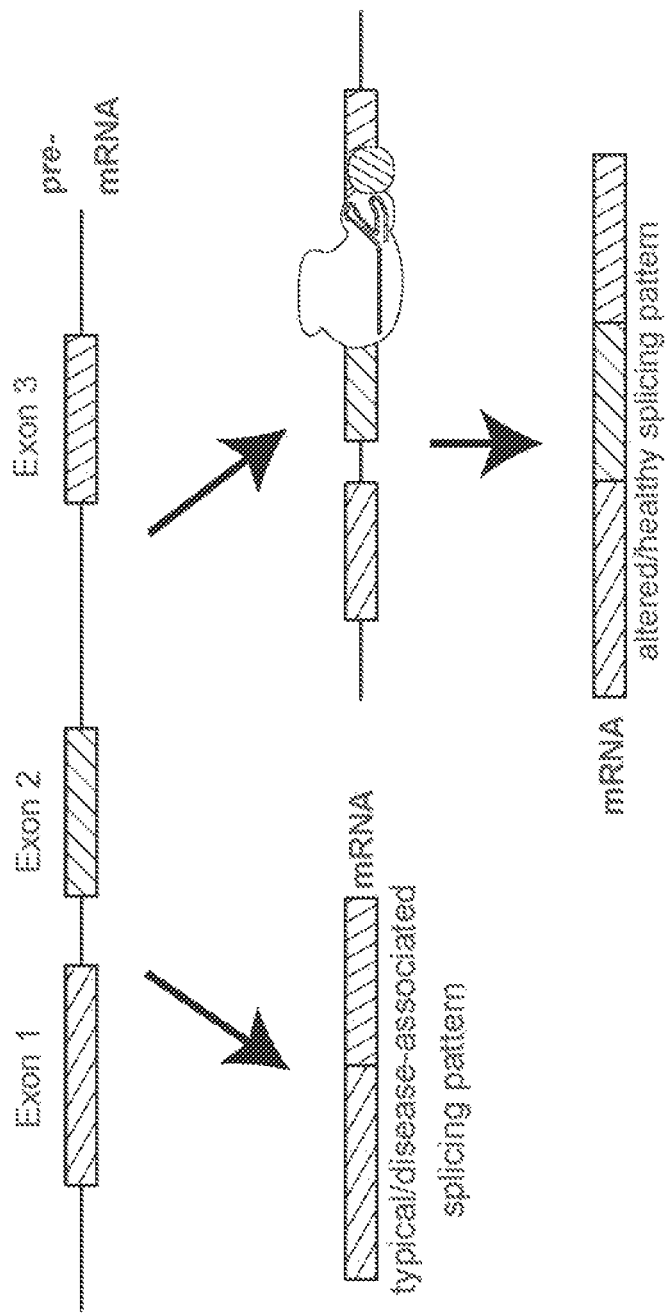
Figure 7B:
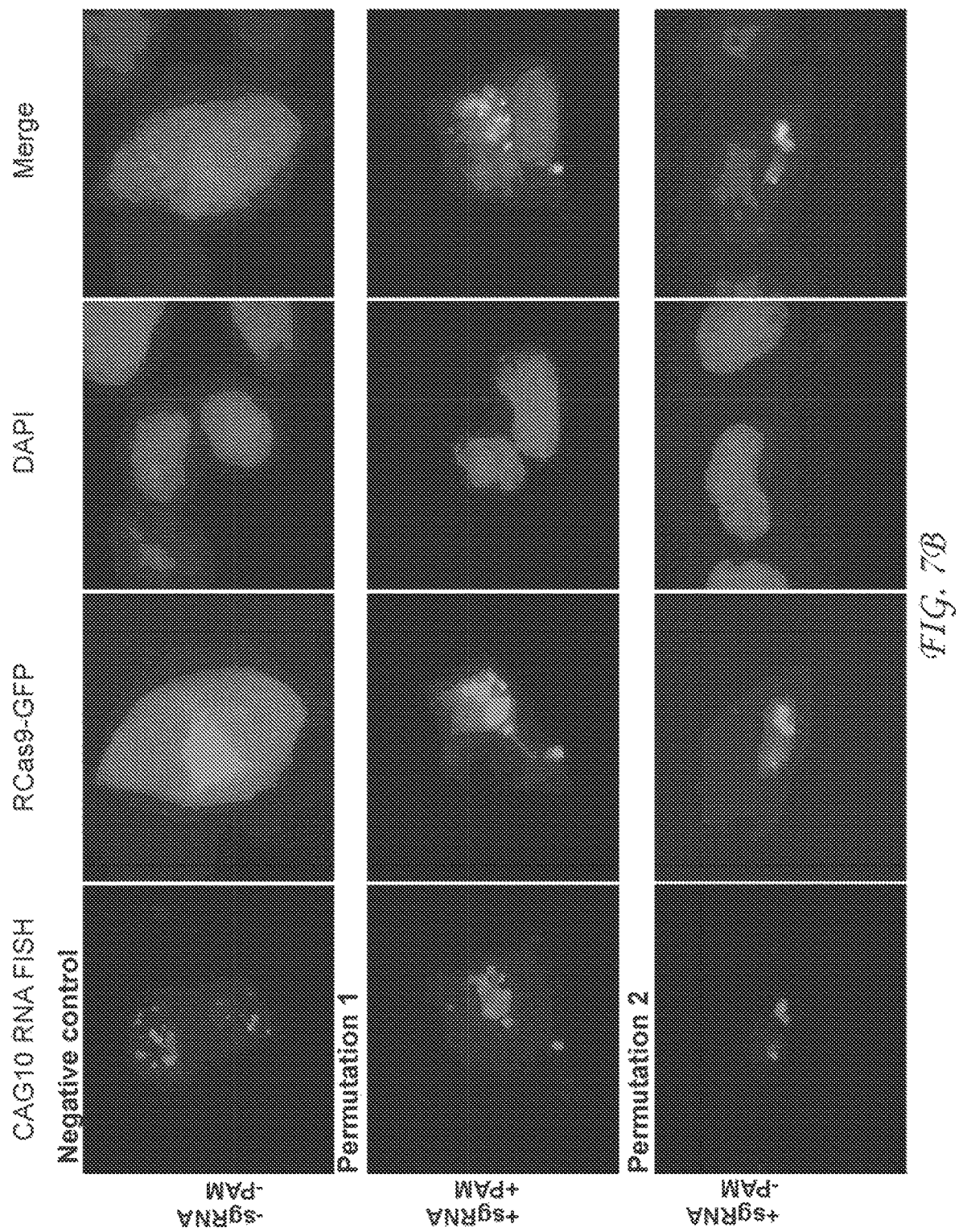
FIG. 7B. Data demonstrating efficient recognition of repeat-containing RNA (Use case 1). Results continued in FIG. 7C. By fusing Cas9 to a fluorescent protein, both permutations 1 and 2 produce signal distributions that reveal presence and location of CUG repeat-containing RNAs. RCas9 measurements of these repeats are compared to an established means to track CUG repeats (CUG RNA fluorescence in situ hybridization, "FISH"). Detailed methods are described below.
Figure 7C:
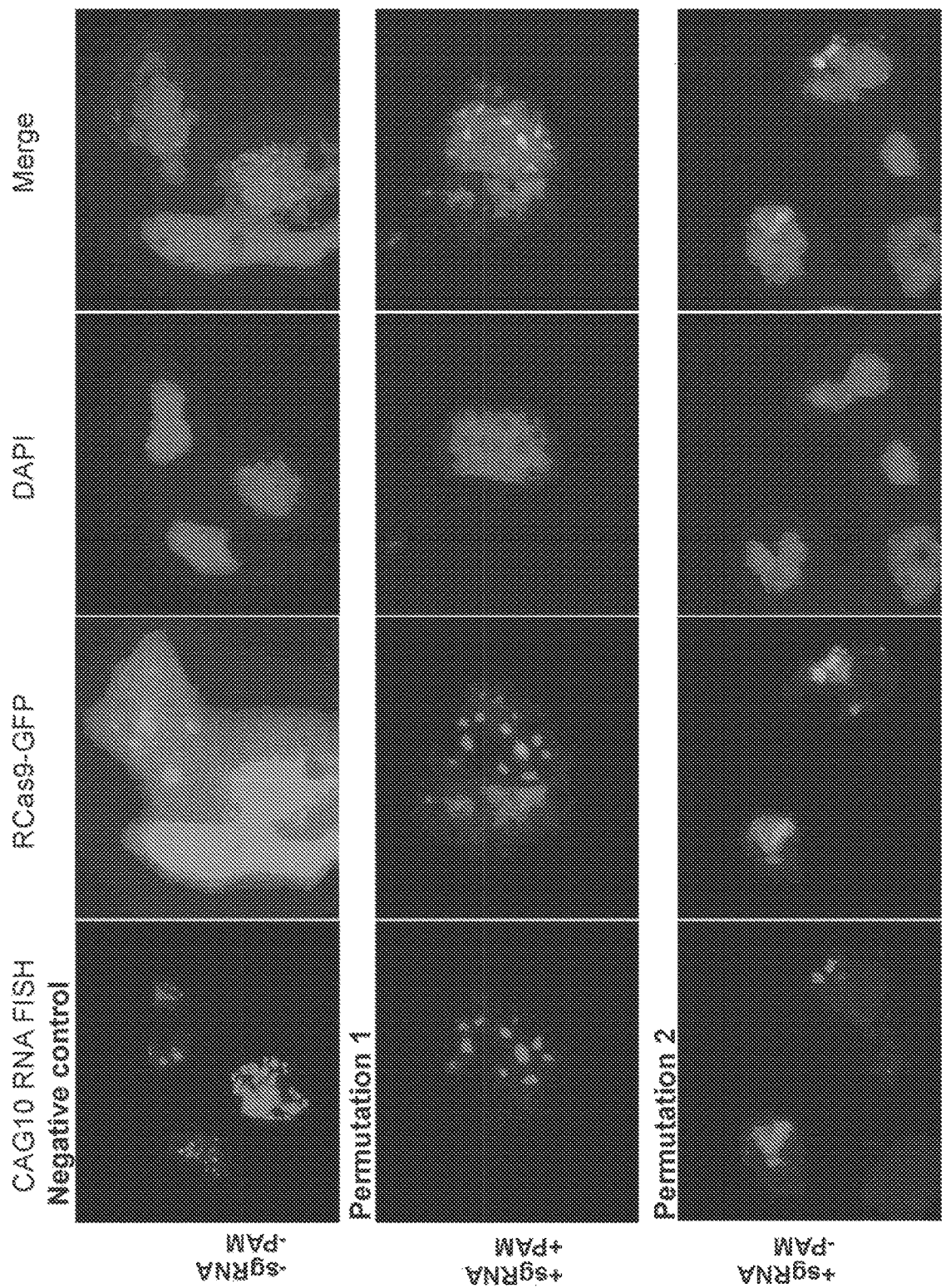
FIG. 7C. Data demonstrating efficient recognition of repeat-containing RNA (Use case 1). Results continued from FIG. 7B.
Figure 7E:
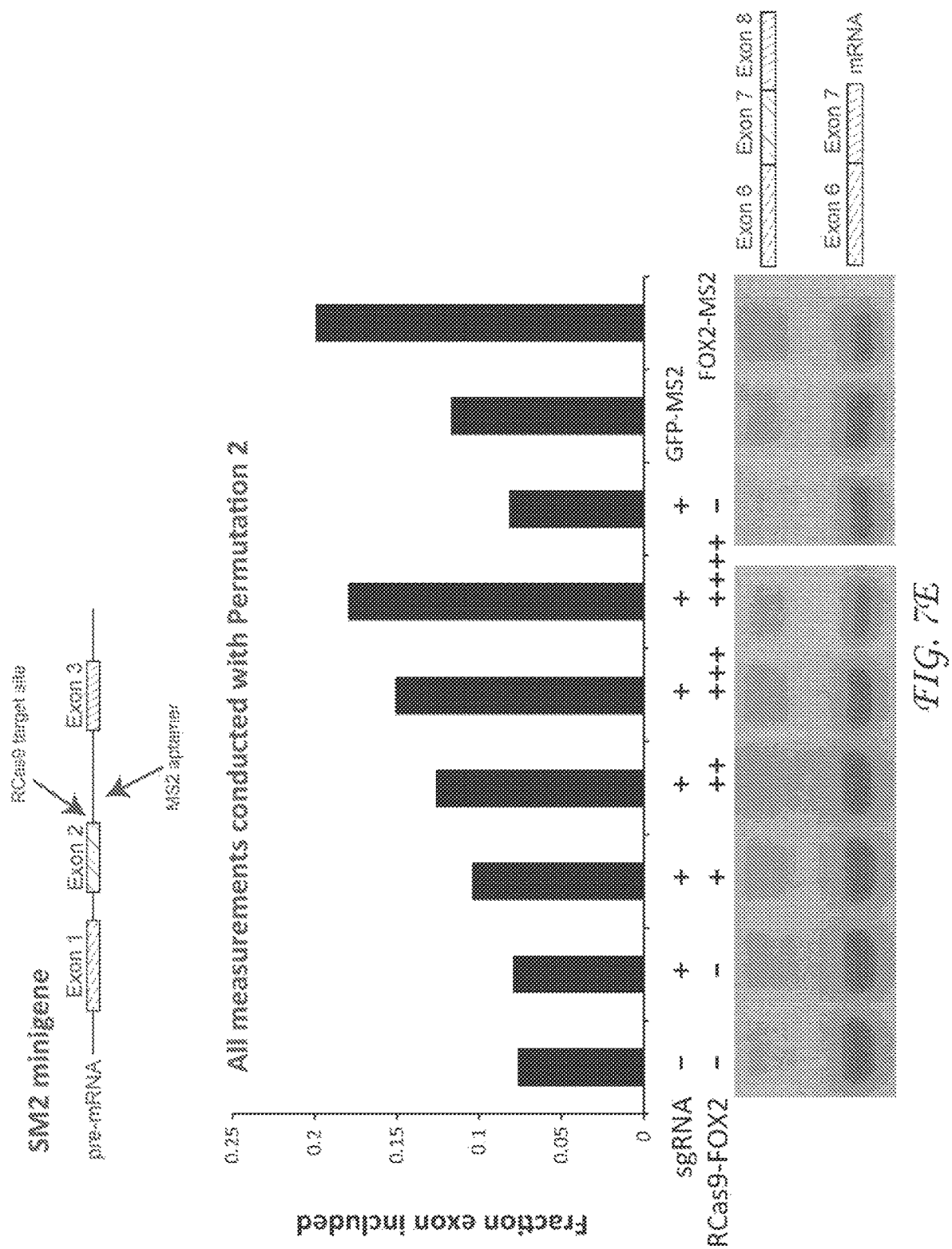
FIG. 7E. Data demonstrating alteration of RNA splicing using an exemplary RCas9 system (use case 3). Here, the splicing of a pre-mRNA composed of a minigene for human SMN2 carrying exons 6-8. By targeting RCas9 fused to FOX2 downstream of exon 7, inclusion of the differentially-spliced exon 7 is promoted. Promotion of inclusion of this exon is known to be an effective therapeutic for spinal muscular atrophy. The bar graph is a quantification of an RT-PCR for the SMN2 minigene. The minigene carries an MS2 aptamer site adjacent to the RCas9 binding sites which is strongly bound by MS2 coat protein fused to FOX2 (MS2-FOX2). This serves as a positive control to demonstrate that this exon is regulated by FOX2 binding. A negative control, also displayed on the far right side of the bar graph, involving replacement of FOX2 with GFP shows that FOX2 is required for regulation of this exon.

In all experiments, Lipofectamine 3000 (Life Technologies, Carlsbad, Calif.) was used according to the manufacturer's direction. For 100 ng total transfected plasmid in a 96w format, 5 ng of Cas9 plasmid and 25 ng sgRNA plasmid were transfected. In the imaging experiments, the GFP-tagged version of Cas9 was used with 20 ng of CAG or GGGGCC (SEQ ID NO: 19) repeat plasmid. In the cleavage experiments, the PIN-tagged version of Cas9 with used with the same amount of repeat plasmid. In the RNA splicing experiments, varied amounts of pCDNA 3.1 FOX2-dCas9-2xNLS were transfected ranging from 0 to 25 ng per well in 96w format. FIGS. 7B-C, F-G was generated from experiments conducted in COS-7 cells and Figure D-E was conducted in HEK293T cells.

Figure 7F:
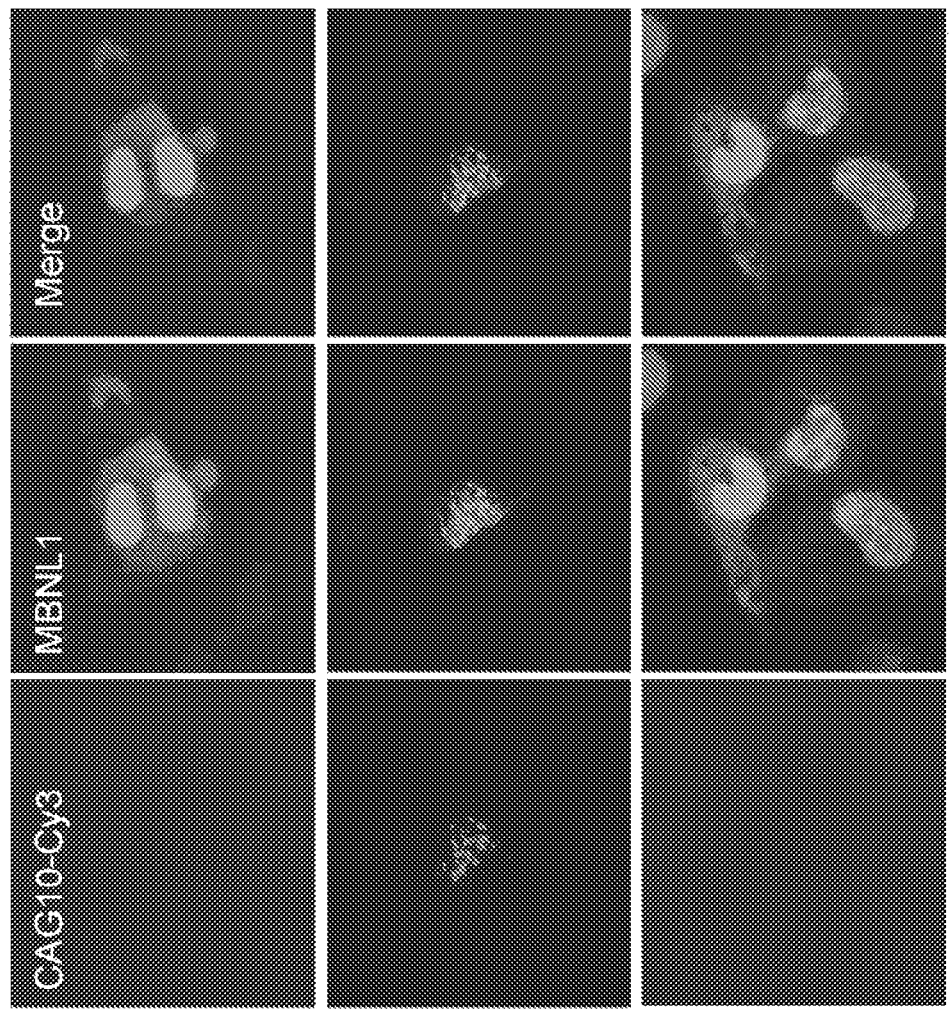
FIG. 7F. Data demonstrating cleavage of RNA using an exemplary RCas9 system (use case 2). A molecular hallmark of type 1 myotonic dystrophy (DM1) is the association of MBNL1 protein within CTG repeat RNA foci (Ho et al, 2005, J Cell Sci; Batra et al, 2014, Mol Cell). Here it is demonstrated that permutation 1 of the RCas9 system causes a redistribution of MBNL1 protein that is identical to the distribution observed without the repeat RNA present (compare the middle and bottom rows).
Figure 7G:
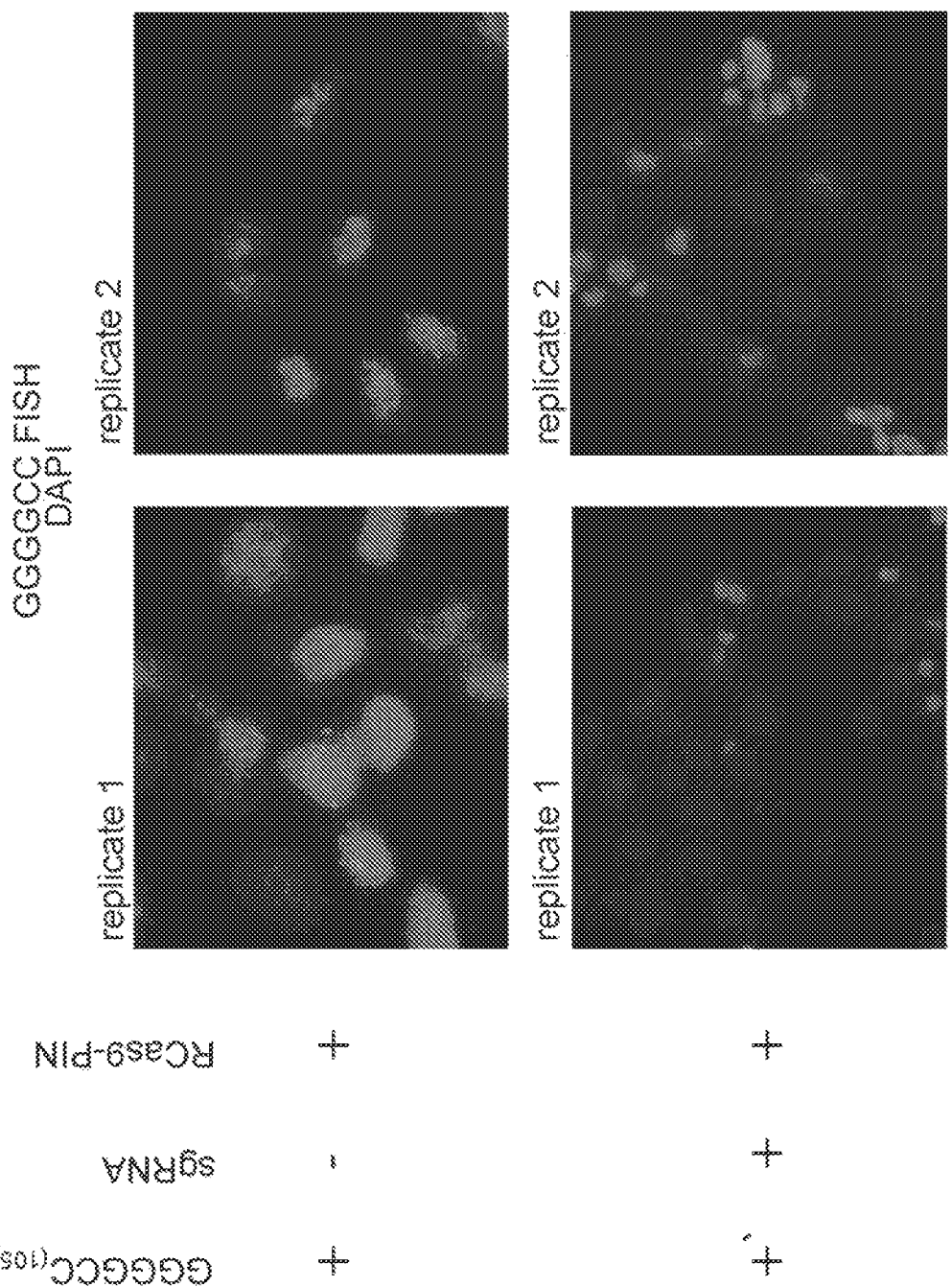
FIG. 7G. Data demonstrating cleavage of RNA using an exemplary RCas9 system (use case 2). Here, the RNA that causes C9 or 172-linked ALS (composed of repeating GGGGCC (SEQ ID NO: 19) RNA bases) was targeted in living human cells using permutation 2 of the RCas9 system. Application of the permutation 2 of the RNA-cleaving RCas9 system (use case 2) resulted in a large reduction of the amount of so that the repeat RNA is undetectable via FISH (bottom images).
Figure 8A:
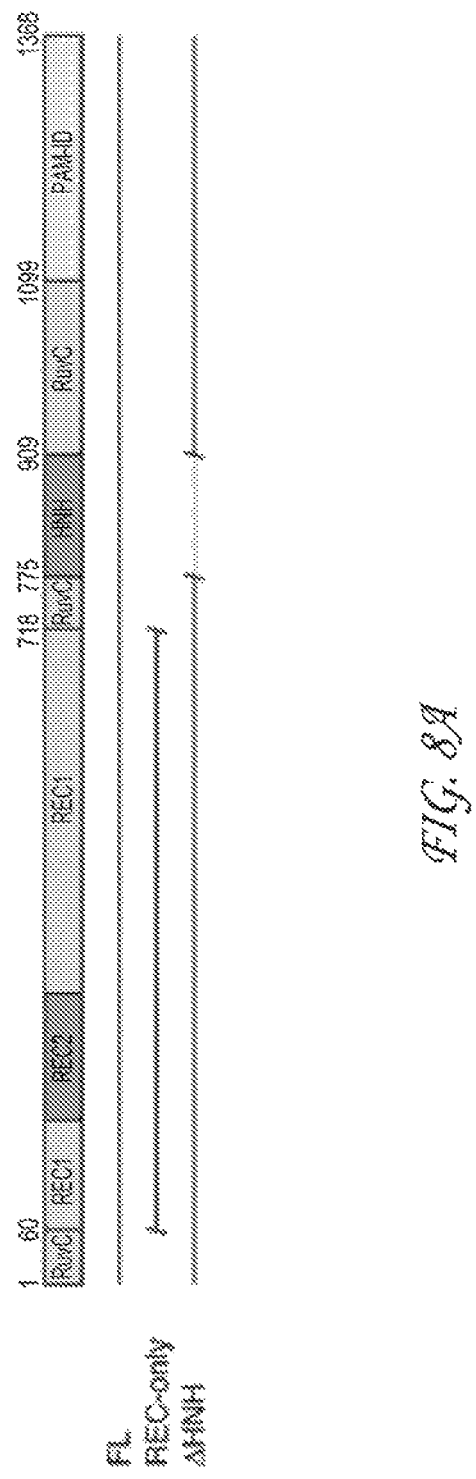
FIG. 8A. Full-Length and Truncated Cas9 Proteins. Domain structure map describing the truncation of Cas9 protein in a manner that maintains the ability of RNA-targeting Cas9 to destroy the pathogenic CTG repeat expansion RNA. This novel variant of the Cas9 protein has never been previously demonstrated and is distinct from full-length Cas9 or other Cas proteins that have been previously used in the art. In addition, this truncated Cas9 (referred to as "ΔHNH") facilitates therapeutic applications of the RCas9 system via packaging and delivery in adeno-associated viruses (AAV). AAV are an increasingly-utilized means to delivery encoded therapeutic systems such as RCas9 but delivered DNA is limited to ~4.5 kb. This truncated version of Cas9 facilitates packaging of the entire RCas9 system in a single AAV vector, facilitating a host of therapeutic applications for RCas9. Full-length Cas9 domain structure shown on top followed by Cas9 truncation variants "Rec-only" and "ΔHNH" domain structure below. The ΔHNH truncation is missing residues 775-909 from the full-length (FL) Cas9 protein.
Figure 8B:
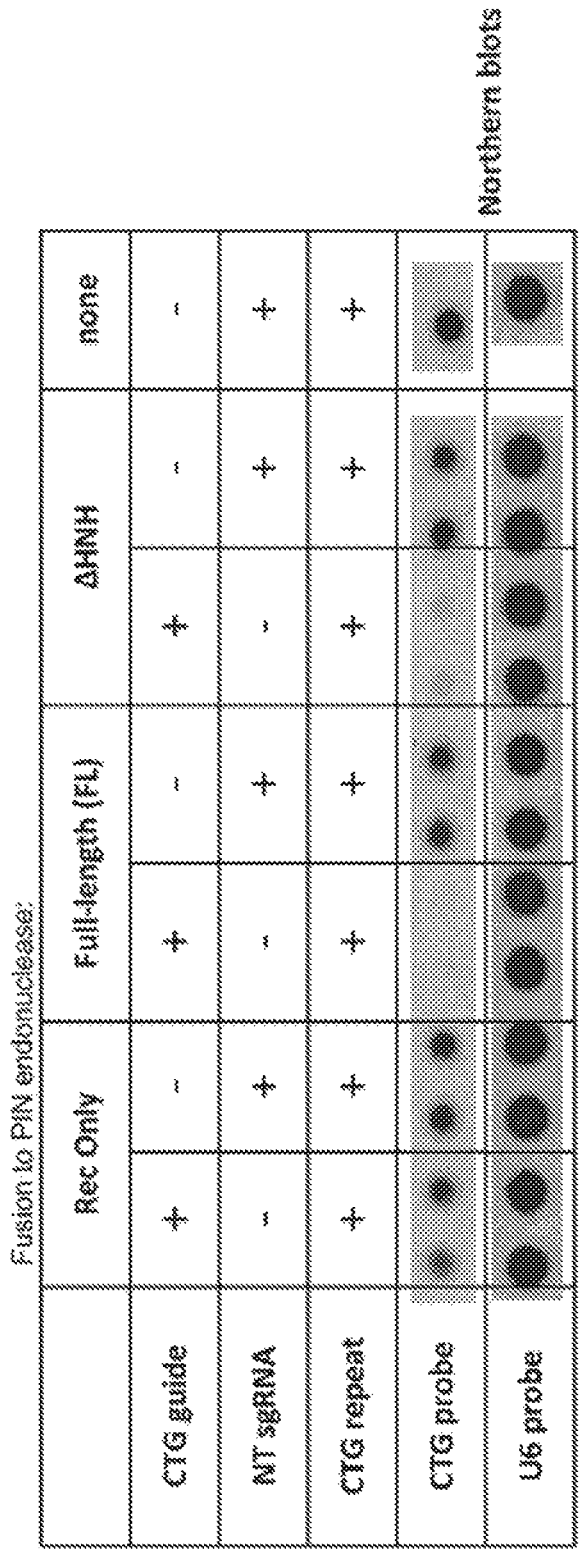
FIG. 8B. Data demonstrating CTG repeat degradation using an RCas9 system with a full-length Cas9 protein compared to an RCas9 system with a truncated Cas9 protein. COSM6 cells were transfected with the RNA-targeting Cas9 system (Cas9 protein or truncated version fused to the PIN endonuclease with a single guide RNA (sgRNA) targeting the CTG repeat or a non-targeting (NT) sgRNA) with a plasmid encoding CTG repeat. The ability of the RCas9 system in various truncated permutations was compared via Northern blot for the CTG repeat RNA with U6 snRNA as a loading control. Both full-length Cas9 and ΔHNH fused to the PIN domain support cleavage of the CTG repeat RNA but only in the presence of the sgRNA targeting the repeat.
Figure 8C:
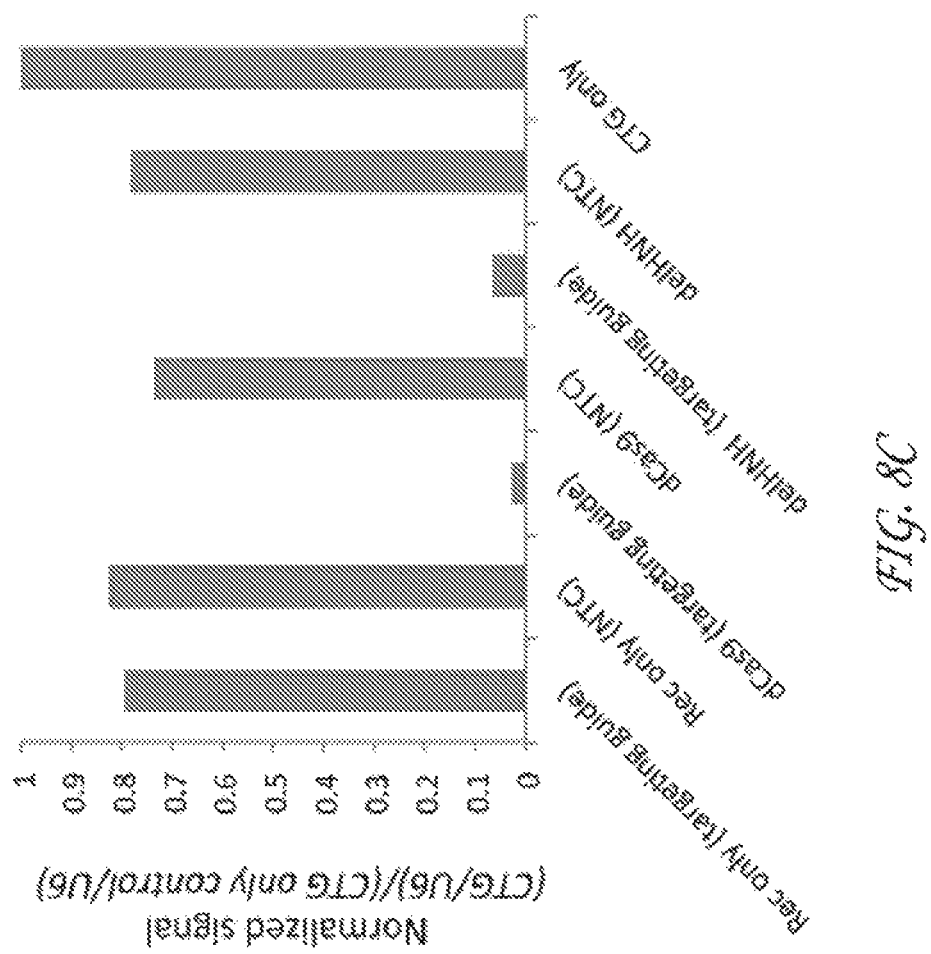
FIG. 8C. Quantification of the Northern blot signal from 8B. Both full length Cas9 and ΔHNH Cas9 truncations support efficient cleavage of the CTG RNA (>95% loss).

For the MBNL1 redistribution experiment (FIG. 7F) either pcDNA 3.1 MBNL1-EGFP alone, or pcDNA 3.1 MBNL1-EGFP, pCDNA 3.1 $CTG^{105}$ and RCas9-PIN, or pcDNA 3.1 MBNL1-EGFP, pCDNA 3.1 $CTG^{105}$, sgRNA and RCas9-PIN were transfected in CosM6 cells using Lipofectamine 3000 using manufacturer's protocol. Cells were washed with PBS, fixed with 4% PFA for 10 minutes, and permeabilized with cold 70% ethanol overnight at 4° C. Cells were rehydrated with 2× SSC with 40% formamide for 15 minutes. The cells were subjected to RNA FISH using CAG10-Cy3 probe as described previously. The EGFP and Cy3 fluorescence were visualized using a Zeiss fluorescence microscope at 20× and 60× magnifications.

PAMmers were composed of mixed 2'OMe RNA and DNA bases and purified by HPLC (Integrated DNA Technologies, Coralville Iowa).

Cell Lines

HEK293T and COS-7 cells were grown in Dulbecco's modified eagle medium (DMEM) supplemented with 10% fetal bovine serum, glutamax, penicillin/streptomycin and non-essential amino acids (Invitrogen). Cells were passaged every 3-4 days with TrypLE EXPRESS (Invitrogen) using standard methods and maintained in a humidified incubator at 37° C. with 5% $CO_2$.

RT-PCR

For the SMN2 minigene splicing experiments, RNA was extracted using Qiagen RNAeasy™ columns, subjected to DNAse treatment, reverse transcription (Superscript III™, Life Technologies), and PCR (Phusion polymerase, Life Technologies) according to manufacturer's directions. The PCR products were run on agarose gels and imaged using Sybr Safe gel stain (Life Technologies) with a UV imager.

RNA FISH

Media was removed from the cell culture slides and cells were washed gently with PBS (pH7.4). Cells were fixed with 4% PFA at room temperature for 10 minutes and subsequently washed at RT with PBS 5 times 3 min each. Slides were incubated in pre-chilled 70% ethanol overnight at 4° C. Ethanol was decanted and slides were rehydrated slides in 40% formamide in 2× SSC for 10 minutes at RT (20 ml deionized formamide, 5 ml 20× SSC, 25 ml ultrapure/DEPC water). While incubation is going lyophilized DNA probe (CAG10-cy3 (SEQ ID NO: 23) or GGGGCC-cy3 (SEQ ID NO: 19)) was reconstituted in water to the concentration of 500 ng/ul. Required volume of probe was pipetted into a PCR tube, heated at 99 C for 10 minutes and immediately cooled on ice for 10 minutes. Incubate cells for prehyb with the required volume of prehyb buffer (see recipe) at 37° C. for 15 mins in a humidified chamber or an incubator. The probe was added to the hybridization buffer (see recipe below). Cells were hybridized with DNA probe made in prehyb buffer (Hyb buffer=prehyb buffer+probe) at 37° C. for 2 hours in a humidified chamber or an incubator. Cells were washed 3× with 40% formamide/2× SSC at 37-37° C. for 30 min each. Wash sections with PBS at RT for 5 mins and then mounted them with mounting medium VECTASHIELD™ with DAPI (vector labs H-1200).

Northern Dot Blot

MATERIALS: Bio-Rad Bio-Dot™ Apparatus 1706545), HYBOND+ nylon membrane (GE HealthCare), Whatman paper.

SOLUTIONS 10 mM EDTA, 20× SSC (Lonza 51205), 10× SSC (diluted with RNase Free water from 20× SSC), 37% Formaldehyde, dH2O RNA was extracted using Tri reagent (Sigma Aldrich) as per manufacturer's protocol. 5 ug of RNA was used per lane. RNA can be stored at −80 C for 6 months until needed.

For sample preparation, 5 ug (for each sample) of RNA resuspended in RNase Free water was diluted to 50 ul with RNase Free water. 30 ul 20× SSC, and 20 ul of 37% formaldehyde were added to each sample. The samples were incubated at 60 C for 30 minutes and then kept on ice until needed.

The Bio-Rad Bio-Dot™ Apparatus (1706545) was assembled as per manufacturer's protocol, washed with ethanol by passing ethanol through the wells and dried. The apparatus was then disassembled. The Hybond+™ nylon membrane and 3 pieces of whatman paper were cut to the size of the Bio-Dot. The Hybond+ membrane was soaked in RNase Free water for 5 minutes and then transferred to 10× SSC buffer for 5 minutes. The Bio-Dot apparatus was then reassembled as following: From the top down >Hybond+ nylon membrane, 3× Whatman™ papers, Gasket, Gasket support plate, vaccum manifold were assembled and the apparatus was screwed tight and connected to a lab vacuum assembly. The vacuum was turned and a quiet seal was taken as the sign of a good seal. The wells to be used were hydrated and tested by passing 200 ul of 10× SSC twice while the vacuum is on. The sample was then applied for 5 minutes with vacuum off, and then the vaccum was turned on. After the samples were passed through the membrane by the vacuum, the wells were washed with 200 ul of 10× SCC twice. The vacuum was turned off, the Bio-Dot assembly was disassembled and the membrane was crosslinked in the UV STRATALINKER™ using the "Auto-Crosslink" setting which is equivalent to 1200 mJ with sample side up. At this point, the membrane can be dried and stored at RT for up to a month.

For probing, the membrane was hydrated with 10× SSC, and the washed with 1× SSC (diluted from 20× SSC with RNase Free water). The membrane was pre-hybridized with 10 ml Express-Hyb™ hybridization solution (Clonetech 636831) containing 500 ul of 1 mg/ml yeast tRNA (Thermo Fisher Scientific 15401-029) in a borosilicate hybridization tube (Thermo Scientific ELED-110113) in a hybridization oven (Thermo Scientific 6240TS) for 2 hours at 50 C.

During Pre-hybridization step, the CAG 10 (CAG CAG CAG CAG CAG CAG CAG CAG CAG CAG) (SEQ ID NO: 23) DNA probe was end-labeled with gamma-P32 ATP (Perkin Elmer BLU502Z) using T4 PNK in the following reaction:

20 ul 500 ng/ul CAG10 probe
10 ul 10× PNK buffer (NEB)
5 ul T4-PNK (NEB)
5 ul gamma-P32 ATP (Perkin Elemer)
60 ul Water The reaction was incubated at 37 C for 30 minutes. The probe was cleaned using the GE Lifesciences G-50 columns (28-9034-08) as per manufacturer's protocol. The probe was boiled at 100 C for 5 minutes and then kept on ice until use. The probe was directly added to the Pre-hybridization buffer (after 2 hours of pre-hybridization) and the hybridization was carried out at 45 C overnight (12-16 hours). After hybridization, the express-hyb buffer was decanted and the membrane was taken out into a small glass square baking dish/reservoir and washed with 1× SSC containing 0.1% SDS for 10 minutes at room temperature. 3 more washes were done with 0.5× SSC containing 0.1% SDS for 10 minutes each at room temperature. The membrane was then blotted with KimWipes™ (KimTech) and wrapped in a Saran wrap. The membrane was exposed to autoradiography film (Thermo Fisher Scientific) to an autoradiography cassette (GE Healthcare) with an intensifying screen (GE Healthcare) at −80 C for 4 hours.

TABLE 6

| PAMmer (PAM sequence in bold) and sgRNA sequences | |
|---|---|
| PAMmer, CAG repeat | mTGmCTmGCmTGmTGGmCTmGCmTGmCTmGCmTGmCTmGC (SEQ ID NO: 20) |
| sgRNA, CAG repeat | GTGCTGCTGCTGCTGCTGCTGGUUUAAGAGCAUUGCUGGAAACAGCAUAGCAA GUUUAAAUAAGGCUAGUCCGUUAUCAACUUGAAAAAGUGGCACCGAGUCGGUG CUUUUUUU (SEQ ID NO: 21) |
| U6 promoter-2x-Bbsi-sgRNA scaffold | TGTACAAAAAAGCAGGCTTTAAAGGAACCAATTCAGTCGACTGGATCCGGTAC CAAGGTCGGGCAGGAAGAGGGCCTATTTCCCATGATTCCTTCATATTTGCATA TACGATACAAGGCTGTTAGAGAGATAATTAGAATTAATTTGACTGTAAACACA AAGATATTAGTACAAAATACGTGACGTAGAAAGTAATAATTTCTTGGGTAGTT TGCAGTTTTAAAATTATGTTTTAAAATGGACTATCATATGCTTACCGTAACTT GAAAGTATTTCGATTTCTTGGCTTTATATATCTTGTGGAAAGGACGAAACACC GGGTCTTCGAGAAGACCTGTTTAAGAGCTATGCTGGAAACAGCATAGCAAGTT TAAATAAGGCTAGTCCGTTATCAACTTGAAAAAGTGGCACCGAGTCGGTGCTT TTTTT (SEQ ID NO: 22) |

Buffers Recipes:

20× Standard Sodium Citrate (SSC) Buffer:

| Component | Recipe |
|---|---|
| 3M sodium chloride (FW 58.44) | 175.3 g |
| 300 mM sodium citrate (FW 294.1) | 88.2 g |
| d2H2O | up to 1 L |

(pH to 7.0 with HCl and bring to final volume with d2H2O)

Formamide/SSC Buffer:

| Component | Recipe |
|---|---|
| 40% formamide (OmniPur deionized formamide, EMD Cat.# 4650) | 20 mL |

-continued

| Component | Recipe |
|---|---|
| 2X SSC | 5 mL of 20X SSC |
| d2H2O | 25 mL |

Prehybridization Buffer:

| Component | Recipe |
|---|---|
| 40% formamide (OmniPur deionized formamide, EMD Cat.# 4650) | 400 µL |
| 2X SSC buffer | 100 µL of 20X SSC |
| 200 µg/mL BSA | 20 µL of 10 mg/mL BSA |
| 10% dextran sulfate (Sigma, Cat.# D8906-10G) | 100 mg |
| 2 mM vanadyl sulfate (Aldrich 20,486-2) | 10 µL of 200 mM vanadyl sulfate |
| 1 mg/mL yeast tRNA (Invitrogen Cat. # 15401-029) | 100 µL of 10 mg/mL yeast tRNA |
| d2H2O | Up to 1 mL (usually 320 µL) |

Vortex vigorously until dextran sulfate has dissolved. Solution will be viscous. Alternatively, 200 nM vanadyl adenosine complex can be used instead of vanadyl sulfate. Vanadyl complex is an RNase inhibitor that can either be made or purchased from NEB (Cat. #S1402S). Alternatively, RNAsin can be used.

Hybridization Buffer:

| Component | Recipe |
|---|---|
| 40% formamide (OmniPur deionized formamide, EMD Cat.# 4650) | 400 µL |
| 2X SSC Buffer | 100 µL of 20X SSC |
| 200 µg/mL BSA | 20 µL of 10 mg/mL BSA |
| 10% dextran sulfate (Sigma, Cat.# D8906-10G) | 100 mg |
| 2 mM vanadyl sulfate (Aldrich 20,486-2) | 10 µL of 200 mM vanadyl sulfate |
| 1 mg/mL yeast tRNA (Invitrogen Cat. # 15401-029) | 100 µL of 10 mg/mL yeast tRNA |
| 500 pg/µL probe | 1 µL of 500 ng/uL probe |
| d2H2O | Up to 1 mL (usually 319 µL) |

Prepare initially without probe. Vortex vigorously until dextran sulfate has dissolved. Solution will be viscous. Add denatured probe to pre-chilled buffer.

Example 6: Using an RNA-Targeting Cas9 Systems for Targeted Destruction of Disease-Causing RNAs in Humans and/or Animal Models An RNA-targeting Cas9 system is used to treat a human patient suffering from a disease caused by an RNA microsatellite repeat expansion (such as microsatellite repeat expansion RNAs that cause myotonic dystrophy, C9orf72-linked ALS, and Huntington's disease). In alternative embodiments, the RNA-targeting Cas9 system, or nucleoprotein complex as provided herein, comprises two components: 1) a nuclease-inactive Cas9-polypeptide, optionally fused to an effector polypeptide and/or detectable moiety, and 2) a single guide RNA (sgRNA) targeting the repeat-containing sequence.

The effector polypeptide can be, but is not limited to, one of the following proteins: an RNA cleaving domain (endonuclease) such as a PIN domain-containing protein; a fluorescent protein; or an RNA splicing domain (splicing factor) such as RBFOX2 domain-containing protein or a protein known to influence RNA splicing.

The single guide RNA can be, but is not limited to, one of the following: an sgRNA targeting the CTG repeat-containing RNA that causes myotonic dystrophy; an sgRNA targeting the GGGGCC repeat-containing RNA that causes C9orf72-linked ALS; an sgRNA targeting the CAG repeat-containing RNA that causes Huntington's disease; or an sgRNA targeting the other diseases caused by repeat-containing RNA (microsatellite repeat expansion diseases such as Fragile X syndrome, spinocerebellar ataxias, Fragile X-associated tremor/ataxia syndrome, Spinal-bulbar muscular dystrophy, Oculopharyngeal muscular dystrophy, and others).

In alternative embodiments, the RNA-targeting Cas9 system is encoded in DNA carried by a vector, e.g., an adenovirus or an adeno-associated virus (AAV), and can be delivered to appropriate tissues via one of the following methods: use of specific AAV serotypes that display specific tissue tropism (such as AAV-9 targeting neurons muscle); injection of naked DNA encoding the RCas9 system into tissue such as muscle or liver; use of nanoparticles composed of lipids, polymers, or other synthetic or natural materials that carry DNA or RNA encoding the therapeutic RCas9 system; or any of the above where the RCas9 system is split between two separate viruses or DNA molecules so that: one virus encodes the Cas9 protein and the other virus encodes the sgRNA; or one virus encodes a portion of the Cas9 protein while the other virus encodes the another portion of the Cas9 protein and the sgRNA. In embodiments in which the portions of Cas9 are encoded on separate vectors, the encoded portions of Cas9 can interact with one another so as to form a functional Cas9 protein. For example, in some embodiments, the portions of Cas9 are engineered to complement via protein splicing or complementation to generate a functional Cas9 protein (see Wright et al., Rational design of a split-Cas9 enzyme complex. PNAS 112:2984-2989 (2015), the content of which is hereby incorporated by reference in its entirety).

In alternative embodiments, to use exemplary RNA-targeting Cas9 systems as provided herein in treatment of a human subject or animal, the vector, e.g., the AVV, encoding the RNA-targeting Cas9 system can, for example, be injected by the following methods:

1. Skeletal muscle tissue (intramuscular) at multiple sites simultaneously (relevant indication: myotonic dystrophy)—injection of $10^{11}$-$10^{14}$ GC (genome copies) per injection into major muscle group such as the abdominal muscles, biceps, deltoids, erector spinae, gastrocnemius, soleus, gluteus, hamstrings, latissimus dorsi, rhomboids, obliques, pectoralis, quadriceps, trapezius and/or triceps;

2. Intravenous delivery of a muscle-targeted AAV serotype such as AAV-9 or AAV-6 or a novel muscle-targeted serotype (relevant indication: myotonic dystrophy)—injection of $10^{11}$-$10^{14}$ GC per injection for a total of $10^{12}$-$10^{17}$ GC delivered;

3. Subpial spinal injection of AAV-6, AAV-9 or another serotype displaying neuronal tropism (relevant indication: ALS)—injection of $10^{11}$-$10^{17}$ GC in a single or multiple doses;

4. Intracranial injection of AAV-6, AAV-9 or another serotype displaying neuronal tropism (relevant indication: Huntington's disease, spinocerebellar ataxias, Fragile X syndrome)—injection of $10^{11}$-$10^{17}$ GC in a single or multiple doses.

Example 7: Treating Myotonic Dystrophy in Human Subjects

In some embodiments for treating myotonic dystrophy in a human subject, the modified RCas9 endonuclease system, the nucleic acid, the genetic construct, or the viral vector (such as a lentiviral or AAV vector) may be formulated by methods known in the art. In addition, any route of administration may be envisioned. In alternative embodiments, the RCas9 endonuclease system, the nucleic acid, the genetic construct and the viral vector (such as a lentiviral or AAV vector) is administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. Any dose or frequency of administration that provides the therapeutic effect described herein is suitable for use in the present treatment. In a particular embodiment, the subject is administered a viral vector encoding the RCas9 endonuclease system according to the disclosure by the intramuscular route. In a specific variant of this embodiment, the vector is an AAV vector as defined above, in particular an AAV9 vector. In some embodiments, the human subject may receive a single injection of the vector. Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. In addition, the pharmaceutical composition may comprise nanoparticles that contain the RCas9 endonuclease system of the present disclosure.

Example 8: Treating Myotonic Dystrophy in Mouse Models and Measuring the Effects of such Treatments Mouse models which can be used include: HSALR transgenic mice that express 250 CUG repeats in the human skeletal actin 3'UTR; GGGGCC (G4C2) transgenic mice; and various human HTT transgenic mouse models.

The gastronemius or tibialis anterior muscles of adult mice are injected respectively with 30 to 100 µi of physiological solution containing or not AAV vectors (AAV-6, AAV-2, or AAV-9). For each mouse, one muscle is injected with AAV GFP-ACT3 and the contralateral muscle is injected with control AAV containing any transgene (MCS) or GFP or vehicle alone (PBS). Six weeks after injections, the isometric contractile properties of the muscles are measured as previously described. Then, the mice are killed, muscles are collected and snap-frozen in liquid nitrogen-cooled isopentane and stored at −80° C.

At the physiological level, it has been established that myotonia observed in the DM1 mouse model results from abnormal splicing of muscle-specific chloride channel Clc-1 exon 7a. Myotonia that is characterized by muscle hyper-excitability that leads to persistent electrical discharges and delayed force relaxation. One means to assess the efficacy of a myontic dystrophy therapeutic is to measure splicing of Clc-1 exon 7a via RNA sequencing or RT-PCR. Further, the effect of the therapeutic on muscle force relaxation can be determined after induced-contraction compared to control contralateral muscles. Reversal of myotonic dystrophy-related electrical activity in muscles will be assessed using electromyography in mice under general anesthesia using 30 gauge concentric needle electrotrode in hindlimb muscles (tibialis anterior, gastrocnemius, and vastus muscles) and forelimb muscles (flexor compartment of distal forelimb, triceps). At least ten needle insertions are performed for each muscle and myotonic discharges will be graded on a 4-point scale where 0 relates to no myotonia, 1, occasional myotonic discharge in <50% of insertions, 2, myotonic discharge in >50% of insertions, or 3, myotonic discharge in nearly all insertions.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together. etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

All references listed herein are expressly incorporated herein by reference in their entireties, including the following references:

REFERENCES

Bashor C J, Helman N C, Yan S, Lim W A. 2008, Using engineered scaffold interactions to reshape MAP kinase pathway signaling dynamics. *Science* 319: 1539-43.

Batra et al, 2014, Loss of MBNL Leads to Disruption of Developmentally Regulated Alternative Polyadenylation in RNA-Mediated Disease; Mol Cell. 56(2): 311-322.

Bennett C. F., and Swayze, E. E. (2010), RNA targeting therapeutics: molecular mechanisms of antisense oligonucleotides as a therapeutic platform. Annu Rev Pharmacol Toxicol 50, 259-293.

Bertrand, E., Chartrand, P., Schaefer, M., Shenoy, S. M., Singer, R. H., and Long, R. M. (1998). Localization of ASH1 mRNA particles in living yeast. Mol Cell 2, 437-445.

Beuth B, Pennell S, Arnvig K B, Martin S R, et al. 2005. Structure of a Mycobacterium tuberculosis NusA-RNA complex. *EMBO J* 24: 3576-87.

Braddock D T, Louis J M, Baber J L, Levens D. et al. 2002. Structure and dynamics of KH domains from FBP bound to single-stranded DNA. *Nature* 415: 1051-6.

Buchan, J. R., and Parker, R. (2009). Eukaryotic stress granules: the ins and outs of translation. Mol Cell 36, 932-941.

Buxbaum, A. R., Wu, B., and Singer, R. H. (2014). Single beta-actin mRNA detection in neurons reveals a mechanism for regulating its translatability. Science 343, 419-422.

Cencie R, Miura H, Malina A, Robert F, et al. 2014. Protospacer adjacent motif (PAM)-distal sequences engage CRISPR Cas9 DNA target cleavage. *PLoS One* 9: e109213.

Chen, B., Gilbert, L. A., Cimini, B. A., Schnitzbauer, J., Zhang, W., Li, G. W., Park, J., Blackburn, E. H., Weissman, J. S., Qi, L. S., Huang, B. (2013). Dynamic imaging of genomic loci in living human cells by an optimized CRISPR/Cas system. Cell 155, 1479-1491.

Cheong, C. G., and Hall, T. M. (2006). Engineering RNA sequence specificity of Pumilio repeats. Proc Natl Acad Sci USA 103, 13635-13639.

Cho S W, Kim S, Kim J M, Kim J S. 2013. Targeted genome engineering in human cells with the Cas9 RNA-guided endonuclease. *Nat Biotechnol* 31: 230-2.

Chou, H. H., Hsia, A. P., Mooney, D. L., and Schnable, P. S. (2004). Picky: oligo microarray design for large genomes. Bioinformatics 20, 2893-2902.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

DeJesus-Hernandez M, Mackenzie I R, Boeve B F, Boxer A L, et al. 2011. Expanded GGGGCC hexanucleotide repeat in noncoding region of C9ORF72 causes chromosome 9p-linked FTD and ALS. *Neuron* 72: 245-56.

Delebecque, C. J., Lindner, A. B., Silver, P. A., and Aldaye, F. A. (2011). Organization of intracellular reactions with rationally designed RNA assemblies. Science 333, 470-474.

Donnelly C J, Willis D E, Xu M, Tep C, et al. 2011. Limited availability of ZBP1 restricts axonal mRNA localization and nerve regeneration capacity. *EMBO J* 30: 4665-77.

Doudna lab patent: https://patentscope.wipo.int/search/en/detail.jsf?docId=WO2015089277&recNum=2&maxRec=2924&office=&prevFilter=&sortOption=&queryString=EN_ALL %3Anmr+AND+PA %3A %22THE+REGENTS+OF+THE+UNIVERSITY+OF+CALIFORNIA %22&tab=PCT+Biblio Dow, L. E., Fisher, J., O'Rourke, K. P., Muley, A., Kastenhuber, E. R., Livshits, G., Tschaharganeh, D. F., Socci, N. D., and Lowe, S. W. (2015). Inducible in vivo genome editing with CRISPR-Cas9. Nat Biotechnol 33, 390-394.

Dow L E, Fisher J, O'Rourke K P, Muley A, et al. 2015. Inducible in vivo genome editing with CRISPR-Cas9. *Nature Biotechnol doi:*10.1038/nbt.3155.

Dueber J E, Wu G C, Malmirchegini G R, Moon T S, et al. 2009. Synthetic protein scaffolds provide modular control over metabolic flux. *Nat Biotechnol* 27: 753-9.

Esvelt, K. M., Mali, P., Braff, J. L., Moosburner, M., Yaung, S. J., and Church, G. M. (2013). Orthogonal Cas9 proteins for RNA-guided gene regulation and editing. Nat Methods 10, 1116-1121.

Filipovska A, Razif M F, Nygard K K, Rackham O. 2011. A universal code for RNA recognition by PUF proteins. *Nat Chem Biol* 7: 425-7.

Fouts, D. E., Truc, H. L., and Celander, D. W. (1997). Functional recognition of fragmented operator sites by R17/MS2 coat protein, a translational repressor. Nucleic Acids Res 25, 4464-4473.

Fu, Y., Sander, J. D., Reyon, D., Cascio, V. M., and Joung, J. K. (2014). Improving CRISPR-Cas nuclease specificity using truncated guide RNAs. Nat Biotechnol 32, 279-284.

Fusco D, Accornero N., Lavoie B, Shenoy S M, et al. 2003. Single mRNA molecules demonstrate probabilistic movement in living mammalian cells. *Curr Biol:* 13: 161-7.

Garcia, J. F., and Parker, R. (2015). MS2 coat proteins bound to yeast mRNAs block 5' to 3' degradation and trap mRNA decay products: implications for the localization of mRNAs by MS2-MCP system. RNA 21, 1393-1395.

Geisler S, Coller J. 2013. RNA in unexpected places: long non-coding RNA functions in diverse cellular contexts. *Nat Rev Mol Cell Biol* 14: 699-712.

Gerstberger S, Hafner M, Ascano M, Tuschl T. 2014. Evolutionary conservation and expression of human RNA-binding proteins and their role in human genetic disease. *Adv Exp Med Biol* 825: 1-55.

Gilbert L A, Larson M H, Morsut L., Liu Z., et al. 2013. CRISPR-mediated modular RNA-guided regulation of transcription in eukaryotes. *Cell* 154: 442-51.

Graveley B R, Maniatis T. 1998. Arginine/serine-rich domains of SR proteins can function as activators of pre-mRNA splicing. *Mol Cell* 1: 765-71.

Hale, C. R., Zhao, P., Olson, S., Duff, M. O., Graveley, B. R., Wells, L., Terns, R. M., and Terns, M. P. (2009). RNA-guided RNA cleavage by a CRISPR RNA-Cas protein complex. Cell 139, 945-956.

Halo et al "NanoFlares for the detection, isolation, and culture of live tumor cells from human blood" PNAS doi: 10.1073/pnas.1418637111.

Hendel, A., Bak, R. O., Clark, J. T., Kennedy, A. B., Ryan, D. E., Roy, S., Steinfeld, I., Lunstad, B. D., Kaiser, R. J., Wilkens, A. B., Bacchetta, R., Tsalenko, A., Dellinger, D., Bruhn, L., Porteus, M. H. (2015). Chemically modified guide RNAs enhance CRISP-Cas genome editing in human primary cells. Nature Biotechnology 33, 985-989.

Ho et al. 2005. Colocalization of muscleblind with RNA foci is separable from mis-regulation of alternative splicing in myotonic dystrophy. J Cell Sci. 118(13): 2923-2933.

Hua Y, Vickers T A, Okunola H L, Bennett C F, et al. 2008. Antisense masking of an hnRNP A1/A2 intronic splicing silencer corrects SMN2 splicing in transgenic mice. *Am J Hum Genet* 82: 834-48.

Hua Y, Sahashi K, Hung G, Rigo F, et al. 2010. Antisense correction of SMN2 splicing in the CNS rescues necrosis in a type III SMA mouse model. *Genes Dev* 24: 1634-44.

Hua et al "Peripheral SMN restoration is essential for long-term rescue of a severe spinal muscular atrophy mouse model." Nature. 2011 Oct. 5;478(7367):123-6. doi: 10.1038/nature10485.

Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using as CRISPR-Cas system. Nat Biotechnol 31, 227-229.

Jiang F, Taylor D W, Chen J S, Kornfeld J E, Zhou K, Thompson A J, Nogales E, Doudna J A. Structures of a CRISPR-Cas9 R-loop complex primed for DNA cleavage. *Science.* 2016;351(6275):867-71.

Jinek M, East A, Cheng A, Lin S, et al. 2013. RNA-programmed genome editing in human cells. *eLife* 2: e00471.

Kanadia R N, Johnstone K A, Mankodi A, Lungu C, Thornton C A, Esson D, Timmers A M, Hauswirth W W, Swanson M S. A muscleblind knockout model for myotonic dystrophy. Science. 2003;302(5652):1978-80.

Kedersha N, Anderson P. 2007. Mammalian stress granules and processing bodies. *Methods Enzymol* 431: 61-81.

Kuscu C, Arslan S, Singh R, Thorpe J, et al. 2014. Genome-wide analysis reveals characteristics of off-target sites bound by the Cas9 endonuclease. *Nat Biotechnol* 32: 677-83.

Laird-Offringa I A, Belasco J G. 1995. Analysis of RNA-binding proteins by in vitro genetic selection: identification of an amino acid residue important for locking U1A onto its RNA target. *Proc Natl Acad Sci USA* 92: 11859-63.

Li, D., Qiu, Z., Shao, Y., Chen, Y., Guan, Y., Liu, M., Li, Y., Gao, N., Wang, L., Lu, X., et al. (2013a). Heritable gene targeting in the mouse and rat using a CRISPR-Cas system. Nat Biotechnol 31, 681-683.

Li, Y. R., King, O. D., Shorter, J., and Gitler, A. D. (2013b). Stress granules as crucibles of ALS pathogenesis. J Cell Biol 201, 361-372.

Lionnet T, Czaplinski K, Darzacq X, Shav-Tal Y, et al. 2011. A transgenic mouse for in vivo detection of endogenous labeled mRNA. *Nature Methods* 8: 165-70.

Long C, Amoasii L, Mireault A A, McAnally J R, Li H, Sanchez-Ortiz E, Bhattacharyya S, Shelton J M, Basel-Duby R, Olson E N. Postnatal genome editing partially restores dystrophin expression in a mouse model of muscular dystrophy. Science. 2016;351(6271):400-3.

Lovei M T, Ghanem D, Marr H, Arnold J, et al. 2013. Rbfox proteins regulate alternative mRNA splicing through evolutionarily conserved RNA bridges. *Nat Struct Mol Biol* 20: 1434-42.

Lu J, Getz G, Miska E A, Alvarez-Saavedra E, et. al. 2005. MicroRNA expression profiles classify human cancers. *Nature* 435: 834-8.

MacKenzie T A, Schwartz G N, Calderone H M, Graveel C R, et al. 2014. Stromal Expression of miR-21 Identifies High-Risk Group in Triple-Negative Breast Cancer. *Am J Pathol* 184: 3217-25.

Maddalo D, Manchado E, Concepcion C P, Bonetti C, et al. 2014. In vivo engineering of oncogenic chromosomal rearrangements with the CRISPR/Cas9 system. *Nature* 516: 423-7.

Mali P, Yang L H, Esvelt K M, Aach J, et al. 2013. RNA-Guided Human Genome Engineering via Cas9. *Science* 339: 823-6.

Manders, E. M., Stap, J., Brakenhoff, G. J., van Driel, R., and Aten, J. A. (1992). Dynamics of three-dimensional replication patterns during the S-phase, analysed by double labelling of DNA and confocal microscopy. J Cell Sci 103 (Pt 3), 857-862.

Meng L, Ward A J, Chun S, Bennett C F, et al. 2015. Towards a therapy for Angelman syndrome by targeting a long non-coding RNA. *Nature* 518: 409-12.

Miyanohara A, Kamizato K, Juhas S, Juhasova J, Navarro M, Marsala S, Lukacova N, Hruska-Plochan M, Curtis E, Gabel B, Ciacci J, Ahrens E T, Kaspar B K, Cleveland D, Marsala M. Potent spinal parenchymal AAV9-mediated gene delivery by subpial injection in adult rats and pigs. Mol Ther Methods Clin Dev. 2016;3:16046.

Mouisel E, Blondet B, Escourrou P, Chatonnet A, Molgo J, Ferry A. Outcome of acetylcholinesterase deficiency for neuromuscular functioning. Neurosci Res. 2006;55(4):389-96.

Muddashetty R S, Nalavadi V C, Gross C, Yao X, et al. 2011. Reversible inhibition of PSD-95 mRNA translation by miR-125a, FMRP phosphorylation, and mGluR signaling. *Mol Cell* 42: 673-88.

Nakayama, T., Fish, M. B., Fisher, M., Oomen-Hajagos, J., Thomsen, G. H., and Grainger, R. M. (2013). Simple and efficient CRISPR/Cas9-mediated targeted mutagenesis in Xenopus tropicalis. Genesis 51, 835-843.

Nissim-Rafinia M, Kerem B. 2002. Splicing regulation as a potential genetic modifier. *Trends Genet* 18: 123-7.

O'Connell, M. R., Oakes, B. L., Sternberg, S. H., East-Seletsky, A., Kaplan, M., and Doudna, J. A. (2014). Programmable RNA recognition and cleavage by CRISPR/Cas9. Nature 516, 263-266.

Orengo J P, Chambon P, Metzger D, Mosier D R, Snipes G J, Cooper T A. Expanded CTG repeats within the DMPK 3' UTR causes severe skeletal muscle wasting in an inducible mouse model for myotonic dystrophy. Proc Natl Acad Sci USA. 2008;105(7):2646-51.

Ozawa T, Natori Y, Sato M, Umezawa Y. 2007. Imaging dynamics of endogenous mitochondrial RNA in single living cells. *Nat Methods* 4: 413-9.

Paige J S, Wu K Y, Jaffrey S R. 2011. RNA mimics of green fluorescent protein. *Science* 333: 642-6.

Park H Y, Lim H, Yoon Y J, Follenzi A, et al. 2014. Visualization of dynamics of single endogenous mRNA labeled in live mouse. *Science* 343: 422-4.

Pasca S P, Portmann T, Voineagu I, Yazawa M, et al. 2011. Using iPSC-derived neurons to uncover cellular phenotypes associated with Timothy syndrome. *Nat Med* 17: 1657-62.

Passini M A, Bu J, Richards A M, Kinnecom C, et al. 2011. Antisense oligonucleotides delivered to the mouse CNS ameliorate symptoms of severe spinal muscular atrophy. *Science Transl Med* 3: 72ra18.

Price, A. A., Sampson, T. R., Ratner, H. K., Grakoui, A., and Weiss, D. S. (2015). Cas9-mediated targeting of viral RNA in eukaryotic cells. Proc Natl Acad Sci USA 112, 6164-6169.

Qi, L. S., Larson, M. H., Gilbert, L. A., Doudna, J. A., Weissman, J. S., Arkin, A. P., and Lim, W. A. (2013). Repurposing CRISPR as an RNA-guided platform for sequence-specific control of gene expression. Cell 152, 1173-1183.

Rackham O, Brown C M. 2004. Visualization of RNA-protein interactions in living cells: FMRP and IMP1 interact on mRNAs. *EMBO J* 123: 3346-55.

Rath A K, Rentmeister A. 2014. Genetically encoded tools for RNA imaging in living cells. *Curr Opin Biotechnol* 31C: 42-9.

Renton A E, Majounie E, Waite A, Simon-Sanchez J, et al. 2011. A hexanucleotide repeat expansion in C9ORF72 is the cause of chromosome 9p21-linked ALS-FTD. *Neuron* 72: 257-68.

Sachdeva, G., Garg, A., Godding, D., Way, J. C., and Silver, P. A. (2014). In vivo co-localization of enzymes on RNA scaffolds increases metabolic production in a geometrically dependent manner. Nucleic Acids Res 42, 9493-9503.

Sampson, T. R., Saroj, S. D., Llewellyn, A. C., Tzeng, Y. L., and Weiss, D. S. (2013). A CRISPR/Cas system mediates bacterial innate immune evasion and virulence. Nature 497, 254-257.

Sander, J. D., and Joung, J. K. (2014). CRISPR-Cas systems for editing, regulating and targeting genomes. Nat. Biotechnol 32, 347-355.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat. Methods 9, 676-682.

Shestakova E A, Singer R H, Condeelis J. 2001. The physiological significance of beta-actin mRNA localization in determining cell polarity and directional motility. *Proc Natl Acad Sci USA* 98: 7045-50.

Shin I, Ray J, Gupta V, Ilgu M, et al. 2014. Live-cell imaging of Pol II promoter activity to monitor gene expression with RNA IMAGEtag reporters. *Nucleic Acids Res* 42: e90.

Staals R H, Zhu Y, Taylor D W, Kornfeld J E, et al. 2014. RNA Targeting by the Type III-A CRISPR-Cas Csm Complex of *Thermus thermophilus*. *Mol Cell* 56: 518-30.

Stepto A, Gallo J M, Shaw C E, Hirth F. Modelling C9ORF72 hexanucleotide repeat expansion in amyotrophic lateral sclerosis and frontotemporal dementia. Acta Neuropathol. 2014;127(3):377-89.

Sternberg, S. H., Redding, S., Jinek, M., Greene, E. C., and Doudna, J. A. (2014). DNA interrogation by the CRISPR RNA-guided endonuclease Cas9. Nature 507, 62-67.

Strack R L, Disney M D, Jaffrey S R. 2013. A superfolding Spinach2 reveals the dynamic nature of trinucleotide repeat-containing RNA. *Nat Methods* 10: 1219-24.

Sunbul M, Jaschke A. 2013. Contact-mediated quenching for RNA imaging in bacteria with fluorophore-binding aptamer. *Angew Chem Int Ed Engl* 52: 13401-4.

Swiech, L., Heidenreich, M., Banerjee, A., Habib, N., Li, Y., Trombetta, J., Sur, M., and Zhang, F. (2015). In vivo interrogation of gene function in the mammalian brain using CRISPR-Cas9. Nat Biotechnol 33, 102-106.

The ENCODE Project Consortium. 2012. An integrated encyclopedia of DNA elements in the human genome. *Nature* 489: 57-74.

Tourriere, H., Chebli, K., Zekri, L., Courselaud, B., Blanchard, J. M., Bertrand, E., and Tazi, J. (2003). The RasGAP-associated endoribonuclease G3BP assembles stress granules. J Cell Biol 160, 823-831.

Tyagi S, Kramer F R. 1996. Molecular beacons: Probes that fluoresce upon hybridization. *Nat Biotechnol* 14: 303-8.

Unsworth, H., Raguz, S., Edwards, H. J., Higgins, C. F., and Yague, E. (2010). mRNA escape from stress granule sequestration is dictated by localization to the endoplasmic reticulum. FASEB J 24, 3370-3380.

Urnov, F. D., Rebar, E. J., Holmes, M. C., Zhang, H. S., and Gregory, P. D. (2010). Genome editing with engineered zinc finger nucleases. Nat Rev Genet 11, 636-646.

Wang X, Zamore P D, Hall T M. 2001. Crystal structure of a Pumilio homology domain. *Mol Cell* 7: 855-65.

Wang, X., McLachlan, J., Zamore, P. D., and Hall, T. M. (2002). Modular recognition of RNA by a human pumilio-homology domain. Cell 110, 501-512.

Wang Y, Cheong C G, Hall T M, Wang Z. 2009. Engineering splicing factors with designed specificities. *Nat Methods* 6: 825-830.

Wernersson, R., and Nielsen, H. B. (2005). OligoWiz 2.0—integrating sequence feature annotation into the design of microarray probes. Nucleic Acids Res 33, W611-615.

Weyn-Vanhentenryck S M, Mele A, Yan Q, Sun S, et al. 2014. HITS-CLIP and integrative modeling define the Rbfox splicing-regulatory network linked to brain development and autism. *Cell Rep* 6: 1139-52.

Wheeler T M, Lueck J D, Swanson, M S, Dirksen R T, Thornton C A. Correction of ClC-1 splicing eliminates chloride channelopathy and myotonia in mouse models of myotonic dystrophy. J Clin Invest. 2007;117(12):3952-7.

Wiedenheft, B., Sternberg, S. H., and Doudna, J. A. (2012). RNA-guided genetic silencing systems in bacteria and archaea. Nature 482, 331-338.

Wright A V, Sternberg S H, Taylor D W, Staahl B T, Bardales J A, Kornfeld J E, Doudna J A. Rational design of a split-Cas9 enzyme complex. Proc Natl Acad Sci USA. 2015;112(10):2984-9.

Wu X, Kriz A J, Sharp P A. Target specificity of the CRISPR-Cas9 system. *Quant Biol.* 2014;2(2):59-70.

Yang, D., Xu, J., Zhu, T., Fan, J., Lai, L., Zhang, J., and Chen, Y. E. (2014). Effective gene targeting in rabbits using RNA-guided Cas9 nucleases. J Mol Cell Biol 6, 97-99.

Yang Y, Wang L, Bell P, McMenamin D, He Z, White J, Yu H, Xu C, Morizono H, Musunuru K, Batshaw M L, Wilson J M. A dual AAV system enables the Cas9-mediated correction of a metabolic liver disease in newborn mice. Nat. Biotechnol. 2016;34(3):334-8.

Yeo G W, Confal N G, Liang T Y, Peng G E, et al. 2009. An RNA code for the FOX2 splicing regulator revealed by mapping RNA-protein interactions in stem cells. *Nat Struct Mol. Biol* 16: 130-7.

Zhang W, Wang Y, Doug S, Choudhury R, et al. 2014. Treatment of type 1 myotonic dystrophy by engineering site-specific RNA endonucleases that target (CUG)(n) repeats. *Molecular therapy: J Am Soc Gene Ther* 22: 312-20.

Zuris, J. A., Thompson, D. B., Shu, Y., Guilinger, J. P., Bessen, J. L., Hu, J. H., Maeder, M. L., Joung, J. K., Chen, Z. Y., and Liu, D. R. (2015). Cationic lipid-mediated delivery of proteins enables efficient protein-based genome editing in vitro and in vivo. Nat Biotechnol 33, 73-80.

What is claimed is:

1. A method of altering target RNA in a cell, the method comprising:
   administering to the cell a 2-component RNA targeting system comprising:
   (a) nucleic acid sequence encoding a truncated nuclease-inactive RNA-targeted Cas9 (RCas9) polypeptide, wherein the truncated nuclease-inactive RCas9 polypeptide lacks all or part of its HNH domain compared to the wild-type (WT) Cas9 protein; and
   (b) a single guide RNA (sgRNA) sequence comprising:
   (i) on its 5' end, an RNA sequence that hybridizes to or binds to the target RNA sequence comprising a repeat sequence selected from the group consisting of CUG, CCUG, CAG, and GGGGCC; and
   (ii) on its 3' end, an RNA sequence capable of binding to or associating with the truncated nuclease-inactive RCas9 polypeptide, wherein the RNA sequence capable of binding to or associating with the truncated nuclease-inactive RCas9 polypeptide comprises or is derived from the wild type guide RNA of an archaeal or a bacterial organism from which the truncated nuclease-inactive RCas9 is derived,
   wherein the RNA targeting system exclusively recognizes and alters the target RNA in the cell in the absence of PAMmers.

2. The method of claim 1, wherein the truncated nuclease-inactive RCas9 is missing residues 775-909 from full-length Cas9 protein.

3. The method of claim 1, wherein the sequences of a) and b) are in a single vector.

4. The method of claim 3, wherein the sequences of a) and b) are a size of less than about 4.5 kb, or a size of less than about 4.7 kb.

5. The method of claim 1, wherein the nuclease-inactive RCas9 polypeptide and the RNA sequence capable of binding to or associating with the nuclease-inactive RCas9 polypeptide comprises or is derived from *Haloferax mediteranii, Mycobacterium tuberculosis, Francisella tularensis* subsp. *novicida, Pasteurella multocida, Neisseria meningitidis, Campylobacter jejune, Streptococcus thermophilus, Campylobacterlari, Mycoplasma gallisepticum* str. F, *Nitratifractor salsuginis* str. DSM 16511, *Parvibaculum lavamentivorans, Roseburia intestinalis, Neisseria cinerea, Gluconacetobacter diazotrophicus, Azospirillum* B510, *Sphaerochaeta globus* str. Buddy, *Flavobacterium columnare, Fluviicola taffensis, Bacteroides coprophilus, Mycoplasma mobile, Lactobacillus farciminis, Streptococcus pasteurianus, Lactobacillus johnsonii, Staphylococcus pseudintermedius, Filifactor alocis, Treponema denticola, Legionella pneumophila* str. Paris, *Sutterella wadsworthensis, Corynebacter diphtheriae, Streptococcus aureus*, and *Natronobacterium gregoryi*.

6. The method of claim 1, wherein the 5' end of the sgRNA is between about 15 to 25 nucleotides in length, and wherein the RNA sequence of the RCas9 polypeptide scaffold is between about 85 and 100 nucleotides in length.

7. The method of claim 1, wherein the truncated nuclease-inactive RCas9 polypeptide is linked to an effector polypeptide, a targeting agent, an enzyme, a detectable moiety, or a combination thereof.

8. The method of claim 7, wherein the effector polypeptide comprises an RNA modifying polypeptide.

9. The method of claim 7, wherein the targeting agent comprises:
(a) a cytoplasmic polyadenylation element binding protein (CPEB), a zinc finger binding protein (ZBP), TIA-1, PSF, the DNA-binding domain (DBD) of PSF, fragile X mental retardation protein (FMRP), IMP1, IMP2, 1MP3, a cytoskeleton binding protein, a transmembrane protein, or
(b) an engineered protein comprising a combination of domains of the proteins of (a).

10. The method of claim 8, wherein the RNA modifying polypeptide comprises a splicing factor or an RNA splicing domain, a RBFOX2 domain-containing protein, a protein known to influence RNA splicing, an RNA cleaving domain or a PIN domain-containing protein.

11. The method of claim 10, wherein the RNA cleaving domain comprises an endonuclease.

12. The method of claim 11, wherein the truncated nuclease-inactive RCas9 lacks all of its HNH domain.

13. The method of claim 1, wherein the sequence of a) comprises a promoter.

14. The method of claim 1, wherein the sequence of b) comprises the U6 polymerase III promoter.

15. The method of claim 1, wherein the sequence of b) comprises one or more point mutations that remove the transcription termination sequence.

16. A method of altering target RNA in a cell, the method comprising administering to the cell an engineered nucleoprotein complex comprising:
(a) a nuclease-inactive RNA-targeted Cas9 (RCas9) polypeptide, wherein the nuclease-inactive RCas9 polypeptide:
(i) lacks all or part of an HNH domain, all or part of RuvC nuclease domain, all or part of a Cas9 polypeptide DNase active site, all or part of a $\beta\beta\alpha$-metal fold comprising the Cas9 polypeptide active site, or a combination thereof as compared to the corresponding wild type (WT) Cas9 polypeptide;
(ii) lacks DNase, DNA cleaving activity, or nickase activity; and
(iii) has a reduced polypeptide size as compared to the corresponding wild type (WT) Cas9 polypeptide that permits packaging of the RCas9-coding nucleotide in a delivery vector;
and
(b) a recombinant or synthetic single guide RNA (sgRNA) comprising:
(i) on its 5' end, an RNA sequence that hybridizes to or binds to the target RNA sequence, wherein the target RNA sequence comprises a repeat sequence, wherein the RNA sequence that hybridizes to or binds to the target RNA sequence is capable of hybridizing or binding to the repeat sequence, and wherein the repeat sequence is CUG, CCUG, CAG, GGGGCC, or any combination thereof;
and
(ii) on its 3' end:
(1) an RNA sequence capable of binding to or associating with the nuclease-inactive RCas9 polypeptide, or
(2) a linker that covalently links or non-covalently links the 5' RNA sequence of the sgRNA with the nuclease-inactive RCas9 polypeptide,
wherein the engineered nucleoprotein complex recognizes and alters target RNA in the cell in the absence of a PAMmer.

17. The method of claim 16, wherein the nuclease-inactive RCas9 polypeptide is covalently linked to an effector polypeptide, a detectable moiety, or an RNA modifying polypeptide.

18. The method of claim 16, wherein said RNA modifying polypeptide comprises a splicing factor or an RNA splicing domain, a RBFOX2 domain-containing protein, an RNA cleaving domain or a PIN domain-containing protein.

19. The method of claim 16, wherein said sgRNA comprises one or more point mutations that remove the transcription termination sequence or a portion thereof.

20. The method of claim 16, wherein said sgRNA comprises one or more of methylphosphonate, thiophosponoaceteate, and phosphorothioate linkages that reduce nuclease activity on the target RNA.

\* \* \* \* \*

SEQUENCE LISTING

<160> NUMBER OF SEQ ID NOS: 39

<210> SEQ ID NO 1
<211> LENGTH: 20
<212> TYPE: RNA
<213> ORGANISM: Artificial Sequence
<220> FEATURE:
<223> OTHER INFORMATION: Guide sequence

<400> SEQUENCE: 1
ggacucccca gcagugaggg                                           20

<210> SEQ ID NO 2
<211> LENGTH: 20
<212> TYPE: RNA
<213> ORGANISM: Artificial Sequence
<220> FEATURE:
<223> OTHER INFORMATION: Guide sequence

<400> SEQUENCE: 2
ggacucccca gcaguguccc                                           20

<210> SEQ ID NO 3
<211> LENGTH: 20
<212> TYPE: RNA
<213> ORGANISM: Artificial Sequence
<220> FEATURE:
<223> OTHER INFORMATION: Guide sequence

<400> SEQUENCE: 3
ggacucccca gcucacuccc                                           20

<210> SEQ ID NO 4
<211> LENGTH: 20
<212> TYPE: RNA
<213> ORGANISM: Artificial Sequence
<220> FEATURE:
<223> OTHER INFORMATION: Guide sequence

<400> SEQUENCE: 4
ggacucccgu cgucacuccc                                           20

<210> SEQ ID NO 5
<211> LENGTH: 39
<212> TYPE: DNA
<213> ORGANISM: Artificial Sequence
<220> FEATURE:
<223> OTHER INFORMATION: GAPDH mRNA 3'UTR

<400> SEQUENCE: 5
cacaagagga agagagagac cctcactgct ggggagtcc                      39

<210> SEQ ID NO 6
<211> LENGTH: 39
<212> TYPE: DNA
<213> ORGANISM: Artificial Sequence
<220> FEATURE:
<223> OTHER INFORMATION: Beta-actin mRNA 3'UTR

<400> SEQUENCE: 6
gaaggtgaca gcagtcggtt ggagcgagca tcccccaaa                         39

<210> SEQ ID NO 7
<211> LENGTH: 39
<212> TYPE: DNA
<213> ORGANISM: Artificial Sequence
<220> FEATURE:
<223> OTHER INFORMATION: Gamma2 bacteriophage

<400> SEQUENCE: 7
gctcaatttt gacagcggtc atggcattcc acttatcac                         39

<210> SEQ ID NO 8
<211> LENGTH: 40
<212> TYPE: DNA
<213> ORGANISM: Artificial Sequence
<220> FEATURE:
<223> OTHER INFORMATION: PAMmer, beta-actin 3'UTR

<400> SEQUENCE: 8
mucmgcmucm camuggmgam ctmgcmugmu cmacmctmuc                        40

<210> SEQ ID NO 9
<211> LENGTH: 114
<212> TYPE: DNA
<213> ORGANISM: Artificial Sequence
<220> FEATURE:
<223> OTHER INFORMATION: sgRNA, beta-actin 3'UTR

<400> SEQUENCE: 9
gtttggggga tgctcgctcc agtttaagag ctatgctgga acagcatag caagtttaaa   60 taaggctagt ccgttatcaa cttgaaaaag tggcaccgag tcggtgcttt tttt        114

<210> SEQ ID NO 10
<211> LENGTH: 40
<212> TYPE: DNA
<213> ORGANISM: Artificial Sequence
<220> FEATURE:
<223> OTHER INFORMATION: PAMmer, GAPDH 3'UTR

<400> SEQUENCE: 10
magmugmagm ggmcggmctm ctmctmucmc tmctmugmug                        40

<210> SEQ ID NO 11
<211> LENGTH: 113
<212> TYPE: DNA
<213> ORGANISM: Artificial Sequence
<220> FEATURE:
<223> OTHER INFORMATION: sgRNA, GAPDH 3'UTR

<400> SEQUENCE: 11
ggactcccca gcagtgaggg gtttaagagc tatgctggaa acagcatagc aagtttaaat  60
aaggctagtc cgttatcaac ttgaaaaagt ggcaccgagt cggtgctttt ttt         113

<210> SEQ ID NO 12

```
<211> LENGTH: 40
<212> TYPE: DNA
<213> ORGANISM: Artificial Sequence
<220> FEATURE:
<223> OTHER INFORMATION: PAMmer, gamma2 bacteriophage

<400> SEQUENCE: 12
matmgcmcam ugmuggmgcm ugmucmaama amutmgamgc                      40

<210> SEQ ID NO 13
<211> LENGTH: 113
<212> TYPE: DNA
<213> ORGANISM: Artificial Sequence
<220> FEATURE:
<223> OTHER INFORMATION: sgRNA, gamma2 bacteriophage

<400> SEQUENCE: 13
gtgataagtg gaatgccatg gtttaagagc tatgctggaa acagcatagc aagtttaaat      60
aaggctagtc cgttatcaac ttgaaaaagt ggcaccgagt cggtgctttt ttt            113

<210> SEQ ID NO 14
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 14
aaggtgaagg tcggagtcaa c                                           21

<210> SEQ ID NO 15
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 15
ggggtcattg atggcaacaa ta                                          22

<210> SEQ ID NO 16
<211> LENGTH: 20
<212> TYPE: DNA
<213> ORGANISM: Artificial Sequence
<220> FEATURE:
<223> OTHER INFORMATION: Renilla luciferase forward primer

<400> SEQUENCE: 16
gtaacgctgc ctccagctac                                             20

<210> SEQ ID NO 17
<211> LENGTH: 20
<212> TYPE: DNA
<213> ORGANISM: Artificial Sequence
<220> FEATURE:
<223> OTHER INFORMATION: Renilla luciferase reverse primer

<400> SEQUENCE: 17
gtggcccaca aagatgattt                                             20

<210> SEQ ID NO 18
<211> LENGTH: 4
<212> TYPE: DNA
<213> ORGANISM: Artificial Sequence
<220> FEATURE:
<223> OTHER INFORMATION: sgRNA target
```

```
<400> SEQUENCE: 18 cctg                                                                    4

<210> SEQ ID NO 19
<211> LENGTH: 6
<212> TYPE: DNA
<213> ORGANISM: Artificial Sequence
<220> FEATURE:
<223> OTHER INFORMATION: sgRNA target

<400> SEQUENCE: 19 ggggcc                                                                  6

<210> SEQ ID NO 20
<211> LENGTH: 40
<212> TYPE: DNA
<213> ORGANISM: Artificial Sequence
<220> FEATURE:
<223> OTHER INFORMATION: PAMmer, CAG repeat

<400> SEQUENCE: 20
mtgmctmgcm tgmtggmctm gcmtgmctmg cmtgmctmgc                             40

<210> SEQ ID NO 21
<211> LENGTH: 114
<212> TYPE: DNA
<213> ORGANISM: Artificial Sequence
<220> FEATURE:
<223> OTHER INFORMATION: sgRNA, CAG repeat

<400> SEQUENCE: 21
gtgctgctgc tgctgctgct gguuuaagag cuaugcugga aacagcauag caaguuuaaa       60
uaaggcuagu ccguuaucaa cuugaaaaag uggcaccgag ucggugcuuu uuuu            114

<210> SEQ ID NO 22
<211> LENGTH: 429
<212> TYPE: DNA
<213> ORGANISM: Artificial Sequence
<220> FEATURE:
<223> OTHER INFORMATION: U6 promoter-2xBbsi-sgRNA scaffold

<400> SEQUENCE: 22
tgtacaaaaa agcaggcttt aaaggaacca attcagtcga ctggatccgg taccaaggtc       60
gggcaggaag agggcctatt tcccatgatt ccttcatatt tgcatatacg atacaaggct     120
gttagagaga taattagaat taatttgact gtaaacacaa agatattagt acaaaatacg     180
tgacgtagaa agtaataatt tcttgggtag tttgcagttt taaaattatg ttttaaaatg     240
gactatcata tgcttaccgt aacttgaaag tatttcgatt tcttggcttt atatatcttg     300
tggaaaggac gaaacaccgg gtcttcgaga agacctgttt aagagctatg ctggaaacag     360
catagcaagt ttaaataagg ctagtccgtt atcaacttga aaagtggca ccgagtcggt      420 gctttttt                                                             429

<210> SEQ ID NO 23
<211> LENGTH: 30
<212> TYPE: DNA
<213> ORGANISM: Artificial Sequence
<220> FEATURE:
<223> OTHER INFORMATION: CAG 10 probe
```

<400> SEQUENCE: 23
cagcagcagc agcagcagca gcagcagcag                30

<210> SEQ ID NO 24
<211> LENGTH: 154
<212> TYPE: PRT
<213> ORGANISM: Artificial Sequence
<220> FEATURE:
<223> OTHER INFORMATION: Split Venus (N-terminal portion, residues
      2-155) (I152L reduced background complementation mutant)

<400> SEQUENCE: 24

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Leu Thr Ala
145                 150

<210> SEQ ID NO 25
<211> LENGTH: 172
<212> TYPE: PRT
<213> ORGANISM: Artificial Sequence
<220> FEATURE:
<223> OTHER INFORMATION: Split Venus (N-terminal portion, residues
      2-173)

<400> SEQUENCE: 25

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Leu Ile Cys
        35                  40                  45

Thr Thr Gly Lys Leu Pro Val Pro Trp Pro Thr Leu Val Thr Thr Leu
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

```
Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu
                165                 170

<210> SEQ ID NO 26
<211> LENGTH: 99
<212> TYPE: PRT
<213> ORGANISM: Artificial Sequence
<220> FEATURE:
<223> OTHER INFORMATION: Split Venus (C-terminal portion, Feature of aa
      16-99 as residues 155-238)

<400> SEQUENCE: 26

Ala Cys Lys Ile Pro Asn Asp Leu Lys Gln Lys Val Met Asn His Asp
1               5                   10                  15

Lys Gln Lys Asn Gly Ile Lys Ala Asn Phe Lys Ile Arg His Asn Ile
            20                  25                  30

Glu Asp Gly Gly Val Gln Leu Ala Asp His Tyr Gln Gln Asn Thr Pro
        35                  40                  45

Ile Gly Asp Gly Pro Val Leu Leu Pro Asp Asn His Tyr Leu Ser Tyr
    50                  55                  60

Gln Ser Lys Leu Ser Lys Asp Pro Asn Glu Lys Arg Asp His Met Val
65                  70                  75                  80

Leu Leu Glu Phe Val Thr Ala Ala Gly Ile Thr Leu Gly Met Asp Glu
                85                  90                  95

Leu Tyr Lys

<210> SEQ ID NO 27
<211> LENGTH: 183
<212> TYPE: PRT
<213> ORGANISM: Artificial Sequence
<220> FEATURE:
<223> OTHER INFORMATION: PIN domain (from human SMG6)

<400> SEQUENCE: 27

Gln Met Glu Leu Glu Ile Arg Pro Leu Phe Leu Val Pro Asp Thr Asn
1               5                   10                  15

Gly Phe Ile Asp His Leu Ala Ser Leu Ala Arg Leu Leu Glu Ser Arg
            20                  25                  30

Lys Tyr Ile Leu Val Val Pro Leu Ile Val Ile Asn Glu Leu Asp Gly
        35                  40                  45

Leu Ala Lys Gly Gln Glu Thr Asp His Arg Ala Gly Gly Tyr Ala Arg
    50                  55                  60

Val Val Gln Glu Lys Ala Arg Lys Ser Ile Glu Phe Leu Glu Gln Arg
65                  70                  75                  80

Phe Glu Ser Arg Asp Ser Cys Leu Arg Ala Leu Thr Ser Arg Gly Asn
                85                  90                  95

Glu Leu Glu Ser Ile Ala Phe Arg Ser Glu Asp Ile Thr Gly Gln Leu
            100                 105                 110

Gly Asn Asn Asp Asp Leu Ile Leu Ser Cys Cys Leu His Tyr Cys Lys
        115                 120                 125
```

```
Asp Lys Ala Lys Asp Phe Met Pro Ala Ser Lys Glu Glu Pro Ile Arg
    130                 135                 140

Leu Leu Arg Glu Val Val Leu Leu Thr Asp Asp Arg Asn Leu Arg Val
145                 150                 155                 160

Lys Ala Leu Thr Arg Asn Val Pro Val Arg Asp Ile Pro Ala Phe Leu
                165                 170                 175

Thr Trp Ala Gln Val Gly Ser
            180

<210> SEQ ID NO 28
<211> LENGTH: 418
<212> TYPE: PRT
<213> ORGANISM: Artificial Sequence
<220> FEATURE:
<223> OTHER INFORMATION: Human RBFOX1

<400> SEQUENCE: 28

Met Leu Ala Ser Gln Gly Val Leu Leu His Pro Tyr Gly Val Pro Met
1               5                   10                  15

Ile Val Pro Ala Ala Pro Tyr Leu Pro Gly Leu Ile Gln Gly Asn Gln
            20                  25                  30

Glu Ala Ala Ala Ala Pro Asp Thr Met Ala Gln Pro Tyr Ala Ser Ala
        35                  40                  45

Gln Phe Ala Pro Pro Gln Asn Gly Ile Pro Ala Glu Tyr Thr Ala Pro
    50                  55                  60

His Pro His Pro Ala Pro Glu Tyr Thr Gly Gln Thr Thr Val Pro Glu
65                  70                  75                  80

His Thr Leu Asn Leu Tyr Pro Pro Ala Gln Thr His Ser Glu Gln Ser
                85                  90                  95

Pro Ala Asp Thr Ser Ala Gln Thr Val Ser Gly Thr Ala Thr Gln Thr
            100                 105                 110

Asp Asp Ala Ala Pro Thr Asp Gly Gln Pro Gln Thr Gln Pro Ser Glu
        115                 120                 125

Asn Thr Glu Asn Lys Ser Gln Pro Lys Arg Leu His Val Ser Asn Ile
    130                 135                 140

Pro Phe Arg Phe Arg Asp Pro Asp Leu Arg Gln Met Phe Gly Gln Phe
145                 150                 155                 160

Gly Lys Ile Leu Asp Val Glu Ile Ile Phe Asn Glu Arg Gly Ser Lys
                165                 170                 175

Gly Phe Gly Phe Val Thr Phe Glu Asn Ser Ala Asp Ala Asp Arg Ala
            180                 185                 190

Arg Glu Lys Leu His Gly Thr Val Val Glu Gly Arg Lys Ile Glu Val
        195                 200                 205

Asn Asn Ala Thr Ala Arg Val Met Thr Asn Lys Lys Thr Val Asn Pro
    210                 215                 220

Tyr Thr Asn Gly Trp Lys Leu Asn Pro Val Val Gly Ala Val Tyr Ser
225                 230                 235                 240

Pro Glu Phe Tyr Ala Gly Thr Val Leu Leu Cys Gln Ala Asn Gln Glu
                245                 250                 255

Gly Ser Ser Met Tyr Ser Ala Pro Ser Ser Leu Val Tyr Thr Ser Ala
            260                 265                 270

Met Pro Gly Phe Pro Tyr Pro Ala Ala Thr Ala Ala Ala Ala Tyr Arg
        275                 280                 285

Gly Ala His Leu Arg Gly Arg Gly Arg Thr Val Tyr Asn Thr Phe Arg
    290                 295                 300
```

```
Ala Ala Ala Pro Pro Pro Ile Pro Ala Tyr Gly Gly Val Val Tyr
305                 310                 315                 320

Gln Glu Pro Val Tyr Gly Asn Lys Leu Leu Gln Gly Gly Tyr Ala Ala
                325                 330                 335

Tyr Arg Tyr Ala Gln Pro Thr Pro Ala Thr Ala Ala Tyr Ser Asp
            340                 345                 350

Ser Tyr Gly Arg Val Tyr Ala Ala Asp Pro Tyr His His Ala Leu Ala
        355                 360                 365

Pro Ala Pro Thr Tyr Gly Val Gly Ala Met Asn Ala Phe Ala Pro Leu
    370                 375                 380

Thr Asp Ala Lys Thr Arg Ser His Ala Asp Asp Val Gly Leu Val Leu
385                 390                 395                 400

Ser Ser Leu Gln Ala Ser Ile Tyr Arg Gly Gly Tyr Asn Arg Phe Ala
                405                 410                 415

Pro Tyr

<210> SEQ ID NO 29
<211> LENGTH: 380
<212> TYPE: PRT
<213> ORGANISM: Artificial Sequence
<220> FEATURE:
<223> OTHER INFORMATION: Human RBFOX2

<400> SEQUENCE: 29

Met Glu Lys Lys Lys Met Val Thr Gln Gly Asn Gln Glu Pro Thr Thr
1               5                   10                  15

Thr Pro Asp Ala Met Val Gln Pro Phe Thr Thr Ile Pro Phe Pro Pro
            20                  25                  30

Pro Pro Gln Asn Gly Ile Pro Thr Glu Tyr Gly Val Pro His Thr Gln
        35                  40                  45

Asp Tyr Ala Gly Gln Thr Gly Glu His Asn Leu Thr Leu Tyr Gly Ser
    50                  55                  60

Thr Gln Ala His Gly Glu Gln Ser Ser Asn Ser Pro Ser Thr Gln Asn
65                  70                  75                  80

Gly Ser Leu Thr Thr Glu Gly Gly Ala Gln Thr Asp Gly Gln Gln Ser
                85                  90                  95

Gln Thr Gln Ser Ser Glu Asn Ser Glu Ser Lys Ser Thr Pro Lys Arg
            100                 105                 110

Leu His Val Ser Asn Ile Pro Phe Arg Phe Arg Asp Pro Asp Leu Arg
        115                 120                 125

Gln Met Phe Gly Gln Phe Gly Lys Ile Leu Asp Val Glu Ile Ile Phe
    130                 135                 140

Asn Glu Arg Gly Ser Lys Gly Phe Gly Phe Val Thr Phe Glu Asn Ser
145                 150                 155                 160

Ala Asp Ala Asp Arg Ala Arg Glu Lys Leu His Gly Thr Val Val Glu
                165                 170                 175

Gly Arg Lys Ile Glu Val Asn Asn Ala Thr Ala Arg Val Met Thr Asn
            180                 185                 190

Lys Lys Met Val Thr Pro Tyr Ala Asn Gly Trp Lys Leu Ser Pro Val
        195                 200                 205

Val Gly Ala Val Tyr Gly Pro Glu Leu Tyr Ala Ala Ser Ser Phe Gln
    210                 215                 220

Ala Asp Val Ser Leu Gly Asn Asp Ala Ala Val Pro Leu Ser Gly Arg
225                 230                 235                 240
```

```
Gly Gly Ile Asn Thr Tyr Ile Pro Leu Ile Ser Leu Pro Leu Val Pro
                245                 250                 255

Gly Phe Pro Tyr Pro Thr Ala Ala Thr Thr Ala Ala Ala Phe Arg Gly
            260                 265                 270

Ala His Leu Arg Gly Arg Gly Arg Thr Val Tyr Gly Ala Val Arg Ala
            275                 280                 285

Val Pro Pro Thr Ala Ile Pro Ala Tyr Pro Gly Val Val Tyr Gln Asp
    290                 295                 300

Gly Phe Tyr Gly Ala Asp Leu Tyr Gly Gly Ala Ala Tyr Arg Tyr
305                 310                 315                 320

Ala Gln Pro Ala Thr Ala Thr Ala Ala Thr Ala Ala Ala Ala Ala
            325                 330                 335

Ala Ala Tyr Ser Asp Gly Tyr Gly Arg Val Tyr Thr Ala Asp Pro Tyr
            340                 345                 350

His Ala Leu Ala Pro Ala Ala Ser Tyr Gly Val Gly Ala Val Ala Ser
            355                 360                 365

Leu Tyr Arg Gly Gly Tyr Ser Arg Phe Ala Pro Tyr
            370                 375                 380

<210> SEQ ID NO 30
<211> LENGTH: 238
<212> TYPE: PRT
<213> ORGANISM: Artificial Sequence
<220> FEATURE:
<223> OTHER INFORMATION: EGFP

<400> SEQUENCE: 30

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220
```

```
Thr Ala Ala Gly Ile Thr Leu Gly Met Asp Glu Leu Tyr Lys
225                 230                 235

<210> SEQ ID NO 31
<211> LENGTH: 1382
<212> TYPE: PRT
<213> ORGANISM: Streptococcus pyogenes

<400> SEQUENCE: 31

Arg Thr Met Asp Lys Lys Tyr Ser Ile Gly Leu Ala Ile Gly Thr Asn
1               5                   10                  15

Ser Val Gly Trp Ala Val Ile Thr Asp Glu Tyr Lys Val Pro Ser Lys
            20                  25                  30

Lys Phe Lys Val Leu Gly Asn Thr Asp Arg His Ser Ile Lys Lys Asn
        35                  40                  45

Leu Ile Gly Ala Leu Leu Phe Asp Ser Gly Glu Thr Ala Glu Ala Thr
    50                  55                  60

Arg Leu Lys Arg Thr Ala Arg Arg Arg Tyr Thr Arg Arg Lys Asn Arg
65                  70                  75                  80

Ile Cys Tyr Leu Gln Glu Ile Phe Ser Asn Glu Met Ala Lys Val Asp
                85                  90                  95

Asp Ser Phe Phe His Arg Leu Glu Glu Ser Phe Leu Val Glu Glu Asp
            100                 105                 110

Lys Lys His Glu Arg His Pro Ile Phe Gly Asn Ile Val Asp Glu Val
        115                 120                 125

Ala Tyr His Glu Lys Tyr Pro Thr Ile Tyr His Leu Arg Lys Lys Leu
    130                 135                 140

Val Asp Ser Thr Asp Lys Ala Asp Leu Arg Leu Ile Tyr Leu Ala Leu
145                 150                 155                 160

Ala His Met Ile Lys Phe Arg Gly His Phe Leu Ile Glu Gly Asp Leu
                165                 170                 175

Asn Pro Asp Asn Ser Asp Val Asp Lys Leu Phe Ile Gln Leu Val Gln
            180                 185                 190

Thr Tyr Asn Gln Leu Phe Glu Glu Asn Pro Ile Asn Ala Ser Gly Val
        195                 200                 205

Asp Ala Lys Ala Ile Leu Ser Ala Arg Leu Ser Lys Ser Arg Arg Leu
    210                 215                 220

Glu Asn Leu Ile Ala Gln Leu Pro Gly Glu Lys Lys Asn Gly Leu Phe
225                 230                 235                 240

Gly Asn Leu Ile Ala Leu Ser Leu Gly Leu Thr Pro Asn Phe Lys Ser
                245                 250                 255

Asn Phe Asp Leu Ala Glu Asp Ala Lys Leu Gln Leu Ser Lys Asp Thr
            260                 265                 270

Tyr Asp Asp Asp Leu Asp Asn Leu Leu Ala Gln Ile Gly Asp Gln Tyr
        275                 280                 285

Ala Asp Leu Phe Leu Ala Ala Lys Asn Leu Ser Asp Ala Ile Leu Leu
    290                 295                 300

Ser Asp Ile Leu Arg Val Asn Thr Glu Ile Thr Lys Ala Pro Leu Ser
305                 310                 315                 320

Ala Ser Met Ile Lys Arg Tyr Asp Glu His His Gln Asp Leu Thr Leu
                325                 330                 335

Leu Lys Ala Leu Val Arg Gln Gln Leu Pro Glu Lys Tyr Lys Glu Ile
            340                 345                 350

Phe Phe Asp Gln Ser Lys Asn Gly Tyr Ala Gly Tyr Ile Asp Gly Gly
        355                 360                 365
```

```
Ala Ser Gln Glu Glu Phe Tyr Lys Phe Ile Lys Pro Ile Leu Glu Lys
    370                 375                 380

Met Asp Gly Thr Glu Glu Leu Leu Val Lys Leu Asn Arg Glu Asp Leu
385                 390                 395                 400

Leu Arg Lys Gln Arg Thr Phe Asp Asn Gly Ser Ile Pro His Gln Ile
            405                 410                 415

His Leu Gly Glu Leu His Ala Ile Leu Arg Arg Gln Glu Asp Phe Tyr
                420                 425                 430

Pro Phe Leu Lys Asp Asn Arg Glu Lys Ile Glu Lys Ile Leu Thr Phe
            435                 440                 445

Arg Ile Pro Tyr Tyr Val Gly Pro Leu Ala Arg Gly Asn Ser Arg Phe
    450                 455                 460

Ala Trp Met Thr Arg Lys Ser Glu Glu Thr Ile Thr Pro Trp Asn Phe
465                 470                 475                 480

Glu Glu Val Val Asp Lys Gly Ala Ser Ala Gln Ser Phe Ile Glu Arg
                485                 490                 495

Met Thr Asn Phe Asp Lys Asn Leu Pro Asn Glu Lys Val Leu Pro Lys
                500                 505                 510

His Ser Leu Leu Tyr Glu Tyr Phe Thr Val Tyr Asn Glu Leu Thr Lys
            515                 520                 525

Val Lys Tyr Val Thr Glu Gly Met Arg Lys Pro Ala Phe Leu Ser Gly
    530                 535                 540

Glu Gln Lys Lys Ala Ile Val Asp Leu Leu Phe Lys Thr Asn Arg Lys
545                 550                 555                 560

Val Thr Val Lys Gln Leu Lys Glu Asp Tyr Phe Lys Lys Ile Glu Cys
                565                 570                 575

Phe Asp Ser Val Glu Ile Ser Gly Val Glu Asp Arg Phe Asn Ala Ser
            580                 585                 590

Leu Gly Thr Tyr His Asp Leu Leu Lys Ile Ile Lys Asp Lys Asp Phe
    595                 600                 605

Leu Asp Asn Glu Glu Asn Glu Asp Ile Leu Glu Asp Ile Val Leu Thr
610                 615                 620

Leu Thr Leu Phe Glu Asp Arg Glu Met Ile Glu Glu Arg Leu Lys Thr
625                 630                 635                 640

Tyr Ala His Leu Phe Asp Asp Lys Val Met Lys Gln Leu Lys Arg Arg
            645                 650                 655

Arg Tyr Thr Gly Trp Gly Arg Leu Ser Arg Lys Leu Ile Asn Gly Ile
    660                 665                 670

Arg Asp Lys Gln Ser Gly Lys Thr Ile Leu Asp Phe Leu Lys Ser Asp
            675                 680                 685

Gly Phe Ala Asn Arg Asn Phe Met Gln Leu Ile His Asp Asp Ser Leu
    690                 695                 700

Thr Phe Lys Glu Asp Ile Gln Lys Ala Gln Val Ser Gly Gln Gly Asp
705                 710                 715                 720

Ser Leu His Glu His Ile Ala Asn Leu Ala Gly Ser Pro Ala Ile Lys
                725                 730                 735

Lys Gly Ile Leu Gln Thr Val Lys Val Val Asp Glu Leu Val Lys Val
            740                 745                 750

Met Gly Arg His Lys Pro Glu Asn Ile Val Ile Glu Met Ala Arg Glu
    755                 760                 765

Asn Gln Thr Thr Gln Lys Gly Gln Lys Asn Ser Arg Glu Arg Met Lys
770                 775                 780
```

-continued

Arg Ile Glu Glu Gly Ile Lys Glu Leu Gly Ser Gln Ile Leu Lys Glu
785                 790                 795                 800

His Pro Val Glu Asn Thr Gln Leu Gln Asn Glu Lys Leu Tyr Leu Tyr
            805                 810                 815

Tyr Leu Gln Asn Gly Arg Asp Met Tyr Val Asp Gln Glu Leu Asp Ile
        820                 825                 830

Asn Arg Leu Ser Asp Tyr Asp Val Asp Ala Ile Val Pro Gln Ser Phe
    835                 840                 845

Leu Lys Asp Asp Ser Ile Asp Asn Lys Val Leu Thr Arg Ser Asp Lys
850                 855                 860

Asn Arg Gly Lys Ser Asp Asn Val Pro Ser Glu Glu Val Val Lys Lys
865                 870                 875                 880

Met Lys Asn Tyr Trp Arg Gln Leu Leu Asn Ala Lys Leu Ile Thr Gln
            885                 890                 895

Arg Lys Phe Asp Asn Leu Thr Lys Ala Glu Arg Gly Gly Leu Ser Glu
        900                 905                 910

Leu Asp Lys Ala Gly Phe Ile Arg Gln Leu Val Gln Thr Arg Gln
    915                 920                 925

Ile Thr Lys His Val Ala Gln Ile Leu Asp Ser Arg Met Asn Thr Lys
930                 935                 940

Tyr Asp Glu Asn Asp Lys Leu Ile Arg Glu Val Lys Val Ile Thr Leu
945                 950                 955                 960

Lys Ser Lys Leu Val Ser Asp Phe Arg Lys Asp Phe Gln Phe Tyr Lys
            965                 970                 975

Val Arg Glu Ile Asn Asn Tyr His His Ala His Asp Ala Tyr Leu Asn
        980                 985                 990

Ala Val Val Gly Thr Ala Leu Ile Lys Lys Tyr Pro Lys Leu Glu Ser
    995                 1000                1005

Glu Phe Val Tyr Gly Asp Tyr Lys Val Tyr Asp Val Arg Lys Met Ile
1010                1015                1020

Ala Lys Ser Glu Gln Glu Ile Gly Lys Ala Thr Ala Lys Tyr Phe Phe
1025                1030                1035                1040

Tyr Ser Asn Ile Met Asn Phe Phe Lys Thr Glu Ile Thr Leu Ala Asn
            1045                1050                1055

Gly Glu Ile Arg Lys Arg Pro Leu Ile Glu Thr Asn Gly Glu Thr Gly
        1060                1065                1070

Glu Ile Val Trp Asp Lys Gly Arg Asp Phe Ala Thr Val Arg Lys Val
    1075                1080                1085

Leu Ser Met Pro Gln Val Asn Ile Val Lys Lys Thr Glu Val Gln Thr
1090                1095                1100

Gly Gly Phe Ser Lys Glu Ser Ile Leu Pro Lys Arg Asn Ser Asp Lys
1105                1110                1115                1120

Leu Ile Ala Arg Lys Lys Asp Trp Asp Pro Lys Lys Tyr Gly Gly Phe
            1125                1130                1135

Asp Ser Pro Thr Val Ala Tyr Ser Val Leu Val Val Ala Lys Val Glu
        1140                1145                1150

Lys Gly Lys Ser Lys Lys Leu Lys Ser Val Lys Glu Leu Leu Gly Ile
    1155                1160                1165

Thr Ile Met Glu Arg Ser Ser Phe Glu Lys Asn Pro Ile Asp Phe Leu
1170                1175                1180

Glu Ala Lys Gly Tyr Lys Glu Val Lys Lys Asp Leu Ile Ile Lys Leu
1185                1190                1195                1200

```
Pro Lys Tyr Ser Leu Phe Glu Leu Glu Asn Gly Arg Lys Arg Met Leu
            1205                1210                1215

Ala Ser Ala Gly Glu Leu Gln Lys Gly Asn Glu Leu Ala Leu Pro Ser
        1220                1225                1230

Lys Tyr Val Asn Phe Leu Tyr Leu Ala Ser His Tyr Glu Lys Leu Lys
        1235                1240                1245

Gly Ser Pro Glu Asp Asn Glu Gln Lys Gln Leu Phe Val Glu Gln His
        1250                1255                1260

Lys His Tyr Leu Asp Glu Ile Ile Glu Gln Ile Ser Glu Phe Ser Lys
1265                1270                1275                1280

Arg Val Ile Leu Ala Asp Ala Asn Leu Asp Lys Val Leu Ser Ala Tyr
                1285                1290                1295

Asn Lys His Arg Asp Lys Pro Ile Arg Glu Gln Ala Glu Asn Ile Ile
                1300                1305                1310

His Leu Phe Thr Leu Thr Asn Leu Gly Ala Pro Ala Ala Phe Lys Tyr
                1315                1320                1325

Phe Asp Thr Thr Ile Asp Arg Lys Arg Tyr Thr Ser Thr Lys Glu Val
                1330                1335                1340

Leu Asp Ala Thr Leu Ile His Gln Ser Ile Thr Gly Leu Tyr Glu Thr
1345                1350                1355                1360

Arg Ile Asp Leu Ser Gln Leu Gly Gly Asp Ala Tyr Pro Tyr Asp Val
                1365                1370                1375

Pro Asp Tyr Ala Ser Leu
            1380

<210> SEQ ID NO 32
<211> LENGTH: 1641
<212> TYPE: PRT
<213> ORGANISM: Artificial Sequence
<220> FEATURE:
<223> OTHER INFORMATION: dCas9-2xNLS-EGFP

<400> SEQUENCE: 32

Arg Thr Met Asp Lys Lys Tyr Ser Ile Gly Leu Ala Ile Gly Thr Asn
1               5                   10                  15

Ser Val Gly Trp Ala Val Ile Thr Asp Glu Tyr Lys Val Pro Ser Lys
            20                  25                  30

Lys Phe Lys Val Leu Gly Asn Thr Asp Arg His Ser Ile Lys Lys Asn
        35                  40                  45

Leu Ile Gly Ala Leu Leu Phe Asp Ser Gly Glu Thr Ala Glu Ala Thr
    50                  55                  60

Arg Leu Lys Arg Thr Ala Arg Arg Tyr Thr Arg Arg Lys Asn Arg
65                  70                  75                  80

Ile Cys Tyr Leu Gln Glu Ile Phe Ser Asn Glu Met Ala Lys Val Asp
                85                  90                  95

Asp Ser Phe Phe His Arg Leu Glu Glu Ser Phe Leu Val Glu Glu Asp
            100                 105                 110

Lys Lys His Glu Arg His Pro Ile Phe Gly Asn Ile Val Asp Glu Val
        115                 120                 125

Ala Tyr His Glu Lys Tyr Pro Thr Ile Tyr His Leu Arg Lys Lys Leu
    130                 135                 140

Val Asp Ser Thr Asp Lys Ala Asp Leu Arg Leu Ile Tyr Leu Ala Leu
145                 150                 155                 160

Ala His Met Ile Lys Phe Arg Gly His Phe Leu Ile Glu Gly Asp Leu
                165                 170                 175
```

```
Asn Pro Asp Asn Ser Asp Val Asp Lys Leu Phe Ile Gln Leu Val Gln
            180                 185                 190

Thr Tyr Asn Gln Leu Phe Glu Glu Asn Pro Ile Asn Ala Ser Gly Val
        195                 200                 205

Asp Ala Lys Ala Ile Leu Ser Ala Arg Leu Ser Lys Ser Arg Arg Leu
    210                 215                 220

Glu Asn Leu Ile Ala Gln Leu Pro Gly Glu Lys Lys Asn Gly Leu Phe
225                 230                 235                 240

Gly Asn Leu Ile Ala Leu Ser Leu Gly Leu Thr Pro Asn Phe Lys Ser
                245                 250                 255

Asn Phe Asp Leu Ala Glu Asp Ala Lys Leu Gln Leu Ser Lys Asp Thr
            260                 265                 270

Tyr Asp Asp Asp Leu Asp Asn Leu Leu Ala Gln Ile Gly Asp Gln Tyr
        275                 280                 285

Ala Asp Leu Phe Leu Ala Ala Lys Asn Leu Ser Asp Ala Ile Leu Leu
    290                 295                 300

Ser Asp Ile Leu Arg Val Asn Thr Glu Ile Thr Lys Ala Pro Leu Ser
305                 310                 315                 320

Ala Ser Met Ile Lys Arg Tyr Asp Glu His His Gln Asp Leu Thr Leu
                325                 330                 335

Leu Lys Ala Leu Val Arg Gln Gln Leu Pro Glu Lys Tyr Lys Glu Ile
            340                 345                 350

Phe Phe Asp Gln Ser Lys Asn Gly Tyr Ala Gly Tyr Ile Asp Gly Gly
        355                 360                 365

Ala Ser Gln Glu Glu Phe Tyr Lys Phe Ile Lys Pro Ile Leu Glu Lys
    370                 375                 380

Met Asp Gly Thr Glu Glu Leu Leu Val Lys Leu Asn Arg Glu Asp Leu
385                 390                 395                 400

Leu Arg Lys Gln Arg Thr Phe Asp Asn Gly Ser Ile Pro His Gln Ile
                405                 410                 415

His Leu Gly Glu Leu His Ala Ile Leu Arg Arg Gln Glu Asp Phe Tyr
            420                 425                 430

Pro Phe Leu Lys Asp Asn Arg Glu Lys Ile Glu Lys Ile Leu Thr Phe
        435                 440                 445

Arg Ile Pro Tyr Tyr Val Gly Pro Leu Ala Arg Gly Asn Ser Arg Phe
    450                 455                 460

Ala Trp Met Thr Arg Lys Ser Glu Glu Thr Ile Thr Pro Trp Asn Phe
465                 470                 475                 480

Glu Glu Val Val Asp Lys Gly Ala Ser Ala Gln Ser Phe Ile Glu Arg
                485                 490                 495

Met Thr Asn Phe Asp Lys Asn Leu Pro Asn Glu Lys Val Leu Pro Lys
            500                 505                 510

His Ser Leu Leu Tyr Glu Tyr Phe Thr Val Tyr Asn Glu Leu Thr Lys
        515                 520                 525

Val Lys Tyr Val Thr Glu Gly Met Arg Lys Pro Ala Phe Leu Ser Gly
    530                 535                 540

Glu Gln Lys Lys Ala Ile Val Asp Leu Leu Phe Lys Thr Asn Arg Lys
545                 550                 555                 560

Val Thr Val Lys Gln Leu Lys Glu Asp Tyr Phe Lys Lys Ile Glu Cys
                565                 570                 575

Phe Asp Ser Val Glu Ile Ser Gly Val Glu Asp Arg Phe Asn Ala Ser
            580                 585                 590
```

```
Leu Gly Thr Tyr His Asp Leu Leu Lys Ile Ile Lys Asp Lys Asp Phe
            595                 600                 605

Leu Asp Asn Glu Glu Asn Glu Asp Ile Leu Glu Asp Ile Val Leu Thr
610                 615                 620

Leu Thr Leu Phe Glu Asp Arg Glu Met Ile Glu Glu Arg Leu Lys Thr
625                 630                 635                 640

Tyr Ala His Leu Phe Asp Asp Lys Val Met Lys Gln Leu Lys Arg Arg
                645                 650                 655

Arg Tyr Thr Gly Trp Gly Arg Leu Ser Arg Lys Leu Ile Asn Gly Ile
            660                 665                 670

Arg Asp Lys Gln Ser Gly Lys Thr Ile Leu Asp Phe Leu Lys Ser Asp
        675                 680                 685

Gly Phe Ala Asn Arg Asn Phe Met Gln Leu Ile His Asp Asp Ser Leu
690                 695                 700

Thr Phe Lys Glu Asp Ile Gln Lys Ala Gln Val Ser Gly Gln Gly Asp
705                 710                 715                 720

Ser Leu His Glu His Ile Ala Asn Leu Ala Gly Ser Pro Ala Ile Lys
                725                 730                 735

Lys Gly Ile Leu Gln Thr Val Lys Val Val Asp Glu Leu Val Lys Val
            740                 745                 750

Met Gly Arg His Lys Pro Glu Asn Ile Val Ile Glu Met Ala Arg Glu
        755                 760                 765

Asn Gln Thr Thr Gln Lys Gly Gln Lys Asn Ser Arg Glu Arg Met Lys
770                 775                 780

Arg Ile Glu Glu Gly Ile Lys Glu Leu Gly Ser Gln Ile Leu Lys Glu
785                 790                 795                 800

His Pro Val Glu Asn Thr Gln Leu Gln Asn Glu Lys Leu Tyr Leu Tyr
                805                 810                 815

Tyr Leu Gln Asn Gly Arg Asp Met Tyr Val Asp Gln Glu Leu Asp Ile
            820                 825                 830

Asn Arg Leu Ser Asp Tyr Asp Val Asp Ala Ile Val Pro Gln Ser Phe
        835                 840                 845

Leu Lys Asp Asp Ser Ile Asp Asn Lys Val Leu Thr Arg Ser Asp Lys
850                 855                 860

Asn Arg Gly Lys Ser Asp Asn Val Pro Ser Glu Glu Val Val Lys Lys
865                 870                 875                 880

Met Lys Asn Tyr Trp Arg Gln Leu Leu Asn Ala Lys Leu Ile Thr Gln
                885                 890                 895

Arg Lys Phe Asp Asn Leu Thr Lys Ala Glu Arg Gly Gly Leu Ser Glu
            900                 905                 910

Leu Asp Lys Ala Gly Phe Ile Lys Arg Gln Leu Val Glu Thr Arg Gln
        915                 920                 925

Ile Thr Lys His Val Ala Gln Ile Leu Asp Ser Arg Met Asn Thr Lys
930                 935                 940

Tyr Asp Glu Asn Asp Lys Leu Ile Arg Glu Val Lys Val Ile Thr Leu
945                 950                 955                 960

Lys Ser Lys Leu Val Ser Asp Phe Arg Lys Asp Phe Gln Phe Tyr Lys
                965                 970                 975

Val Arg Glu Ile Asn Asn Tyr His His Ala His Asp Ala Tyr Leu Asn
            980                 985                 990

Ala Val Val Gly Thr Ala Leu Ile Lys Lys Tyr Pro Lys Leu Glu Ser
        995                 1000                1005
```

```
Glu Phe Val Tyr Gly Asp Tyr Lys Val Tyr Asp Val Arg Lys Met Ile
    1010                1015                1020

Ala Lys Ser Glu Gln Glu Ile Gly Lys Ala Thr Ala Lys Tyr Phe Phe
1025                1030                1035                1040

Tyr Ser Asn Ile Met Asn Phe Phe Lys Thr Glu Ile Thr Leu Ala Asn
                1045                1050                1055

Gly Glu Ile Arg Lys Arg Pro Leu Ile Glu Thr Asn Gly Glu Thr Gly
                1060                1065                1070

Glu Ile Val Trp Asp Lys Gly Arg Asp Phe Ala Thr Val Arg Lys Val
            1075                1080                1085

Leu Ser Met Pro Gln Val Asn Ile Val Lys Lys Thr Glu Val Gln Thr
        1090                1095                1100

Gly Gly Phe Ser Lys Glu Ser Ile Leu Pro Lys Arg Asn Ser Asp Lys
1105                1110                1115                1120

Leu Ile Ala Arg Lys Lys Asp Trp Asp Pro Lys Lys Tyr Gly Gly Phe
                1125                1130                1135

Asp Ser Pro Thr Val Ala Tyr Ser Val Leu Val Val Ala Lys Val Glu
            1140                1145                1150

Lys Gly Lys Ser Lys Lys Leu Lys Ser Val Lys Glu Leu Leu Gly Ile
        1155                1160                1165

Thr Ile Met Glu Arg Ser Ser Phe Glu Lys Asn Pro Ile Asp Phe Leu
    1170                1175                1180

Glu Ala Lys Gly Tyr Lys Glu Val Lys Lys Asp Leu Ile Ile Lys Leu
1185                1190                1195                1200

Pro Lys Tyr Ser Leu Phe Glu Leu Glu Asn Gly Arg Lys Arg Met Leu
                1205                1210                1215

Ala Ser Ala Gly Glu Leu Gln Lys Gly Asn Glu Leu Ala Leu Pro Ser
            1220                1225                1230

Lys Tyr Val Asn Phe Leu Tyr Leu Ala Ser His Tyr Glu Lys Leu Lys
        1235                1240                1245

Gly Ser Pro Glu Asp Asn Glu Gln Lys Gln Leu Phe Val Glu Gln His
    1250                1255                1260

Lys His Tyr Leu Asp Glu Ile Ile Glu Gln Ile Ser Glu Phe Ser Lys
1265                1270                1275                1280

Arg Val Ile Leu Ala Asp Ala Asn Leu Asp Lys Val Leu Ser Ala Tyr
                1285                1290                1295

Asn Lys His Arg Asp Lys Pro Ile Arg Glu Gln Ala Glu Asn Ile Ile
            1300                1305                1310

His Leu Phe Thr Leu Thr Asn Leu Gly Ala Pro Ala Ala Phe Lys Tyr
        1315                1320                1325

Phe Asp Thr Thr Ile Asp Arg Lys Arg Tyr Thr Ser Thr Lys Glu Val
    1330                1335                1340

Leu Asp Ala Thr Leu Ile His Gln Ser Ile Thr Gly Leu Tyr Glu Thr
1345                1350                1355                1360

Arg Ile Asp Leu Ser Gln Leu Gly Gly Asp Ala Tyr Pro Tyr Asp Val
                1365                1370                1375

Pro Asp Tyr Ala Ser Leu Gly Ser Gly Ser Pro Lys Lys Lys Arg Lys
            1380                1385                1390

Val Glu Asp Pro Lys Lys Lys Arg Lys Val Asp Val Ser Lys Gly Glu
        1395                1400                1405

Glu Leu Phe Thr Gly Val Val Pro Ile Leu Val Glu Leu Asp Gly Asp
    1410                1415                1420
```

-continued

Val Asn Gly His Lys Phe Ser Val Ser Gly Glu Gly Glu Gly Asp Ala
1425                1430                1435                1440

Thr Tyr Gly Lys Leu Thr Leu Lys Phe Ile Cys Thr Thr Gly Lys Leu
            1445                1450                1455

Pro Val Pro Trp Pro Thr Leu Val Thr Thr Leu Thr Tyr Gly Val Gln
            1460                1465                1470

Cys Phe Ser Arg Tyr Pro Asp His Met Lys Gln His Asp Phe Phe Lys
            1475                1480                1485

Ser Ala Met Pro Glu Gly Tyr Val Gln Glu Arg Thr Ile Phe Phe Lys
            1490                1495                1500

Asp Asp Gly Asn Tyr Lys Thr Arg Ala Glu Val Lys Phe Glu Gly Asp
1505                1510                1515                1520

Thr Leu Val Asn Arg Ile Glu Leu Lys Gly Ile Asp Phe Lys Glu Asp
                1525                1530                1535

Gly Asn Ile Leu Gly His Lys Leu Glu Tyr Asn Tyr Asn Ser His Asn
                1540                1545                1550

Val Tyr Ile Met Ala Asp Lys Gln Lys Asn Gly Ile Lys Val Asn Phe
            1555                1560                1565

Lys Ile Arg His Asn Ile Glu Asp Gly Ser Val Gln Leu Ala Asp His
            1570                1575                1580

Tyr Gln Gln Asn Thr Pro Ile Gly Asp Gly Pro Val Leu Leu Pro Asp
1585                1590                1595                1600

Asn His Tyr Leu Ser Thr Gln Ser Ala Leu Ser Lys Asp Pro Asn Glu
                1605                1610                1615

Lys Arg Asp His Met Val Leu Leu Glu Phe Val Thr Ala Ala Gly Ile
                1620                1625                1630

Thr Leu Gly Met Asp Glu Leu Tyr Lys
            1635                1640

<210> SEQ ID NO 33
<211> LENGTH: 1599
<212> TYPE: PRT
<213> ORGANISM: Artificial Sequence
<220> FEATURE:
<223> OTHER INFORMATION: PIN-XTEN-dCas9-2xNLS

<400> SEQUENCE: 33

Gln Met Glu Leu Glu Ile Arg Pro Leu Phe Leu Val Pro Asp Thr Asn
1               5                   10                  15

Gly Phe Ile Asp His Leu Ala Ser Leu Ala Arg Leu Leu Glu Ser Arg
            20                  25                  30

Lys Tyr Ile Leu Val Val Pro Leu Ile Val Ile Asn Glu Leu Asp Gly
        35                  40                  45

Leu Ala Lys Gly Gln Glu Thr Asp His Arg Ala Gly Gly Tyr Ala Arg
    50                  55                  60

Val Val Gln Glu Lys Ala Arg Lys Ser Ile Glu Phe Leu Glu Gln Arg
65                  70                  75                  80

Phe Glu Ser Arg Asp Ser Cys Leu Arg Ala Leu Thr Ser Arg Gly Asn
                85                  90                  95

Glu Leu Glu Ser Ile Ala Phe Arg Ser Glu Asp Ile Thr Gly Gln Leu
            100                 105                 110

Gly Asn Asn Asp Asp Leu Ile Leu Ser Cys Cys Leu His Tyr Cys Lys
        115                 120                 125

Asp Lys Ala Lys Asp Phe Met Pro Ala Ser Lys Glu Glu Pro Ile Arg
    130                 135                 140

```
Leu Leu Arg Glu Val Val Leu Leu Thr Asp Asp Arg Asn Leu Arg Val
145                 150                 155                 160

Lys Ala Leu Thr Arg Asn Val Pro Val Arg Asp Ile Pro Ala Phe Leu
                165                 170                 175

Thr Trp Ala Gln Val Gly Ser Gly Ser Glu Thr Pro Gly Thr Ser Glu
            180                 185                 190

Ser Ala Thr Pro Glu Ser Asp Lys Lys Tyr Ser Ile Gly Leu Ala Ile
        195                 200                 205

Gly Thr Asn Ser Val Gly Trp Ala Val Ile Thr Asp Glu Tyr Lys Val
    210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
                260                 265                 270

Lys Asn Arg Ile Cys Tyr Leu Gln Glu Ile Phe Ser Asn Glu Met Ala
            275                 280                 285

Lys Val Asp Asp Ser Phe Phe His Arg Leu Glu Glu Ser Phe Leu Val
290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
            340                 345                 350

Leu Ala Leu Ala His Met Ile Lys Phe Arg Gly His Phe Leu Ile Glu
        355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
                420                 425                 430

Gly Leu Phe Gly Asn Leu Ile Ala Leu Ser Leu Gly Leu Thr Pro Asn
            435                 440                 445

Phe Lys Ser Asn Phe Asp Leu Ala Glu Asp Ala Lys Leu Gln Leu Ser
450                 455                 460

Lys Asp Thr Tyr Asp Asp Asp Leu Asp Asn Leu Leu Ala Gln Ile Gly
465                 470                 475                 480

Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
        515                 520                 525

Leu Thr Leu Leu Lys Ala Leu Val Arg Gln Gln Leu Pro Glu Lys Tyr
    530                 535                 540

Lys Glu Ile Phe Phe Asp Gln Ser Lys Asn Gly Tyr Ala Gly Tyr Ile
545                 550                 555                 560
```

```
Asp Gly Gly Ala Ser Gln Glu Glu Phe Tyr Lys Phe Ile Lys Pro Ile
            565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
            595                 600                 605

His Gln Ile His Leu Gly Glu Leu His Ala Ile Leu Arg Arg Gln Glu
            610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
            645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
            675                 680                 685

Ile Glu Arg Met Thr Asn Phe Asp Lys Asn Leu Pro Asn Glu Lys Val
            690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
            725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
            755                 760                 765

Ile Glu Cys Phe Asp Ser Val Glu Ile Ser Gly Val Glu Asp Arg Phe
            770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
            805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
            835                 840                 845

Lys Arg Arg Arg Tyr Thr Gly Trp Gly Arg Leu Ser Arg Lys Leu Ile
            850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
            885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
            915                 920                 925

Ala Ile Lys Lys Gly Ile Leu Gln Thr Val Lys Val Val Asp Glu Leu
            930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
            965                 970                 975
```

-continued

Arg Met Lys Arg Ile Glu Glu Gly Ile Lys Glu Leu Gly Ser Gln Ile
          980                 985                 990

Leu Lys Glu His Pro Val Glu Asn Thr Gln Leu Gln Asn Glu Lys Leu
        995                 1000                1005

Tyr Leu Tyr Tyr Leu Gln Asn Gly Arg Asp Met Tyr Val Asp Gln Glu
        1010                1015                1020

Leu Asp Ile Asn Arg Leu Ser Asp Tyr Asp Val Asp Ala Ile Val Pro
1025                1030                1035                1040

Gln Ser Phe Leu Lys Asp Asp Ser Ile Asp Asn Lys Val Leu Thr Arg
                1045                1050                1055

Ser Asp Lys Asn Arg Gly Lys Ser Asp Asn Val Pro Ser Glu Glu Val
                1060                1065                1070

Val Lys Lys Met Lys Asn Tyr Trp Arg Gln Leu Leu Asn Ala Lys Leu
                1075                1080                1085

Ile Thr Gln Arg Lys Phe Asp Asn Leu Thr Lys Ala Glu Arg Gly Gly
                1090                1095                1100

Leu Ser Glu Leu Asp Lys Ala Gly Phe Ile Lys Arg Gln Leu Val Glu
1105                1110                1115                1120

Thr Arg Gln Ile Thr Lys His Val Ala Gln Ile Leu Asp Ser Arg Met
                1125                1130                1135

Asn Thr Lys Tyr Asp Glu Asn Asp Lys Leu Ile Arg Glu Val Lys Val
                1140                1145                1150

Ile Thr Leu Lys Ser Lys Leu Val Ser Asp Phe Arg Lys Asp Phe Gln
                1155                1160                1165

Phe Tyr Lys Val Arg Glu Ile Asn Asn Tyr His His Ala His Asp Ala
        1170                1175                1180

Tyr Leu Asn Ala Val Val Gly Thr Ala Leu Ile Lys Lys Tyr Pro Lys
1185                1190                1195                1200

Leu Glu Ser Glu Phe Val Tyr Gly Asp Tyr Lys Val Tyr Asp Val Arg
                1205                1210                1215

Lys Met Ile Ala Lys Ser Glu Gln Glu Ile Gly Lys Ala Thr Ala Lys
                1220                1225                1230

Tyr Phe Phe Tyr Ser Asn Ile Met Asn Phe Phe Lys Thr Glu Ile Thr
                1235                1240                1245

Leu Ala Asn Gly Glu Ile Arg Lys Arg Pro Leu Ile Glu Thr Asn Gly
1250                1255                1260

Glu Thr Gly Glu Ile Val Trp Asp Lys Gly Arg Asp Phe Ala Thr Val
1265                1270                1275                1280

Arg Lys Val Leu Ser Met Pro Gln Val Asn Ile Val Lys Lys Thr Glu
                1285                1290                1295

Val Gln Thr Gly Gly Phe Ser Lys Glu Ser Ile Leu Pro Lys Arg Asn
                1300                1305                1310

Ser Asp Lys Leu Ile Ala Arg Lys Lys Asp Trp Asp Pro Lys Lys Tyr
                1315                1320                1325

Gly Gly Phe Asp Ser Pro Thr Val Ala Tyr Ser Val Leu Val Val Ala
                1330                1335                1340

Lys Val Glu Lys Gly Lys Ser Lys Lys Leu Lys Ser Val Lys Glu Leu
1345                1350                1355                1360

Leu Gly Ile Thr Ile Met Glu Arg Ser Ser Phe Glu Lys Asn Pro Ile
                1365                1370                1375

Asp Phe Leu Glu Ala Lys Gly Tyr Lys Glu Val Lys Lys Asp Leu Ile
                1380                1385                1390

-continued

```
Ile Lys Leu Pro Lys Tyr Ser Leu Phe Glu Leu Glu Asn Gly Arg Lys
        1395                1400                1405

Arg Met Leu Ala Ser Ala Gly Glu Leu Gln Lys Gly Asn Glu Leu Ala
    1410                1415                1420

Leu Pro Ser Lys Tyr Val Asn Phe Leu Tyr Leu Ala Ser His Tyr Glu
1425                1430                1435                1440

Lys Leu Lys Gly Ser Pro Glu Asp Asn Glu Gln Lys Gln Leu Phe Val
            1445                1450                1455

Glu Gln His Lys His Tyr Leu Asp Glu Ile Ile Glu Gln Ile Ser Glu
        1460                1465                1470

Phe Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala Glu
1490                1495                1500

Asn Ile Ile His Leu Phe Thr Leu Thr Asn Leu Gly Ala Pro Ala Ala
1505                1510                1515                1520

Phe Lys Tyr Phe Asp Thr Thr Ile Asp Arg Lys Arg Tyr Thr Ser Thr
            1525                1530                1535

Lys Glu Val Leu Asp Ala Thr Leu Ile His Gln Ser Ile Thr Gly Leu
        1540                1545                1550

Tyr Glu Thr Arg Ile Asp Leu Ser Gln Leu Gly Gly Asp Ala Tyr Pro
    1555                1560                1565

Tyr Asp Val Pro Asp Tyr Ala Ser Leu Gly Ser Gly Ser Pro Lys Lys
        1570                1575                1580

Lys Arg Lys Val Glu Asp Pro Lys Lys Lys Arg Lys Val Asp Val
1585                1590                1595

<210> SEQ ID NO 34
<211> LENGTH: 1419
<212> TYPE: PRT
<213> ORGANISM: Artificial Sequence
<220> FEATURE:
<223> OTHER INFORMATION: Telomerase-binding protein EST1A encoded by
      SMG6 gene

<400> SEQUENCE: 34

Met Ala Glu Gly Leu Glu Arg Val Arg Ile Ser Ala Ser Glu Leu Arg
1               5                   10                  15

Gly Ile Leu Ala Thr Leu Ala Pro Gln Ala Gly Ser Arg Glu Asn Met
            20                  25                  30

Lys Glu Leu Lys Glu Ala Arg Pro Arg Lys Asp Asn Arg Arg Pro Asp
        35                  40                  45

Leu Glu Ile Tyr Lys Pro Gly Leu Ser Arg Leu Arg Asn Lys Pro Lys
    50                  55                  60

Ile Lys Glu Pro Pro Gly Ser Glu Glu Phe Lys Asp Glu Ile Val Asn
65                  70                  75                  80

Asp Arg Asp Cys Ser Ala Val Glu Asn Gly Thr Gln Pro Val Lys Asp
                85                  90                  95

Val Cys Lys Glu Leu Asn Asn Gln Glu Gln Asn Gly Pro Ile Asp Pro
            100                 105                 110

Glu Asn Asn Arg Gly Gln Glu Ser Phe Pro Arg Thr Ala Gly Gln Glu
        115                 120                 125

Asp Arg Ser Leu Lys Ile Ile Lys Arg Thr Lys Lys Pro Asp Leu Gln
    130                 135                 140
```

```
Ile Tyr Gln Pro Gly Arg Arg Leu Gln Thr Val Ser Lys Glu Ser Ala
145                 150                 155                 160

Ser Arg Val Glu Glu Glu Val Leu Asn Gln Val Glu Gln Leu Arg
            165                 170                 175

Val Glu Glu Asp Glu Cys Arg Gly Asn Val Ala Lys Glu Val Ala
        180                 185                 190

Asn Lys Pro Asp Arg Ala Glu Ile Glu Lys Ser Pro Gly Gly Arg
        195                 200                 205

Val Gly Ala Ala Lys Gly Glu Lys Gly Lys Arg Met Gly Lys Gly Glu
210                 215                 220

Gly Val Arg Glu Thr His Asp Asp Pro Ala Arg Gly Arg Pro Gly Ser
225                 230                 235                 240

Ala Lys Arg Tyr Ser Arg Ser Asp Lys Arg Arg Asn Arg Tyr Arg Thr
                245                 250                 255

Arg Ser Thr Ser Ser Ala Gly Ser Asn Asn Ser Ala Glu Gly Ala Gly
            260                 265                 270

Leu Thr Asp Asn Gly Cys Arg Arg Arg Gln Asp Arg Thr Lys Glu
        275                 280                 285

Arg Pro Arg Leu Lys Lys Gln Val Ser Val Ser Ser Thr Asp Ser Leu
        290                 295                 300

Asp Glu Asp Arg Ile Asp Glu Pro Asp Gly Leu Gly Pro Arg Arg Ser
305                 310                 315                 320

Ser Glu Arg Lys Arg His Leu Glu Arg Asn Trp Ser Arg Gly Glu
            325                 330                 335

Gly Glu Gln Lys Asn Ser Ala Lys Glu Tyr Arg Gly Thr Leu Arg Val
            340                 345                 350

Thr Phe Asp Ala Glu Ala Met Asn Lys Glu Ser Pro Met Val Arg Ser
        355                 360                 365

Ala Arg Asp Asp Met Asp Arg Gly Lys Pro Lys Gly Leu Ser Ser
        370                 375                 380

Gly Gly Lys Gly Ser Glu Lys Gln Glu Ser Lys Asn Pro Lys Gln Glu
385                 390                 395                 400

Leu Arg Gly Arg Gly Arg Gly Ile Leu Ile Leu Pro Ala His Thr Thr
                405                 410                 415

Leu Ser Val Asn Ser Ala Gly Ser Pro Glu Ser Ala Pro Leu Gly Pro
            420                 425                 430

Arg Leu Leu Phe Gly Ser Gly Ser Lys Gly Ser Arg Ser Trp Gly Arg
        435                 440                 445

Gly Gly Thr Thr Arg Arg Leu Trp Asp Pro Asn Asn Pro Asp Gln Lys
    450                 455                 460

Pro Ala Leu Lys Thr Gln Thr Pro Gln Leu His Phe Leu Asp Thr Asp
465                 470                 475                 480

Asp Glu Val Ser Pro Thr Ser Trp Gly Asp Ser Arg Gln Ala Gln Ala
            485                 490                 495

Ser Tyr Tyr Lys Phe Gln Asn Ser Asp Asn Pro Tyr Tyr Pro Arg
        500                 505                 510

Thr Pro Gly Pro Ala Ser Gln Tyr Pro Tyr Thr Gly Tyr Asn Pro Leu
        515                 520                 525

Gln Tyr Pro Val Gly Pro Thr Asn Gly Val Tyr Pro Gly Pro Tyr Tyr
        530                 535                 540

Pro Gly Tyr Pro Thr Pro Ser Gly Gln Tyr Val Cys Ser Pro Leu Pro
545                 550                 555                 560
```

```
Thr Ser Thr Met Ser Pro Glu Glu Val Glu Gln His Met Arg Asn Leu
                565                 570                 575
Gln Gln Gln Glu Leu His Arg Leu Leu Arg Val Ala Asp Asn Gln Glu
            580                 585                 590
Leu Gln Leu Ser Asn Leu Leu Ser Arg Asp Arg Ile Ser Pro Glu Gly
            595                 600                 605
Leu Glu Lys Met Ala Gln Leu Arg Ala Glu Leu Leu Gln Leu Tyr Glu
            610                 615                 620
Arg Cys Ile Leu Leu Asp Ile Glu Phe Ser Asn Gln Asn Val Asp
625                 630                 635                 640
Gln Ile Leu Trp Lys Asn Ala Phe Tyr Gln Val Ile Glu Lys Phe Arg
                645                 650                 655
Gln Leu Val Lys Asp Pro Asn Val Glu Asn Pro Glu Gln Ile Arg Asn
            660                 665                 670
Arg Leu Glu Leu Leu Asp Glu Gly Ser Asp Phe Phe Asp Ser Leu
            675                 680                 685
Leu Gln Lys Leu Gln Val Thr Tyr Lys Phe Lys Leu Glu Asp Tyr Met
            690                 695                 700
Asp Gly Leu Ala Ile Arg Ser Lys Pro Leu Arg Lys Thr Val Lys Tyr
705                 710                 715                 720
Ala Leu Ile Ser Ala Gln Arg Cys Met Ile Cys Gln Gly Asp Ile Ala
                725                 730                 735
Arg Tyr Arg Glu Gln Ala Ser Asp Thr Ala Asn Tyr Gly Lys Ala Arg
            740                 745                 750
Ser Trp Tyr Leu Lys Ala Gln His Ile Ala Pro Lys Asn Gly Arg Pro
            755                 760                 765
Tyr Asn Gln Leu Ala Leu Leu Ala Val Tyr Thr Arg Arg Lys Leu Asp
            770                 775                 780
Ala Val Tyr Tyr Tyr Met Arg Ser Leu Ala Ala Ser Asn Pro Ile Leu
785                 790                 795                 800
Thr Ala Lys Glu Ser Leu Met Ser Leu Phe Glu Glu Thr Lys Arg Lys
                805                 810                 815
Ala Glu Gln Met Glu Lys Lys Gln His Glu Glu Phe Asp Leu Ser Pro
            820                 825                 830
Asp Gln Trp Arg Lys Gly Lys Lys Ser Thr Phe Arg His Val Gly Asp
            835                 840                 845
Asp Thr Thr Arg Leu Glu Ile Trp Ile His Pro Ser His Pro Arg Ser
            850                 855                 860
Ser Gln Gly Thr Glu Ser Gly Lys Asp Ser Glu Gln Glu Asn Gly Leu
865                 870                 875                 880
Gly Ser Leu Ser Pro Ser Asp Leu Asn Lys Arg Phe Ile Leu Ser Phe
                885                 890                 895
Leu His Ala His Gly Lys Leu Phe Thr Arg Ile Gly Met Glu Thr Phe
            900                 905                 910
Pro Ala Val Ala Glu Lys Val Leu Lys Glu Phe Gln Val Leu Leu Gln
            915                 920                 925
His Ser Pro Ser Pro Ile Gly Ser Thr Arg Met Leu Gln Leu Met Thr
            930                 935                 940
Ile Asn Met Phe Ala Val His Asn Ser Gln Leu Lys Asp Cys Phe Ser
945                 950                 955                 960
Glu Glu Cys Arg Ser Val Ile Gln Glu Gln Ala Ala Ala Leu Gly Leu
                965                 970                 975
```

```
Ala Met Phe Ser Leu Leu Val Arg Arg Cys Thr Cys Leu Leu Lys Glu
            980                 985                 990

Ser Ala Lys Ala Gln Leu Ser Ser Pro Glu Asp Gln Asp Gln Asp
        995                 1000                1005

Asp Ile Lys Val Ser Ser Phe Val Pro Asp Leu Lys Glu Leu Leu Pro
    1010                1015                1020

Ser Val Lys Val Trp Ser Asp Trp Met Leu Gly Tyr Pro Asp Thr Trp
1025                1030                1035                1040

Asn Pro Pro Thr Ser Leu Asp Leu Pro Ser His Val Ala Val Asp
            1045                1050                1055

Val Trp Ser Thr Leu Ala Asp Phe Cys Asn Ile Leu Thr Ala Val Asn
            1060                1065                1070

Gln Ser Glu Val Pro Leu Tyr Lys Asp Pro Asp Asp Leu Thr Leu
        1075                1080                1085

Leu Ile Leu Glu Glu Asp Arg Leu Leu Ser Gly Phe Val Pro Leu Leu
        1090                1095                1100

Ala Ala Pro Gln Asp Pro Cys Tyr Val Glu Lys Thr Ser Asp Lys Val
1105                1110                1115                1120

Ile Ala Ala Asp Cys Lys Arg Val Thr Val Leu Lys Tyr Phe Leu Glu
            1125                1130                1135

Ala Leu Cys Gly Gln Glu Glu Pro Leu Leu Ala Phe Lys Gly Gly Lys
            1140                1145                1150

Tyr Val Ser Val Ala Pro Val Pro Asp Thr Met Gly Lys Glu Met Gly
        1155                1160                1165

Ser Gln Glu Gly Thr Arg Leu Glu Asp Glu Glu Asp Val Val Ile
        1170                1175                1180

Glu Asp Phe Glu Glu Asp Ser Glu Ala Glu Gly Ser Gly Gly Glu Asp
1185                1190                1195                1200

Asp Ile Arg Glu Leu Arg Ala Lys Lys Leu Ala Leu Ala Arg Lys Ile
            1205                1210                1215

Ala Glu Gln Gln Arg Arg Gln Glu Lys Ile Gln Ala Val Leu Glu Asp
            1220                1225                1230

His Ser Gln Met Arg Gln Met Glu Leu Glu Ile Arg Pro Leu Phe Leu
        1235                1240                1245

Val Pro Asp Thr Asn Gly Phe Ile Asp His Leu Ala Ser Leu Ala Arg
        1250                1255                1260

Leu Leu Glu Ser Arg Lys Tyr Ile Leu Val Val Pro Leu Ile Val Ile
1265                1270                1275                1280

Asn Glu Leu Asp Gly Leu Ala Lys Gly Gln Glu Thr Asp His Arg Ala
            1285                1290                1295

Gly Gly Tyr Ala Arg Val Val Gln Glu Lys Ala Arg Lys Ser Ile Glu
            1300                1305                1310

Phe Leu Glu Gln Arg Phe Glu Ser Arg Asp Ser Cys Leu Arg Ala Leu
        1315                1320                1325

Thr Ser Arg Gly Asn Glu Leu Glu Ser Ile Ala Phe Arg Ser Glu Asp
        1330                1335                1340

Ile Thr Gly Gln Leu Gly Asn Asn Asp Asp Leu Ile Leu Ser Cys Cys
1345                1350                1355                1360

Leu His Tyr Cys Lys Asp Lys Ala Lys Asp Phe Met Pro Ala Ser Lys
            1365                1370                1375

Glu Glu Pro Ile Arg Leu Leu Arg Glu Val Val Leu Leu Thr Asp Asp
            1380                1385                1390
```

```
Arg Asn Leu Arg Val Lys Ala Leu Thr Arg Asn Val Pro Val Arg Asp
        1395                1400                1405

Ile Pro Ala Phe Leu Thr Trp Ala Gln Val Gly
    1410                1415

<210> SEQ ID NO 35
<211> LENGTH: 152
<212> TYPE: PRT
<213> ORGANISM: Artificial Sequence
<220> FEATURE:
<223> OTHER INFORMATION: PIN domain

<400> SEQUENCE: 35

Leu Phe Leu Val Pro Asp Thr Asn Gly Phe Ile Asp His Leu Ala Ser
1               5                   10                  15

Leu Ala Arg Leu Leu Glu Ser Arg Lys Tyr Ile Leu Val Val Pro Leu
            20                  25                  30

Ile Val Ile Asn Glu Leu Asp Gly Leu Ala Lys Gly Gln Glu Thr Asp
        35                  40                  45

His Arg Ala Gly Gly Tyr Ala Arg Val Val Gln Lys Ala Arg Lys
    50                  55                  60

Ser Ile Glu Phe Leu Gln Arg Phe Glu Ser Arg Asp Ser Cys Leu
65                  70                  75                  80

Arg Ala Leu Thr Ser Arg Gly Asn Glu Leu Glu Ser Ile Ala Phe Arg
            85                  90                  95

Ser Glu Asp Ile Thr Gly Gln Leu Gly Asn Asn Asp Leu Ile Leu
            100                 105                 110

Ser Cys Cys Leu His Tyr Cys Lys Asp Lys Ala Lys Asp Phe Met Pro
            115                 120                 125

Ala Ser Lys Glu Glu Pro Ile Arg Leu Leu Arg Glu Val Val Leu Leu
    130                 135                 140

Thr Asp Asp Arg Asn Leu Arg Val
145                 150

<210> SEQ ID NO 36
<211> LENGTH: 16
<212> TYPE: PRT
<213> ORGANISM: Artificial Sequence
<220> FEATURE:
<223> OTHER INFORMATION: XTEN linker

<400> SEQUENCE: 36

Ser Gly Ser Glu Thr Pro Gly Thr Ser Glu Ser Ala Thr Pro Glu Ser
1               5                   10                  15

<210> SEQ ID NO 37
<211> LENGTH: 1600
<212> TYPE: PRT
<213> ORGANISM: Artificial Sequence
<220> FEATURE:
<223> OTHER INFORMATION: PIN-XTEN-dCas9

<400> SEQUENCE: 37

Met Gln Met Glu Leu Glu Ile Arg Pro Leu Phe Leu Val Pro Asp Thr
1               5                   10                  15

Asn Gly Phe Ile Asp His Leu Ala Ser Leu Ala Arg Leu Leu Glu Ser
            20                  25                  30

Arg Lys Tyr Ile Leu Val Val Pro Leu Ile Val Ile Asn Glu Leu Asp
        35                  40                  45
```

```
Gly Leu Ala Lys Gly Gln Glu Thr Asp His Arg Ala Gly Gly Tyr Ala
             50                  55                  60

Arg Val Val Gln Glu Lys Ala Arg Lys Ser Ile Glu Phe Leu Glu Gln
 65                  70                  75                  80

Arg Phe Glu Ser Arg Asp Ser Cys Leu Arg Ala Leu Thr Ser Arg Gly
                 85                  90                  95

Asn Glu Leu Glu Ser Ile Ala Phe Arg Ser Glu Asp Ile Thr Gly Gln
                100                 105                 110

Leu Gly Asn Asn Asp Asp Leu Ile Leu Ser Cys Cys Leu His Tyr Cys
            115                 120                 125

Lys Asp Lys Ala Lys Asp Phe Met Pro Ala Ser Lys Glu Glu Pro Ile
130                 135                 140

Arg Leu Leu Arg Glu Val Val Leu Leu Thr Asp Asp Arg Asn Leu Arg
145                 150                 155                 160

Val Lys Ala Leu Thr Arg Asn Val Pro Val Arg Asp Ile Pro Ala Phe
                165                 170                 175

Leu Thr Trp Ala Gln Val Gly Ser Gly Ser Glu Thr Pro Gly Thr Ser
                180                 185                 190

Glu Ser Ala Thr Pro Glu Ser Asp Lys Lys Tyr Ser Ile Gly Leu Ala
            195                 200                 205

Ile Gly Thr Asn Ser Val Gly Trp Ala Val Ile Thr Asp Glu Tyr Lys
        210                 215                 220

Val Pro Ser Lys Lys Phe Lys Val Leu Gly Asn Thr Asp Arg His Ser
225                 230                 235                 240

Ile Lys Lys Asn Leu Ile Gly Ala Leu Leu Phe Asp Ser Gly Glu Thr
                245                 250                 255

Ala Glu Ala Thr Arg Leu Lys Arg Thr Ala Arg Arg Arg Tyr Thr Arg
                260                 265                 270

Arg Lys Asn Arg Ile Cys Tyr Leu Gln Glu Ile Phe Ser Asn Glu Met
            275                 280                 285

Ala Lys Val Asp Asp Ser Phe Phe His Arg Leu Glu Glu Ser Phe Leu
290                 295                 300

Val Glu Glu Asp Lys Lys His Glu Arg His Pro Ile Phe Gly Asn Ile
305                 310                 315                 320

Val Asp Glu Val Ala Tyr His Glu Lys Tyr Pro Thr Ile Tyr His Leu
                325                 330                 335

Arg Lys Lys Leu Val Asp Ser Thr Asp Lys Ala Asp Leu Arg Leu Ile
            340                 345                 350

Tyr Leu Ala Leu Ala His Met Ile Lys Phe Arg Gly His Phe Leu Ile
        355                 360                 365

Glu Gly Asp Leu Asn Pro Asp Asn Ser Asp Val Asp Lys Leu Phe Ile
    370                 375                 380

Gln Leu Val Gln Thr Tyr Asn Gln Leu Phe Glu Glu Asn Pro Ile Asn
385                 390                 395                 400

Ala Ser Gly Val Asp Ala Lys Ala Ile Leu Ser Ala Arg Leu Ser Lys
                405                 410                 415

Ser Arg Arg Leu Glu Asn Leu Ile Ala Gln Leu Pro Gly Glu Lys Lys
            420                 425                 430

Asn Gly Leu Phe Gly Asn Leu Ile Ala Leu Ser Leu Gly Leu Thr Pro
        435                 440                 445

Asn Phe Lys Ser Asn Phe Asp Leu Ala Glu Asp Ala Lys Leu Gln Leu
    450                 455                 460
```

```
Ser Lys Asp Thr Tyr Asp Asp Leu Asp Asn Leu Leu Ala Gln Ile
465                 470                 475                 480

Gly Asp Gln Tyr Ala Asp Leu Phe Leu Ala Lys Asn Leu Ser Asp
            485                 490                 495

Ala Ile Leu Leu Ser Asp Ile Leu Arg Val Asn Thr Glu Ile Thr Lys
                500                 505                 510

Ala Pro Leu Ser Ala Ser Met Ile Lys Arg Tyr Asp Glu His His Gln
            515                 520                 525

Asp Leu Thr Leu Leu Lys Ala Leu Val Arg Gln Gln Leu Pro Glu Lys
        530                 535                 540

Tyr Lys Glu Ile Phe Phe Asp Gln Ser Lys Asn Gly Tyr Ala Gly Tyr
545                 550                 555                 560

Ile Asp Gly Gly Ala Ser Gln Glu Glu Phe Tyr Lys Phe Ile Lys Pro
            565                 570                 575

Ile Leu Glu Lys Met Asp Gly Thr Glu Glu Leu Leu Val Lys Leu Asn
                580                 585                 590

Arg Glu Asp Leu Leu Arg Lys Gln Arg Thr Phe Asp Asn Gly Ser Ile
        595                 600                 605

Pro His Gln Ile His Leu Gly Glu Leu His Ala Ile Leu Arg Arg Gln
    610                 615                 620

Glu Asp Phe Tyr Pro Phe Leu Lys Asp Asn Arg Glu Lys Ile Glu Lys
625                 630                 635                 640

Ile Leu Thr Phe Arg Ile Pro Tyr Tyr Val Gly Pro Leu Ala Arg Gly
                645                 650                 655

Asn Ser Arg Phe Ala Trp Met Thr Arg Lys Ser Glu Glu Thr Ile Thr
            660                 665                 670

Pro Trp Asn Phe Glu Glu Val Val Asp Lys Gly Ala Ser Ala Gln Ser
        675                 680                 685

Phe Ile Glu Arg Met Thr Asn Phe Asp Lys Asn Leu Pro Asn Glu Lys
690                 695                 700

Val Leu Pro Lys His Ser Leu Leu Tyr Glu Tyr Phe Thr Val Tyr Asn
705                 710                 715                 720

Glu Leu Thr Lys Val Lys Tyr Val Thr Glu Gly Met Arg Lys Pro Ala
            725                 730                 735

Phe Leu Ser Gly Glu Gln Lys Lys Ala Ile Val Asp Leu Leu Phe Lys
            740                 745                 750

Thr Asn Arg Lys Val Thr Val Lys Gln Leu Lys Glu Asp Tyr Phe Lys
            755                 760                 765

Lys Ile Glu Cys Phe Asp Ser Val Glu Ile Ser Gly Val Glu Asp Arg
770                 775                 780

Phe Asn Ala Ser Leu Gly Thr Tyr His Asp Leu Leu Lys Ile Ile Lys
785                 790                 795                 800

Asp Lys Asp Phe Leu Asp Asn Glu Glu Asn Glu Asp Ile Leu Glu Asp
            805                 810                 815

Ile Val Leu Thr Leu Thr Leu Phe Glu Asp Arg Glu Met Ile Glu Glu
                820                 825                 830

Arg Leu Lys Thr Tyr Ala His Leu Phe Asp Asp Lys Val Met Lys Gln
            835                 840                 845

Leu Lys Arg Arg Arg Tyr Thr Gly Trp Gly Arg Leu Ser Arg Lys Leu
    850                 855                 860

Ile Asn Gly Ile Arg Asp Lys Gln Ser Gly Lys Thr Ile Leu Asp Phe
865                 870                 875                 880
```

Leu Lys Ser Asp Gly Phe Ala Asn Arg Asn Phe Met Gln Leu Ile His
            885                 890                 895

Asp Asp Ser Leu Thr Phe Lys Glu Asp Ile Gln Lys Ala Gln Val Ser
            900                 905                 910

Gly Gln Gly Asp Ser Leu His Glu His Ile Ala Asn Leu Ala Gly Ser
            915                 920                 925

Pro Ala Ile Lys Lys Gly Ile Leu Gln Thr Val Lys Val Asp Glu
            930                 935                 940

Leu Val Lys Val Met Gly Arg His Lys Pro Glu Asn Ile Val Ile Glu
945                 950                 955                 960

Met Ala Arg Glu Asn Gln Thr Thr Gln Lys Gly Gln Lys Asn Ser Arg
            965                 970                 975

Glu Arg Met Lys Arg Ile Glu Glu Gly Ile Lys Glu Leu Gly Ser Gln
            980                 985                 990

Ile Leu Lys Glu His Pro Val Glu Asn Thr Gln Leu Gln Asn Glu Lys
            995                 1000                1005

Leu Tyr Leu Tyr Tyr Leu Gln Asn Gly Arg Asp Met Tyr Val Asp Gln
            1010                1015                1020

Glu Leu Asp Ile Asn Arg Leu Ser Asp Tyr Asp Val Asp Ala Ile Val
1025                1030                1035                1040

Pro Gln Ser Phe Leu Lys Asp Asp Ser Ile Asp Asn Lys Val Leu Thr
            1045                1050                1055

Arg Ser Asp Lys Asn Arg Gly Lys Ser Asp Asn Val Pro Ser Glu Glu
            1060                1065                1070

Val Val Lys Lys Met Lys Asn Tyr Trp Arg Gln Leu Leu Asn Ala Lys
            1075                1080                1085

Leu Ile Thr Gln Arg Lys Phe Asp Asn Leu Thr Lys Ala Glu Arg Gly
            1090                1095                1100

Gly Leu Ser Glu Leu Asp Lys Ala Gly Phe Ile Lys Arg Gln Leu Val
1105                1110                1115                1120

Glu Thr Arg Gln Ile Thr Lys His Val Ala Gln Ile Leu Asp Ser Arg
            1125                1130                1135

Met Asn Thr Lys Tyr Asp Glu Asn Asp Lys Leu Ile Arg Glu Val Lys
            1140                1145                1150

Val Ile Thr Leu Lys Ser Lys Leu Val Ser Asp Phe Arg Lys Asp Phe
            1155                1160                1165

Gln Phe Tyr Lys Val Arg Glu Ile Asn Asn Tyr His His Ala His Asp
            1170                1175                1180

Ala Tyr Leu Asn Ala Val Val Gly Thr Ala Leu Ile Lys Lys Tyr Pro
1185                1190                1195                1200

Lys Leu Glu Ser Glu Phe Val Tyr Gly Asp Tyr Lys Val Tyr Asp Val
            1205                1210                1215

Arg Lys Met Ile Ala Lys Ser Glu Gln Glu Ile Gly Lys Ala Thr Ala
            1220                1225                1230

Lys Tyr Phe Phe Tyr Ser Asn Ile Met Asn Phe Phe Lys Thr Glu Ile
            1235                1240                1245

Thr Leu Ala Asn Gly Glu Ile Arg Lys Arg Pro Leu Ile Glu Thr Asn
            1250                1255                1260

Gly Glu Thr Gly Glu Ile Val Trp Asp Lys Gly Arg Asp Phe Ala Thr
1265                1270                1275                1280

Val Arg Lys Val Leu Ser Met Pro Gln Val Asn Ile Val Lys Lys Thr
            1285                1290                1295

Glu Val Gln Thr Gly Gly Phe Ser Lys Glu Ser Ile Leu Pro Lys Arg
            1300            1305            1310

Asn Ser Asp Lys Leu Ile Ala Arg Lys Lys Asp Trp Asp Pro Lys Lys
        1315            1320            1325

Tyr Gly Gly Phe Asp Ser Pro Thr Val Ala Tyr Ser Val Leu Val Val
    1330            1335            1340

Ala Lys Val Glu Lys Gly Lys Ser Lys Lys Leu Lys Ser Val Lys Glu
1345            1350            1355            1360

Leu Leu Gly Ile Thr Ile Met Glu Arg Ser Ser Phe Glu Lys Asn Pro
            1365            1370            1375

Ile Asp Phe Leu Glu Ala Lys Gly Tyr Lys Glu Val Lys Lys Asp Leu
        1380            1385            1390

Ile Ile Lys Leu Pro Lys Tyr Ser Leu Phe Glu Leu Glu Asn Gly Arg
            1395            1400            1405

Lys Arg Met Leu Ala Ser Ala Gly Glu Leu Gln Lys Gly Asn Glu Leu
        1410            1415            1420

Ala Leu Pro Ser Lys Tyr Val Asn Phe Leu Tyr Leu Ala Ser His Tyr
1425            1430            1435            1440

Glu Lys Leu Lys Gly Ser Pro Glu Asp Asn Glu Gln Lys Gln Leu Phe
            1445            1450            1455

Val Glu Gln His Lys His Tyr Leu Asp Glu Ile Ile Glu Gln Ile Ser
        1460            1465            1470

Glu Phe Ser Lys Arg Val Ile Leu Ala Asp Ala Asn Leu Asp Lys Val
            1475            1480            1485

Leu Ser Ala Tyr Asn Lys His Arg Asp Lys Pro Ile Arg Glu Gln Ala
        1490            1495            1500

Glu Asn Ile Ile His Leu Phe Thr Leu Thr Asn Leu Gly Ala Pro Ala
1505            1510            1515            1520

Ala Phe Lys Tyr Phe Asp Thr Thr Ile Asp Arg Lys Arg Tyr Thr Ser
            1525            1530            1535

Thr Lys Glu Val Leu Asp Ala Thr Leu Ile His Gln Ser Ile Thr Gly
        1540            1545            1550

Leu Tyr Glu Thr Arg Ile Asp Leu Ser Gln Leu Gly Gly Asp Ala Tyr
        1555            1560            1565

Pro Tyr Asp Val Pro Asp Tyr Ala Ser Leu Gly Ser Gly Ser Pro Lys
    1570            1575            1580

Lys Lys Arg Lys Val Glu Asp Pro Lys Lys Lys Arg Lys Val Asp Val
1585            1590            1595            1600

<210> SEQ ID NO 38
<211> LENGTH: 1470
<212> TYPE: PRT
<213> ORGANISM: Artificial Sequence
<220> FEATURE:
<223> OTHER INFORMATION: PIN-XTEN-dCas9(delta HNH)-2xNLS

<400> SEQUENCE: 38

Gln Met Glu Leu Glu Ile Arg Pro Leu Phe Leu Val Pro Asp Thr Asn
1               5                   10                  15

Gly Phe Ile Asp His Leu Ala Ser Leu Ala Arg Leu Leu Glu Ser Arg
            20                  25                  30

Lys Tyr Ile Leu Val Val Pro Leu Ile Val Ile Asn Glu Leu Asp Gly
        35                  40                  45

Leu Ala Lys Gly Gln Glu Thr Asp His Arg Ala Gly Gly Tyr Ala Arg
    50                  55                  60

```
Val Val Gln Glu Lys Ala Arg Lys Ser Ile Glu Phe Leu Glu Gln Arg
 65                  70                  75                  80

Phe Glu Ser Arg Asp Ser Cys Leu Arg Ala Leu Thr Ser Arg Gly Asn
                 85                  90                  95

Glu Leu Glu Ser Ile Ala Phe Arg Ser Glu Asp Ile Thr Gly Gln Leu
            100                 105                 110

Gly Asn Asn Asp Asp Leu Ile Leu Ser Cys Cys Leu His Tyr Cys Lys
            115                 120                 125

Asp Lys Ala Lys Asp Phe Met Pro Ala Ser Lys Glu Pro Ile Arg
    130                 135                 140

Leu Leu Arg Glu Val Val Leu Leu Thr Asp Asp Arg Asn Leu Arg Val
145                 150                 155                 160

Lys Ala Leu Thr Arg Asn Val Pro Val Arg Asp Ile Pro Ala Phe Leu
                165                 170                 175

Thr Trp Ala Gln Val Gly Ser Gly Ser Glu Thr Pro Gly Thr Ser Glu
                180                 185                 190

Ser Ala Thr Pro Glu Ser Asp Lys Lys Tyr Ser Ile Gly Leu Ala Ile
            195                 200                 205

Gly Thr Asn Ser Val Gly Trp Ala Val Ile Thr Asp Glu Tyr Lys Val
210                 215                 220

Pro Ser Lys Lys Phe Lys Val Leu Gly Asn Thr Asp Arg His Ser Ile
225                 230                 235                 240

Lys Lys Asn Leu Ile Gly Ala Leu Leu Phe Asp Ser Gly Glu Thr Ala
                245                 250                 255

Glu Ala Thr Arg Leu Lys Arg Thr Ala Arg Arg Arg Tyr Thr Arg Arg
            260                 265                 270

Lys Asn Arg Ile Cys Tyr Leu Gln Glu Ile Phe Ser Asn Glu Met Ala
            275                 280                 285

Lys Val Asp Asp Ser Phe Phe His Arg Leu Glu Glu Ser Phe Leu Val
    290                 295                 300

Glu Glu Asp Lys Lys His Glu Arg His Pro Ile Phe Gly Asn Ile Val
305                 310                 315                 320

Asp Glu Val Ala Tyr His Glu Lys Tyr Pro Thr Ile Tyr His Leu Arg
                325                 330                 335

Lys Lys Leu Val Asp Ser Thr Asp Lys Ala Asp Leu Arg Leu Ile Tyr
                340                 345                 350

Leu Ala Leu Ala His Met Ile Lys Phe Arg Gly His Phe Leu Ile Glu
            355                 360                 365

Gly Asp Leu Asn Pro Asp Asn Ser Asp Val Asp Lys Leu Phe Ile Gln
    370                 375                 380

Leu Val Gln Thr Tyr Asn Gln Leu Phe Glu Glu Asn Pro Ile Asn Ala
385                 390                 395                 400

Ser Gly Val Asp Ala Lys Ala Ile Leu Ser Ala Arg Leu Ser Lys Ser
                405                 410                 415

Arg Arg Leu Glu Asn Leu Ile Ala Gln Leu Pro Gly Glu Lys Lys Asn
            420                 425                 430

Gly Leu Phe Gly Asn Leu Ile Ala Leu Ser Leu Gly Leu Thr Pro Asn
            435                 440                 445

Phe Lys Ser Asn Phe Asp Leu Ala Glu Asp Ala Lys Leu Gln Leu Ser
    450                 455                 460

Lys Asp Thr Tyr Asp Asp Asp Leu Asp Asn Leu Leu Ala Gln Ile Gly
465                 470                 475                 480
```

```
Asp Gln Tyr Ala Asp Leu Phe Leu Ala Ala Lys Asn Leu Ser Asp Ala
                485                 490                 495

Ile Leu Leu Ser Asp Ile Leu Arg Val Asn Thr Glu Ile Thr Lys Ala
            500                 505                 510

Pro Leu Ser Ala Ser Met Ile Lys Arg Tyr Asp Glu His His Gln Asp
            515                 520                 525

Leu Thr Leu Leu Lys Ala Leu Val Arg Gln Gln Leu Pro Glu Lys Tyr
        530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
            595                 600                 605

His Gln Ile His Leu Gly Glu Leu His Ala Ile Leu Arg Arg Gln Glu
        610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
            675                 680                 685

Ile Glu Arg Met Thr Asn Phe Asp Lys Asn Leu Pro Asn Glu Lys Val
        690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
            755                 760                 765

Ile Glu Cys Phe Asp Ser Val Glu Ile Ser Gly Val Glu Asp Arg Phe
        770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
        850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895
```

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925

Ala Ile Lys Lys Gly Ile Leu Gln Thr Val Lys Val Val Asp Glu Leu
    930                 935                 940

Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Gly Ser Gly
                965                 970                 975

Ser Gly Leu Asp Lys Ala Gly Phe Ile Lys Arg Gln Leu Val Glu Thr
            980                 985                 990

Arg Gln Ile Thr Lys His Val Ala Gln Ile Leu Asp Ser Arg Met Asn
        995                 1000                1005

Thr Lys Tyr Asp Glu Asn Asp Lys Leu Ile Arg Glu Val Lys Val Ile
    1010                1015                1020

Thr Leu Lys Ser Lys Leu Val Ser Asp Phe Arg Lys Asp Phe Gln Phe
1025                1030                1035                1040

Tyr Lys Val Arg Glu Ile Asn Asn Tyr His His Ala His Asp Ala Tyr
                1045                1050                1055

Leu Asn Ala Val Val Gly Thr Ala Leu Ile Lys Lys Tyr Pro Lys Leu
            1060                1065                1070

Glu Ser Glu Phe Val Tyr Gly Asp Tyr Lys Val Tyr Asp Val Arg Lys
        1075                1080                1085

Met Ile Ala Lys Ser Glu Gln Glu Ile Gly Lys Ala Thr Ala Lys Tyr
    1090                1095                1100

Phe Phe Tyr Ser Asn Ile Met Asn Phe Phe Lys Thr Glu Ile Thr Leu
1105                1110                1115                1120

Ala Asn Gly Glu Ile Arg Lys Arg Pro Leu Ile Glu Thr Asn Gly Glu
                1125                1130                1135

Thr Gly Glu Ile Val Trp Asp Lys Gly Arg Asp Phe Ala Thr Val Arg
            1140                1145                1150

Lys Val Leu Ser Met Pro Gln Val Asn Ile Val Lys Lys Thr Glu Val
        1155                1160                1165

Gln Thr Gly Gly Phe Ser Lys Glu Ser Ile Leu Pro Lys Arg Asn Ser
    1170                1175                1180

Asp Lys Leu Ile Ala Arg Lys Lys Asp Trp Pro Lys Lys Tyr Gly
1185                1190                1195                1200

Gly Phe Asp Ser Pro Thr Val Ala Tyr Ser Val Leu Val Val Ala Lys
                1205                1210                1215

Val Glu Lys Gly Lys Ser Lys Lys Leu Lys Ser Val Lys Glu Leu Leu
            1220                1225                1230

Gly Ile Thr Ile Met Glu Arg Ser Ser Phe Glu Lys Asn Pro Ile Asp
        1235                1240                1245

Phe Leu Glu Ala Lys Gly Tyr Lys Glu Val Lys Lys Asp Leu Ile Ile
    1250                1255                1260

Lys Leu Pro Lys Tyr Ser Leu Phe Glu Leu Glu Asn Gly Arg Lys Arg
1265                1270                1275                1280

Met Leu Ala Ser Ala Gly Glu Leu Gln Lys Gly Asn Glu Leu Ala Leu
                1285                1290                1295

Pro Ser Lys Tyr Val Asn Phe Leu Tyr Leu Ala Ser His Tyr Glu Lys
            1300                1305                1310

-continued

Leu Lys Gly Ser Pro Glu Asp Asn Glu Gln Lys Gln Leu Phe Val Glu
            1315                1320                1325

Gln His Lys His Tyr Leu Asp Glu Ile Ile Glu Gln Ile Ser Glu Phe
        1330                1335                1340

Ser Lys Arg Val Ile Leu Ala Asp Ala Asn Leu Asp Lys Val Leu Ser
1345                1350                1355                1360

Ala Tyr Asn Lys His Arg Asp Lys Pro Ile Arg Glu Gln Ala Glu Asn
                1365                1370                1375

Ile Ile His Leu Phe Thr Leu Thr Asn Leu Gly Ala Pro Ala Ala Phe
            1380                1385                1390

Lys Tyr Phe Asp Thr Thr Ile Asp Arg Lys Arg Tyr Thr Ser Thr Lys
        1395                1400                1405

Glu Val Leu Asp Ala Thr Leu Ile His Gln Ser Ile Thr Gly Leu Tyr
    1410                1415                1420

Glu Thr Arg Ile Asp Leu Ser Gln Leu Gly Gly Asp Ala Tyr Pro Tyr
1425                1430                1435                1440

Asp Val Pro Asp Tyr Ala Ser Leu Gly Ser Gly Ser Pro Lys Lys Lys
                1445                1450                1455

Arg Lys Val Glu Asp Pro Lys Lys Lys Arg Lys Val Asp Val
            1460                1465                1470

<210> SEQ ID NO 39
<211> LENGTH: 1354
<212> TYPE: PRT
<213> ORGANISM: Artificial Sequence
<220> FEATURE:
<223> OTHER INFORMATION: Streptococcus pyogenes dCas9 (D10A, H840A)

<400> SEQUENCE: 39

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

```
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
            645                 650                 655

Thr Gly Trp Gly Arg Leu Ser Arg Lys Leu Ile Asn Gly Ile Arg Asp
        660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr Ser
1025                1030                1035                1040
```

-continued

```
Asn Ile Met Asn Phe Phe Lys Thr Glu Ile Thr Leu Ala Asn Gly Glu
            1045                1050                1055
Ile Arg Lys Arg Pro Leu Ile Glu Thr Asn Gly Glu Thr Gly Glu Ile
            1060                1065                1070
Val Trp Asp Lys Gly Arg Asp Phe Ala Thr Val Arg Lys Val Leu Ser
        1075                1080                1085
Met Pro Gln Val Asn Ile Val Lys Lys Thr Glu Val Gln Thr Gly Gly
    1090                1095                1100
Phe Ser Lys Glu Ser Ile Leu Pro Lys Arg Asn Ser Asp Lys Leu Ile
1105                1110                1115                1120
Ala Arg Lys Lys Asp Trp Asp Pro Lys Lys Tyr Gly Gly Phe Asp Ser
            1125                1130                1135
Pro Thr Val Ala Tyr Ser Val Leu Val Val Ala Lys Val Glu Lys Gly
            1140                1145                1150
Lys Ser Lys Lys Leu Lys Ser Val Lys Glu Leu Leu Gly Ile Thr Ile
            1155                1160                1165
Met Glu Arg Ser Ser Phe Glu Lys Asn Pro Ile Asp Phe Leu Glu Ala
        1170                1175                1180
Lys Gly Tyr Lys Glu Val Lys Lys Asp Leu Ile Ile Lys Leu Pro Lys
1185                1190                1195                1200
Tyr Ser Leu Phe Glu Leu Glu Asn Gly Arg Lys Arg Met Leu Ala Ser
            1205                1210                1215
Ala Gly Glu Leu Gln Lys Gly Asn Glu Leu Ala Leu Pro Ser Lys Tyr
            1220                1225                1230
Val Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys His
    1250                1255                1260
Tyr Leu Asp Glu Ile Ile Glu Gln Ile Ser Glu Phe Ser Lys Arg Val
1265                1270                1275                1280
Ile Leu Ala Asp Ala Asn Leu Asp Lys Val Leu Ser Ala Tyr Asn Lys
            1285                1290                1295
His Arg Asp Lys Pro Ile Arg Glu Gln Ala Glu Asn Ile Ile His Leu
            1300                1305                1310
Phe Thr Leu Thr Asn Leu Gly Ala Pro Ala Ala Phe Lys Tyr Phe Asp
        1315                1320                1325
Thr Thr Ile Asp Arg Lys Arg Tyr Thr Ser Thr Lys Glu Val Leu Asp
    1330                1335                1340
Ala Thr Leu Ile His Gln Ser Ile Thr Gly
1345                1350
```